(12) United States Patent
Silver et al.

(10) Patent No.: US 6,664,090 B1
(45) Date of Patent: Dec. 16, 2003

(54) CARBOXYLESTERASE NUCLEIC ACID MOLECULES, PROTEINS AND USES THEREOF

(75) Inventors: Gary M. Silver, Fort Collins, CO (US); Nancy Wisnewski, Fort Collins, CO (US); Kevin S. Brandt, Ft Collins, CO (US)

(73) Assignee: Heska Corporation, Fort Collins, CO (US)

(*) Notice: Subject to any disclaimer, the term of this patent is extended or adjusted under 35 U.S.C. 154(b) by 0 days.

(21) Appl. No.: 09/403,942

(22) PCT Filed: Nov. 10, 1997

(86) PCT No.: PCT/US97/20598
§ 371 (c)(1),
(2), (4) Date: May 2, 2000

(87) PCT Pub. No.: WO98/21324
PCT Pub. Date: May 22, 1998

Related U.S. Application Data

(63) Continuation-in-part of application No. 08/747,221, filed on Nov. 12, 1996, now Pat. No. 6,063,610.

(51) Int. Cl.[7] ........................... C12N 9/18; C07H 21/04; C12Q 1/44
(52) U.S. Cl. ........................ 435/197; 435/183; 435/196; 435/19; 435/320.1; 435/69.2; 435/252.3; 435/325; 536/23.1; 536/23.2; 536/24.31; 530/350
(58) Field of Search ............................... 435/183, 196, 435/197, 69.2, 19, 320.1, 252.3, 325; 536/23.1, 23.2, 24.31; 530/350

(56) References Cited

PUBLICATIONS

Ngo et al., Computational Complexity, Protein Structure Prediction, and the Levinthal Paradox, in The Protein Folding Problem and Tertiary Structure Prediction, 1994, Merz et al. (ed.), Birkhauser, Boston, MA, pp. 433 and 492–495.*
Roslavtseva et al., Interaction of O–octyl–S–(carbomethoxy–methylmercaptomethyl) methylthiophosphonate (Sh–205) with esterases of various insect species, Journal of Evolutionary Biochemistry and Physiology, vol 27, No. 6, pp. 537–541, Nov./Dec., 1991.*
Argentine, J.A. et al. "Characterization of a salivary gland–specific esterase in the vector mosquito, Aedes aeqypti," Insect Biochem Mol Biol. 1995 May;25(5):621–30.
Bonning et al., "Further Development of a recombinant baculovirus insecticide expressing the enzyme juvenile hormone esterase from heliothis virescens," 1992, pp. 453–458, Insect Biochem. Molec. Biol., 22:5.
Bonning et al., "Insect control by use of recombinant baculovirus expressing juvenile hormone esterase," 1994, pp. 368–383, Natural and engineered pest management agents, by Paul A. Hedin, et al., American Chemical Society, Washington, DC.

Booth, G.M. et al., "A comparative study of the effects of selective inhibitors on esterase isozymes from the mosquito Anopheles punctipennis," Comp Biochem Physiol B. 44(4):1185–95 (1973).
Borovsky, D., "Oostatic hormone inhibits biosynthesis of midgut proteolytic enzymes and egg developments in mosquitoes," 1988, pp. 187–210, Archives of insect biochemistry and physiology, 7.
Cao et al., "A comparative study of esterase isoenzymes from three species of fleas," 1991, pp. 209–212, Chinese Journal of Parasitology and Parasitic diseases, 9(3).
Chen et al., "Purification and characterization of carboxylesterases of a rice brown planthopper, nilaparvata lugens stal," 1994 pp. 347–355, Insect Biochem. Molec. Biol. 24:4.
Cooke, P.H. et al., "Amino acid polymorphisms for esterase–6 in Drosophila melanogaster," Proc Natl Acad Sci U S A. 1989 Feb.;86(4):1426–30.
Eldridge et al., "Insecticidal properties of genetically engineered baculoviruses expressing an insect juvenile hormone esterase gene," 1992, pp. 1583–1591, Applied and Environmental Microbiology, 58:5.
Hanzlik et al., "Isolation and sequencing of cDNA clones coding for juvenile hormone esterase from Heliothis virescens. Evidence for a catalytic mechanism for the serine carboxylesterases different from that of the serine proteases," J Biol Chem. 1989 Jul. 25;264(21):12419–25.
Harshman, L.G. et al., "Cloning, characterization, and genetics of the juvenile hormone esterase gene from the Heliothis virescens," Insect Biochem Mol Biol. 1994 Jul.;24(7):671–6.
Hinkle, N.C. et al., "Mechanisms of insecticide resistance in a strain of cat fleas," J Entomol Sci, 30:43–48 (1995).
Jones, G. et al., "Structure, expression and gene sequence of a juvenile hormone esterase–related protein from metamorphosing larvae of Trichoplusia ni," Biochem J. 1994 Sep. 15;302 ( Pt 3):827–35.
Ketterman A.J. et al., "Purification and characterization of a carboxylesterase involved in insecticide resistance from the mosquito Culex quinquefasciatus," Biochem J. 287 ( Pt 2):355–60 (1992).

(List continued on next page.)

Primary Examiner—Richard Hutson
(74) Attorney, Agent, or Firm—Heska Corporation

(57) ABSTRACT

The present invention relates to arthropod esterase proteins; to arthropod esterase nucleic acid molecules, including those that encode such esterase proteins; to antibodies raised against such esterase proteins; and to other compounds that inhibit arthropod esterase activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from hematophagous arthropod infestation.

12 Claims, 5 Drawing Sheets

PUBLICATIONS

McCutchen, B.F. et al., "Characterization of a spectrophotometric assay for juvenile hormone esterase," *Insect Biochem Mol Biol.* 1995 Jan.;25(1):119–26.

Mouches, C. et al., "Characterization of amplification core and esterase B1 gene responsible for insecticide resistance in Culex," *Proc Natl Acad Sci U S A.* 1990 Apr.;87(7):2574–8.

Mumby, S.M. et al., "Synthesis and bioassay of carbamate inhibitors of the juvenile hormone hydrolyzing esterases from the housefly, *Musca domestica*," *J Agric Food Chem*, 27:763–765 (1979).

Sparks, T.C. et al., "Comparative inhibition of the juvenile hormone estarases from *Thrichoplusia ni, Tenebrio molitor*, and *Musca domestica*," *Pesticide Biochemistry and Psyhiology*, 14:290–302 (1980).

Turchetto, M. et al., "In vitro study of estarase inhibition in the midge *Chironomus thummi* Kieff," *Boll Zool* 48:335–339 (1981).

Valaitis, A.P., "Use of concanavalin A in the purification of juvenile hormone esterase from the hemolymph and the fat body of *lymantria dispar*," 1992, pp. 639–648, *Insect Biochem. Molec. Biol.* 22:7.

Vaughan, A. et al., "Mosquito carboxylesterase Est alpha 2(1) (A2). Cloning and sequence of the full–length cDNA for a major insecticide resistance gene worldwide in the mosquito *Culex quinquefasciatus*," *J Biol Chem.* 1995 Jul. 14;270(28):17044–9.

Venkataraman, V. et al., "Regulation of juvenile hormone esterase gene transcription by juvenile hormone," *Dev Genet.* 1994:15(5):391–400.

Venkatesh et al., "Characterization of affinity–purified juvenile hormone esterase from the plasma of the tobacco hornworm, *Manduca sexta*," *J Biol Chem.* 1990 Dec. 15;265(35):21727–32.

Ward, V.K. et al., "Analysis of the catalytic mechanism of juvenile hormone esterase by site–directed mutagenesis," *Int J Biochem.* 1992 Dec.;24(12):1933–41.

Whyard, S. et al., "Characterization of a novel esterase conferring insecticide resistance in the mosquito *Culex tarsalis*," *Arch Insect Biochem Physiol.* 29(4):329–42 (1995).

Whyard, S. et al., "Insecticide resistance and malathion carboxylesterase in the sheep blowfly, *Lucilia cuprina*," *Biochem Genet.* 1994 Feb.;32(1–2):9–24.

Wu, S–H. et al., "Ethyl octylphosphonofluoridate and analogs: optimized inhibitors of neuropathy target esterase," *Chem Res Toxicol.* 8(8):1070–5 (1995).

Yan, B. et al., "Rat kidney carboxylesterase. Cloning, sequencing, cellular localization, and relationship to rat liver hydrolase," *J Biol Chem.* 269(47):29688–96 (1994).

GenBank accession No. L40608 for *Plasmodium falciparum* (strain Dd2) variant–specific surface protein (var–1) gene. (1995).

* cited by examiner

MW

148-

60-

42-

30-

22-

UF 1st Instar
Fed 1st Instar
3rd Instar
Prepupae
ABF Whole Adult
ACF Whole Adult

Fig. 3

CARBOXYLESTERASE NUCLEIC ACID MOLECULES, PROTEINS AND USES THEREOF

This Application is a 371 of PCT/US97/20598, filed Nov. 10, 1997, which is a continuation-in-part of application Ser. No. 08/747,221, filed Nov. 12, 1996, now issued as U.S. Pat. No. 6,063,610.

FIELD OF THE INVENTION

The present invention relates to arthropod esterase nucleic acid molecules, proteins encoded by such nucleic acid molecules, antibodies raised against such proteins, and inhibitors of such proteins. The present invention also includes therapeutic compositions comprising such nucleic acid molecules, proteins, antibodies, and/or other inhibitors, as well as their use to protect an animal from hematophagous arthropod infestation.

BACKGROUND OF THE INVENTION

Hematophagous arthropod infestation of animals is a health and economic concern because hematophagous arthropods are known to cause and/or transmit a variety of diseases. Hematophagous arthropods directly cause a variety of diseases, including allergies, and also carry a variety of infectious agents including, but not limited to, endoparasites (e.g., nematodes, cestodes, trematodes and protozoa), bacteria and viruses.

In particular, the bites of hematophagous arthropods are a problem for animals maintained as pets because the infestation becomes a source of annoyance not only for the pet but also for the pet owner who may find his or her home generally contaminated with insects. As such, hematophagous arthropods are a problem not only when they are on an animal but also when they are in the general environment of the animal.

Bites from hematophagous arthropods are a particular problem because they not only can lead to disease transmission but also can cause a hypersensitive response in animals which is manifested as disease. For example, bites from fleas can cause an allergic disease called flea allergic (or allergy) dermatitis (FAD). A hypersensitive response in animals typically results in localized tissue inflammation and damage, causing substantial discomfort to the animal.

The medical importance of arthropod infestation has prompted the development of reagents capable of controlling arthropod infestation. Commonly encountered methods to control arthropod infestation are generally focused on use of insecticides. While some of these products are efficacious, most, at best, offer protection of a very limited duration. Furthermore, many of the methods are often not successful in reducing arthropod populations. In particular, insecticides have been used to prevent hematophagous arthropod infestation of animals by adding such insecticides to shampoos, powders, collars, sprays, foggers and liquid bath treatments (i.e., dips). Reduction of hematophagous arthropod infestation on the pet has been unsuccessful for one or more of the following reasons: (1) failure of owner compliance (frequent administration is required); (2) behavioral or physiological intolerance of the pet to the pesticide product or means of administration; and (3) the emergence of hematophagous arthropod populations resistant to the prescribed dose of pesticide. However, hematophagous arthropod populations have been found to become resistant to insecticides.

Prior investigators have described insect carboxylesterase (CE) protein biochemistry, for example, Chen et al., *Insect Biochem. Molec. Biol.*, 24:347–355, 1994; Whyard et al., *Biochemical Genetics*, 32:924, 1994 and Argentine et al., *Insect Biochem. Molec Biol*, 25:621–630, 1995. Other investigators have disclosed certain insect CE amino acid sequences, for example, Mouches et al., *Proc Natl Acacd Sci USA*, 87:2574–2578, 1990 and Cooke et al., *Proc Natl Acad Sci USA*, 86:1426–1430, 1989, and nucleic acid sequence (Vaughn et al., *J. Biol. Chem.*, 270:17044–17049, 1995).

Prior investigators have described certain insect juvenile hormone esterase (JHE) nucleic acid and amino acid sequences: for example, sequence for *Heliothis virescens* is disclosed by Hanzlik et al., *J. Biol. Chem.*, 264:12419–12425, 1989; Eldridge et al., *App Environ Microbiol*, 58:1583–1591, 1992; Bonning et al., *Insect Biochem. Molec. Biol.*, 22:453–458, 1992; Bonning et al., *Natural and Engineered Pest Management Agents*, pp. 368–383, 1994 and Harshman et al., *Insect Biochem. Molec. Biol*, 24:671–676, 1994; sequence for *Manduca sexta*'s disclosed by Vankatesh et al., *J Biol Chem*, 265:21727–21732, 1990; sequence for *Trichoplusia ni* is disclosed by Venkataraman et al., *Dev. Genet.*, 15:391–400, 1994 and Jones et al., *Biochem. J.*, 302:827–835, 1994; and sequence for *Lymantria dispar* is disclosed by Valaitis, *Insect Biochem. Molec. Biol.*, 22:639–648, 1992.

Identification of an esterase of the present invention is unexpected, however, because even the most similar nucleic acid sequence identified by previous investigators could not be used to identify an esterase of the present invention. In addition, identification of an esterase protein of the present invention is unexpected because a protein fraction from flea prepupal larvae that was obtained by monitoring for serine protease activity surprisingly also contained esterase proteins of the present invention.

In summary, there remains a need to develop a reagent and a method to protect animals or plants from hematophagous arthropod infestation.

SUMMARY OF THE INVENTION

The present invention relates to a novel product and process for protection of animals or plants from arthropod infestation. According to the present invention there are provided arthropod esterase proteins and mimetopes thereof; arthropod nucleic acid molecules, including those that encode such proteins; antibodies raised against such esterase proteins (i.e., anti-arthropod esterase antibodies); and compounds that inhibit arthropod esterase activity (i.e, inhibitory compounds or inhibitors).

The present invention also includes methods to obtain such proteins, mimetopes, nucleic acid molecules, antibodies and inhibitory compounds. Also included in the present invention are therapeutic compositions comprising such proteins, mimetopes, nucleic acid molecules, antibodies, and/or inhibitory compounds, as well as use of such therapeutic compositions to protect animals from arthropod infestation.

Identification of an esterase of the present invention is unexpected, however, because the most similar nucleic acid sequence identified by previous investigators could not be used to identify an esterase of the present invention. In addition, identification of an esterase protein of the present invention is unexpected because a protein fraction from flea prepupal larvae that was obtained by monitoring for serine protease activity surprisingly also contained esterase proteins of the present invention.

One embodiment of the present invention is an isolated nucleic acid molecule that hybridizes under stringent hybridization conditions with a gene comprising a nucleic acid sequence including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74.

The present invention also includes a nucleic acid molecule that hybridizes under stringent hybridization conditions with a nucleic acid molecule encoding a protein comprising at least one of the following amino acid sequences: SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:39, SEQ ID NO:53, SEQ ID NO:54, SEQ ID NO:55, SEQ ID NO:58, SEQ ID NO:68, SEQ ID NO:73 and/or SEQ ID NO:74; and particularly a nucleic acid molecule that hybridizes with a nucleic acid sequence that is a complement of a nucleic acid sequence encoding any of the amino acid sequences. A preferred nucleic acid molecule of the present invention includes a nucleic acid molecule comprising a nucleic acid sequence including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74, and allelic variants thereof.

The present invention also includes an isolated carboxylesterase nucleic acid molecule comprising a nucleic acid sequence encoding a protein comprising an amino acid sequence including SEQ ID NO:5, SEQ ID NO:19, SEQ ID NO:39, SEQ ID NO:40, SEQ ID NO:41, SEQ ID NO:42, SEQ ID NO:43, SEQ ID NO:44 and/or SEQ ID NO:53, SEQ ID NO:39, SEQ ID NO:40, SEQ ID NO:41, SEQ ID NO:42, SEQ ID NO:43 and SEQ ID NO:44 represent N-terminal amino acid sequences of carboxylesterases isolated from prepupal flea larvae, the production of which are described in the Examples of the present application.

The present invention also relates to recombinant molecules, recombinant viruses and recombinant cells that include a nucleic acid molecule of the present invention. Also included are methods to produce such nucleic acid molecules, recombinant molecules, recombinant viruses and recombinant cells.

Another embodiment of the present invention includes an isolated esterase protein that is encoded by a nucleic acid molecule that hybridizes under stringent hybridization conditions to (a) a nucleic acid molecule that includes at least one of the following nucleic acid sequences: SEQ ID NO:3, SEQ ID NO:6, SEQ ID NO:9, SEQ ID NO:12, SEQ ID NO:15, SEQ ID NO:17, SEQ ID NO:20, SEQ ID NO:22, SEQ ID NO:26, SEQ ID NO:29, SEQ ID NO:32, SEQ ID NO:35, SEQ ID NO:38, SEQ ID NO:52, SEQ ID NO:59, SEQ ID NO:61, SEQ ID NO:69, and SEQ ID NO:71; and/or (b) a nucleic acid molecule encoding a protein including at least one of the following amino acid sequences: SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55 and SEQ ID NO:74. One embodiment is a carboxylesterase protein encoded by a nucleic acid molecule that hybridizes under stringent hybridization conditions to a nucleic acid molecule that encodes a protein comprising at least one of the following amino acid sequences: SEQ ID NO:5, SEQ ID NO:19, SEQ ID NO:39, SEQ ID NO:40, SEQ ID NO:41, SEQ ID NO:42, SEQ ID NO:43, SEQ ID NO:44 and/or SEQ ID NO:53. Preferred proteins of the present invention are isolated flea proteins including at least one of the following amino acid sequences: SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55, SEQ ID NO:58, SEQ ID NO:68, SEQ ID NO:73 and SEQ ID NO:74; also included are proteins encoded by allelic variants of nucleic acid molecules encoding proteins comprising any of the above-listed amino acid sequences.

The present invention also relates to mimetopes of arthropod esterase proteins as well as to isolated antibodies that selectively bind to arthropod esterase proteins or mimetopes thereof. Also included are methods, including recombinant methods, to produce proteins, mimetopes and antibodies of the present invention.

The present invention also includes a formulation of flea carboxylesterase proteins, in which the proteins, when submitted to 14% Tris-glycine SDS-PAGE, comprise a fractionation profile as depicted in FIG. 3, in which the proteins have carboxylesterase activity.

Also included in the present invention is a formulation of flea carboxylesterase proteins, in which the proteins, when submitted to IEF-PAGE, comprise a fractionation profile as depicted in FIG. 4, lane 3, lane 4, lane 5, lane 6 and/or lane 7, wherein the proteins have carboxylesterase activity.

Another embodiment of the present invention is an isolated flea protein or a formulation of flea proteins that hydrolyzes α-napthyl acetate to produce α-napthol, when the protein is incubated in the presence of α-napthyl acetate contained in 20 mM Tris at pH 8.0 for about 15 minutes at about 37° C.

Yet another embodiment of the present invention is an isolated flea protein or a formulation of flea proteins that hydrolyzes the methyl ester group of juvenile hormone to produce a juvenile hormone acid.

Another embodiment of the present invention is a method to identify a compound capable of inhibiting flea carboxylesterase activity, the method comprising: (a) contacting an isolated flea carboxylesterase with a putative inhibitory compound under conditions in which, in the absence of the compound, the protein has carboxylesterase activity; and (b) determining if the putative inhibitory compound inhibits the activity. Also included in the present invention is a test kit to identify a compound capable of inhibiting flea carboxylesterase activity, the test kit comprising an isolated flea carboxylesterase protein having esterase activity and a means for determining the extent of inhibition of the activity in the presence of a putative inhibitory compound.

Yet another embodiment of the present invention is a therapeutic composition that is capable of reducing hematophagous ectoparasite infestation. Such a therapeutic composition includes at least one of the following protective compounds: an isolated hematophagous ectoparasite carboxylesterase protein or a mimetope thereof, an isolated carboxylesterase nucleic acid molecule that hybridizes under stringent hybridization conditions with a *Ctenocephalides felis* carboxylesterase gene, an isolated antibody that selectively binds to a hematophagous ectoparasite carboxylesterase protein, and an inhibitor of carboxylesterase activity identified by its ability to inhibit the activity of a flea carboxylesterase. A therapeutic composition of the present invention can also include an excipient, an adjuvant and/or a carrier. Preferred esterase nucleic acid molecule compounds of the present invention include naked nucleic acid vaccines, recombinant virus vaccines and recombinant cell vaccines. Also included in the present invention is a method to protect an animal from hematophagous ectoparasite infestation comprising the step of administering to the animal a therapeutic composition of the present invention.

BRIEF DESCRIPTION OF THE FIGURES

FIG. 3 depicts SDS-PAGE analysis of carboxylesterase activity of certain esterase proteins of the present invention.

DETAILED DESCRIPTION OF THE INVENTION

The present invention provides for isolated arthropod esterase proteins, isolated arthropod esterase nucleic acid molecules, antibodies directed against arthropod esterase proteins and other inhibitors of arthropod esterase activity. As used herein, the terms isolated arthropod esterase proteins and isolated arthropod esterase nucleic acid molecules refers to esterase proteins and esterase nucleic acid molecules derived from arthropods and, as such, can be obtained from their natural source or can be produced using, for example, recombinant nucleic acid technology or chemical synthesis. Also included in the present invention is the use of these proteins, nucleic acid molecules, antibodies and inhibitors as therapeutic compositions to protect animals from hematophagous ectoparasite infestation as well as in other applications, such as those disclosed below.

Arthropod esterase proteins and nucleic acid molecules of the present invention have utility because they represent novel targets for anti-arthropod vaccines and drugs. The products and processes of the present invention are advantageous because they enable the inhibition of arthropod development, metamorphosis, feeding, digestion and reproduction processes that involve esterases. While not being bound by theory, it is believed that expression of arthropod esterase proteins are developmentally regulated, thereby suggesting that esterase proteins are involved in arthropod development and/or reproduction. The present invention is particularly advantageous because the proteins of the present invention were identified in larval fleas, thereby suggesting the importance of the proteins as developmental proteins.

Figure 1:
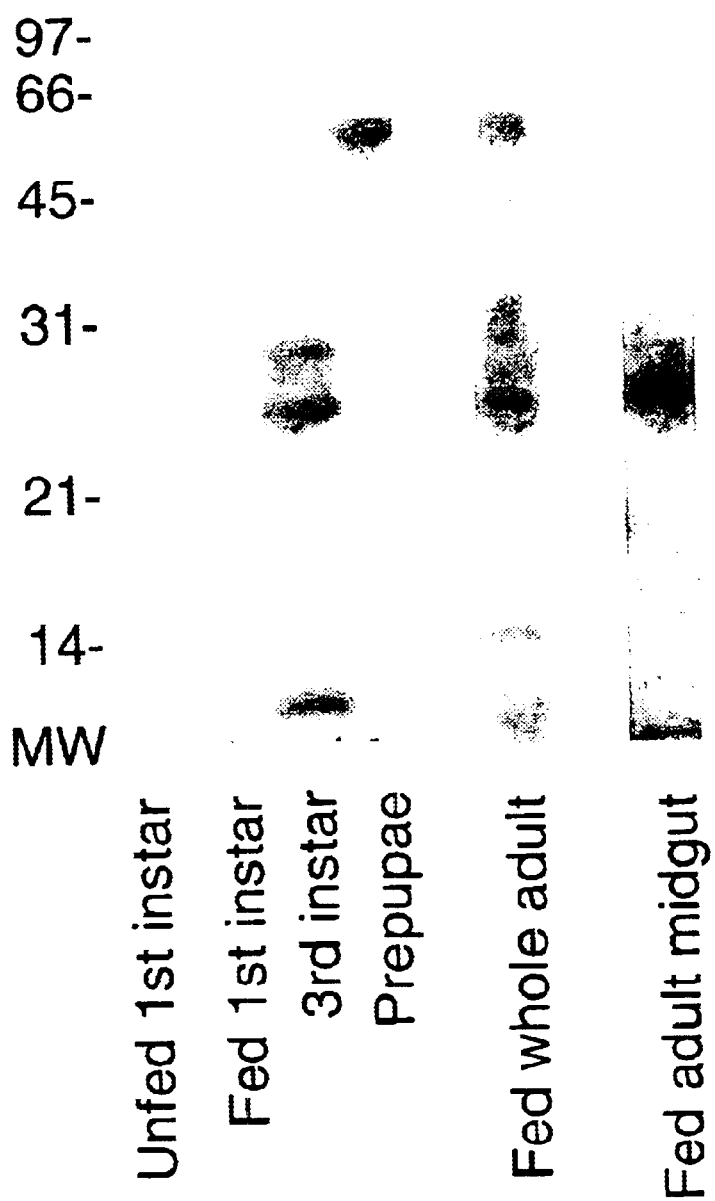
FIG. 1 depicts SDS-PAGE analysis of DFP-labeled esterase proteins.

One embodiment of the present invention is an esterase formulation that includes one or more esterase proteins capable of binding to diisopropylfluorophosphate (DFP). A preferred embodiment of an esterase formulation of the present invention comprises one or more arthropod esterase proteins that range in molecular weight from about 20 kilodaltons (kD) to about 200 kD, more preferably from about 40 kD to about 100 kD, and even more preferably from about 60 kD to about 75 kD, as determined by SDS-PAGE (sodium dodecyl sulfate polyacrylamide gel electrophoresis). An even more preferred formulation includes one or more flea esterase proteins having elution (or migration) patterns as shown in FIG. 1.

Another embodiment of the present invention is a formulation comprising one or more hematophagous ectoparasite carboxylesterase (CE) proteins. The present invention includes the discovery that such a formulation has general CE activity. General CE activity can be identified using methods known to those of skill in the art and described in the Examples section herein. A suitable formulation of the present invention comprises one or more flea proteins capable of hydrolyzing α-napthyl acetate to produce α-napthol when the proteins are incubated in the presence of α-napthyl acetate contained in 20 mm Tris at pH 8.0 for about 15 minutes at about 37° C. General CE activity can be identified following such incubation by detecting the production of from about 0.3 to about 2.5 absorbance units in the presence of Fast Blue when measured at 590 nm.

A preferred CE formulation of the present invention includes one or more flea CE proteins having acidic to neutral isoelectric points, or pI values. An isoelectric pH, or pI, value refers to the pH value at which a molecule has no net electric charge and fails to move in an electric field. A preferred formulation of the present invention includes one or more proteins having a pI value ranging from about pI 2 to about 10, more preferably from about pI 3 to about 8, and even more preferably from about pI 4.7 to about 5.2, as determined by IEF-PAGE.

An esterase formulation, including a CE formulation, of the present invention can be prepared by a method that includes the steps of: (a) preparing an extract by isolating flea tissue, homogenizing the tissue by sonication and clarifying the extract by centrifugation at a low speed spin, e.g., about 18,000 rpm for about 30 minutes; (b) recovering soluble proteins from said centrifuged extract and applying the proteins to a p-aminobenzamidine agarose bead column; (c) recovering unbound protein from the column and clarifying by filtration; (d) applying the clarified protein to a gel filtration column and eluting and collecting fractions with esterase activity; (e) dilayzing the eluate against 20 mM MES buffer, pH 6.0, containing 10 mM NaCl; (f) applying the dialysate to a cation exchange chromatography column, eluting protein bound to the column with a linear grader of from about 10 mM NaCl to about 1 M NaCl in 20 mM MES buffer, pH 6, and collecting fractions having esterase activity; (g) adjusting the pH of the resulting fractions to pH 7 and applying the fractions to an anion exchange chromatography column; (h) eluting protein bound to the column with a linear gradient of from about 0 to about 1 M NaCl in 25 mM Tris buffer, pH 6.8 and collecting fractions having esterase activity, such activity elutes from the column at about 170 mM NaCl.

Tissue can be obtained from unfed fleas or from fleas that recently consumed a blood meal (i.e., blood-fed fleas). Such flea tissues are referred to herein as, respectively, unfed flea and fed flea tissue. Preferred flea tissue from which to obtain an esterase formulation of the present invention includes pre-pupal larval tissue, wandering flea larvae, 3rd instar tissue, fed adult tissue and unfed adult tissue.

In a preferred embodiment, a CE formulation of the present invention comprises a flea protein comprising amino acid sequence SEQ ID NO:5, SEQ ID NO:19, SEQ ID NO:39, SEQ ID NO:40, SEQ ID NO:41, SEQ ID NO:42, SEQ ID NO:43, SEQ ID NO:44 and/or SEQ ID NO:53.

Another embodiment of the present invention is a juvenile hormone esterase (JHE) formulation comprising one or more arthropod JHE proteins, the arthropod being of the order Hemiptera, Anoplura, Malloplaga, Diptera, Siphonaptera, Parasitiformes, Acariformes and Acarina. The present invention includes the discovery that such a formulation has JHE activity. JHE activity can be identified using methods known to those of skill in the art and described in the Examples section herein. A suitable formulation of the present invention comprises one or more arthropod proteins capable of hydrolyzing a methyl ester group of juvenile hormone to produce a juvenile hormone acid. Preferably, such a protein is capable of releasing of at least about 120 counts per minute when such a protein is incubated in the presence of $^3$H-juvenile hormone to create a reaction mixture, the reaction mixture is combined with isooctane, the aqueous phase is recovered and the amount of $^3$H-juvenile hormone present in that phase is determined. Such a protein is also preferably capable of causing release of methane thiol when such protein is incubated in the presence of methyl 1-heptylthioacetothioate (HEPTAT) using the method generally disclosed in McCutohen et al., *Insect Biochem. Molec. Biol.*, Vol. 25, No. 1, pg 119–126, 1995, which is incorporated in its entirety by this reference.

In one embodiment, a juvenile hormone esterase formulation of the present invention comprises a protein comprising amino acid sequence SEQ ID NO:74.

According to the present invention, an arthropod that is not of the order lepidoptera includes an arthropod of the order Hemiptera, Anoplura, Mallophaga, Diptera, Siphonaptera, Parasitiformes, Acariformes and Acarina. Preferred arthropods include *Hemiptera cimicidae, Hemiptera reduviidae, Anoplura pediculidae, Anoplura pthiridae, Diptera culicidae, Diptera simuliidae, Diptera psychodidae, Diptera ceratopogonidae, Diptera chaoboridae, Diptera tabanidae, Diptera rhagionidae, athericidae, Diptera chloropidae, Diptera muscidae, Diptera hippoboscidae, Diptera calliphoridae, Diptera sarcophagidae, Diptera oestridae, Diptera gastrophilidae, Diptera cuterebridae, Siphonaptera ceratophyllidae, Siphonaptera leptopsyllidae, Siphonaptera pulicidae, Siphonaptera tungidae, Parasitiformes dermanyssidae, Acariformes tetranychidae, Acariformes cheyletide, Acarifomies demodicidae, Acariformes erythracidae, Acariformes trombiculidae, Acariformes psoroptidae, Acariformes sarcoptidae, Acarina argasidae* and *Acarina ixodidae*. Preferred *Diptera muscidae* include Musca, Hydrotaea, Stomoxys Haematobia. Preferred Siphonaptera include *Ceratophyllidae nosopsyllus, Ceratophyllidae diamanus, Ceratophyllidae ceratophyllus, Leptopsyllidae leptopsylla, Pulicidae pulex, Pulicidae ctenocephalides, Pulicidae xenopsylla, Pulicidae echidnophaga* and *Tungidae tunga*. Preferred *Parasitiformes dermanyssidae* include Ornithonyssus and Liponyssoicles. Preferred Acarina include *Argasidae argas, Argasidae ornithodoros, Argasidae otobius, Argasidae ixodes, Ixodidae hyalomma, Ixodidae nosomma, Ixodidae rhipicephalus, Ixodidae boophilus, Ixodidae dermacentor, Ixodidae haemaphysalus, Ixodidae amblyomma* and *Ixodidae anocentor*.

One embodiment of a JHE formulation of the present invention is one or more arthropod JHE proteins that range in molecular weight from about 20 kD to about 200 kD, more preferably from about 40 kD to about 100 kD, and even more preferably from about 60 kD to about 75 kD, as determined by SDS-PAGE (sodium dodecyl sulfate polyacrylamide gel electrophoresis).

A JHE formulator of the present invention can be prepared by a method that includes the steps of: (a) preparing soluble proteins from arthropod extracts as described above for CE purification and purifying such soluble proteins by gel filtration; (b) collecting fractions having JHE activity from the gel filtration step, loading the fractions onto a cation exchange column, eluting the cation exchange column with a linear gradient of from about 10 mM NaCl to about 1 M NaCl in 20 mM MES buffer, pH 6 and collecting fractions having JHE activity; (c) adjusting the pH of the collected fractions to about pH 7 are dialyzed against about 10 mM phosphate buffer (pH 7.2) containing about 10 mM NaCl; (d) applying the dialysate to a hydroxyapatite column, eluting protein bound to the column with a linear gradient of from about 10 mM phosphate buffer (pH 7.2) containing 10 mM NaCl to about 0.5 M phosphate buffer (pH 6.5) containing 10 mM NaCl and collecting fractions having JHE activity; (e) dialyzing the fractions against 20 mM Tris buffer (pH 8.0) containing 10 mM NaCl; (f) applying the dialysate an anion exchange chromatography column and eluting protein bound to the column with a linear gradient of from about 10 mM to about 1 M NaCl in 20 mM Tris buffer, pH 8 and collecting fractions containing JHE activity.

A JHE formulation of the present invention can be prepared by a method that includes the steps of (a) preparing flea extracts as described herein in the Examples section and applying the extract to p-aminobenzamidine linked agarose beads and collecting protein not bound to the beads; (b) applying the unbound protein to a Superdex 200 HR gel filtration column and collecting fractions having JHE activity; (c) applying the fractions to an anion exchange chromatography column, eluting the anion exchange column with a linear gradient of 0 to 1 M NaCl in 25 mM Tris buffer, pH 6.8 and collecting fractions having JHE activity; (d) dialyzing the fractions overnight against about 1 L of 20 mM Tris buffer, pH 8.0, containing 10 mM NaCl; (e) applying the dialysate to a Poros 10 HQ anion exchange column, eluting the column with buffer containing about 120 mM NaCl and collecting fractions having JHE activity.

Suitable arthropods from which to isolate a JHE formulation of the present invention include, but are not limited to agricultural pests, stored product pests, forest pests, structural pests or animal health pests. Suitable agricultural pests of the present invention include, but are not limited to Colorado potato beetles, corn earworms, fleahoppers, weevils, pink boll worms, cotton aphids, beet amryworms, lygus bugs, hessian flies, sod webworms, whites grubs, diamond back moths, white flies, plauthoppers, leafloppers, mealy bugs, mormon crickets and mole crickets. Suitable stored product pests of the present invention include, but are not limited to dermestids, anobeids, saw toothed grain beetles, indian mealmoths, flour beetles, long-horn wood boring beetles and metallic wood boring beetles. Suitable forest pests of the present invention include, but are not limited to southern pine bark bettles, gypsy moths, elm beetles, ambrosia bettles, bag worms, tent worms and tussock moths. Suitable structural pests of the present invention include, but are not limited to, bess beetles, termites, fire ants, carpenter ants, wasps, hornets, cockroaches, silverfish, *Musca domestica* and *Musca autumnalis*. Suitable animal health pests of the present invention include, but are not limited to fleas, ticks, mosquitoes, black flies, lice, true bugs, sand flies, Psychodidae, tsetse flies, sheep blow flies, cattle grub, mites, horn flies, heel flies, deer flies, Culicoides and warble flies. Preferred arthropods from which to isolate a JHE formulation of the present invention include fleas, midges, mosquitos, sand flies, black flies, horse flies, snipe flies, louse flies, horn flies, deer flies, tsetse flies, buffalo flies, blow flies, stable flies, myiasis-causing flies, biting gnats, lice, mites, bee, wasps, ants, true bugs and ticks, preferably fleas, ticks and blow flies, and more preferably fleas. Preferred fleas from which to isolate JHE proteins include Ctenocephalides, Ceratophyllus, Diamanus, Echidnophga, Nosopsyllus, Pulex, Tunga, Oropsylla, Orchopeus and Xenopsylla. More preferred fleas include *Ctenocephalides felis, Ctenocephalides canis, Ctenocephalides pulicidae, Pulex irritans, Oropsylla (Thrassis) bacchi, Oropsylla (Diamanus) montana, Orchopeus howardi, Xenopsylla cheopis* and *Pulex simulans*, with *C. felis* being even more preferred.

Suitable tissue from which to isolate a JHE formulation of the present invention includes unfed fleas or fleas that recently consumed a blood meal (i.e., blood-fed fleas). Such flea tissues are referred to herein as, respectively, unfed flea and fed flea tissue. Preferred flea tissue from which to obtain a JHE formulation of the present invention includes pre-pupal larval tissue, 3rd instar tissue, fed or unfed adult tissue, with unfed adult gut tissue being more preferred than fed or unfed whole adult tissue. It is of note that a JHE formulation of the present invention obtained from pre-pupal larval tissue does not hydrolyze α-napthyl acetate.

Another embodiment of the present invention is an esterase formulation comprising a combination of one or more arthropod CE and JHE proteins of the present invention. Suitable arthropods from which to isolate a combined CE and JHE formulation include those arthropods described herein for the isolation of a JHE formulation of the present invention. Preferred arthropods from which to isolate a combined CE and JHE formulation include fleas, midges, mosquitos, sand flies, black flies, horse flies, horn flies, deer flies, tsetse flies, buffalo flies, blow flies, stable flies, mylasis-causing flies, biting gnats, lice, bee, wasps, ants, true bugs and ticks, preferably fleas, ticks and blow flies, and more preferably fleas. Suitable flea tissue from which to isolate a combined CE and JHE formulation of the present invention includes 3rd instar tissue, fed or unfed adult tissue and unfed adult tissue, with unfed adult gut tissue being more preferred than fed or unfed whole adult tissue.

In one embodiment, a formulation of the present invention comprises an esterase having both CE and JHE activity. Preferably, a formulation of the present invention that comprises an esterase having both CE and JHE activity comprises a flea protein comprising amino acid sequence SEQ ID NO:8 and/or SEQ ID NO:37.

Another embodiment of the present invention is an isolated protein comprising an arthropod esterase protein. It is to be noted that the term "a" or "an" entity refers to one or more of that entity; for example, a protein refers to one or more proteins or at least one protein. As such, the terms "a" (or "an"), "one or more" and "at least one" can be used interchangeably herein. It is also to be noted that the terms "comprising", "including", and "having" can be used interchangeably. Furthermore, a compound "selected from the group consisting of" refers to one or more of the compounds in the list that follows, including mixtures (i.e., combinations) of two or more of the compounds. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology or can be produced by chemical synthesis.

As used herein, an isolated arthropod esterase protein can be a full-length protein or any homolog of such a protein. An isolated protein of the present invention, including a homolog, can be identified in a straight-forward manner by the protein's ability to elicit an immune response against arthropod esterase proteins, to hydrolyze α-napthyl acetate, to hydrolyze the methyl ester group of juvenile hormone or bind to DFP. Esterase proteins of the present invention include CE and JHE proteins. As such, an esterase protein of the present invention can comprise a protein capable of hydrolyzing α-napthyl acetate, hydrolyzing the methyl ester group of juvenile hormone and/or binding to DFP. Examples of esterase homologs include esterase proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homolog includes at least one epitope capable of eliciting an immune response against an arthropod esterase protein. That is, when the homolog is administered to an animal as an immunogen, using techniques known to those skilled in the art, the animal will produce an immune response against at least one epitope of a natural arthropod esterase protein. The ability of a protein to effect an immune response, can be measured using techniques known to those skilled in the art. Esterase protein homologs of the present invention also include esterase proteins that hydrolyze α-napthyl acetate and/or that hydrolyze the methyl ester group of juvenile hormone.

Arthropod esterase protein homologs can be the result of natural allelic variation or natural mutation. Esterase protein homologs of the present invention can also be produced using techniques known in the art including, but not limited to, direct modifications to the protein or modifications to the gene encoding the protein using, for example, classic or recombinant nucleic acid techniques to effect random or targeted mutagenesis.

Isolated esterase proteins of the present invention have the further characteristic of being encoded by nucleic acid molecules that hybridize under stringent hybridization conditions to a gene encoding a *Ctenocephalides felis* protein (i.e., a *C. felis* esterase gene). As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989; Sambrook et al., *ibid*., is incorporated by reference herein in its entirety. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinikoth et al., *ibid*., is incorporated by reference herein in its entirety.

As used herein, a *C. felis* esterase gene includes all nucleic acid sequences related to a natural *C. felis* esterase gene such as regulatory regions that control production of the *C. felis* esterase protein encoded by that gene (such as, but not limited to, transcription, translation or post-translation control regions) as well as the coding region itself. In one embodiment, a *C. felis* esterase gene of the present invention includes the nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74. Nucleic acid sequence SEQ ID NO:1 represents the deduced sequence of the coding strand of a PCR amplified nucleic acid molecule denoted herein as nfE1$_{401}$, the production of which is disclosed in the Examples. The complement of SEQ ID NO:1 (represented herein by SEQ ID NO:3) refers to the nucleic acid sequence of the strand complementary to the strand having SEQ ID NO:1, which can easily be determined by those skilled in the art. Likewise, a nucleic acid sequence complement of any nucleic acid sequence of the present invention refers to the nucleic acid sequence of the nucleic acid strand that is complementary to (i.e., can form a complete double helix with) the strand for which the sequence is cited.

Nucleic acid sequence SEQ ID NO:4 represents the deduced sequence of the coding strand of a PCR amplified nucleic acid molecule denoted herein as nfE2$_{364}$, the production of which is disclosed in the Examples. The complement of SEQ ID NO:4 is represented herein by SEQ ID NO:6.

Nucleic acid sequence SEQ ID NO:7 represents the deduced sequence of the coding strand of a PCR amplified nucleic acid molecule denoted herein as nfE3$_{421}$, the production of which is disclosed in the Examples. The complement of SEQ ID NO:7 is represented herein by SEQ ID NO:9.

Nucleic acid sequence SEQ ID NO:10 represents the deduced sequence of the coding strand of a PCR amplified nucleic acid molecule denoted herein as nfE4$_{524}$, the production of which is disclosed in the Examples. The complement of SEQ ID NO:10 is represented herein by SEQ ID NO:12.

Nucleic acid sequence SEQ ID NO:13 represents the deduced sequence of the coding strand of an apparent coding region of a complementary DNA (cDNA) nucleic acid molecule denoted herein as nfE5$_{1982}$, the production of which is disclosed in the Examples. The complement of SEQ ID NO:13 is represented herein by SEQ ID NO:15.

Nucleic acid sequence SEQ ID NO:18 represents the deduced sequence of the coding strand of an apparent coding region of a cDNA nucleic acid molecule denoted herein as nfE6$_{1792}$, the production of which is disclosed in the Examples. The complement of SEQ ID NO:18 is represented herein by SEQ ID NO:20.

Nucleic acid sequence SEQ ID NO:24 represents the deduced sequence of the coding strand of an apparent coding region of a cDNA nucleic acid molecule denoted herein as nfE7$_{2836}$, the production of which is disclosed in the Examples. The complement of SEQ ID NO:24 is represented herein by SEQ ID NO:26.

Nucleic acid sequence SEQ ID NO:30 represents the deduced sequence of the coding strand of an apparent coding region of a cDNA nucleic acid molecule denoted herein as nfE8$_{2801}$, the production of which is disclosed in the Examples. The complement of SEQ ID NO:30 is represented herein by SEQ ID NO:32.

Nucleic acid sequence SEQ ID NO:36 represents the deduced sequence of the coding strand of an apparent coding region of a cDNA nucleic acid molecule denoted herein as nfE9$_{2007}$, the production of which is disclosed in the Examples. The complement of SEQ ID NO:36 is represented herein by SEQ ID NO:38.

Nucleic acid sequence SEQ ID NO:57 represents the deduced sequence of the coding strand of an apparent coding region of a cDNA nucleic acid molecule denoted herein as nfE5$_{2144}$, the production of which is disclosed in the Examples. The complement of SEQ ID NO:57 is represented herein by SEQ ID NO:59.

Nucleic acid sequence SEQ ID NO:67 represents the deduced sequence of the coding strand of an apparent coding region of a cDNA nucleic acid molecule denoted herein as nfE10$_{1987}$, the production of which is disclosed in the Examples. The complement of SEQ ID NO:67 is represented herein by SEQ ID NO:69.

It should be noted that since nucleic acid sequencing technology is not entirely error-free, the nucleic acid sequences and amino acid sequences presented herein represent, respectively, apparent nucleic acid sequences of nucleic acid molecules of the present invention and apparent amino acid sequences of esterase proteins of the present invention.

In another embodiment, a *C. felis* esterase gene can be an allelic variant that includes a similar but not identical sequence to SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74. An allelic variant of a *C. felis* esterase gene is a gene that occurs at essentially the same locus (or loci) in the genome as the gene including SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given arthropod since the genome is diploid and/or among a group of two or more arthropods.

The minimal size of an esterase protein homolog of the present invention is a size sufficient to be encoded by a nucleic acid molecule capable of forming a stable hybrid (i.e., hybridize under stringent hybridization conditions) with the complementary sequence of a nucleic acid molecule encoding the corresponding natural protein. As such, the size of the nucleic acid molecule encoding such a protein homolog is dependent on nucleic acid composition and percent homology between the nucleic acid molecule and complementary sequence. It should also be noted that the extent of homology required to form a stable hybrid can vary depending on whether the homologous sequences are interspersed throughout the nucleic acid molecules or are clustered (i.e., localized) in distinct regions on the nucleic acid molecules. The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode an esterase protein homolog of the present invention is from about 12 to about 18 nucleotides in length. Thus, the minimal size of an esterase protein homolog of the present invention is from about 4 to about 6 amino acids in length. There is no limit, other than a practical limit, on the maximal size of such a nucleic acid molecule in that the nucleic acid molecule can include a portion of a gene, an entire gene, multiple genes, or portions thereof. The preferred size of a protein encoded by a nucleic acid molecule of the present invention depends on whether a full-length, fusion, multivalent, or functional portion of such a protein is desired.

One embodiment of the present invention includes an arthropod esterase protein having CE enzyme activity. Such a CE protein preferably includes: a catalytic triad of serine—histidine—glutamic acid as well as the essential amino acids arginine and aspartic acid at positions similar to those described for juvenile hormone esterase, for example by Ward et al., 1992, *Int J Biochem* 24: 1933–1941; this reference is incorporated by reference herein in its entirety. Analysis of the apparent full-length protein sequences disclosed herein indicates that each of these amino acid sequences includes these amino acid motifs, as well as surrounding consensus sequences.

Suitable arthropods from which to isolate esterase proteins having general CE activity of the present invention (including isolation of the natural protein or production of the protein by recombinant or synthetic techniques) preferably include insects and acarines but not Culicidae, Drosophilidae, Calliphoridae, Sphingidae, Lymantriidae, Noctuidae, Fulgoroidae and Aphididae. Preferred arthropods from which to isolate CE proteins having general CE activity include fleas, ticks, black flies, lice, true bugs, sand flies, Psychodidae, tsetse flies, cattle grub, mites, horn flies, heel flies, deer flies, Culicoides and warble flies. Preferred arthropods from which to isolate an esterase proteins having general CE activity include fleas, midges, sand flies, black flies, horse flies, snipe flies, louse flies, horn flies, deer flies, tsetse flies, buffalo flies, blow flies, stable flies, myiasis-causing flies, biting gnats, lice, mites, bee, wasps, ants, true bugs and ticks, preferably fleas, ticks and blow flies, and more preferably fleas. Preferred fleas from which to isolate esterase proteins having general CE activity include Ctenocephalides, Ceratophyllus, Diamanus, Echidnophga, Nosopsyllus, Pulex, Tunga, Oropsylla, Orchopeus and Xenopsylla. More preferred fleas include *Ctenocephalides felis, Ctenocephalides canis, Ctenocephalides pulicidae, Pulex irritans, Oropsylla (Thrassis) bacchi, Oropsylla (Diamanus) montana, Orchopeus howardi, Xenopsylla cheopis* and *Pulex simulans*, with *C. felis* being even more preferred.

A preferred arthropod esterase protein of the present invention is a compound that when administered to an animal in an effective manner, is capable of protecting that animal from hematophagous ectoparasite infestation. In accordance with the present invention, the ability of an esterase protein of the present invention to protect an animal from hematophagous ectoparasite infestation refers to the ability of that protein to, for example, treat, ameliorate and/or prevent infestation caused by hematophagous arthropods. In particular, the phrase "to protect an animal from hematophagous ectoparasite infestation" refers to reducing the potential for hematophagous ectoparasite population expansion on and around the animal (i.e., reducing the hematophagous ectoparasite burden). Preferably, the hematophagous ectoparasite population size is decreased, optimally to an extent that the animal is no longer bothered by hematophagous ectoparasites. A host animal, as used herein, is an animal from which hematophagous ectoparasites can feed by attaching to and feeding through the skin of the animal. Hematophagous ectoparasites, and other ectoparasites, can live on a host animal for an extended period of time or can attach temporarily to an animal in order to feed. At any given time, a certain percentage of a hematophagous ectoparasite population can be on a host animal whereas the remainder can be in the environment of the animal. Such an environment can include not only adult hematophagous ectoparasites, but also hematophagous ectoparasite eggs and/or hematophagous ectoparasite larvae. The environment can be of any size such that hematophagous ectoparasites in the environment are able to jump onto and off of a host animal. For example, the environment of an animal can include plants, such as crops, from which hematophagous ectoparasites infest an animal. As such, it is desirable not only to reduce the hematophagous ectoparasite burden on an animal per se, but also to reduce the hematophagous ectoparasite burden in the environment of the animal. In one embodiment, an esterase protein of the present invention can elicit an immune response (including a humoral and/or cellular immune response) against a hematophagous ectoparasite.

Suitable hematophagous ectoparasites to target include any hematophagous ectoparasite that is essentially incapable of infesting an animal administered an esterase protein of the present invention. As such, a hematophagous ectoparasite to target includes any hematophagous ectoparasite that produces a protein having one or more epitopes that can be targeted by a humoral and/or cellular immune response against an esterase protein of the present invention and/or that can be targeted by a compound that otherwise inhibits esterase activity (e.g., a compound that inhibits hydrolysis of α-napthyl acetate, hydrolysis of the methyl ester group of juvenile hormone, and/or binds to DFP), thereby resulting in the decreased ability of the hematophagous ectoparasite to infest an animal. Preferred hematophagous ectoparasite to target include ectoparasites disclosed herein as being useful in the production of esterase proteins of the present invention.

The present invention also includes mimetopes of esterase proteins of the present invention. As used herein, a mimetope of an esterase protein of the present invention refers to any compound that is able to mimic the activity of such a protein (e.g., ability, to elicit an immune response against an arthropod esterase protein of the present invention and/or ability to inhibit esterase activity), often because the mimetope has a structure that mimics the esterase protein. It is to be noted, however, that the mimetope need not have a structure similar to an esterase protein as long as the mimetope functionally mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); synthetic or natural organic or inorganic molecules, including nucleic acids; and/or any other peptidomimetic compounds. Mimetopes of the present invention can be designed using computer-generated structures of esterase proteins of the present invention. Mimetopes can also be obtained by generating random samples of molecules, such as oligonucleotides, peptides or other organic molecules, and screening such samples by affinity chromatography techniques using the corresponding binding partner, (e.g., an esterase substrate, an esterase substrate analog, or an anti-esterase antibody). A preferred mimetope is a peptidomimetic compound that is structurally and/or functionally similar to an esterase protein of the present invention, particularly to the active site of the esterase protein.

The present invention also includes mimetopes of esterase proteins of the present invention. As used herein, a mimetope of an esterase protein of the present invention refers to any compound that is able to mimic the activity of such an esterase protein, often because the mimetope has a structure that mimics the esterase protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

One embodiment of an arthropod esterase protein of the present invention is a fusion protein that includes an arthropod esterase protein-containing domain attached to one or more fusion segments. Suitable fusion segments for use with the present invention include, but are not limited to, segments that can: enhance a protein's stability; act as an immunopotentiator to enhance an immune response against an esterase protein; and/or assist purification of an esterase protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the esterase-containing domain of the protein and can be susceptible to cleavage in order to enable straight-forward recovery of an esterase protein. Fusion proteins are preferably produced by culturing a recombinant cell transformed with a fusion nucleic acid molecule that encodes a protein including the fusion segment attached to either the carboxyl and/or amino terminal end of an esterase-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies). More preferred fusion segments include metal binding domains, such as a poly-histidine segment; a amaltose binding domain; a strep tag peptide, such as that available from Biometra in Tampa, Fla.; and an S10 peptide. Examples of particularly preferred fusion proteins of the present invention include PHIS-PfE6$_{540}$, PHIS-PfE7$_{275}$, PHIS-PfE7$_{570}$, PHIS-PfE8$_{570}$ and PHIS-PfE9$_{528}$, production of which are disclosed herein.

In another embodiment, an arthropod esterase protein of the present invention also includes at least one additional protein segment that is capable of protecting an animal from hematophagous ectoparasite infestations. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds, or portions thereof, capable of protecting an animal from hematophagous ectoparasite infestation by, for example, targeting two different arthropod proteins.

Examples of multivalent protective compounds include, but are not limited to, an esterase protein of the present invention attached to one or more compounds protective against one or more arthropod compounds. Preferred second compounds are proteinaceous compounds that effect active immunization (e.g., antigen vaccines), passive immunization (e.g., antibodies), or that otherwise inhibit a arthropod activity that when inhibited can reduce hematophagous ectoparasite burden oil and around an animal. Examples of second compounds include a compound that inhibits binding between an arthropod protein and its ligand (e.g., a compound that inhibits flea ATPase activity or a compound that inhibits binding of a peptide or steroid hormone to its receptor), a compound that inhibits hormone (including peptide or steroid hormone) synthesis, a compound that inhibits vitellogenesis (including production of vitellin and/or transport and maturation thereof into a major egg yolk protein), a compound that inhibits fat body function, a compound that inhibits muscle action, a compound that inhibits the nervous system, a compound that inhibits the immune system and/or a compound that inhibits hematophagous ectoparasite feeding. Examples of second compounds also include proteins obtained from different stages of hematophagous ectoparasite development. Particular examples of second compounds include, but are not limited to, serine proteases, cysteine proteases, aminopeptidases, serine protease inhibitor proteins, calreticulins, larval serum proteins and echdysone receptors, as well as antibodies to and inhibitors of such proteins. In one embodiment, an arthropod esterase protein of the present invention is attached to one or more additional compounds protective against hematophagous ectoparasite infestation. In another embodiment, one or more protective compounds, such as those listed above, can be included in a multivalent vaccine comprising an arthropod esterase protein of the present invention and one or more other protective molecules as separate compounds.

A preferred isolated protein of the present invention is a protein encoded by a nucleic acid molecule that hybridizes under stringent hybridization conditions with nucleic acid molecules $nfE1_{401}$, $nfE2_{364}$, $nfE3_{421}$, $nfE4_{524}$, $nfE5_{1982}$, $nfE5_{1515}$, $nfE5_{2144}$, $nfE5_{1650}$, $nfE6_{1488}$, $nfE6_{1792}$, $nfE6_{1650}$, $nfE7_{2836}$, $nfE7_{1788}$, $nfE7_{1710}$, $nfE7_{650}$, $nfE8_{2801}$, $nfE8_{1785}$, $nfE8_{1710}$, $nfE9_{2007}$, $nfE9_{1584}$, $nfE9_{1540}$, $nfE10_{1987}$ and/or $nfE10_{1590}$. A further preferred isolated protein is encoded by a nucleic acid molecule that hybridizes under stringent hybridization conditions with a nucleic acid molecule having nucleic acid sequence SEQ ID NO:3, SEQ ID NO:6, SEQ ID NO:9, SEQ ID NO:12, SEQ ID NO:15, SEQ ID NO:17, SEQ ID NO:20, SEQ ID NO:22, SEQ ID NO:26, SEQ ID NO:29, SEQ ID NO:32, SEQ ID NO:35, SEQ ID NO:38, SEQ ID NO:52, SEQ ID NO:59, SEQ ID NO:61, SEQ ID NO:69 and/or SEQ ID NO:71.

Translation of SEQ ID NO:1 suggests that nucleic acid molecule $nfE1_{401}$ encodes a non-full-length arthropod esterase protein of about 103 amino acids, referred to herein as $PfE1_{103}$, represented by SEQ ID NO:2, assuming the first codon spans from nucleotide 92 through nucleotide 94 of SEQ ID NO:1.

Comparison of amino acid sequence SEQ ID NO:2 (i.e., the amino acid sequence of $PfE1_{103}$) with amino acid sequences reported in GenBank indicates that SEQ ID NO:2, showed the most homology, i.e., about 33% identity, between SEQ ID NO:2 and alpha esterase protein from *Drosophila melanogaster*.

Translation of SEQ ID NO:4 suggests that nucleic acid molecule $nfE2_{364}$ encodes a non-full-length arthropod esterase protein of about 121 amino acids, referred to herein as $PfE2_{121}$, represented by SEQ ID NO:5, assuming the first codon spans from nucleotide 2 through nucleotide 4 of SEQ ID NO:4.

Comparison of amino acid sequence SEQ ID NO:5 (i.e., the amino acid sequence of $PfE2_{121}$) with amino acid sequences reported in GenBank indicates that SEQ ID NO:5, showed the most homology, i.e., about 38% identity, between SEQ ID NO:5 and alpha esterase protein from *Drosophila melanogaster*.

Translation of SEQ ID NO:7 suggests that nucleic acid molecule $nfE3_{421}$ encodes a non-full-length arthropod esterase protein of about 103 amino acids, referred to herein as $PfE3_{103}$, represented by SEQ ID NO:8, assuming the first codon spans from nucleotide 113 through nucleotide 115 of SEQ ID NO:7.

Comparison of amino acid sequence SEQ ID NO:8 (i.e., the amino acid sequence of $PfE3_{103}$) with amino acid sequences reported in GenBank indicates that SEQ ID NO:8, showed the most homology, i.e., about 39% identity, between SEQ ID NO:8 and alpha esterase protein from *Drosophila melanogaster*.

Translation of SEQ ID NO:10 suggests that nucleic acid molecule $nfE4_{524}$ encodes a non-full-length arthropod esterase protein of about 137 amino acids, referred to herein as $PfE4_{137}$, represented by SEQ ID NO:11, assuming the first codon spans from nucleotide 113 through nucleotide 115 of SEQ ID NO:10.

Comparison of amino acid sequence SEQ ID NO:11 (i.e., the amino acid sequence of $PfE4_{137}$) with amino acid sequences reported in GenBank indicates that SEQ ID NO:11, showed the most homology, i.e., about 30% identity, between SEQ ID NO:11 and *Leptinotarsa decemlineata* acetylcholinesterase.

Translation of SEQ ID NO:57 suggests that nucleic acid molecule $nfE5_{2144}$ encodes a full-length arthropod esterase protein of about 550 amino acids, referred to herein as $nfE8_{550}$, represented by SEQ ID NO:58, assuming an open reading frame in which the initiation codon spans from nucleotide 30 through nucleotide 32 of SEQ ID NO:57 and the termination (stop) codon spans from nucleotide 1680 through nucleotide 1682 of SEQ ID NO:57. The complement of SEQ ID NO:57 is represented herein by SEQ ID NO:59. The coding region encoding $PfE5_{550}$ is represented by the nucleic acid molecule $nfE5_{1650}$, having a coding strand with the nucleic acid sequence represented by SEQ ID NO:60 and a complementary strand with nucleic acid sequence SEQ ID NO:61. The deduced amino acid sequence of $PfE5_{550}$ (i.e., SEQ ID NO:58) predicts that $PfE5_{550}$ has an estimated molecular weight of about 61.8 kD and an estimated pI of about 5.5.

Comparison of amino acid sequence SEQ ID NO:58 (i.e., the amino acid sequence of $PfE5_{550}$) with amino acid sequences reported in GenBank indicates that SEQ ID NO:58 showed the most homology, i.e., about 36% identity between SEQ ID NO:58 and *Drosophila melanogaster* alpha esterase protein.

Translation of SEQ ID NO:18 suggests that nucleic acid molecule $nfE6_{1792}$ encodes a full-length arthropod esterase protein of about 550 amino acids, referred to herein as $PfE6_{550}$, represented by SEQ ID NO:19, assuming an open reading frame having an initiation codon spanning from nucleotide 49 through nucleotide 51 of SEQ ID NO:18 and a stop codon spanning from nucleotide 1699 through nucleotide 1701 of SEQ ID NO:18. The coding region encoding $PfE6_{550}$, is represented by nucleic acid molecule $nfE6_{1650}$, having a coding strand with the nucleic acid sequence represented by SEQ ID NO:21 and a complementary strand with nucleic acid sequence SEQ ID NO:22. The proposed mature protein, denoted herein as $PfE6_{530}$, contains about 530 amino acids which is represented herein as SEQ ID NO:53. The nucleic acid molecule encoding $PfE6_{530}$ is denoted herein as $nfE6_{1590}$ and has a coding strand having the nucleic acid sequence SEQ ID NO:23. The deduced amino acid sequence SEQ ID NO:19 suggests a protein having a molecular weight of about 61.8 kD and an estimated pI of about 5.5.

Comparison of amino acid sequence SEQ ID NO:19 (i.e., the amino acid sequence of $PfE6_{550}$) with amino acid sequences reported in GenBank indicates that SEQ ID NO:19 showed the most homology, i.e., about 28% identity between SEQ ID NO:19 and *Drosophila melanogaster* alpha esterase protein.

Translation of SEQ ID NO:24 suggests that nucleic acid molecule $nfE7_{2836}$ encodes a full-length arthropod esterase protein of about 596 amino acids, referred to herein as $PfE7_{596}$, represented by SEQ ID NO:25, assuming an open reading frame having an initiation codon spanning from nucleotide 99 through nucleotide 101 of SEQ ID NO:24 and a stop codon spanning from nucleotide 1887 through nucleotide 1889 of SEQ ID NO:24. The coding region encoding $PfE7_{596}$, is represented by nucleic acid molecule $nfE7_{1788}$, having a coding strand with the nucleic acid sequence represented by SEQ ID NO:28 and a complementary strand with nucleic acid sequence SEQ ID NO:29. The proposed mature protein, denoted herein as $PfE7_{570}$, contains about 570 amino acids which is represented herein as SEQ ID NO:54. The nucleic acid molecule encoding $PfE7_{570}$ is denoted herein as $nfE7_{1710}$ and has a coding strand having the nucleic acid sequence SEQ ID NO:27. The deduced amino acid sequence SEQ ID NO:25 suggests a protein having a molecular weight of about 68.7 kD and an estimated pI of about 6.1.

Comparison of amino acid sequence SEQ ID NO:25 (i.e., the amino acid sequence of PfE7596) with amino acid sequences reported in GenBank indicates that SEQ ID NO:25 showed the most homology, i.e., about 27% identity between SEQ ID NO:25 and *Drosophila melanogaster* alpha esterase protein.

Translation of SEQ ID NO:30 suggests that nucleic acid molecule nfE8$_{2801}$ encodes a full-length arthropod esterase protein of about 595 amino acids, referred to herein as PfE8$_{595}$, represented by SEQ ID NO:31, assuming an open reading frame having an initiation codon spanning from nucleotide 99 through nucleotide 101 of SEQ ID NO:30 and a stop codon spanning from nucleotide 1884 through nucleotide 1886 of SEQ ID NO:30. The coding region encoding PfE8$_{595}$, is represented by nucleic acid molecule nfE8$_{1785}$, having a coding strand with the nucleic acid sequence represented by SEQ ID NO:34 and a complementary strand with nucleic acid sequence SEQ ID NO:35. The proposed mature protein, denoted herein as PfE8$_{570}$, contains about 570 amino acids which is represented herein as SEQ ID NO:55. The nucleic acid molecule encoding PfE8$_{570}$ is denoted herein as nf8$_{1710}$ and has a coding strand having the nucleic acid sequence SEQ ID NO:33. The deduced amino acid sequence SEQ ID NO:31 suggests a protein having a molecular weight of about 68.6 kD and an estimated pI of about 6.1.

Comparison of amino acid sequence SEQ ID NO:31 (i.e., the amino acid sequence of PfE8$_{595}$) with amino acid sequences reported in GenBank indicates that SEQ ID NO:31 showed the most homology, i.e., about 28% identity between SEQ ID NO:31 and estalpha-2 esterase of *Culex pipiens quinquefasciatus*.

Translation of SEQ ID NO:36 suggests that nucleic acid molecule nfE9$_{2007}$ encodes a full-length arthropod esterase protein of about 528 amino acids, referred to herein as PfE9$_{528}$, represented by SEQ ID NO:37, assuming an open reading frame having an initiation codon spanning from nucleotide 11 through nucleotide 13 of SEQ ID NO:36 and a stop codon spanning from nucleotide 1595 through nucleotide 1597 of SEQ ID NO:36. The coding region encoding PfE9$_{528}$, is represented by nucleic acid molecule nfE9$_{1584}$, having a coding strand with the nucleic acid sequence represented by SEQ ID NO:51 and a complementary strand with nucleic acid sequence SEQ ID NO:52. The deduced amino acid sequence SEQ ID NO:37 suggests a protein hatting a molecular weight of about 60 kD and an estimated pI of about 5.43.

Comparison of amino acid sequence SEQ ID NO:37 (i.e., the amino acid sequence of PfE9$_{528}$) with amino acid sequences reported in GenBank indicates that SEQ ID NO:37 showed the most homology, i.e., about 37% identity between SEQ ID NO:37 and alpha esterase protein from *Drosophila melanogaster*.

Translation of SEQ ID NO:67 suggests that nucleic acid molecule nfE10$_{1987}$ encodes a full-length flea esterase protein of about 530 amino acids, referred to herein as PfE10$_{530}$, having amino acid sequence SEQ ID NO:68, assuming an open reading frame in which the initiation codon spans from nucleotide 231 through nucleotide 233 of SEQ ID NO:67 and a stop codon spanning from nucleotide 1821 through nucleotide 1823 of SEQ ID NO:67. The complement of SEQ ID NO:67 is represented herein by SEQ ID NO:69. The coding region encoding PfE10$_{530}$, is represented by nucleic acid molecule nfE10$_{1590}$, having a coding strand with the nucleic acid sequence represented by SEQ ID NO:70 and a complementary strand with nucleic acid sequence SEQ ID NO:71. The amino acid sequence of PfE10$_{530}$ (i.e., SEQ ID NO:68) predicts that PfE10$_{530}$ has an estimated molecular weight of about 59.5 kD and an estimated pI of about 5.5.

Comparison of amino acid sequence SEQ ID NO:68 (i.e., the amino acid sequence of PfE10$_{530}$) with amino acid sequences reported in GenBank indicates that SEQ ID NO:68 showed the most homology, i.e., about 30% identity between SEQ ID NO:68 and *Culex pipeis* esterase b1 precurser protein (swissprot #P16854).

More preferred arthropod esterase proteins of the present invention include proteins comprising amino acid sequences that are at least about 40%, preferably at least about 45%, more preferably at least about 50%, even more preferably at least about 55%, even more preferably at least about 60%, even more preferably at least about 70%, even more preferably at least about 80%, even more preferably at least about 90%, and even more preferably at least about 95%, identical to amino acid sequence SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55, SEQ ID NO:58, SEQ ID NO:68, SEQ ID NO:73 and/or SEQ ID NO:74.

More preferred arthropod esterase proteins of the present invention include proteins encoded by a nucleic acid molecule comprising at least a portion of nfE1$_{401}$, nfE2$_{364}$, nfE3$_{421}$, nfE4$_{524}$, nfE5$_{1982}$, nfE5$_{1515}$, nfE5$_{2144}$, nfE5$_{1650}$, nfE6$_{1488}$, nfE6$_{1792}$, nfE6$_{1650}$, nfE7$_{2836}$, nfE7$_{1788}$, nfE7$_{1710}$, nfE7$_{650}$, nfE8$_{2801}$, nfE8$_{1785}$, nfE8$_{1710}$, nfE9$_{1584}$, nfE9$_{1540}$, nfE10$_{1987}$ and/or nfE10$_{1590}$, or of allelic variants of such nucleic acid molecules. More preferred is an esterase protein encoded by nfE1$_{401}$, nfE2$_{364}$, nfE3$_{421}$, nfE4$_{524}$, nfE5$_{1982}$, nfE5$_{1515}$, nfE5$_{2144}$, nfE5$_{650}$, nfE6$_{1488}$, nfE6$_{1792}$, nfE6$_{1650}$, nfE7$_{2836}$, nfE7$_{1788}$, nfE7$_{1710}$, nfE7$_{650}$, nfE8$_{2801}$, nfE8$_{1785}$, nfE8$_{1710}$, nfE9$_{2007}$, nfE9$_{1584}$, nfE9$_{1540}$, nfE10$_{1987}$ and/or nfE10$_{1590}$, or by an allelic variant of such nucleic acid molecules. Particularly preferred arthropod esterase proteins are PfE1$_{103}$, PfE2$_{121}$, PfE3$_{103}$, PfE4$_{137}$, PfE5$_{505}$, PfE5$_{550}$, PfE6$_{550}$, PfE6$_{530}$, PfE7$_{596}$, PfE7$_{570}$, PfE8$_{595}$, PfE8$_{570}$, PfE9$_{528}$ and PfE10$_{530}$.

In one embodiment, a preferred esterase protein of the present invention is encoded by at least a portion of SEQ ID NO:1, SEQ ID NO:4, SEQ ID NO:7, SEQ ID NO:10, SEQ ID NO:13, SEQ ID NO:16, SEQ ID NO:18, SEQ ID NO:21, SEQ ID NO:23, SEQ ID NO:24, SEQ ID NO:27, SEQ ID NO:28, SEQ ID NO:30, SEQ ID NO:33, SEQ ID NO:34, SEQ ID NO:36, SEQ ID NO:51, SEQ ID NO:57, SEQ ID NO:60 and/or SEQ ID NO:67, and, as such, has an amino acid sequence that includes at least a portion of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:53, SEQ ID NO:54, SEQ ID NO:55, SEQ ID NO:58 and/or SEQ ID NO:68. Also preferred is a protein encoded by an allelic variant of a nucleic acid molecule comprising at least a portion of the above-listed nucleic acid sequences.

Particularly preferred esterase proteins of the present invention include SEQ ID NO:2, SEQ ID NO:5, SEQ ID NO:8, SEQ ID NO:10, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55, SEQ ID NO:58, SEQ ID NO:68, SEQ ID NO:73 and/or SEQ ID NO:74 (including, but not limited to, the proteins consisting of such sequences, fusion proteins and multivalent proteins) and proteins encoded by allelic variants of SEQ ID NO:1, SEQ ID NO:4, SEQ ID NO:7, SEQ ID NO:10, SEQ ID NO:13, SEQ ID NO:16, SEQ ID NO:18, SEQ ID NO:21, SEQ ID NO:23, SEQ ID NO:24, SEQ ID NO:27, SEQ ID NO:28, SEQ ID NO:30, SEQ ID NO:33, SEQ ID NO:34, SEQ ID NO:36, SEQ ID NO:51, SEQ ID NO:57, SEQ ID NO:60 and/or SEQ ID NO:67.

Another embodiment of the present invention is an isolated nucleic acid molecule that hybridizes under stringent hybridization conditions with a *C. felis* esterase gene. The identifying characteristics of such a gene are heretofore described. A nucleic acid molecule of the present invention can include an isolated natural arthropod esterase gene or a homolog thereof, the latter of which is described in more detail below. A nucleic acid molecule of the present invention can include one or more regulatory regions, full-length or partial coding regions, or combinations thereof. The minimal size of a nucleic acid molecule of the present invention is the minimal size that can form a stable hybrid with a *C. felis* esterase gene under stringent hybridization conditions.

In accordance with the present invention, an isolated nucleic acid molecule is a nucleic acid molecule that has been removed from its natural milieu (i.e., that has been subject to human manipulation) and can include DNA, RNA, or derivatives of either DNA or RNA. As such, "isolated" does not reflect the extent to which the nucleic acid molecule has been purified. An isolated arthropod esterase nucleic acid molecule of the present invention can be isolated from its natural source or can be produced using recombinant DNA technology (e.g., polymerase chain reaction (PCR) amplification, cloning) or chemical synthesis. Isolated esterase nucleic acid molecules can include, for example, natural allelic variants and nucleic acid molecules modified by nucleotide insertions, deletions, substitutions, and/or inversions in a manner such that the modifications do not substantially interfere with the nucleic acid molecule's ability to encode an esterase protein of the present invention or to form stable hybrids under stringent conditions with natural gene isolates.

An arthropod esterase nucleic acid molecule homolog can be produced using a number of methods known to those skilled in the art (see, for example, Sambrook et al., *ibid.*). For example, nucleic acid molecules can be modified using a variety of techniques including, but not limited to, classic mutagenesis and recombinant DNA techniques (e.g., site-directed mutagenesis, chemical treatment, restriction enzyme cleavage, ligation of nucleic acid fragments and/or PCR amplification), synthesis of oligonucleotide mixtures and ligation of mixture groups to "build" a mixture of nucleic acid molecules and combinations thereof. Nucleic acid molecule homologs can be selected by hybridization with a *C. felis* esterase gene or by screening for the function of a protein encoded by the nucleic acid molecule (e.g., ability to elicit an immune response against at least one epitope of an arthropod esterase protein, hydrolyze α-napthyl acetate, hydrolyze the methyl ester group of juvenile hormone and/or bind to DFP).

An isolated nucleic acid molecule of the present invention can include a nucleic acid sequence that encodes at least one arthropod esterase protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding an arthropod esterase protein.

A preferred nucleic acid molecule of the present invention, when administered to an animal, is capable of protecting that animal from infestation by a hematophagous ectoparasite. As will be disclosed in more detail below, such a nucleic acid molecule can be, or can encode, an antisense RNA, a molecule capable of triple helix formation, a ribozyme, or other nucleic acid-based drug compound. In additional embodiments, a nucleic acid molecule of the present invention can encode a protective esterase protein (e.g., an esterase protein of the present invention), the nucleic acid molecule being delivered to the animal, for example, by direct injection (i.e, as a naked nucleic acid) or in a vehicle such as a recombinant virus vaccine or a recombinant cell vaccine.

One embodiment of the present invention is an esterase nucleic acid molecule that hybridizes under stringent hybridization conditions with nucleic acid molecule $nfE1_{401}$ and preferably with a nucleic acid molecule having nucleic acid sequence SEQ ID NO:1 and/or SEQ ID NO:3.

Another embodiment of the present invention is an esterase nucleic acid molecule that hybridizes under stringent hybridization conditions ith nucleic acid molecule $nfE2_{364}$ and preferably with a nucleic acid molecule having nucleic acid sequence SEQ ID NO:4 and/or SEQ ID NO:6.

Another embodiment of the present invention is an esterase nucleic acid molecule that hybridizes under stringent hybridization conditions with nucleic acid molecule $nfE3_{421}$ and preferably with a nucleic acid molecule having nucleic acid sequence SEQ ID NO:7 and/or SEQ ID NO:9.

Another embodiment of the present invention is an esterase nucleic acid molecule that hybridizes under stringent hybridization conditions with nucleic acid molecule $nfE4_{524}$ and preferably with a nucleic acid molecule having nucleic acid sequence SEQ ID NO:10 and/or SEQ ID NO:12.

Another embodiment of the present invention is an esterase nucleic acid molecule that hybridizes under stringent hybridization conditions with nucleic acid molecule $nfF5_{2144}$ and preferably with a nucleic acid molecule having nucleic acid sequence SEQ ID NO:57 and/or SEQ ID NO:59.

Another embodiment of the present invention is an esterase nucleic acid molecule that hybridizes under stringent hybridization conditions with nucleic acid molecule $nfE6_{1792}$ and preferably with a nucleic acid molecule having nucleic acid sequence SEQ ID NO:18 and/or SEQ ID NO:20.

Another embodiment of the present invention is an esterase nucleic acid molecule that hybridizes under stringent hybridization conditions with nucleic acid molecule $nfE7_{2836}$ and preferably with a nucleic acid molecule having nucleic acid sequence SEQ ID NO:24 and/or SEQ ID NO:26.

Another embodiment of the present invention is an esterase nucleic acid molecule that hybridizes under stringent hybridization conditions with nucleic acid molecule $nfE8_{2801}$ and preferably with a nucleic acid molecule having nucleic acid sequence SEQ ID NO:30 and/or SEQ ID NO:32.

Another embodiment of the present invention is an esterase nucleic acid molecule that hybridizes under stringent hybridization conditions with nucleic acid molecule nfE9$_{2007}$ and preferably with a nucleic acid molecule having nucleic acid sequence SEQ ID NO:36 and/or SEQ ID NO:38.

Another embodiment of the present invention is an esterase nucleic acid molecule that hybridizes under stringent hybridization conditions with nucleic acid molecule nfE10$_{1987}$ and preferably with a nucleic acid molecule having nucleic acid sequence SEQ ID NO:67 and/or SEQ ID NO:69.

Comparison of nucleic acid sequence SEQ ID NO:1 (i.e., the nucleic acid sequence of nfE1$_{401}$) with nucleic acid sequences reported in GenBank indicates that SEQ ID NO:1 showed no identifiable identity with any sequence reported in GenBank.

Comparison of nucleic acid sequence SEQ ID NO:4 (i.e., the coding strand of nucleic acid sequence of nfE2$_{364}$) with nucleic acid sequences reported in GenBank indicates that SEQ ID NO:4 showed the most homolog, i.e., about 43% identity, between SEQ ID NO:4 and a *H. virescens* juvenile hormone esterase gene.

Comparison of nucleic acid sequence SEQ ID NO:7 (i.e., the coding strand of nucleic acid sequence of nfE3$_{421}$) with nucleic acid sequences reported in GenBank indicates that SEQ ID NO:7 showed the most homolog, i.e., about 53% identity, between SEQ ID NO:7 and a *Torpedo marmorata* acetylcholinesterase gene.

Comparison of nucleic acid sequence SEQ ID NO:10 (i.e., the coding strand of nucleic acid sequence of nfE4$_{524}$) with nucleic acid sequences reported in GenBank indicates that SEQ ID NO:10 showed the most homolog, i.e., about 47% identity, between SEQ ID NO:10 and an *Anas platyrhyncos* thioesterase B gene.

Comparison of nucleic acid sequence SEQ ID NO:57 (i.e., the coding strand of nucleic acid sequence of nfE5$_{2144}$) with nucleic acid sequences reported in GenBank indicates that SEQ ID NO:57 showed the most homolog, i.e., about 41% identity, between SEQ ID NO:57 and a esterase mRNA from *Myzus persicae*.

Comparison of nucleic acid sequence SEQ ID NO:18 (i.e., the coding strand of nucleic acid sequence of nfE6$_{1792}$) with nucleic acid sequences reported in GenBank indicates that SEQ ID NO:18 showed the most homolog, i.e., about 41% identity, between SEQ ID NO:18 and a esterase gene from *Myzus persicae*.

Comparison of nucleic acid sequence SEQ ID NO:24 (i.e., the coding strand of nucleic acid sequence of nfE7$_{2836}$) with nucleic acid sequences reported in GenBank indicates that SEQ ID NO:24 showed the most homolog, i.e., about 48% identity, between SEQ ID NO:24 and an *Anas platyrhyncos* thioesterase B gene.

Comparison of nucleic acid sequence SEQ ID NO:30 (i.e., the coding strand of nucleic acid sequence of nfE8$_{2801}$) with nucleic acid sequences reported in GenBank indicates that SEQ ID NO:30 showed the most homolog, i.e., about 46% identity, between SEQ ID NO:30 and a *Mus musculus* carboxyl ester lipase gene.

Comparison of nucleic acid sequence SEQ ID NO:36 (i.e., the coding strand of nucleic acid sequence of nfE9$_{2007}$) with nucleic acid sequences reported in GenBank indicates that SEQ ID NO:36 showed the most homolog, i.e., about 47% identity, between SEQ ID NO:36 and a hamster mRNA for CE precursor gene.

Comparison of nucleic acid sequence SEQ ID NO:67 with nucleic acid sequences reported in GenBank indicates that SEQ ID NO:67 showed the most homology, i.e., about 48% identity, between SEQ ID NO:67 and a *Lucilia cuprina* alpha esterase gene (genembl #U56636) gene.

Preferred arthropod esterase nucleic acid molecules include nucleic acid molecules having a nucleic acid sequence that is at least about 55%, preferably at least about 60%, more preferably at least about 65%, more preferably at least about 70%, more preferably at least about 75%, more preferably at least about 80%, more preferably at least about 90%, and even more preferably at least about 95% identical to nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74.

Another preferred nucleic acid molecule of the present intention includes at least a portion of nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:58, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74, that is capable of hybridizing to a *C. felis* esterase gene of the present invention, as well as allelic variants thereof. A more preferred nucleic acid molecule includes the nucleic acid sequence SEQ ID NO:1, SEQ ID NO:3, SEQ ID NO:4, SEQ ID NO:6, SEQ ID NO:7, SEQ ID NO:9, SEQ ID NO:10, SEQ ID NO:12, SEQ ID NO:13, SEQ ID NO:15, SEQ ID NO:16, SEQ ID NO:17, SEQ ID NO:18, SEQ ID NO:20, SEQ ID NO:21, SEQ ID NO:22, SEQ ID NO:23, SEQ ID NO:24, SEQ ID NO:26, SEQ ID NO:27, SEQ ID NO:28, SEQ ID NO:29, SEQ ID NO:30, SEQ ID NO:32, SEQ ID NO:33, SEQ ID NO:34, SEQ ID NO:35, SEQ ID NO:36, SEQ ID NO:38, SEQ ID NO:51, SEQ ID NO:52, SEQ ID NO:57, SEQ ID NO:59, SEQ ID NO:60, SEQ ID NO:61, SEQ ID NO:67, SEQ ID NO:69, SEQ ID NO:70, SEQ ID NO:71, SEQ ID NO:72, SEQ ID NO:76 and/or a nucleic acid molecule encoding a protein comprising amino acid sequence SEQ ID NO:74, as well as allelic variants thereof. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound. Particularly preferred nucleic acid molecules include nfE1$_{401}$, nfE2$_{364}$, nfE3$_{421}$, nfE4$_{524}$, nfE5$_{1982}$, nfE5$_{1515}$, nfE5$_{2144}$, nfE5$_{1650}$, nfE6$_{1488}$, nf6$_{1792}$, nfE6$_{1650}$, nfE7$_{2836}$, nfE7$_{1788}$, nfE7$_{1710}$, nfE7$_{650}$, nfE8$_{2801}$, nfE8$_{1785}$, nfE8$_{1710}$, nfE9$_{2007}$, nfE9$_{1584}$, nfE9$_{1540}$, nfE10$_{1987}$ and nfE10$_{1590}$.

The present invention also includes a nucleic acid molecule encoding a protein having at least a portion of SEQ ID NO:2, SEQ ID NO:5, SEQ ID NO:8, SEQ ID NO:11, SEQ ID NO:14, SEQ ID NO:19, SEQ ID NO:25, SEQ ID NO:31, SEQ ID NO:37, SEQ ID NO:39, SEQ ID NO:40, SEQ ID NO:41, SEQ ID NO:42, SEQ ID NO:43, SEQ ID NO:44, SEQ ID NO:53, SEQ ID NO:54, SEQ ID NO:55, SEQ ID NO:58, SEQ ID NO:68, SEQ ID NO:73 and/or SEQ ID NO:74, including nucleic acid molecules that have been modified to accommodate codon usage properties of the cells in which such nucleic acid molecules are to be expressed.

Knowing the nucleic acid sequences of certain arthropod esterase nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain esterase nucleic acid molecules from other arthropods. Such nucleic acid molecules can be obtained in a variety of ways including screening appropriate expression libraries with antibodies of the present invention; traditional cloning techniques using oligonucleotide probes of the present invention to screen appropriate libraries or DNA; and PCR amplification of appropriate libraries or DNA using oligonucleotide primers of the present invention. Preferred libraries to screen or from which to amplify nucleic acid molecule include flea pre-pupal, 3rd instar or adult cDNA libraries as well as genomic DNA libraries. Similarly, preferred DNA sources to screen or from which to amplify nucleic acid molecules include flea pre-pupal, 3rd instar or adult cDNA and genomic DNA. Techniques to clone and amplify genes are disclosed, for example, in Sambrook et al., *ibid.*

The present invention also includes nucleic acid molecules that are oligonucleotides capable of hybridizing, under stringent hybridization conditions, with complementary regions of other, preferably longer, nucleic acid molecules of the present invention such as those comprising arthropod esterase genes or other arthropod esterase nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. Minimal size characteristics are disclosed herein. The present invention includes oligonucleotides that can be used as, for example, probes to identify nucleic acid molecules, primers to produce nucleic acid molecules or therapeutic reagents to inhibit esterase protein production or activity (e.g., as antisense-, triplex formation-, ribozyme- and/or RNA drug-based reagents). The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulation of arthropod esterase nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, but not limited to, tac, lac, trp, trc, oxy-pro, omp/lpp, rmB, bacteriophage lambda (such as lambda $p_L$ and lambda $p_R$ and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukinis). Transcription control sequences of the present invention can also include naturally occurring transcription control sequences naturally associated with arthropods, such as, *C. felis*.

Suitable and preferred nucleic acid molecules to include in recombinant vectors of the present invention are as disclosed herein. Preferred nucleic acid molecules to include in recombinant vectors, and particularly in recombinant molecules, include $nfE1_{401}$, $nfE2_{364}$, $nfE3_{421}$, $nfE4_{524}$, $nfE5_{1982}$, $nfE5_{1515}$, $nfE5_{2144}$, $nfE6_{1488}$, $nfE6_{1792}$, $nfE6_{1650}$, $nfE7_{2836}$, $nfE7_{1788}$, $nfE7_{1710}$, $nfE7_{650}$, $nfE8_{2801}$, $nfE8_{1785}$, $nfE8_{1710}$, $nfE9_{2007}$, $nfE9_{1584}$, $nfE9_{1540}$, $nfE10_{1987}$ and/or $nfE10_{1590}$. Particularly preferred recombinant molecules of the present invention include $pCro\text{-}nfE6_{1488}$, $pTrc\text{-}nfE7_{650}$, $pTrc\text{-}nfE7_{1710}$, $pTrc\text{-}nfE8_{1710}$, $pTrc\text{-}nfE5_{1650}$, $pTrc\text{-}nfE9_{1540}$, $pFB\text{-}nfE6_{1679}$, $pVL\text{-}nfE7_{1802}$, $pVL\text{-}fE8_{1792}$ and $pVL\text{-}nfE9_{1600}$, the production of which are described in the Examples section.

Recombinant molecules of the present invention may also (a) contain secretory signals (i.e., signal segment nucleic acid sequences) to enable an expressed arthropod protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments, as well as natural signal sequences. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include arthropod esterase nucleic acid molecules disclosed herein. Particularly preferred nucleic acid molecules with which to transform a cell include $nfE1_{401}$, $nfE2_{364}$, $nfE3_{421}$, $nfE4_{524}$, $nfE5_{1982}$, $nfE5_{1515}$, $nfE5_{2144}$, $nfE6_{1488}$, $nfE6_{1792}$, $nfE6_{1650}$, $nfE7_{2836}$, $nfE7_{1788}$, $nfE7_{1710}$, $nfE7_{650}$, $nfE8_{2801}$, $nfE8_{1785}$, $nfE8_{1710}$, $nfE9_{2007}$, $nfE9_{1584}$, $nfE9_{1540}$, $nfE10_{1987}$ and/or $nfE10_{1590}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing arthropod esterase proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite, other insect, other animal and plant cells. Preferred host cells include bacterial, mycobacterial, yeast, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (normal dog kidney cell line for canine herpesvirus cultivation), CRFK cells (normal cat kidney cell line for feline herpesvirus cultivation), CV-1 cells (African monkey kidney cell line used, for example, to culture raccoon poxvirus), COS (e.g., COS-7) cells, and Vero cells. Particularly preferred host cells are *Escherichia coli*, including *E. coli* K-12 derivatives; *Salmonella typhi*; *Salmonella typhimurium* including attenuated strains such as $UK\text{-}1_x3987$ and $SR\text{-}11_x4072$; *Spodoptera frugiperda*; *Trichoplusia ni*; BHK cells; MDCK cells; CRFK cells; CV-1 cells; COS cells; Vero cells; and non-tumorgenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, $LMTK^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences. The phrase operatively linked refers to insertion of a nucleic acid molecule into an expression vector in a manner such that the molecule is able to be expressed when transformed into a host cell.

A recombinant molecule of the present invention is a molecule that can include at least one of any nucleic acid molecule heretofore described operatively linked to at least one of any transcription control sequence capable of effectively regulating expression of the nucleic acid molecule(s) in the cell to be transformed, examples of which are disclosed herein. Particularly preferred recombinant molecules include $pCro\text{-}nfE6_{1488}$, $pTrc\text{-}nfE7_{650}$, $pTrc\text{-}nfE7_{1710}$, $pTrc\text{-}nfE8_{1710}$, $pTrc\text{-}nfE5_{1650}$, $pTrc\text{-}nfE9_{1540}$, $pFB\text{-}nfE6_{1679}$, $pVL\text{-}nfE7_{1802}$, $pVL\text{-}fE8_{1792}$ and $pVL\text{-}nfE9_{1600}$.

A recombinant cell of the present invention includes any cell transformed with at least one of any nucleic acid molecule of the present invention. Suitable and preferred a nucleic acid molecules as well as suitable and preferred recombinant molecules with which to transform cells are disclosed herein. Particularly preferred recombinant cells include *E. coli*:$pCro\text{-}nfE6_{1488}$, *E. coli*:$pTrc\text{-}nfE7_{1710}$, *E. coli*:$pTrc\text{-}nf7_{650}$, *E. coli*:$pTrc\text{-}nfE8_{1710}$, *E. coli*:$pTrc\text{-}nfE5_{1650}$, *E. coli*:$pTrc\text{-}nfE9_{1540}$, *S. fugiperda*:$pVL\text{-}nfE7_{1802}$, *S. fugiperda*:$pVL\text{-}nfE8_{1792}$, *S. fugiperda*:$pVL\text{-}nfE9_{1600}$ and *S. fugiperda*:$pFB\text{-}nfE6_{1679}$. Details regarding the production of these recombinant cells are disclosed herein.

Recombinant cells of the present invention can also be co-transformed with one or more recombinant molecules including arthropod esterase nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated esterase proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective medium refers to any medium in which a cell is cultured to produce an arthropod esterase protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the perplasmic space in *E. coli*; or be retained on the outer surface of a cell or viral membrane. The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to an arthropod esterase protein of the present invention or a mimetope thereof (i.e., anti-arthropod esterase antibodies). As used herein, the term "selectively binds to" an esterase protein refers to the ability of antibodies of the present invention to preferentially bind to specified proteins and mimetopes thereof of the present invention. Binding can be measured using a variety of methods standard in the art including enzyme immunoassays (e.g., ELISA), immiiunioblot assays, etc.; see, for example, Sambrook et al., *ibid*. An anti-arthropod esterase antibody preferably selectively binds to an arthropod esterase protein in such a way as to reduce the activity of that protein.

Isolated antibodies of the present invention can include antibodies in a bodily fluid (such as, but not limited to, serum), or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce arthropod esterase proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from arthropods susceptible to treatment by such antibodies and/or (b) as tools to screen expression libraries and/or to recover desired proteins of the present invention from a mixture of proteins and other contaminants. Furthermore, antibodies of the present invention can be used to target cytotoxic agents to hematophagous ectoparasites such as those discloses herein, in order to directly kill such hematophiagous ectoparasites. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from infestation by hematophagous ectoparasite. Therapeutic compositions of the present invention include at least one of the following protective compounds: an isolated hematophagous arthropod esterase protein (including a peptide); a mimetope of such a protein; an isolated nucleic acid molecule that hybridizes under stringent hybridization conditions with a *Ctenocephalides felis* esterase gene; an isolated antibody that selectively binds to an hematophagous arthropod esterase protein; and inhibitors of hematophagous arthropod esterase activity (including esterase substrate analogs). As used herein, a protective compound refers to a compound that, when administered to an animal in an effective manner, is able to treat, ameliorate, and/or prevent disease caused by an arthropod of the present invention. Preferred arthropods to target are heretofore disclosed. Examples of proteins, nucleic acid molecules, antibodies and inhibitors of the present invention are disclosed herein.

A preferred therapeutic composition of the present invention includes at least one of the following protective compounds: an isolated hematophagous ectoparasite carboxylesterase protein (including a peptide); a mimetope of such a protein; an isolated hematophagous ectoparasite carboxylesterase nucleic acid molecule that hybridizes under stringent hybridization conditions with a *Ctenocephalides felis* carboxylesterase gene; an isolated antibody that selectively binds to a hematophagous ectoparasite carboxylesterase protein; and an inhibitor of carboxylesterase activity identified by its ability to inhibit the activity of a flea carboxylesterase (including a substrate analog).

Suitable inhibitors of esterase activity are compounds that interact directly with an esterase protein's active site, thereby inhibiting that esterase's activity, usually by binding to or otherwise interacting with or otherwise modifying the esterase's active site. Esterase inhibitors can also interact with other regions of the esterase protein to inhibit esterase activity, for example, by allosteric interaction. Inhibitors of esterases are usually relatively small compounds and as such differ from anti-esterase antibodies. Preferably, an esterase inhibitor of the present invention is identified by its ability to bind to, or otherwise interact with, a flea esterase protein, thereby inhibiting the activity of the flea esterase.

Esterase inhibitors can be used directly as compounds in compositions of the present invention to treat animals as long as such compounds are not harmful to host animals being treated. Esterase inhibitors can also be used to identify preferred types of arthropod esterases to target using compositions of the present invention, for example by affinity chromatography. Preferred esterase inhibitors of the present invention include, but are not limited to, flea esterase substrate analogs, and other molecules that bind to a flea esterase (e.g., to an allosteric site) in such a manner that esterase activity of the flea esterase is inhibited; examples include, but are not limited to, juvenile hormone analogs and cholinesterase inhibitors as well as other neural transmission inhibitors. An esterase substrate analog refers to a compound that interacts with (e.g., binds to, associates with, modifies) the active site of an esterase protein. A preferred esterase substrate analog inhibits esterase activity. Esterase substrate analogs can be of any inorganic or organic composition, and, as such, can be, but are not limited to, peptides, nucleic acids, and peptidomimetic compounds. Esterase substrate analogs can be, but need not be, structurally similar to an esterase's natural substrate as long as they can interact with the active site of that esterase protein. Esterase substrate analogs can be designed using computer-generated structures of esterase proteins of the present invention or computer structures of esterases' natural substrates. Substrate analogs can also be obtained by generating random samples of molecules, such as oligonucleotides, peptides, peptidomimetic compounds, or other inorganic or organic molecules, and screening such samples by affinity chromatography techniques using the corresponding binding partner, (e.g., a flea esterase). A preferred esterase substrate analog is a peptidomimetic compound (i.e., a compound that is structurally and/or functionally similar to a natural substrate of an esterase of the present invention, particularly to the region of the substrate that interacts with the esterase active site, but that inhibits esterase activity upon interacting with the esterase active site).

Esterase peptides, mimetopes and substrate analogs, as well as other protective compounds, can be used directly as compounds in compositions of the present invention to treat animals as long as such compounds are not handful to the animals being treated.

The present invention also includes a therapeutic composition comprising at least one arthropod esterase-based compound of the present invention in combination with at least one additional compound protective against hematophagous ectoparasite infestation. Examples of such compounds are disclosed herein.

In one embodiment, a therapeutic composition of the present invention cell be used to protect an animal from hematophagous ectoparasite infestation by administering such composition to a hematophagous ectoparasite, such as to a flea, in order to prevent infestation. Such administration could be oral, or by application to the environment (e.g., spraying). Examples of such compositions include, but are not limited to, transgenic vectors capable of producing at least one therapeutic composition of the present invention. In another embodiment, a hematophagous ectoparasite, such as a flea, can ingest therapeutic compositions, or products thereof, present in the blood of a host animal that has been administered a therapeutic composition of the present invention.

Compositions of the present invention can be administered to any animal susceptible to hematophagous ectoparasite infestation (i.e., a host animal), including warm-blooded animals. Preferred animals to treat include mammals and birds, with cats, dogs, humans, cattle, chinchillas, ferrets, goats, mice, minks, rabbits, raccoons, rats, sheep, squirrels, swine, chickens, ostriches, quail and turkeys as well as other furry animals, pets, zoo animals, work animals and/or food animals, being more preferred. Particularly preferred animals to protect are cats and dogs.

In accordance with the present invention, a host animal (i.e., an animal that is or is capable of being infested with a hematophagous ectoparasite) is treated by administering to the animal a therapeutic composition of the present invention in such a ,manner that the composition itself (e.g., an esterase inhibitor, an esterase synthesis suppressor (i.e., a compound that decreases the production of esterase in the hematophagous ectoparasite), an esterase mimetope, or an anti-esterase antibody) or a product generated by the animal in response to administration of the composition (e.g., antibodies produced in response to administration of an arthropod esterase protein or nucleic acid molecule, or conversion of ail inactive inhibitor "prodrug" to an active esterase inhibitor) ultimately enters the hematophagous ectoparasite. A host animal is preferably treated in such a way that the compound or product thereof enters the blood stream of the animal. Hematophagous ectoparasites are then exposed to the composition or product when they feed from the animal. For example, flea esterase inibitors administered to an animal are administered in such a way that the inhibitors enter the blood stream of the animal, where they can be taken up by feeding fleas. In another embodiment, when a host animal is administered an arthropod esterase protein or nucleic acid molecule, the treated animal mounts an immune response resulting in the production of antibodies against the esterase (i.e., anti-esterase antibodies) which circulate in the animal's blood stream and are taken up by hematophagous ectoparasites upon feeding. Blood taken up by hematophagous ectoparasites enters the hematophagous ectoparasites where compounds of the present invention, or products thereof, such as anti-esterase antibodies, esterase inhibitors, esterase mimetopes and/or esterase synthesis suppressors, interact with, and reduce esterase activity in the hematophagous ectoparasite.

The present invention also includes the ability to reduce larval hematophagous ectoparasite infestation in that when hematophagous ectoparasites feed from a host animal that has been administered a therapeutic composition of the present invention, at least a portion of compounds of the present invention, or products thereof, in the blood taken up by the hematophagous ectoparasite are excreted by the hematophagous ectoparasite in feces, which is subsequently ingested by hematophagous ectoparasite larvae. In particular, it is of note that flea larvae obtain most, if not all, of their nutrition from flea feces.

In accordance with the present invention, reducing esterase activity in a hematophagous ectoparasite can lead to a number of outcomes that reduce hematophagous ectoparasite burden on treated animals and their surrounding environments. Such outcomes include, but are not limited to, (a) reducing the viability of hematophagous ectoparasites that feed from the treated animal, (b) reducing the fecundity of female hematophagous ectoparasites that feed from the treated animal, (c) reducing the reproductive capacity of male hematophagous ectoparasites that feed from the treated animal, (d) reducing the viability of eggs laid by female hematophagous ectoparasites that feed from the treated animal, (e) altering the blood feeding behavior of hematophagous ectoparasites that feed from the treated animal (e.g., hematophagous ectoparasites take up less volume per feeding or feed less frequently), (f) reducing the viability of hematophagous ectoparasite larvae, for example due to the feeding of larvae from feces of hematorhagous ectoparasites that feed from the treated animal and (g) altering the development of hematophagous ectoparasite larvae (e.g., by decreasing feeding behavior, inhibiting growth, inhibiting (e.g., slowing or blocking) molting, and/or otherwise inhibiting maturation to adults).

Therapeutic compositions of the present invention also include excipients in which protective compounds are formulated. An excipient can be any material that the animal to be treated can tolerate. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thmerosal or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, dog serum albumin, cat serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta, RANTES (regulated upon activation, normal T cell expressed and presumably secreted), macrophage inflammatory proteins (e.g., MIP-1 alpha and MIP-1 beta), and Leishmania elongation initiating factor (LEIF); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposopheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of an animal at a constant rate sufficient to attain therapeutic dose levels of the composition to protect an animal from hematophagous ectoparasite infestation. The therapeutic composition is preferably released over a period of time ranging from about 1 to about 12 months. A preferred controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (µg) to about milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 µg to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal, intraocular and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid vaccine (e.g., as naked DNA or RNA molecules, such as is taught, for example in Wolff et al., 1990, *Science* 247, 1465–1468) or (b) administering a nucleic acid molecule packaged as a recombinant virus vaccine or as a recombinant cell vaccine (i.e., the nucleic acid molecule is delivered by a viral or cellular vechicle).

A naked nucleic acid vaccine of the present invention includes a nucleic acid molecule of the present invention and preferably includes a recombinant molecule of the present invention that preferably is replication, or otherwise amplification, competent. A naked nucleic acid vaccine of the present invention can comprise one or more nucleic acid molecules of the present invention in the form of, for example, a bicistronic recombinant molecule having, for example one or more internal ribosome entry sites. Preferred naked nucleic acid vaccines include at least a portion of a viral genome (i.e., a viral vector). Preferred viral vectors include those based on alphaviruses, poxviruses, adenoviruses, herpesviruses, and retroviruses, with those based on alphaviruses (such as Sindbis or Semliki virus), species-specific herpesviruses and species-specific poxviruses being particularly preferred. Any suitable transcription control sequence can be used, including those disclosed as suitable for protein production. Particularly preferred transcription control sequence include cytomegalovirus intermediate early (preferably in conjunction with Intron-A), *Rous Sarcoma* Virus long terminal repeat, and tissue-specific transcription control sequences, as well as transcription control sequences endogenous to viral vectors if viral vectors are used. The incorporation of "strong" poly(A) sequences are also preferred.

Naked nucleic acid vaccines of the present invention can be administered in a variety of ways, with intramuscular, subcutaneous, intradermal, transdermal, intranasal and oral routes of administration being preferred. A preferred single dose of a naked nucleic acid vaccines ranges from about 1 nanogram (ng) to about 100 µg, depending on the route of administration and/or method of delivery, as can be determined by those skilled in the art. Suitable delivery methods include, for example, by injection, as drops aerosolized and/or topically. Naked DNA of the present invention can be contained in an aqueous excipient (e.g., phosphate buffered saline) alone or a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging-deficient and/or encodes an attenuated virus. A number of recombinant viruses can be used, including, but not limited to, those based on alphaviruses, poxviruses, adenoviruses, herpesviruses, and retroviruses. Preferred recombinant virus vaccines are those based on alphaviruses (such as Sindbis virus), raccoon poxviruscs, species-specific herpesviruses and species-specific poxviruses. An example of methods to produce and use alphavirus recombinant virus vaccines is disclosed in PCT Publication No. WO 94/17813, by Xiong et al., published Aug. 18, 1994, which is incorporated by reference herein in its entirety.

When administered to an animal, a recombinant virus vaccine of the present invention infects cells within the immunized animal and directs the production of a protective protein or RNA nucleic acid molecule that is capable of protecting the animal from hematophagous ectoparasite infestation. For example, a recombinant virus vaccine comprising an arthropod CE nucleic acid molecule of the present invention is administered according to a protocol that results in the animal producing a sufficient immune response to protect itself from hematophagous ectoparasite infestation. A preferred single dose of a recombinant virus vaccine of the present invention is from about $1 \times 10^4$ to about $1 \times 10^7$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from hematophagous ectoparasite infestation can be tested in a variety of ways including, but not limited to, detection of anti-arthropod esterase antibodies (using, for example, proteins or mimetopes of the present invention), detection of cellular immunity within the treated animal, or challenge of the treated animal with hematophagous ectoparasites to determine whether, for example, the feeding, fecundity or viability of hematophagous ectoparasites feeding from the treated animal is disrupted. Challenge studies can include attachment of chambers containing hematophagous ectoparasites onto the skin of the treated animal. In one embodiment, therapeutic compositions can be tested in animal models such as mice. Such techniques are known to those skilled in the art.

One preferred embodiment of the present invention is the use of arthropod protective compounds, such as proteins, mimetopes, nucleic acid molecules, antibodies and inhibitory compounds of the present invention, to protect an animal from hematophagous ectoparasite, and particularly flea, infestation. Preferred protective compounds of the present invention include, but are not limited to, *C. felis* esterase nucleic acid molecules, *C. felis* esterase proteins and mimetopes thereof, anti-*C. felis* esterase antibodies, and inhibitors of *C. felis* esterase activity. More preferred protective compounds of the present invention include, but are not limited to, CE or JHE formulations of the present invention, *C. felis* CE nucleic acid molecules, *C. felis* CE proteins and mimetopes thereof, anti-flea CE antibodies, anti-flea JHE antibodies, inhibitors of *C. felis* CE activity and inhibitors of flea JHE activity. Additional protection may be obtained by administering additional protective compounds, including other proteins, mimetopes, nucleic acid molecules, antibodies and inhibitory compounds, as disclosed herein.

One therapeutic composition of the present invention includes an inhibitor of arthropod esterase activity, i.e., a compound capable of substantially interfering with the function of an arthropod esterase susceptible to inhibition by an inhibitor of arthropod esterase activity. An inhibitor of esterase activity can be identified using arthropod esterase proteins of the present invention. One embodiment of the present invention is a method to identify a compound capable of inhibiting esterase activity of an arthropod. Such a method includes the steps of (a) contacting (e.g., combining, mixing) an isolated flea esterase protein, preferably a *C. felis* esterase protein of the present invention, with a putative inhibitory compound under conditions in which, in the absence of the compound, the protein has esterase activity, and (b) determining if the putative inhibitory compound inhibits the esterase activity. Putative inhibitory compounds to screen include small organic molecules, antibodies (including mimetopes thereof) and substrate analogs. Methods to determine esterase activity are known to those skilled in the art; see, for example, the Examples section of the present application.

The present invention also includes a test kit to identify a compound capable of inhibiting esterase activity of an arthropod. Such a test kit includes an isolated flea esterase protein, preferably a *C. felis* esterase protein, having esterase activity and a means for determining the extent of inhibition of esterase activity in the presence of (i.e., effected by) a putative inhibitory compound. Such compounds are also screened to identify those that are substantially not toxic in host animals.

Esterase inhibitors isolated by such a method, and/or test kit, can be used to inhibit any esterase that is susceptible to such an inhibitor. Preferred esterase proteins to inhibit are those produced by arthropods. A particularly preferred esterase inhibitor of the present invention is capable of protecting an animal from hematophagous ectoparasite infestation. Effective amounts and dosing regimens can be determined using techniques known to those skilled in the art.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., *ibid.*, Borovsky, *Arch Insect Biochem. and Phys.*, 7:187–210, 1988, and related references.

Example 1

This example describes labeling of proteases and esterases with radiolabeled diisopropylfluorophosphate.

Tissue samples were isolated from unfed or bovine blood-fed 1st instar *Ctenocephalides felis* flea larvae; bovine blood-fed or cat blood-fed 3rd instar *Ctenocephalides felis* flea larvae; bovine blood-fed or cat blood-fed *Ctenocephalides felis* prepupal flea larvae; bovine blood-fed or cat blood-fed adult *Ctenocephalides felis* flea midgut tissue, and whole unfed, bovine blood-fed or cat blood-fed adult *Ctenocephalides felis* fleas. The 1st instar, 3rd instar, prepupal and adult midgut tissues were then homogenized by freeze-fracture and sonicated in a Tris buffer comprising 50 mM Tris, pH 8.0 and 100 mM $CaCl_2$. The whole adult flea sample was then homogenized by freeze-fracture and ground with a microtube mortar and pestle. The extracts were centrifuged at about 14,000×g for 20 minutes (min.) and the soluble material recovered. The soluble material was then diluted to a final concentration of about 1 to about 1.2 tissue equivalents per microliter ($\mu$l) of Tris buffer. Each sample was labeled with [1,3-$^3$H]-diisopropylfluorophosphate ($^3$H-DFP) (available from DuPont-NEN, Wilmington, Del.) using the method generally described in Borovsky, *ibid*. About 20 tissue equivalents of each tissue sample were mixed with about 1 $\mu$Ci of $^3$H-DFP and incubated for about 18 hours at 4° C. Proteins contained in each sample were then resolved using a 14% Tris-glycine sodium dodecyl sulfate polyacrylamide gel electrophoresis (SDS-PAGE) (available from Novex, San Diego, Calif.) under reducing conditions. The gel was soaked in Entensify (available from DuPont-NEN) according to manufacturers instructions, and exposed to X-ray film (available from Kodak X-Omat AR, Rochester, N.Y.) for about 3 days at −70° C.

Analysis of the resulting autoradiogram (shown in FIG. 1) indicated that tissue samples from 3rd instar, prepupal larvae and whole adult flea contained proteins that labeled with DFP, having a molecular weight (MW) of about 60 kilodalton (kD). No proteins of this MW were labeled in tissue samples from unfed or fed 1st instar larvae and adult midgut. The results indicated preferred tissue distribution and stage-specific expression of DFP-labeled serine esterases in fleas.

Example 2

This sample describes the identification of general CE activity in flea tissue extracts.

Tissue samples and soluble extracts were prepared as described above in Example 1, except not labelled, from unfed (UF) and bovine blood-fed 1st instar flea larvae, bovine blood-fed 3rd instar flea larvae, bovine blood-fed prepupal flea larvae, unfed whole adult fleas, cat blood-fed adult (ACF) whole fleas, cat blood-fed adult fleas that have had their heads and midguts removed (referred to herein as fed adult partial fleas), unfed adult flea midguts and cat blood-fed adult flea midguts. About 5 tissue equivalents of each tissue were assayed for general CE activity using the following method. Tissue samples of about 5 $\mu$l were added to separate wells of flat-bottomed microtiter plate (available from Becton Dickinson, Lincoln Park, N.J.). A control well was prepared by adding about 5 $\mu$l of Tris buffer to an empty well of the plate. About 95 µl of 25 mM Tris-HCl (pH 8.0) was then added to each sample to increase the volume in each well to about 100 µl. About 100 µl of 0.25 mM α-napthyl acetate (available from Sigma, St. Louis, Mo.) dissolved in 25 mM Tris-HCl (pH 8.0) was then added to each well. The plate was then incubated for about 15 min. at 37° C. Following the incubation, about 40 µl of 0.3% Fast Blue salt BN (tetrazotized o-dianisidine; available from Sigma) dissolved in 3.3% SDS in water was added to each well.

The microtiter plate was then analyzed using a Cambridge Technology, Inc. (Watertown, Pa.) model 7500 Microplate Reader set to 590 nm. The absorbance value for the control sample was subtracted from absorbance values of experimental samples, such that the background value was zero.

Figure 2:
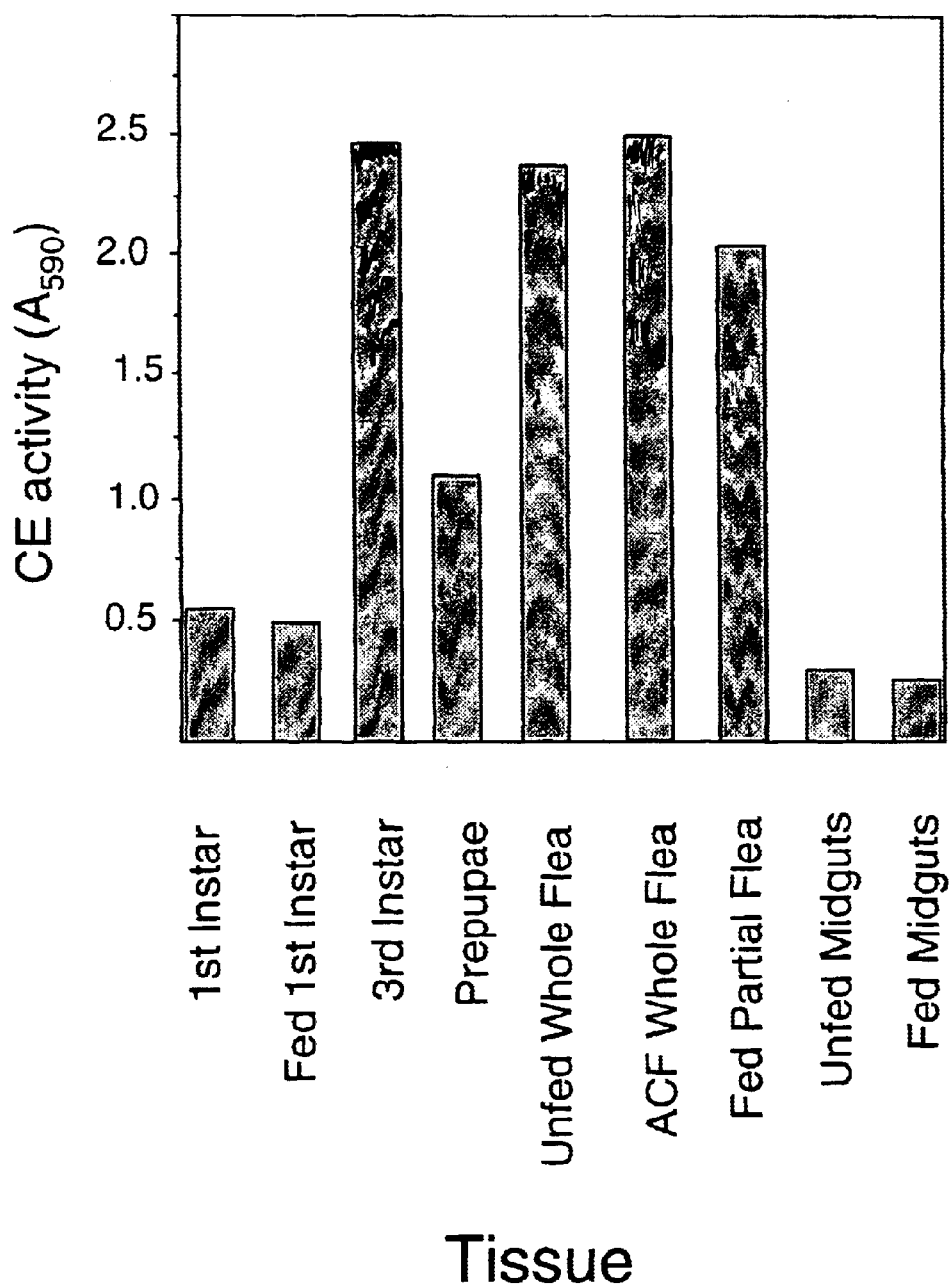
FIG. 2 depicts carboxylesterase activity of certain esterase proteins of the present invention.

The results shown in FIG. 2 indicated that general CE activity was detected in all tissue samples. The level of activity varied, with unfed and fed 1st instar larvae, unified adult flea midguts, and fed adult flea midguts having relatively lower activity than in the other tissues. Thus, the results indicated preferred tissue distribution and stage-specific expression of general CE activity in fleas.

Example 3

This example describes the determination of general CE activity using isoelectric focusing (IEF)-PAGE and non-reducing SDS-PAGE.

A. Non-reducing SDS-PAGE.

Soluble extracts from unfed and bovine blood-fed 1st instar flea larvae, bovine blood-fed 3rd instar flea larvae, bovine blood-fed prepupal flea larvae, bovine blood-fed adult (ABF) whole fleas and cat blood-fed adult whole fleas were prepared using the method described in Example 1. Each soluble extract sample was combined with SDS sample buffer (available from Novex) and proteins in the samples were resolved by gel electrophoresis using 14% Tris-glycine SDS electrophoresis gels (available from Novex). The gels were run at room temperature for about 1 hour at 200 volts. After electrophoresis, the gels were soaked for about for 30 minutes in 50 mM Tris, pH 8.0, containing 2.5% Triton X-100 to renature the proteins. The gels were then soaked in 50 mM Tris, pH 8.0, for about 5 minutes and then stained for about 5 min. in 50 milliliters (ml) of 25 mM Tris, pH 8.0, containing 50 mg Fast blue salt BN and 10 mg α-napthyl acetate (dissolved in 1 ml acetone). Once protein was detected on the stained gels, the gels were rinsed with water and photographed.

B. IEF-PAGE.

Soluble extracts from un fed and bovine blood-fed 1st instar flea larvae, bovine blood-fed 3rd instar flea larvae, bovine blood-fed prepupal flea larvae, unfed and cat blood-fed whole fleas, cat blood-fed adult partial fleas and cat blood-fed adult midguts seere prepared as described above in Section A. The extracts were each combined with IEF sample buffer pH 3–7 (available from Novex) and loaded onto pH 3–7 IEF electrophoresis gels (available from Novex). The gels were electrophoresed at room temperature first for about 1 hour at about 100 volts, then for about 1 hour at about 200 volts, and then for about 30 min. at about 500 volts. Following electrophoresis, the gels were soaked in 25 mM Tris buffer, pH 8.0, for about 5 min. and then stained for about 15 min. in 50 ml of 25 mM Tris buffer, pH 8.0, containing 50 mg Fast blue salt BN and 10 mg α-napthyl acetate (dissolved in 1 ml acetone). Once protein as detected on the stained gels, the gels were rinsed with water and photographed.

C. Results.

Figure 4:
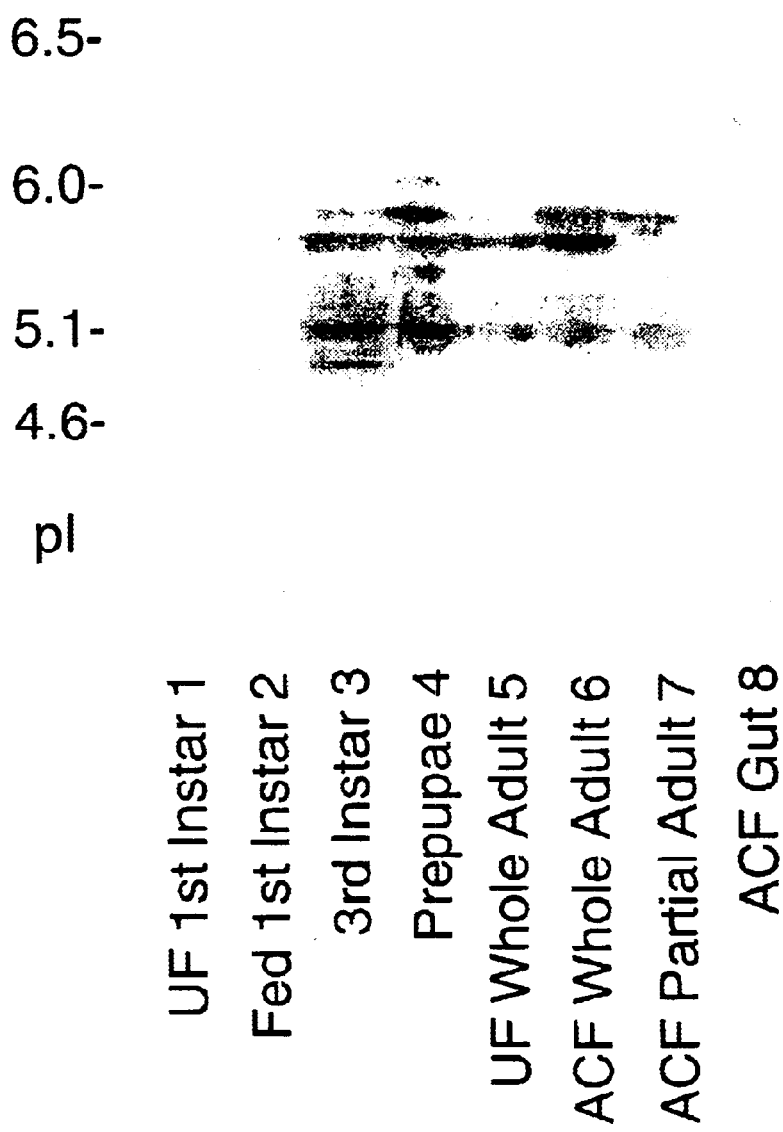
FIG. 4 depicts IEF analysis of certain esterase proteins of the present invention.

The results from gel electrophoresis experiments described above in Sections A and B are shown in FIGS. 3 and 4. The results indicated that certain flea tissues contain proteins having MW's of from about 60 to about 70 kD and native pI values of from about 4.7 to about 5.2 that have CE activity. In particular, CE activity was identified in prepupal larvae and fed adult flea extracts resolved by non-reduced SDS-PAGE. No CE activity was identified in unfed and fed 1st instar larvae or fed 3rd instar larvae extracts (see FIG. 3). When extracts were resolved by native IEF-PAGE, CE activity was identified in fed 3rd instar larvae, prepupal larvae, unfed and fed whole adult flea, and fed adult partial flea extracts (see FIG. 4, lanes 3–7)). No CE activity was identified in unfed or fed 1st instar larvae, or in fed adult flea midgut extracts (see FIG. 4, lanes 1, 2, and 8).

Example 4

This example describes the purification of CE protein from prepupal flea larvae.

About 15,000 bovine blood-fed prepupal flea larvae were collected and the larvae were homogenized in TBS by sonication in 50 ml Oak Ridge centrifuge tubes (available from Nalgene Co., Rochester, N.Y.) by sonicating 4 times 20 seconds each at a setting of 5 of a model W-380 Sonicator (available from Heat Systems-Ultrasonics, Inc.). The sonicates were clarified by centrifugation at 18,000 RPM for 30 minutes to produce an extract. Soluble protein in the extract was removed by aspiration and diluted to a volume of about 20 ml in TBS (equivalent to about 1 larva per µl TBS). The extract was then added to a column containing about 5 ml of p-aminobenzamidine linked to agarose beads (available from Sigma, St. Louis, Mo.) and incubated overnight at 4° C. The column was then washed with about 30 ml TBS to remove unbound protein. The collected unbound protein was then concentrated to a volume of about 20 ml using a Macrosep 10 centrifugal protein concentrator (Filtron Technology Corp., Northborough Mass.) and filtered sequentially through a 1 µm syringe filter and then through a 0.2 µm syringe filter to clarify the sample for chromatography.

Aliquots of about 0.5 ml were loaded onto a 20 ml Superdex 200 HR gel filtration column (available from Pharmacia, Piscataway, N.J.) equilibrated in TBS, operated on a BioLogic liquid chromatography system (available from BioRad, Burlingame, Calif.). About 1 ml fractions were then collected. Repetitive runs were performed until about 30 ml of each fraction was collected. The fractions were analyzed for CE activity using the assay described above in Example 2. In preparation for cation exchange chromatography, fractions having CE activity ($V_e$=16–18 ml) were combined and dialyzed against about 2 liters of 20 mM MES buffer (2-(N-morpholino)ethanesulfonic acid), pH 6.0, containing 10 mM NaCl, for about 1.5 hours, and then against about 1 liter of the same buffer overnight at 4° C. Prior to loading onto the cation exchange chromatography column, the sample was again filtered through a 0.2 µm syringe filter to remove precipitated proteins. The sample was then applied to a Bio-Scale S2 cation exchange column (available from BioRad) at a rate of about 0.5 ml/min. The column was washed with MES buffer until all unbound protein was removed. Protein bound to the column was then eluted with a linear gradient from 10 mM to 1 M NaCl in 20 mM MES buffer, pH 6. Fractions were assayed for CE activity using the assay described above in Example 2. The results indicated that CE activity was not retained on the cation exchange column using the above conditions, and all of the activity was found in the flow-through fractions.

Fractions containing CE activity were pooled and adjusted to pH 7 using 0.5 M Tris, pH 8.0, in preparation for anion exchange chromatography. The pooled fractions were then loaded onto a 4.5 mm×50 mm Poros 10 HQ anion exchange chromatography column (available from PerSeptive Biosystems, Cambridge, Mass.) equilibrated in 25 mM Tris buffer, pH 6.8. The column was washed with the loading buffer, and bound proteins were eluted with a linear gradient of 0 to 1 M NaCl in 25 mM Tris buffer, pH 6.8. Fractions were tested for CE activity using the assay described above in Example 2. The results indicated that CE activity was eluted at about 170 mM NaCl. Fractions containing CE activity were pooled and diafiltered into TBS.

Example 5

This example describes the determination of N-terminal amino acid sequences of carboxylesterases isolated from prepupal flea larvae.

A. Anion Exchange Chromatography Fractions.

Anion exchange chromatography fractions described above in Example 4 that contained proteins having CE activity were pooled, diafiltered into TBS buffer and concentrated 3-fold in a Speed-Vac Concentrator (available from Savant Instruments, Holbrook, N.Y.). Proteins in the concentrated samples were then resolved on a reducing, 10% SDS-PAGE Tris-glycine gel (available from Novex) for 1 hour at about 200 V. The proteins on the gel were then blotted onto a polyvinylidene difluoride (PVDF) membrane (available from Novex) for about 70 min in 10 mM CAPS buffer (3-[cyclohexylamino]-1-propanesulfonic acid; available from Sigma), pH 11, with 0.5 mM dithiothreitol (DTT). The membrane was then stained for 1 minute in 0.1% Coomassie Blue R-250 dissolved in 40% methanol and 1% acetic acid. The membrane was destained in 50% methanol for about 10 minutes, rinsed with MilliQ water and air dried. Three stained protein bands were identified having apparent molecular weights of about 64 kD, 65 kD, and 66 kD, respectively. The portion of the membrane containing each band was excised separately. Protein contained in each membrane segment was subjected to N-terminal amino acid sequencing using a 473A Protein Sequencer (available from Applied Biosystems, Foster City, Calif.) and using standard techniques.

The results indicated that the N-terminal amino acid sequence of the putative 64 kD protein was DPPTVTLPQ-GEL (denoted SEQ ID NO:39); the N-terminal amino acid sequence of the putative 65 kD protein was DPPTVTLPQGELVGKATNEnxk (denoted SEQ ID NO:40); and the N-terminal amino acid sequence of the putative 66 kD protein was DppTVTLPQGEL (denoted SEQ ID NO:41), in which the lower case letters designate uncertainties and "x" designates an undetermined residue.

B. Proteins Resolved by Native IEF-PAGE.

Proteins isolated by anion exchange chromatography as described above in Section A were further resolved by native IEF-PAGE. Proteins were loaded onto a pH 3–10 IEF gel (available from Novex) and separated in Novex's IEF buffers according to Novex's standard procedure (60 min at 100 V; then 60 min at 200 V; and then 30 min at 500 V). Following electrophoresis, part of the gel was stained for CE activity using the method described above in Example 2. The remaining portion of the gel was blotted onto PVDF membrane by reversing the orientation of the gel and membrane so that positively charged proteins migrated to the membrane, electrophoresing the protein for 60 min at 10 V, using 0.7% acetic acid as the transfer buffer. The membrane was stained as described above in Section A. After the membrane was dried, stained protein bands on the membrane were compared to bands on the gel tested for CE activity to identify corresponding bands. Protein bands on the membrane corresponding to proteins having CE activity were excised and submitted to N-terminal sequencing as described in Section A.

N-terminal amino acid sequence was obtained for protein contained in two bands having pI values of about pI 4.8 and about pI 4.9. N-terminal amino acid sequence of the pI 4.8 band was DPPTVTLPQGELVGKALSNen (denoted SEQ ID NO:42) and N-terminal amino acid sequence of the pI 4.9 band was DPPTVTLP (denoted SEQ ID NO:43). A comparison of the N-terminal amino acid sequences identified here and described in Section A indicates closely related proteins having a consensus sequence of DPPTVTLPQGELVGKALTNEnGk (denoted SEQ ID NO:44).

The amino acid sequences of SEQ ID NO:39, SEQ ID NO:40, SEQ ID NO:41, SEQ ID NO:42, SEQ ID NO:43 and SEQ ID NO:44 are substantially contained within SEQ ID NO:5, SEQ ID NO:19 and SEQ ID NO:53, which are described below in Example 11.

Example 6

This example describes partial purification of CE from 3rd instar flea larvae.

Using the extract preparation methods described in Example 1 without labelling, extracts were prepared from about 50,000 bovine blood-fed 3rd instar flea larvae. The extract was then further purified over a p-aminobenzamidine linked agarose bead column using the method also described in Example 1. Collected unbound protein was concentrated to about 70 ml using a 200 ml stirred cell fitted with a YM-10 membrane (available from Amicon, Beverly, Mass.). Seven ml (about 5,000 3rd instar flea larval equivalents) of the concentrated extract was used for the remainder of the purification scheme described in Example 4. Resulting fractions from the anion exchange chromatography column were tested for CE activity using the assay described above in Example 2.

The results indicated that CE activity was eluted in two overlapping peaks at about 120 mM and about 210 mM NaCl.

Example 7

This example describes the identification of JHE activity in different flea tissues.

Tissue samples were prepared as described above in Example 1 from unfed and bovine blood-fed 1st instar flea larvae, bovine blood-fed 3rd instar flea larvae, bovine blood-fed prepupal flea larvae, unfed and cat blood-fed whole adult fleas, cat blood-fed adult partial fleas and cat blood-fed adult flea midguts. About 5 tissue equivalents of each tissue was assayed for JHE activity as follows.

Unlabeled juvenile hormone (JH; available from ICN Biomedicals, Inc., Aurora, Ohio) was diluted in hexane to concentration of about 0.025 M. Labeled 10-$^3$H-juvenile hormone ($^3$H-JH; available from Dupont-NEN) was diluted in hexane to concentration of about 80,000 cpm/$\mu$l. A JH substrate mixture was prepared by mixing about 20 $\mu$l of unlabeled JH with about 80 $\mu$l of $^3$H-JH (about 5 $\mu$Ci) in a 4 ml screw cap vial. The substrate mixture was then covered with nitrogen (i.e., "blanketed") and the solvent contained in the mixture was evaporated by heating the mixture at 35° C. When just dry, about 1 ml of absolute anhydrous ethanol (final concentration $5 \times 10^{-4}$ M, or 6400 cpm/$\mu$l) was added to the vial. The substrate mixture was then stored at −20° C.

About 5 equivalents of each tissue (about 5 $\mu$l of protein) was added into the bottom of a small glass autosampler vial.

About 95 μl of Tris-buffered saline (TBS) was added to each vial to bring the final volume in each vial to about 100 μl. Two control samples were also prepared by adding 100 μl TBS to two separate vials. About 1 μl of the substrate mixture described above was added to all of the vials including the control samples. The final JH concentration in each vial was about $5 \times 10^{-6}$ M. The vials were then capped and spun in a microfuge to bring all of the liquid to the bottom of each vial. The vials were then transferred to a heat block and incubated at 35° C. for about 30 minutes. Following the incubation, enzyme activity was stopped by adding about 50 μl of methanol buffer (methanol:water:concentrated ammonium hydroxide at a 10:9:1 ratio, respectively) to each vial and removing the vials from the heat block.

To measure labeled juvenile hormone acid, about 250 μl isooctane was added to each vial. Each vial was vortexed for about 15 seconds or until an emulsion formed. Each vial was then centrifuged in a microfuge for about 1 minute to separate aqueous and organic phases. About 75 μl of the aqueous layer was removed from each vial and added to about 2 nl Eco-lame scintillation fluid (available from ICN). The amount of $^3$H-juvenile hormone acid contained in each vial was determined using a Beckman LS-1801 liquid scintillation counter (available from Beckman, Fullerton, Calif.).

Figure 5:
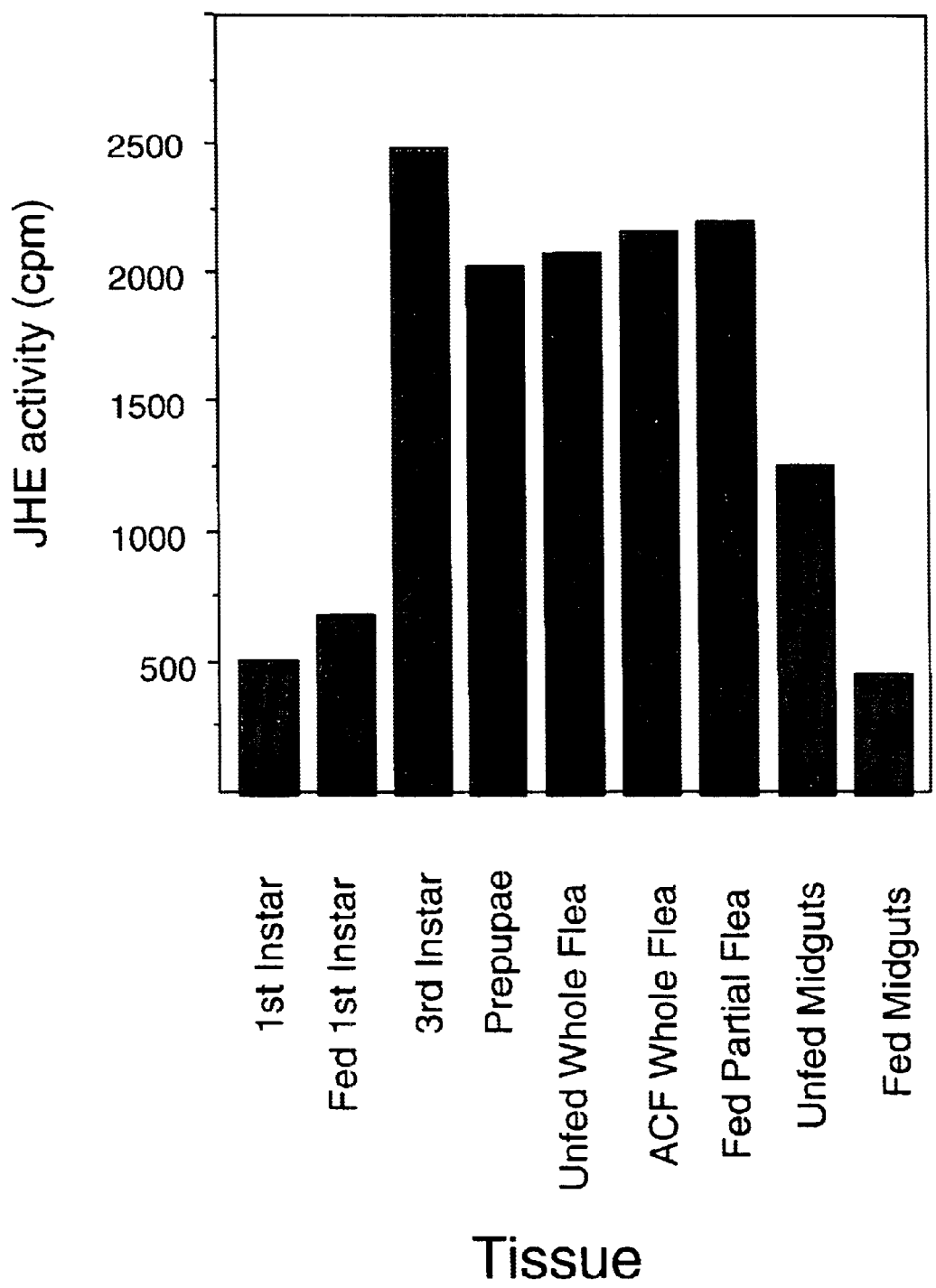
FIG. 5 depicts juvenile hormone esterase activity of certain esterase proteins of the present invention.

The results shown in FIG. 5 indicated that all flea tissues tested contain active JHE. Referring to Example 2, the level of CE activity differed from JHE activity in various tissue samples. The combined JHE and CE data indicated the differential expression of these two enzymatic activities during the development of a flea.

Example 8

This example describes the purification of JHE protein from cat blood-fed adult midguts.

About 23,000 cat blood-fed adult midguts were collected and prepared using the method described in Example 1. The extract was then added in 4 aliquots to columns containing about 3 to about 5 ml of p-aminobenzamidine linked agarose beads (available from Sigma), equilibrated in 50 mM Tris (pH 8.0), 100 mM $CaCl_2$, 400 mM NaCl, and incubated overnight at 4° C. The columns were then washed with about 15 to about 125 ml of the equilibration Tris buffer to removes unbound protein. The collected unbound protein was pooled and then concentrated to a volume of about 5 ml using an Ultrafree-20 10 kD centrifugal concentrator (available from Millipore, Bedford, Mass.) and filtered sequentially through a 0.2 μm centrifugal ultrafiltration membrane (available from Lida, Kenosha, Wis.) to clarify the sample for chromatography.

Aliquots of about 0.5 ml were loaded onto a Superdex 200 HR gel filtration column using the method described in Example 4. Repeated runs were performed until about 10 ml of each fraction was collected. The fractions were analyzed for JHE activity using the assay described in Example 7. In preparation for anion exchange chromatography, fractions having JHE activity ($V_e$=17–18 ml) were combined and dialyzed overnight against about 1 L of 20 mM Tris buffer, pH 8.0, containing 10 mM NaCl. The sample was then loaded onto a Poros 10 HQ anion exchange column using the method described in Example 4. Resulting fractions were tested for JHE activity as described in Example 7.

The results indicated that midgut JHE activity was eluted from the anion exchange column in a single peak at about 120 mM NaCl.

Example 9

This example describes partial purification of JHE from prepupal flea larvae and 3rd instar larvae.

A. JHE Purification From Prepupal Tissue.

Using the extract preparation methods described in Example 1, gel filtration fractions were obtained using a Superdex 200 HR gel filtration column (available from Pharmacia) using the method described in Example 4, from about 15,000 bovine blood-fed prepupal flea larvae. The fractions were analyzed for JHE activity using the assay, described above in Example 7. Those fractions containing protein having JHE activity ($V_e$=16–18 ml) were combined and dialyzed using the method described in Example 8.

The fractions were then further purified by passing the fractions over a Bio-Scale S2 cation exchange column (available from BioRad) at a rate of about 0.5 ml/min. The column was washed with MES until all unbound protein was eluted. Bound protein was then eluted with a linear gradient of 20 mM MES buffer, pH 6.0, containing 10 mM NaCl to 1 M NaCl. Resulting fractions were assayed for JHE activity using the method described in Example 7. The results indicated that proteins having JHE activity using prepupal tissue eluted from the column in about 200 to 300 mM NaCl.

The fractions containing JHE activity were combined and the pH adjusted to pH 7 using 0.5 M Tris buffer (pH 8.0). The fractions were then dialyzed twice against about 1 liter of 10 mM phosphate buffer (pH 7.2) containing 10 mM NaCl at 4° C. The resulting dialyzed fractions were then loaded onto a Bio-Scale CHT2-I Hydroxyapatite Column (available from BioRad) at a rate of about 0.5 ml/min. Unbound protein was washed from the column using the dialysis buffer. Bound protein was then eluted with a linear gradient of from 10 mM phosphate buffer, pH 7.2, containing 10 mM NaCl to 0.5 M phosphate buffer pH 6.5 containing 10 mM NaCl. One ml fractions were collected and each tested for JHE activity by the method described in Example 7.

The results indicated that JHE eluted in 2 overlapping peaks at about 100 mM and 150 mM phosphate. These two JHE activities were designated PP JHE I and PP JHE II, and were kept separate for the remainder of the purification. Both JHE samples, were dialyzed overnight against 20 mM Tris buffer (pH 8.0) containing 10 mM NaCl. The two samples were then loaded, separately, onto a 4.5 mm×50 mm Poros 10 HQ anion exchange chromatography column (available from PerSeptive Biosystems) equilibrated with 20 mM Tris buffer, pH 8.0, containing 10 mM NaCl. Unbound proteins were washed from the column using the same buffer. Bound proteins were eluted with a linear gradient of from 10 mM to 1 M NaCl in 20 mM Tris buffer, pH 8.0. Resulting fractions were tested for JHE activity using the method described in Example 7.

The results indicated that in both samples, JHE activity was eluted from the column in a single peak at about 100 mM NaCl.

B. JHE Purification From 3rd Instar Tissue

Using the procedure described above in Section A, proteins having JHE activity were obtained using about 5,000 bovine blood-fed 3rd instar flea larvae. Following purification by cation exchange, proteins having JHE activity using 3rd instar tissue were found to elute in 2 peaks. The first peak having JHE activity was not retained on the column and also exhibited CE activity (referred to herein as CE/JHE fractions). The second peak having JHE activity eluted from the column in about 100–200 mM NaCl and did not contain CE activity.

The CE/JHE fractions were pooled and adjusted to about pH 7 using 0.5 M Tris, pH 8.0. The fractions were then loaded onto a 4.5 mm×50 mm Poros 10 HQ anion exchange chromatography column (available from PerSeptive Biosystems) and the column was equilibrated in 25 mM Tris buffer, pH 6.8. The column was washed with the same buffer and bound proteins were eluted with a linear gradient of 0 to 1 M NaCl in 25 mM Tris buffer, pH 6.8. Fractions were then tested for JHE activity using the method described in Example 7. JHE activity was eluted in two overlapping peaks at about 120 mM and 210 mM NaCl. The fraction containing JHE activity also contained CE activity when tested using the method described in Example 2.

Fractions from the cation exchange column containing only JHE activity were combined, diluted in 20 mM Tris buffer, pH 8 containing 10 mM NaCl, and concentrated to about 5 ml. The fractions were purified on a Poros 10 HQ anion exchange chromatography column as described immediately above. Fractions were then tested for JHE activity using the method described in Example 7. The JHE activity was eluted in a single peak at about 120 mM. The peak contained no detectable CE activity.

Example 10

This example describes the purification of JHE protein from unfed adult midguts.

About 16,000 unfed adult midguts were collected in 20 mM Tris buffer (pH 7.7), containing 130 mM NaCl, 1 mM sodium EDTA, 1 mM Pefabloc® (available from Boehringer Mannheim, Indianapolis, Ind.), 1 microgram/ml (μg/ml) leupeptin and 1 μg/ml pepstatin. The midguts were homogenized by freeze-fracture and sonication, and then centrifuged at about 14,000×g for 20 min. The soluble material from the centrifugation step was recovered. The soluble material was then concentrated to about 1 ml using an Ultrafree-20 10 kD centrifugal concentrator (available from Millipore) and filtered sequentially through a 0.2 μm centrifugal ultrafiltration membrane to clarify the sample for chromatography. Aliquots of about 0.5 ml were loaded onto a Superdex 200 HR gel filtration column using the method described in Example 4. Repeated column runs were performed until about 2 ml of each fraction was collected. The fractions were analyzed for JHE activity using the assay described in Example 7. In preparation for cation exchange chromatography, fractions having JHE activity ($V_c$=15–17 ml) were combined and dialyzed overnight against about 1 L of 20 mM MES buffer, pH 6.0, containing 10 mM NaCl. The sample was then applied to a Bio-Scale S2 cation exchange column using the method described in Example 4. Fractions of eluate were assayed for JHE activity using the method described in Example 7.

The results indicate that JHE is present in unfed midguts in two forms, one that is not retained on the cation exchange column and one that is bound to the column under low salt conditions at about 100 mM NaCl. The form that was not retained under low salt conditions was shown to have general CE activity using the methods described in Example 2.

Example 11

This example describes the identification of certain esterase nucleic acid molecules of the present invention.

Several flea esterase nucleic acid molecules, representing one or more partial flea esterase genes, were PCR amplified from a flea mixed instar cDNA library or a flea prepupal cDNA library. The flea mixed instar cDNA library was produced using unfed 1st instar, bovine blood-fed 1st instar, bovine blood-fed 2nd instar and bovine blood-fed 3rd instar flea larvae (this combination of tissues is referred to herein as mixed instar larval tissues for purposes of this example). The flea prepupal cDNA library was produced using prepupal flea larvae. For each library, total RNA was extracted from mixed instar or prepupal tissue, respectfully, using an acid-guanidinium-phenol-chloroform method similar to that described by Chomczynski et al., 1987, Anal. Biochem. 162, p. 156–159. Approximately 5,164 mixed instar larvae or 3,653 prepupal larvae were used in each RNA preparation. Poly A+ selected RNA was separated from each total RNA preparation by oligo-dT cellulose chromatography using Poly(A)Quick® mRNA isolation kits (available from Stratagene Cloning Systems, La Jolla, Calif.), according to the method recommended by the manufacturer.

A mixed instar cDNA expression library and a prepupal cDNA expression library were constructed in lambda (λ) Uni-ZAP™XR vector (available from Stratagene Cloning Systems) using Stratagene's ZAP-cDNA Synthesis Kit® protocol. About 6.34 μg of mixed instar poly A+ RNA were used to produce the mixed instar library and about 6.72 μg of prepupal poly A+ RNA were used to produce the prepupal library. The resultant mixed instar library was amplified to a titer of about $2.17 \times 10^{10}$ pfu/ml with about 97% recombinants. The resultant prepupal library was amplified to a titer of about $3.5 \times 10^{10}$ pfu/ml with about 97% recombinants.

A pair of primers was used to amplify DNA from the cDNA libraries. A sense vector primer T-3X (corresponding to the vector in which nucleic acid molecules of the present invention had been ligated), having the nucleic acid sequence AATTAACCCT CACTAAAGGG (available from Gibco BRL, Gaithersburg, Md.; denoted SEQ ID NO:45), was used in combination with a degenerate primer, the design of which was based on a highly conserved esterase amino acid sequence (disclosed in Hanzlik et al., J. Biol. Chem. 264:12419–12423, 1989; I Y/H G G G F/L) located in a region downstream from the mature amino terminus in a number of known esterases. The degenerate primer, referred to herein as FCEF, is an anti-sense primer having the nucleic acid sequence ARDCCDCCDC CRTRDAT (R indicating an A or G; and D indicating an A, G or T; denoted SEQ ID NO:46). The resultant PCR products from the mixed instar cDNA library, obtained using standard PCR conditions (e.g., Sambrook et al., ibid.). were about 550 nucleotides. The resultant PCR products from the prepupal cDNA library were from about 500 nucleotides to about 860 nucleotides.

A. PCR Products.

PCR products were gel purified and cloned into the TA Vector™ (available from InVitrogen Corp., San Diego, Calif.). Approximately 8 clones were identified from the prepupal library and 6 clones were identified from the mixed instar library. These nucleic acid molecules were subjected to nucleic acid sequencing using the Sanger dideoxy chain termination method, as described in Sambrook et al., ibid.

1. Flea esterase clone 1 isolated from the mixed instar cDNA library was determined to comprise nucleic acid molecule $nfE1_{401}$, the nucleic acid sequence of the coding strand which is denoted herein as SEQ ID NO:1. Translation of SEQ ID NO:1 suggests that nucleic acid molecule $nfE1_{401}$ encodes a non-full-length flea esterase protein of about 103 amino acids, referred to herein as $PfE1_{103}$, having amino acid sequence SEQ ID NO:2, assuming an initiation codon spanning from nucleotide 92 through nucleotide 94 of SEQ ID NO:1. The complement of SEQ ID NO:1 is represented herein by SEQ ID NO:3. Comparison of amino acid sequence SEQ ID NO:2 (i.e., the amino acid sequence of $PfE1_{103}$) with amino acid sequences reported in GenBank indicates that SEQ ID NO:2, showed the most homology, i.e., about 33% identity, between SEQ ID NO:2 and alpha esterase protein from *Drosophila melanogaster*.

2. Flea esterase clone 2 isolated from the mixed instar cDNA library was determined to comprise nucleic acid molecule $nfE2_{364}$, the nucleic acid sequence of the coding strand which is denoted herein as SEQ ID NO:4. Translation of SEQ ID NO:4 suggests that nucleic acid molecule $nfE2_{364}$ encodes a non-full-length flea esterase protein of about 121 amino acids, referred to herein as $PfE2_{121}$, having amino acid sequence SEQ ID NO:5, assuming the first codon spans from nucleotide 2 through nucleotide 4 of SEQ ID NO:4. The complement of SEQ ID NO:4 is represented herein by SEQ ID NO:6. Comparison of nucleic acid sequence SEQ ID NO:4 with nucleic acid sequences reported in GenBank indicates that SEQ ID NO:4 showed the most homology, i.e., about 43% identity, between SEQ ID NO:4 and a *H. virescens* JHE gene. Comparison of amino acid sequence SEQ ID NO:5 (i.e., the amino acid sequence of $PfE2_{121}$) with amino acid sequences reported in GenBank indicates that SEQ ID NO:5, showed the most homology, i.e., about 38% identity, between SEQ ID NO:5 and alpha esterase protein from *Drosophila melanogaster*.

3. Flea esterase clone 3 isolated from the prepupal cDNA library was determined to comprise nucleic acid molecule $nfE3_{421}$, the nucleic acid sequence of the coding strand which is denoted herein as SEQ ID NO:7. Translation of SEQ ID NO:7 suggests that nucleic acid molecule $nfE3_{421}$ encodes a non-full-length flea esterase protein of about 103 amino acids, referred to herein as $PfE3_{103}$, hatting amino acid sequence SEQ ID NO:8, assuming an initiation codon spanning from nucleotide 113 through nucleotide 115 of SEQ ID NO:7. The complement of SEQ ID NO:7 is represented herein by SEQ ID NO:9. Comparison of nucleic acid sequence SEQ ID NO:7 with nucleic acid sequences reported in GenBank indicates that SEQ ID NO:7 showed the most homology, i.e., about 53% identity, between SEQ ID NO:7 and a *Torpedo marmorata* acetylcholinesterase gene. Comparison of amino acid sequence SEQ ID NO:8 (i.e., the amino acid sequence of $PfE3_{103}$) with amino acid sequences reported in GenBank indicates that SEQ ID NO:8, showed the most homology, i.e., about 39% identity, between SEQ ID NO:5 and alpha esterase protein from *Drosophila melanogaster*.

4. Flea esterase clone 4 isolated from the prepupal cDNA library was determined to comprise nucleic acid molecule $nfE4_{524}$, the nucleic acid sequence of the coding strand which is denoted herein as SEQ ID NO:10. Translation of SEQ ID NO:10 suggests that nucleic acid molecule $nfE4_{524}$ encodes a non-full-length flea esterase protein of about 137 amino acids, referred to herein as $PfE4_{137}$, having amino acid sequence SEQ ID NO:11, assuming an initiation codon spanning from nucleotide 113 through nucleotide 115 of SEQ ID NO:10. The complement of SEQ ID NO:10 is represented herein by SEQ ID NO:12. Comparison of nucleic acid sequence SEQ ID NO:10 with nucleic acid sequences reported in GenBank indicates that SEQ ID NO:10 showed the most homology, i.e., about 47% identity, between SEQ ID NO:10 and an *Anas platyrhyncos* thioesterase B gene. Comparison of amino acid sequence SEQ ID NO:11 (i.e., the amino acid sequence of $PfE4_{137}$) with amino acid sequences reported in GenBank indicates that SEQ ID NO:11, showed the most homology, i.e., about 30% identity, between SEQ ID NO:11 and *Leptinotarsa decemlineata* acetylcholinesterase.

B. cDNA Clones.

Certain amplified PCR fragments were used as probes to identify full-length flea esterase genes in the prepupal cDNA library.

1. Nucleic acid molecule $nfE2_{364}$ was labeled with $^{32}P$ and used as a probe to screen the mixed instar cDNA library described in Section A, using standard hybridization techniques. Two clones were isolated. A first clone included about a 2300-nucleotide insert, referred to herein as $nfE5_{2300}$. Nucleic acid sequence was obtained using standard techniques from $nfE5_{2300}$, to yield a flea esterase nucleic acid molecule named $nfE5_{1982}$ having a nucleic acid sequence of the coding strand which is denoted herein as SEQ ID NO:13. Translation of SEQ ID NO:13 suggests that nucleic acid molecule $nfE5_{1982}$ encodes a non-full-length flea esterase protein of about 505 amino acids, referred to herein as $PfE5_{505}$, having amino acid sequence SEQ ID NO:14, assuming the first codon spans from nucleotide 1 through nucleotide 3 of SEQ ID NO:13 and the stop codon spans from nucleotide 1518 through nucleotide 1520 of SEQ ID NO:13. The complement of SEQ ID NO:13 is represented herein by SEQ ID NO:15. The amino acid sequence of $PfE5_{505}$ (i.e., SEQ ID NO:14) predicts that $PfE5_{505}$ has an estimated molecular weight of about 56.8 kD and an estimated pI of about 5.5. Tile nucleic acid molecule representing the coding region for $PfE5_{505}$ is referred to herein as $nfE5_{515}$; the nucleic acid sequences of the coding strand and the complementary strand are represented by SEQ ID NO:16 and SEQ ID NO:17, respectively.

The nucleic acid sequence of $nfE5_{1982}$ was used to design primers to use in combination with a vector primer to PCR amplify the 5' terminal fragment of the remainder of the flea esterase coding region from the flea mixed instar cDNA library. A pair of primers was used to amplify DNA from the cDNA library. A sense vector primer T3-X (corresponding to the vector in which nucleic acid molecules of the present invention had been ligated), having the nucleic acid sequence 5' AATTAACCCT CACTAAAGGG 3' (denoted SEQ ID NO:45), was used in combination with an anti-sense primer M6/M265', having the nucleic acid sequence 5' GTGCGTACAC GTTTACTACC 3' (denoted SEQ ID NO:56). The resultant PCR product from the mixed instar cDNA library, obtained using standard PCR conditions (e.g., Sambrook et al., *ibid.*), were about 354 nucleotides.

The PCR product was subjected to DNA sequencing analysis, and a composite sequence representing a full-length flea esterase coding region was deduced. The nucleic acid sequence of the composite nucleic acid molecule, referred to herein as $nfE5_{2144}$ is denoted herein as SEQ ID NO:57. Translation of SEQ ID NO:57 suggests that nucleic acid molecule $nfE5_{2144}$ encodes a full-length flea esterase protein of about 550 amino acids, referred to herein as $PfE5_{550}$, having amino acid sequence SEQ ID NO:58, assuming an open reading frame in which the initiation codon spans from nucleotide 30 through nucleotide 32 of SEQ ID NO:57 and the stop codon spans from nucleotide 1680 through nucleotide 1682 of SEQ ID NO:57. The complement of SEQ ID NO:57 is represented herein by SEQ ID NO:59. The coding region encoding $PfE5_{550}$ is represented by the nucleic acid molecule $nfE5_{1650}$, having a coding strand with the nucleic acid sequence represented by SEQ ID NO:60 and a complementary strand with nucleic acid sequence SEQ ID NO:61. The amino acid sequence of $PfE5_{550}$ (i.e., SEQ ID NO:58) predicts that $PfE5_{550}$ has an estimated molecular weight of about 61.8 kD and an estimated pI of about 5.5.

Comparison of nucleic acid sequence SEQ ID NO:57 with nucleic acid sequences reported in GenBank indicates that SEQ ID NO:57 showed the most homology, i.e., about 41% identity, between SEQ ID NO:57 and a *M. persicae* esterase FE4 mRNA sequence. Comparison of amino acid sequence SEQ ID NO:58 (i.e., the amino acid sequence of PfE5$_{550}$) with amino acid sequences reported in GenBank indicates that SEQ ID NO:58 showed the most homology, i.e., about 36% identity between SEQ ID NO:58 and *Drosophila melanogaster* alpha esterase protein.

A second clone included about a 1900 nucleotide insert, referred to herein as nfE6$_{1900}$. Nucleic acid sequence was obtained using standard techniques from nfE6$_{1900}$, to yield a flea esterase nucleic acid molecule named nfE6$_{1792}$ having a nucleic acid sequence of the coding strand which is denoted herein as SEQ ID NO:18. Translation of SEQ ID NO:18 suggests that nucleic acid molecule nfE6$_{1792}$ encodes a full-length flea esterase protein of about 550 amino acids, referred to herein as PfE6$_{550}$, having amino acid sequence SEQ ID NO:19, assuming an open reading frame in which the initiation codon spans from nucleotide 49 through nucleotide 51 of SEQ ID NO:18 and a stop codon spanning from nucleotide 1699 through nucleotide 1701 of SEQ ID NO:18. The complement of SEQ ID NO:18 is represented herein by SEQ ID NO:20. The coding region encoding PfE6$_{551}$, is represented by nucleic acid molecule nfE6$_{1650}$, having a coding strand with the nucleic acid sequence represented by SEQ ID NO:21 and a complementary strand with nucleic acid sequence SEQ ID NO:22. The proposed mature protein, denoted herein as PfE6$_{530}$, contains about 530 amino acids which is represented herein as SEQ ID NO:53. The nucleic acid molecule encoding PfE6$_{530}$ is denoted herein as nfE6$_{1590}$ and has a coding strand having the nucleic acid sequence SEQ ID NO:23. The amino acid sequence of PfE6$_{550}$ (i.e., SEQ ID NO:19) predicts that PfE6$_{550}$ has an estimated molecular weight of about 61.8 kD and an estimated pI of about 5.5.

Comparison of nucleic acid sequence SEQ ID NO:18 with nucleic acid sequences reported in GenBank indicates that SEQ ID NO:18 showed the most homology, i.e., about 41% identity, between SEQ ID NO:18 and a *Myzus pericae* esterase gene. Comparison of amino acid sequence SEQ ID NO:19 (i.e., the amino acid sequence of PfE6$_{550}$) with amino acid sequences reported in GenBank indicates that SEQ ID NO:19 showed the most homology, i.e., about 28% identity between SEQ ID NO:19 and *Drosophila melanogaster* alpha esterase protein.

2. Nucleic acid molecule nfE4$_{124}$ was labeled with $^{32}$P and used as a probe to screen the prepupal cDNA library described in Example 11, using standard hybridization techniques (e.g., Sambrook et al., *ibid*.). Two clones were isolated. A first clone included about a 3000 nucleotide insert, referred to herein as nfE7$_{3000}$. Nucleic acid sequence was obtained using standard techniques from nfE7$_{3000}$, to yield a flea esterase nucleic acid molecule named nfE7$_{2836}$ having a nucleic acid sequence of the coding strand which is denoted herein as SEQ ID NO:24. Translation of SEQ ID NO:24 suggests that nucleic acid molecule nfE7$_{2836}$ encodes a full-length flea esterase protein of about 596 amino acids, referred to herein as PfE7$_{196}$, having amino acid sequence SEQ ID NO:25, assuming an open reading frame in which the initiation codon spans from nucleotide 99 through nucleotide 101 of SEQ ID NO:24 and a stop codon spanning from nucleotide 1887 through nucleotide 1889 of SEQ ID NO:25. The complement of SEQ ID NO:24 is represented herein by SEQ ID NO:26. The coding region encoding PfE7$_{596}$, is represented by nucleic acid molecule nfE7$_{1788}$, having a coding strand with the nucleic acid sequence represented by SEQ ID NO:28 and a complementary strand with nucleic acid sequence SEQ ID NO:29. The proposed mature protein, denoted herein as PfE7$_{570}$, contains about 570 amino acids which is represented herein as SEQ ID NO:54. The nucleic acid molecule encoding PfE7$_{570}$ is denoted herein as nfE7$_{1710}$ and has a coding strand having the nucleic acid sequence SEQ ID NO:27. The amino acid sequence of PfE7$_{596}$ (i.e., SEQ ID NO:25) predicts that PfE7$_{596}$ has an estimated molecular weight of about 68.7 kD and an estimated pI of about 6.1.

Comparison of nucleic acid sequence SEQ ID NO:24 with nucleic acid sequences reported in GenBank indicates that SEQ ID NO:24 showed the most homology, i.e., about 48% identity, between SEQ ID NO:24 and an *Anas platyrhyncos* thioesterase B gene. Comparison of amino acid sequence SEQ ID NO:25 (i.e., the amino acid sequence of PfE7$_{596}$) With amino acid sequences reported in GenBank indicates that SEQ ID NO:25 showed the most homology, i.e., about 27% identity between SEQ ID NO:25 and *Drosophila melanogaster* alpha esterase protein.

A second clone included about a 3000 nucleotide insert, referred to herein as nfE8$_{3000}$. Nucleic acid sequence was obtained using standard techniques from nfE8$_{3000}$, to yield a flea esterase nucleic acid molecule named nfE8$_{2801}$ having a nucleic acid sequence of the coding strand which is denoted herein as SEQ ID NO:30. Translation of SEQ ID NO:30 suggests that nucleic acid molecule nfE8$_{280}$, encodes a full-length flea esterase protein of about 59: amino acids, referred to herein as PfE8$_{595}$, having amino acid sequence SEQ ID NO:31, assuming an open reading frame in which the initiation codon spans from nucleotide 99 through nucleotide 101 of SEQ ID NO:30 and a stop codon spanning from nucleotide 1884 through nucleotide 1886 of SEQ ID NO:30. The complement of SEQ ID NO:30 is represented herein by SEQ ID NO:32. The coding region encoding PfE8$_{595}$, is represented by nucleic acid molecule nfE8$_{1785}$, having a coding strand with the nucleic acid sequence represented by SEQ ID NO:34 and a complementary strand with nucleic acid sequence SEQ ID NO:35. The proposed mature protein, denoted herein as PfE8$_{570}$, contains about 570 amino acids which is represented herein as SEQ ID NO:55. The nucleic acid molecule encoding PfE8$_{570}$ is denoted herein as nfE8$_{1710}$ and has a coding strand having the nucleic acid sequence SEQ ID NO:33. The amino acid sequence of PfE8$_{595}$ (i.e., SEQ ID NO:31) predicts that PfE8$_{595}$ has an estimated molecular weight of about 68.6 kD and an estimated pI of about 6.1.

Comparison of nucleic acid sequence SEQ ID NO:30 with nucleic acid sequences reported in GenBank indicates that SEQ ID NO:30 showed the most homology, i.e., about 46% identity, between SEQ ID NO:30 and a *Mus musculus* carboxyl ester lipase gene. Comparison of amino acid sequence SEQ ID NO:31 (i.e., the amino acid sequence of PfE8$_{595}$) with amino acid sequences reported in GenBank indicates that SEQ ID NO:31 showed the most homology, i.e., about 28% identity between SEQ ID NO:31 and estalpha-2 esterase of *Culex pipiens quinque fasciatus*.

3. Nucleic acid molecule nfE3$_{421}$ was labeled with $^{32}$P and used as a probe to screen the prepupal cDNA library using standard hybridization techniques (e.g., Sambrook et al., *ibid*.). Two clones were isolated. One clone included about a 1900 nucleotide insert, referred to herein as nfE9$_{1900}$. Nucleic acid sequence as obtained using standard techniques from nfE9$_{1900}$, to yield a flea esterase nucleic acid molecule named nfE9$_{2007}$ having nucleic acid sequence of the coding strand which is denoted herein as SEQ ID NO:36. Translation of SEQ ID NO:36 suggests that nucleic acid molecule nfE9$_{2007}$ encodes a full-length flea esterase protein of about 528 amino acids, referred to herein as PfE9$_{528}$, having amino acid sequence SEQ ID NO:37, assuming an open reading frame in which the initiation codon spans from nucleotide 11 through nucleotide 13 of SEQ ID NO:36 and a stop co ion spanning from nucleotide 1595 through nucleotide 1597 of SEQ ID NO:36. The complement of SEQ ID NO:36 is represented herein by SEQ ID NO:38. The coding region encoding $PfE9_{528}$, is represented by nucleic acid molecule $nfE9_{1584}$, having a coding strand with the nucleic acid sequence represented by SEQ ID NO:51 and a complementary strand with nucleic acid sequence SEQ ID NO:52. The amino acid sequence of $PfE9_{528}$ (i.e., SEQ ID NO:37) predicts that $PfE9_{528}$ has an estimated molecular weight of about 60 kD and an estimated pI of about 5.43.

Comparison of nucleic acid sequence SEQ ID NO:36 with nucleic acid sequences reported in GenBank indicates that SEQ ID NO:36 showed the most homology, i.e., about 47% identity, between SEQ ID NO:36 and a hamster mRNA for carboxylesterase precursor gene. Comparison of amino acid sequence SEQ ID NO:37 (i.e., the amino acid sequence of $PfE9_{528}$) with amino acid sequences reported in GenBank indicates that SEQ ID NO:37 showed the most homology, i.e., about 37% identity between SEQ ID NO:37 and alpha esterase protein from *Drosophila melanogaster.*

As is the case for any of the nucleic acid molecules described in this example, variations between sequences may be due to a number of factors, such as but not limited to, sequencing errors or allelic variation.

4. Nucleic acid molecule $nfE1_{401}$ was labeled with $^{32}P$ and used as a probe to screen the mixed instar cDNA library using standard hybridization techniques (e.g., Sambrook et al., *ibid.*). A clone was isolated that included about a 2000 nucleotide insert, referred to herein as $nfE10_{2000}$. Nucleic acid sequence as obtained using standard techniques from $nfE10_{2000}$, to yield a flea esterase nucleic acid molecule named $nfE10_{1987}$ having nucleic acid sequence of the coding strand which is denoted herein as SEQ ID NO:67. Translation of SEQ ID NO:67 suggests that nucleic acid molecule $nfE10_{1987}$ encodes a full-length flea esterase protein of about 530 amino acids, referred to herein as $PfE10_{530}$, having amino acid sequence SEQ ID NO:68, assuming an open reading frame in which the initiation codon spans from nucleotide 231 through nucleotide 233 of SEQ ID NO:67 and a stop codon spanning from nucleotide 1821 through nucleotide 1823 of SEQ ID NO:67. The complement of SEQ ID NO:67 is represented herein by SEQ ID NO:69. The coding region encoding $PfE10_{530}$, is represented by nucleic acid molecule $nfE10_{1590}$, having a coding strand with the nucleic acid sequence represented by SEQ ID NO:70 and a complementary strand with nucleic acid sequence SEQ ID NO:71. The amino acid sequence of $PfE10_{530}$ (i.e., SEQ ID NO:68) predicts that $PfE10_{530}$ has an estimated molecular weight of about 59.5 kD and an estimated pI of about 5.5.

Comparison of nucleic acid sequence SEQ ID NO:67 with nucleic acid sequences reported in GenBank indicates that SEQ ID NO:67 showed the most homology, i.e., about 48% identity, between SEQ ID NO:67 and a *Lucilia cuprina* alpha esterase gene (genemb1 #U56636) gene. Comparison of amino acid sequence SEQ ID NO:68 (i.e., the amino acid sequence of $PfE10_{530}$) with amino acid sequences reported in GenBank indicates that SEQ ID NO:68 showed the most homology, i.e., about 30% identity between SEQ ID NO:68 and *Culex pipens* esterase b1 precurser protein (swissprot #P16854).

As is the case for any of the nucleic acid molecules described in this example, variations between sequences may be due to a number of factors, such as but not limited to, sequencing errors or allelic variation.

Example 12

This Example demonstrates the production of esterase proteins of the present invention in *E. coli* cells.

A. Flea esterase protein $PHIS-PfE7_{570}$ and flea esterase protein $PHIS-PfE8_{570}$ were produced in the following manner. A pair of primers w,as used to amplify DNA from flea esterase nucleic acid molecule $nfE7_{2836}$ or $nfE8_{2801}$ produced as described in Example 11. A sense primer containing an XhoI site (shown in bold) having the nucleic acid sequence 5' TGTGCTCGAG ATGGGATAAC CTAGAT-CAGC ATTTGTGC 3' (denoted SEQ ID NO:47), was used in combination with an anti-sense primer containing a KpnI site (shown in bold) having the nucleic acid sequence 5' TTAAGGTACC TCATCTAATA CTTCCTTCAT TACAG 3' (denoted SEQ ID NO:48). A PCR product was derived from $nfE7_{2836}$, and is referred to herein as $nfE7_{1710}$, having nucleic acid sequence SEQ ID NO:27. The PCR product was digested with XhoI and KpnI restriction endonucleases, gel purified and subcloned into expression vector pTrcHisB (available from InVitrogen). The resultant recombinant molecule, referred to herein as pTrc-$nfE7_{1710}$, was transformed into *E. coli* HB101 competent cells (available from Gibco BRL) to form recombinant cell *E. coli*:pTrc-$nfE7_{1710}$.

The PCR product derived from $nfE8_{2801}$ using the primers is referred to herein as $nfE8_{1710}$, having nucleic acid sequence SEQ ID NO:33. PCR product $nfE8_{1710}$ was digested with XhoI and KpnI restriction endonucleases, gel purified and subcloned into expression vector pTrcHisB. The resultant recombinant molecule, referred to herein as pTrc-$nfE8_{1710}$, was transformed into *E. coli* HB101 competent cells to form recombinant cell *E. coli*:pTrc-$nfE8_{1710}$.

The recombinant cells were cultured in enriched bacterial growth medium containing 0.1 mg/ml ampicillin and 0.1% glucose at about 32° C. When the cells reached an $OD_{600}$ of about 0.4–0.5, expression of recombinant protein was induced by the addition of 0.5 mM isopropyl-B-D-thiogalactoside (IPTG), and the cells were cultured for about 2 hours at about 32° C. Immunoblot analysis of recombinant cell *E. coli*:pTrc-$nfE7_{2710}$ and *E. coli*:pTrc-$nfE8_{1710}$ lysates using a T7 tag monoclonal antibody (available from Novagen, Inc., Madison, Wis.) directed against the fusion portion of the recombinant $PHIS-PfE7_{570}$ and $PHIS-PfE8_{570}$ fusion proteins identified proteins of appropriate size, namely an about 65 kD protein for each fusion protein.

B. Flea esterase protein $PHIS-PfE6_{540}$ was produced in the following manner. A pair of primers was used to amplify DNA from flea esterase nucleic acid molecule $nfE6_{1792}$ produced as described in Example 11. A sense primer containing an XhoI site having the nucleic acid sequence 5' AAACTCGAGT CCCCCGACTG TAACTTTGC 3' (denoted SEQ ID NO:62; XhoI site shown in bold), was used in combination with an anti-sense primer containing a PstI site having the nucleic acid sequence 5' TCATCTGCAG TTATTGACTG TGCAAAGTTT TTGTGG 3' (denoted SEQ ID NO:63; PstI site shown in bold). A PCR product was derived from $nfE6_{1792}$, and is referred to herein as $nfE6_{1488}$, having nucleic acid sequence SEQ ID NO:76. The PCR product was Digested with XhoI and PstI restriction endonucleases, gel purified and subcloned into expression vector lambda$P_R$/$T^2$ori/S10HIS-RSET-A9, that had been digested with XhoI and PstI and dephosphorylated. The resultant recombinant molecule, referred to herein as pCro-$nfE6_{1488}$, was transformed into *E. coli* HB101 competent cells (available from Gibco BRL) to form recombinant cell *E. coli*:pCro-$nfE6_{1488}$.

The recombinant cells were cultured using the method generally described in Section A of this example, except that the cells were grown under heat shift conditions rather than in the presence of IPTG. The cells were grown at 32° C. for about 2 hours, and then grown at 42° C. Immunoblot analysis of recombinant cell $E.\ coli$:pCro-nfE6$_{1488}$ lysate using a T7 tag monoclonal antibody directed against the fusion portion of the recombinant PHIS-PfE6$_{540}$ fusion protein identified proteins of appropriate size, namely an about 60 kD protein for each fusion protein.

Expression of the recombinant PHIS-PfE6$_{540}$ fusion protein was improved by transforming supercoiled plasmid pCro-nfE6$_{1488}$ DNA harvested from $E.\ coli$:pCro-nfE6$_{1488}$ cells into the BL-21 strain of $E.\ coli$ (available from Novagen). The amount of expression PHIS-PfE6$_{540}$ was confined by immunoblot using the method described immediately above.

$E.\ coli$ cells expressing PHIS-PfE6$_{540}$ protein were harvested from about 2 liters of media and suspended in about 140 ml of 50 mM Tris, pH 8.0, 50 mM NaCl, 0.1 mM phenylmethylsulfonylfluoride (PMSF) (Solubilization Buffer). The cells were broken by passage through a microfluidizer at 30 psi for 30 cycles. Tile sample was centrifuged at about 16,000×g for 30 mile at 4° C. The supernatant (S1) was recovered and the pellet was resuspended in about 80 ml of Solubilization Buffer and centrifuged at about 16,000×g for 30 min at 4° C. The supernatant (S2) was recovered and the pellet was resuspended in about 80 ml of Solubilization Buffer containing 0.1% Triton-X100 and centrifuged at about 16,000×g for 30 min at 4° C. The supematant (S3) was recovered and the pellet was resuspended in about 140 mls 50 mM Tris, pH 8.0, 8 M Urea, 0.1 M PMSF and centrifuged at about 16,000×g. The supernatant (S4) was recovered and the pellet was resuspended in 40 mls 50 mM Tris, 8 M Urea, 0.1 M PMSF. Aliquots of each pellet and supernatant were anally, by SDS-PAGE and immunoblot using the T7 tag monoclonal antibody described above. The results indicated that the PHIS-PfE6$_{540}$ protein was located in the final supematant (S4). The PHIS-PfE6$_{540}$ protein was loaded onto a 5.0 ml, Metal chelating HiTrap column charged with NiCl$_2$ (obtained from Pharmacia Biotech Inc., Piscataway, N.J.), previously equilibrated with 50 mM Tris, 1 mM PMSF, 1 mM β-mercaptoethanol (βME), 8 M urea, pH 8.0 (Buffer A). The column was washed with 10 column volumes (cv) of Buffer A and then with 10 cv with 50 mM Tris, 25 mM sodium acetate, 1 mM PMSF, 1 mM βME, 8 M urea, pH 6.0 (Buffer B) to remove loosely bound proteins. Bound PHIS-PfE6$_{540}$ protein was eluted with 10 cv of 50 mM Tris, 25 mM sodium acetate, 1 mM PMSF, 1 mM βME, 8 M urea, pH 4.0 (Buffer C). Column fractions were analyzed for the presence of PHIS-PfE6$_{540}$ protein by immunoblot using the T7 tag monoclonal antibody as described above. The results indicated that the majority of the PHIS-PfE6$_{540}$ protein was eluted by Buffer C. The fractions containing the PHIS-PfE6$_{540}$ protein were combined and loaded onto a 5 ml SP-Sepharose HiTrap column (obtained from Pharmacia Biotech Inc.) previously equilibrated with 50 mM Tris, 25 mM Sodium Acetate, 1 mM PMSF, 1 mM βME, 8 M Urea, pH 4.5 (SP-Sepharose Buffer). The column was washed with SP-Sepharose Buffer until most of the unbound protein was removed. Bound protein was eluted with an increasing salt gradient to 1 M NaCl over 100 ml (20 cv) in SP-sepharose buffer. Column fractions were analyzed for the presence of PHIS-PfE6$_{540}$, protein by immunoblot using the T7 tag monoclonal antibody as described above. The results indicated that the PHIS-PfE6$_{540}$ protein was eluted at about 0.75 M NaCl.

The purified PHIS-PfE6$_{488}$ protein was used to produce an anti-M6 polyclonal antiserum as follows. Rabbits were immunized with PHIS-PfE6$_{1488}$ protein diluted to a concentration of about 0.1 mg/ml in PBS. One milliliter of the dilution was mixed 1:1 mix with Complete Freunds Adjuvant. In the primary immunization, about 500 μl of the 1:1 mix was injected subcutaneously into 5 different sites (0.1 ml/site) and 500 μl was injected intradermally into 5 different sites (0.1 ml/site) on the rabbit. Booster shots were administered to the rabbit intramuscularly in 4 sites using 250 μl/site of a 1:1 mix of PHIS-PfE6$_{1488}$ protein with Incomplete Freunds Adjuvant. The booster shots were administered at days 14 and 35. Serum samples were obtained prior to immunization (pre-bleed), and at day 14 after primary immunization and day 14 after the first and second boost.

C. Flea esterase protein PHIS-PfE9$_{528}$ was produced in the following manner. A pair of primers was used to amplify DNA from flea esterase nucleic acid molecule nfE9$_{2007}$ produced as described in Example 11. A sense primer containing an BamHI site having the nucleic acid sequence 5'-TTC CGG ATC CGG CTG ATC TAC AAG TGA CTT TG-3' (denoted SEQ ID NO:64; BamHI site shown in bold), was used in combination with an anti-sense primer containing a XhoI site having the nucleic acid sequence 5' TGG TAC TCG AGT CAT AAA AAT TTA TTC CAA AAT C 3' (denoted SEQ ID NO:65; XhoI site shown in bold). A PCR product was derived from nfE9$_{2007}$, and is referred to herein as nfE9$_{1540}$, having nucleic acid sequence SEQ ID NO:51. The PCR product was digested with BamHI and XhoI restriction endonucleases, gel purified and subcloned into expression vector pTrcHisB (available from InVitrogen). The resultant recombinant molecule, referred to herein as pTrc-nfE9$_{5140}$, was transformed into $E.\ coli$ HB101 competent cells (available from Gibco BRL) to form recombinant cell $E.\ coli$:pTrc-nfE9$_{1540}$.

The recombinant cells were cultured using the method described in Section A of this example. Immunoblot analysis of recombinant cell $E.\ coli$:pTrc-nfE9$_{1540}$ lysate using a T7 tag monoclonal antibody directed against the fusion portion of the recombinant PHIS-PfE9$_{528}$ fusion protein identified proteins of appropriate size, namely an about 59 kD protein for each fusion protein.

Expression of the recombinant PHIS-PfE9$_{528}$ fusion protein was improved by transforming supercoiled plasmid pTrc-nfE9$_{1584}$ DNA harvested from $E.\ coli$:pTrc-nfE9$_{1540}$ cells into the BL-21 strain of $E.\ coli$. The amount of expression PHIS-PfE9$_{528}$ was confined by immunoblot using the method described immediately above.

Two liters of media from cultures of $E.\ coli$ cells expressing PHIS-PfE9$_{528}$ protein were harvested and S4 supematant was prepared using the method described above in section B. The PHIS-PfE9$_{528}$ protein contained in the S4 supernatant was loaded onto a 5.0 ml, Metal chelating HiTrap column charged with NiCl$_2$ (available from Pharmacia Biotech Inc., Piscataway, N.J.), previously equilibrated with 50 mM Tris, 1 mM PMSF, 1 mM βME, 8 M urea, pH 8.0 (Buffer A). The column was washed with 5 cv of Buffer A until all unbound protein was removed. Bound protein was eluted with a linear gradient from Buffer A to 50 mM Tris, 1 mM PMSF, 1 mM βME, 8 M urea, 1 M NaCl, pH 4.0. Column fractions were analyzed for the presence of PHIS-PfE9$_{528}$ protein by immunoblot using the T7 tag monoclonal antibody as described above. The results indicated that the majority of the PHIS-PfE9$_{529}$ protein was eluted at about 250 mM NaCl. The fractions containing the PHIS-PfE9$_{528}$ protein were combined and loaded onto a C4-reversed phase column (obtained from Vydak, Hesperia, Calif.), previously equilibrated with 0.05% trifluoroacetic acid (TFA). The column was washed with 0.05% TFA until all unbound protein was removed. Bound proteins were eluted with a linear gradient from 0.05% TFA to 0.05% TFA in acetonitrile. Column fractions were analyzed for the presence of PHIS-PfE9$_{528}$ protein by immunoblot using the T7 tag monoclonal antibody as described above. The results indicated that the PHIS-PfE9$_{528}$ protein was eluted at about 40% acetonitrile. The fractions containing the PHIS-PfE9$_{528}$ protein were combined and loaded onto a 5 ml Q-Sepharose HiTrap column previously equilibrated with 50 mM Tris, 25 mM Sodium Acetate, 1 mM PMSF, 1 mM βME, 8 M Urea, pH 8.5 (Q-Sepharose Buffer). The column was washed with Q-Sepharose Buffer until all unbound protein was removed. Bound protein was eluted with an increasing salt gradient to 1 M NaCl over 100 ml (20 cv) in Q-sepharose buffer. Column fractions were analyzed for the presence of PHIS-PfE9$_{528}$ protein by immunoblot using the T7 tag noncolonial antibody as described above. The results indicated that the PHIS-PfE9$_{528}$ protein was eluted at about 0.3 M NaCl.

The purified PHIS-PfE9$_{528}$ protein was used to produce an anti-P1 polyclonal antiserum as follows. Rabbits were immunized with PHIS-PfE9$_{528}$ protein diluted to a concentration of about 0.1 mg/ml in PBS. One milliliter of the dilution was mixed 1:1 mix with Complete Freunds Adjuvant. In the primary immunization, about 500 µl of the 1:1 mix was injected subcutaneously into 5 different sites (0.1 ml/site) and 500 µl was injected intradermally into 5 different sites (0.1 ml/site) on the rabbit. Booster shots were administered to the rabbit intramuscularly in 4 sites using 250 µl/site of a 1:1 mix of PHIS-PfE9$_{528}$ protein with Incomplete Freunds Adjuvant The booster shots were administered at days 14 and 35. Serum samples were obtained prior to immunization (pre-bleed), and at day 14 after primary immunization and day 14 after the first and second boost.

D. Flea esterase protein PHIS-PfE7$_{275}$ was produced in the following manner. A 650-bp fragment was produced by digesting nfE7$_{2836}$ DNA with the restriction enzymes BamHI and BglII. The BamHI and BglII fragment derived from nfE7$_{2836}$ is referred to herein as nfE7$_{650}$, having nucleic acid sequence SEQ ID NO:72 and amino acid SEQ ID NO:73. The fragment was purified using a Qiaquick™ Kit (available from Qiagen, Santa Clarita, Calif.), according to methods provided by the manufacturer. The purified fragment was subcloned into expression vector pTrcHisC which had been digested with BamHI and BglII. The resultant recombinant molecule, referred to herein as pTrc-nfE7$_{650}$ was transformed into *E. coli* DH-5a competent cells (available from Gibco BRL) to form recombinant cell *E. coli*:pTrc-nfE7$_{650}$.

The recombinant cells were cultured using the method described above in section A. Immunoblot analysis of recombinant cell *E. coli*:pTrc-nfE7$_{650}$ Pulsate using a T7 tag monoclonal antibody directed against the fusion portion of the recombinant PHIS-PfE7$_{275}$ fusion protein identified proteins of appropriate size, namely an about 35 kD protein for each fusion protein.

Expression of the recombinant fusion protein was improved by transforming supercoiled plasmid pTrc-nfE7$_{650}$ DNA harvested from *E. coli*:pTrc-nfE7$_{650}$ cells into the BL-21 strain of *E. coli*. The amount of expression *E. coli*:pTrc-nfE7$_{650}$ was confined by immunoblot using the method described immediately above.

Example 13

This Example demonstrates the production of esterase proteins of the present invention in eukaryotic cells.

A. Recombinant molecule pBv-nfE7$_{1788}$, containing a flea esterase nucleic acid molecule spanning nucleotides from about 99 through about 1886 of SEQ ID NO:24, and pBv-nfE8$^8_{1788}$, containing a flea esterase nucleic acid molecule spanning nucleotides from about 99 through about 1883 of SEQ ID NO:30 each, operatively linked to baculovirus polyhedron transcription control sequences were produced in the following manner. In order to subclone a flea esterase nucleic acid molecule into baculovirus expression vectors, flea esterase nucleic acid molecule-containing fragments were separately PCR amplified from nfE7$_{2836}$ or nfE8$_{2801}$ DNA. A PCR fragment of 1858 nucleotides, named nfE7$_{1858}$, was amplified from nfE7$_{2836}$ using a sense primer E1113 FWD having the nucleic acid sequence 5'-AAAACTGCAG TATAAATATG TTACCTCACA GTAGTG-3' (SEQ ID NO:49; PstI site shown in bold) and an antisense primer E1113/2212 REV having the nucleic acid sequence 5'-TGCTCTAGAT TATCTAATAC TTCCT-TCATT ACAG (SEQ ID NO:50; XbaI site shown in bold). A PCR fragment of 1858 nucleotides, named nfE8$_{1858}$, was amplified from nfE8$_{2801}$ using a sense primer E2212 FWD having the nucleic acid sequence 5'-AAACTGCAG TATAAATATG TTACCTCACA GTGCATTAG-3' (SEQ ID NO:66; PstI site shown in bold), and the antisense primer E1113/2212 REV. The N-terminal primer was designed from the pol h sequence of baculovirus with modifications to enhance expression in the baculovirus system.

In order to produce a baculovirus recombinant molecule capable of directing the production of PfE7$_{596}$, the about 1,802 base pair PCR product (referred to as Bv-nfE7$_{1802}$) was digested with PstI and XbaI and subcloned into unique PstI and XbaI sites of pVL1392 baculovirus shuttle plasmid (available from Pharmingen, San Diego, Calif.) to produce the recombinant molecule referred to herein as pVL-nfE7$_{1802}$.

In order to produce a baculovirus recombinant molecule capable of directing the production of PfE8$_{595}$, the about 1,792 base pair PCR product (referred to as Bv-nfE8$_{1792}$) w,as digested with PstI and XbaI and subcloned into PstI and XbaI digested to produce the recombinant molecule referred to herein as pVL-nfE8$_{1792}$.

The resultant recombinant molecules, pVL-nfE7$_{1802}$ and pVL-nfE8$_{1792}$, were verified for proper insert orientation by restriction mapping. Such a recombinant molecule can be co-transfected with a linear Baculogold baculovirus DNA (available from Pharmingen) into *S. frugiperda* Sf9 cells (available from InVitrogen) to form the recombinant cells denoted *S. frugiperda*:pVL-nfE7$_{1802}$ and *S. frugiperda*:pVL-nfE8$_{1792}$. *S. frugiperda*:pVL-nfE7$_{1802}$ can be cultured in order to produce a flea esterase protein PfE7$_{596}$. *S. frugiperda*:pVL-nfE8$_{1792}$ can be cultured in order to produce a flea esterase protein PfE8$_{595}$.

B. Recombinant molecule pBv-PfE9$_{528}$, containing a flea esterase nucleic acid molecule spanning nucleotides from 14 through 1595 of SEQ ID NO:36, operatively linked to baculovirus polyhedron transcription control sequences were produced in the following manner. In order to subclone a flea esterase nucleic acid molecule into baculovirus expression vectors, a flea esterase nucleic acid molecule-containing fragment was PCR amplified from nfE9$_{2007}$ DNA. A PCR fragment of about 1600 nucleotides, named nfE9$_{1600}$, was amplified from nfE9$_{2007}$ using a sense primer P121B1 Sense having the nucleic acid sequence 5'-CGC GGA TCC GCT GAT CTA CAA GTG ACT TTG C-3' (SEQ ID NO:75; BamHI site shown in bold) and an antisense primer PI21B1 Anti having the nucleic acid sequence 5'-CCG AGC GGC CGC ATA AAA ATT TAT TCC AAA ATC TAA GTC G-3' (SEQ ID NO:76; NotI site shown in bold). The N-terminal primer was designed from the pol h sequence of baculovirus with modifications to enhance expression in the baculovirus system.

In order to produce a baculovirus recombinant molecule capable of directing the production of $PfE9_{528}$, the about 1,600 base pair PCR product (referred to as Bv-$nfE9_{1600}$) was digested with BamHI and NotI and subcloned into unique BamHI and NotI sites of pVL3193 baculovirus shuttle plasmid (available from Pharmingen, San Diego, Calif.) to produce the recombinant molecule referred to herein as pVL-$nfE9_{1600}$.

The resultant recombinant molecule, pVL-$nfE9_{1600}$, was verified for proper insert orientation by restriction mapping. Such a recombinant molecule can be co-transfected with a linear Baculogold baculovirus DNA into *S. frugiperda* Sf9 cells to form the recombinant cells denoted *S. frugiperda*:pVL-$nfE9_{1600}$. *S. frugiperda*:pVL-$nfE9_{1600}$ can be cultured in order to produce a flea esterase protein $PfE9_{529}$.

An immunoblot of supernatant from cultures of *S. frugiperda*:pL-$nfE9_{1600}$ cells producing the flea esterase protein $PfE9_{528}$ was performed using the anti-P1 polyclonal antiserum described in detail in Example 12. Blots were incubated using serum samples from the pre-bleed or from serum collected 14 days after the first boost of the rabbit. Analysis of the supernatent from cultures of *S. frugiperda*:pVL-$nfE9_{1600}$ cells identified an about 66 kD protein C. Recombinant molecule pBv-$PfE6_{530}$, containing a flea esterase nucleic acid molecule spanning nucleotides from 50 through 1701 of SEQ ID NO:18, operatively linked to baculovirus polyhedron transcription control sequences ere produced in the following manner. In order to subclone a flea esterase nucleic acid molecule into baculovirus expression vectors, a flea esterase nucleic acid molecule-containing fragment was PCR amplified from $nfE6_{1792}$ DNA. A PCR fragment of about 1679 nucleotides, named $nfE10_{1679}$, was amplified from $nfE6_{1792}$ using a sense primer M6M32 Sense having the nucleic acid sequence 5'-GCG AGG CCT TAT AAA TAT GTC TCG TGT TAT TTT TTT AAG TTG-3' (SEQ ID NO:75; StuI site shown in bold) and an antisense primer M6M32 Anti having the nucleic acid sequence 5'-GCA CTG CAG TTA TTG ACT GTG CAA AGT TTT TGT GG-3' (SEQ ID NO:76; PstI site shown in bold). The N-terminal primer was designed from the pol h sequence of baculovirus with modifications to enhance expression in the baculovirus system.

In order to produce a baculovirus recombinant molecule capable of directing the production of $PfE6_{530}$, the about 1,679 base pair PCR product (referred to as Bv-$nfE6_{1679}$) was digested with StuI and PstI and subcloned into unique StuI and PstI sites of FAST BAC™ baculovirus shuttle plasmid (obtained from Gibco-BRL) to produce the recombinant molecule referred to herein as pFB-$nfE6_{1679}$.

The resultant recombinant molecule, pFB-$nfE6_{1679}$, was verified for proper insert orientation by restriction mapping. Such a recombinant molecule can be transformed into *E. coli* strain DH10 (obtained from Gibco-BRL) according to the manufacturer's instructions. The pFB-$nfE6_{1679}$ isolated from the transformed DH10 cells can then be co-transfected with a linear Baculogold baculovirus DNA into *S. frugiperda* Sf9 cells to form the recombinant cells denoted *S. frugiperda*:pFB-$nfE6_{1679}$. *S. frugiperda*:pFB-$nfE6_{1679}$ can be cultured in order to produce a flea esterase protein $PfE6_{530}$.

An immunoblot of supernatant from cultures of *S. frugiperda*:pFB-$nf6_{1679}$ cells producing the flea esterase protein $PfE6_{530}$ was performed using the anti-M6 polyclonal antiserum described in detail in Example 12. Blots were incubated using serum samples from the pre-bleed or from serum collected 14 days after the first boost of the rabbit. Analysis of the supematant from cultures of *S. frugiperda*:pFB-$nfE6_{1679}$ cells identified an about 66 kD protein.

N-terminal amino acid sequence was obtained using standard methods for the about 66 kD protein identified using the anti-M6 polyclonal antiserum. The N-terminal amino acid sequence was determined to be identical to the N-terminal amino acid sequence of SEQ ID NO:44.

Example 14

This example describes the purification of carboxylesterase protein from fed flea midguts.

About 43,000 cat blood-fed adult flea midguts were collected and prepared as previously described in Example 1. The extract was then added in 2 aliquots to columns containing about 1 to about 2 ml of p-aminobenzamidine linked agarose beads (available from Sigma), equilibrated in 50 mM Tris (pH 8.0), 400 mM NaCl, and incubated overnight at 4° C. The columns were then drained to remove unbound protein and the two aliquots of unbound protein were combined. The collected unbound protein was then concentrated and diafiltered into a total volume of about 16 ml of 25 mM Tris (pH 8), 10 mM NaCl using an Ultrafree-20 10 kD centrifugal concentrator (available from Millipore; Bedford, Mass.).

Aliquots of about 8 ml were loaded onto an Uno Q6 anion exchange column (available from Bio-Rad, Hercules, Calif.) equilibrated in 25 mM Tris (pH 8), 10 mM NaCl, operated on a BioLogic liquid chromatography system (available from Bio-Rad). The column was washed with 25 mM Tris (pH 8), 10 mM NaCl until all unbound protein was removed. Protein bound to the column was then eluted with a linear gradient from 10 mM to 1 M NaCl in 25 mM Tris, pH 8. Fractions were assayed for CE activity using the assay described previously. The results indicated that CE activity was eluted at about 220 mM NaCl.

Fractions containing CE activity were pooled and diafiltered into a total volume of about 3 ml of 20 mM MES buffer (2-N-morpholino)ethanesulfonic acid), pH 6.0, containing 10 mM NaCl, in preparation for cation exchange chromatography. The sample was then applied to an Uno S1 cation exchange column (available from Bio-Rad) equilibrated in MES buffer. The column was washed with MES buffer until all unbound protein was removed. Protein bound to the column was then eluted with a linear gradient from 10 mM to 1 M, NaCl in 20 mM MES buffer, pH 6. Fractions were assayed for CE activity using the assay described previously. Tile results indicated that CE activity was not retained on the cation exchange column using the above conditions, and all of the activity was found in the flow-through fractions.

Fractions containing CE activity were pooled and diafiltered into a total volume of about 3 ml of 25 mM Tris (pH 8), 10 mM NaCl, in preparation for an additional anion exchange chromatography step. The sample was then applied to a Bio-Scale Q2 anion exchange column (available from Bio-Rad). The column was washed with 25 mM Tris (pH 8), 10 mM NaCl until all unbound protein was removed. Protein bound to the column was then eluted with a linear gradient from 10 mM to 1 M NaCl in 25 mM Tris, pH 8. Fractions were assayed for CE activity using the assay described previously. The results indicated that CE activity was eluted at about 130 mM NaCl.

A fraction containing CE activity was diluted into a total volume of about 4 ml of 10 mM phosphate buffer, pH 7.2 containing 10 mM NaCl, in preparation for hydroxyapatite chromatography. The sample was then applied to a Bio-Scale CHT2-I column (available from Bio-Rad) at a flow rate of about 0.5 ml/min. The column was washed with 10 mM phosphate buffer, pH 7.2 containing 10 mM NaCl until all unbound protein was removed. Protein bound to the column was then eluted with a linear gradient from 10 mM phosphate buffer, pH 7.2 containing 10 mM NaCl to 0.5 M 10 mM phosphate buffer, pH 6.5 containing 10 mM NaCl. Fractions were assayed for CE activity using the assay described previously. The results indicated that CE activity as eluted at about 200 mM phosphate.

Example 15

This example describes the purification of a carboxylesterase protein from wandering flea larvae.

About 120,000 bovine blood-fed adult wandering flea larvae were homogenized in 3 batches of about 40,000 wandering larvae in each batch, in Tris buffered saline (TBS), pH 8.0 as previously described, except that about 1.2 mg of phenylthiourea was added to each ml of TBS during the extraction procedure to inhibit cross linkin, reactions. The extracts were dialyzed against 2 changes of about 2 L of 10 mM phosphate buffer, pH 7.2 containing 10 mM NaCl in preparation for hydroxyapatite batch chromatography. The samples were then filtered through glass Acrodiscs® (available from Gelman Sciences, Ann Arbor, Mich.) and added to 14 g of Macro-Prep Ceramic Hydroxyapatite, Type I, 40 μm beads (available from Bio-Rad), previously equilibrated in 10 mM phosphate buffer, pH 7.2 containing 10 mM NaCl. The extracts and beads were rocked at room temperature for about 30 minutes. Following incubation, the beads were centrifuged for about 5 minutes at 500×g and the supernatants removed. The beads were washed with about 40 ml 10 mM phosphate buffer, pH 7.2 containing 10 mM NaCl, centrifuged as above, and washed and centrifuged again to eliminate all unbound protein. Bound proteins were eluted by washing the beads with about 40 ml of each of 100 mM, 200 mM, 300 mM, and 400 mM phosphate buffer, pH 6.5 containing 10 mM NaCl. Following elution, the supernatants from each concentration of phosphate buffer were tested for juvenile hormone esterase activity as described previously in Example 7. The juvenile hormone esterase activity eluted at different phosphate concentrations in each batch, but the activity was generally found in the 200 mM to 300 mM phosphate fractions.

The fractions that contained the highest juvenile hormone esterase activity were combined and diafiltered into a total volume of about 50 ml of 10 mM phosphate buffer, pH 7.2 containing 10 mM NaCl using a stirred cell concentrator fitted with a YM10 ultrafiltration membrane (available from Anicon, Beverly, Mass.). Aliquots of about 5 ml to 10 ml were applied to a chromatography column containing about 10 ml of Macro-Prep Ceramic Hydroxyapatite, Type I, 20 μm beads, previously equilibrated with 10 mM phosphate buffer, pH 7.2 containing 10 mM NaCl. The column was washed with 10 mM phosphate buffer, pH 7.2 containing 10 mM NaCl until all unbound protein as removed. Protein bound to the column was then eluted with a linear gradient from 10 mM phosphate buffer, pH 7.2 containing 10 mM NaCl to 0.5 M 10 mM phosphate buffer, pH 6.5 containing 10 mM NaCl. Fractions were assayed for carboxylesterase activity using the assay described previously. The results indicated that carboxylesterase activity was eluted at about 160 mM phosphate.

The fractions that contained the highest carboxylesterase activity were combined and diafiltered into a total volume of about 15 ml of 20 mM sodium acetate buffer, pH 4.0 in preparation for cation exchange chromatography. Aliquots of about 3 ml were applied to a PolyCat A cation exchange column (available from PolyLC, Columbia, Md.) equilibrated in 20 mM sodium acetate buffer, pH 6.0, operated on a Waters high performance liquid chromatography system (available from Waters Corporation, Milford, Mass.). The column was washed with 20 mM sodium acetate buffer, pH 6.0 until all unbound protein was removed. Protein bound to the column was then eluted with a linear gradient from 20 mM sodium acetate buffer, pH 6.0 to 20 mM sodium acetate buffer, pH 6.0 containing 1 M NaCl. Fractions were assayed for CE activity using the assay described previously. The results indicated that there were two pools of CE activity. The first pool was not retained on the cation exchange column, and the second pool was eluted at about 170 mM NaCl.

The fractions from the second pool that contained the highest carboxylesterase activity were combined and diafiltered into a total volume of about 10 ml of 25 mM Tris (pH 8), 10 mM NaCl, in preparation for anion exchange chromatography. The sample was then applied to a Bio-Scale Q2 anion exchange column (available from Bio-Rad). The column was washed with 25 mM Tris (pH 8), 10 mM NaCl until all unbound protein was removed. Protein bound to the column was then eluted with a linear gradient from 10 mM to 1 M NaCl in 25 mM Tris, pH 8. Fractions were assayed for carboxylesterase activity using the assay described previously. The results indicated that carboxylesterase activity was eluted at about 350 mM NaCl.

Fractions containing carboxylesterase activity were combined and concentrated to about 175 μl using a Centricon 10 centrifugal concentrator (available from Amicon, Beverly, Mass.) in preparation for size exclusion chromatography. The sample was applied to a Bio-Select SEC 125-5 size exclusion chromatography column (available from Bio-Rad), previously equilibrated in TBS, pH 7.2. About 250 μl fractions were then collected. The fractions were assayed for carboxylesterase activity using the assay described previously. The results indicated that the carboxylesterase activity was eluted in about 5.5 to 6 ml of buffer, corresponding to a molecular weight of about 40 to 100 kDa based on the elution volumes of gel filtration molecular weight standard proteins (available from Sigma, St. Louis, Mo.).

Example 16

This example describes the purification of juvenile hormone esterase activity from unfed adult flea midguts by affinity chromatography.

About 16,000 unfed adult flea midguts were collected in 20 mM Tris buffer (pH 7.7), containing 130 mM NaCl, 1 mM sodium EDTA, 1 mM Pefabloc® (available from Boehringer Mannheim, Indianapolis, Ind.), 1 microgram/ml (μg/ml) leupeptin and 1 μg/ml pepstatin. The midguts were homogenized by freeze-fracture and sonication, and then centrifuged at about 14,000×g for 20 min. The soluble material from the centrifugation step was recovered, diafiltered into Tris buffered saline (TBS), and applied to a disposable plastic column containing about 1 ml of 3-[(4'-mercapto)butylthio]-1,1,1-trifluoropropan-2-one linked Sepharose 6B beads, prepared similarly to the method described by Venkatesh et al. (*J. Biol. Chem.*, Vol. 265, No. 35, 21727–21732, 1990) (the 3-[(4'-mercapto)butylthio]-1, 1,1-trifluoropropan-2-one was a gift from Novartis Corp., Basel, Switzerland; and the Epoxy-activated Sepharose 6B is available from Pharmacia Biotech Inc., Piscataway, N.J.). After overnight incubation at 4° C., the column was drained and the beads were washed with about 10 ml TBS, then about 10 ml TBS containing 0. 1% (w/v) n-octylglucoside (OG; available from Boehringer Mannheim). The pre-column, flow-through, and wash fractions were tested for juvenile hormone esterase activity by the method previously described above in Example 7. The results indicate that the flow-through fraction contained approximately 40% less juvenile hormone esterase activity than the pre-column material, and that the washes contained very little activity.

Bound protein was eluted from the beads by adding about 10 ml of TBS containing 0.1% (w/v) OG and 1 mM 3-octylthio-1,1,1-trifluoropropan-2-one (OTFP; a gift from Novartis Corp.). After a 2 hour incubation at 4° C., about 5 ml of the eluate was collected, and the remaining 5 ml was incubated with the beads overnight at 4° C. The following day, the beads were drained, the eluate collected, and an additional 10 ml of TBS containing 0.1% (w/v) OG and 1 mM OTFP was added to the beads. After an overnight incubation at 4° C., the beads were drained and the eluate collected. Tile final 10 ml elution step was repeated 3 additional times so that we had 6 eluted fractions. The first elution fraction was dialyzed overnight twice against 1 liter of fresh TBS to remove excess OTFP. The second elution fraction was also dialyzed overnight against 1 liter of fresh TBS to remove OTFP. The third through sixth elution fractions were not dialyzed. All six eluted fractions were tested for juvenile hormone esterase activity by the method previously described above in Example 7. The results indicate that only the third elution fraction contained detectable juvenile hormone esterase activity. Analysis of the eluted fractions by silver-stained SDS-PAGE indicated that several proteins were specifically bound to the affinity beads and were eluted by OTFP. The apparent molecular weights of these proteins, as determined by SDS-PAGE, were about 66 kDa, 55 kDa, and 33 kDa. About 3.5 ml of each elution fraction were combined and concentrated to about 110 µl using a Centriplus 10 centrifugal concentrator (available from Amicon, Beverly, Mass.). This pool was separated by SDS-PAGE and blotted onto a polyvinylidene difluoride (PVDF) membrane as described previously in Example 5. The stained protein band at about 66 kDa was excised and subjected to N-terminal sequence analysis as described previously.

The results indicated that the N-terminal amino acid sequence of the putative 66 kDa juvenile hormone esterase protein was DL y/g V k/y/cg v/q/n LQGTLKGKE (denoted herein as SEQ ID NO:74), in which the lower case letters designate uncertainties. Below is shown a comparison between different esterase amino acid sequences of the present invention.

SEQ ID NO:74: DL (y/g) V (k/y/g) (v/q/n) LQGTLKGKE
SEQ ID NO:37: DL Q V T L LQGTLKGKE
(Residues 3–17)

Example 17

This example describes the purification of an active recombinant juvenile hormone esterase protein from baculovirus supematants.

About 1 liter of supernatant from cultures of $S.$ $frugiperda$:pVL-nfE9$_{1600}$ cells producing the flea esterase protein PfE9$_{528}$ was brought to about 50% saturation with ammonium sulfate and centrifuged at about 20000×g for about 30 minutes at 4° C. to pellet the precipitated material. After centrifugation, the pellet was retained and the supernatant was brought to about 100% saturation with ammonium sulfate and centrifuged as above. The material in both pellets were resuspended separately in about 35 ml of Tris buffered saline (TBS), pH 8.0. The resuspended pellets were assayed for the presence of flea esterase protein PfE9$_{528}$ using standard Western blot techniques and a polyclonal antiserum that binds specifically to PfE9$_{528}$ protein. Briefly, a rabbit was immunized with PHIS-PfE9$_{528}$ protein purified from $E.$ $coli$:pTrc-nfE9$_{1584}$ cells (described above in Example 12C) and boosted using standard procedures. The results indicated that the flea esterase protein PfE9$_{528}$ was present in the $S.$ $frugiperda$:pVL-nfE9$_{1600}$ supernatants and the protein was precipitated by adjusting the ammonium sulfate concentration from about 50% saturation to about 100% saturation.

The resuspended flea protein PfE9$_{528}$ was diafiltered into about 10 ml of 25 mM Tris (pH 8.0), 10 mM NaCl using an Ultrafree-20 10 kD centrifugal concentrator in preparation for anion exchange chromatography. Aliquots of about 5 ml were loaded onto an Uno Q6 anion exchange column equilibrated in 25 mM Tris (pH 8.0), 10 mM NaCl. The column was washed with 25 mM Tris (pH 8.0), 10 mM NaCl until most of the unbound protein was removed. Protein bound to the column was then eluted with a linear gradient from 10 mM to 1 M NaCl in 25 mM Tris buffer (pH 8.0). Fractions were assayed for the presence of flea esterase protein PfE9$_{528}$ by the immunoblot method described above. The results indicated that the flea esterase protein PfE9$_{528}$ was eluted at about 200 mM NaCl.

Fractions containing the flea esterase protein PfE9$_{523}$ were pooled and concentrated to about 440 µl using a Centricon 10 kD centrifugal concentrator in preparation for size exclusion chromatography. The sample was applied in 3 aliquots to a Bio-Select SEC 125-5 size exclusion chromatography column (available from Bio-Rad), previously equilibrated in TBS, pH 7.2. The column was eluted with TBS, pH 7.2 at a flow rate of about 0.5 ml/min, and fractions of about 250 µl were collected. The fractions were assayed for the presence of flea esterase protein PfE9$_{528}$ by the immunoblot method described above. The results indicate 't° at the flea esterase protein PfE9$_{528}$ was eluted with about 6 ml of buffer, corresponding to a molecular weight of about 40 to 100 kDa based on the elution volumes of gel filtration molecular weight standard proteins (available from Sigma, St. Louis, Mo.).

Fractions containing flea esterase protein PfE9$_{528}$ were then assayed for juvenile hormone esterase activity as described in Example 7 and carboxylesterase activity as described in Example 2. The results indicated that the purified flea esterase protein PfE9$_{528}$ had both juvenile hormone esterase activity and carboxylesterase activity.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated nucleic acid molecule selected from the group consisting of: (a) a nucleic acid molecule that encodes a protein selected from the group consisting of SEQ ID NO:68 and proteins that are at least 95% identical to SEQ ID NO:68, wherein said protein exhibits carboxylesterase activity; and (b) an isolated nucleic acid molecule fully complementary to a nucleic acid molecule of (a).

2. The nucleic acid molecule of claim 1, wherein said nucleic acid molecule encodes a protein comprising an amino acid sequence SEQ ID NO:68.

3. The nucleic acid molecule of claim 1, wherein said nucleic acid molecule is selected from the group consisting of: SEQ ID NO:67, SEQ ID NO:69, SEQ ID NO:70, and SEQ ID NO:71.

4. A recombinant molecule comprising a nucleic acid molecule as set forth in claim 1 operatively linked to a transcription control sequence.

5. A recombinant virus comprising a nucleic acid molecule as set forth in claim 1.

6. A recombinant cell comprising a nucleic acid molecule as set forth in claim 1.

7. A method to produce a carboxylesterase protein, said method comprising culturing a cell capable of expressing said protein, said protein being encoded by a nucleic acid molecule of claim 1, part (a).

8. An isolated protein comprising an amino acid sequence selected from the group consisting of SEQ ID NO:68 and an amino acid sequence 95% identical to SEQ ID NO:68, wherein said isolated protein has carboxylesterase activity.

9. The protein of claim 8, wherein said protein, when administered to an animal, elicits an immune response against a carboxylesterase protein.

10. The protein of claim 8, wherein said protein is encoded by a nucleic acid molecule selected from the group consisting of: SEQ ID NO:67 and SEQ ID NO:70.

11. A method to identify a compound capable of inhibiting flea carboxylesterase activity, said method comprising:
   (a) contacting an isolated flea carboxylesterase protein of claim 8 with a putative inhibitory compound under conditions in which, in the absence of said compound, said protein has carboxylesterase activity; and
   (b) determining if said putative inhibitory compound inhibits said activity.

12. A test kit to identify a compound capable of inhibiting flea carboxylesterase activity, said test kit comprising an isolated flea carboxylesterase protein of claim 8 having esterase activity and a means for determining the extent of inhibition of said activity in the presence of a putative inhibitory compound.

* * * * *

SEQUENCE LISTING

<160> NUMBER OF SEQ ID NOS: 76

<210> SEQ ID NO 1
<211> LENGTH: 401
<212> TYPE: DNA
<213> ORGANISM: Ctenocephalides felis
<220> FEATURE:
<221> NAME/KEY: CDS
<222> LOCATION: (92)..(400)
<223> OTHER INFORMATION:
<220> FEATURE:
<221> NAME/KEY: misc_feature
<222> LOCATION: (219)..(219)
<223> OTHER INFORMATION: At nucleotide 219, n = unknown
    At amino acid residue 43, Xaa = Ile, Thr, Lys or Arg
<220> FEATURE:
<221> NAME/KEY: misc_feature
<222> LOCATION: (275)..(275)
<223> OTHER INFORMATION: At nucleotide 275, n = unknown
    At amino acid residue 62, Xaa = Gln, Glu or Lys
<220> FEATURE:
<221> NAME/KEY: misc_feature
<222> LOCATION: (329)..(329)
<223> OTHER INFORMATION: At nucleotide 329, n = unknown
    At amino acid residue 80, Xaa = Gln, Glu or Lys
<220> FEATURE:
<221> NAME/KEY: misc_feature
<222> LOCATION: (332)..(332)
<223> OTHER INFORMATION: At nucleotide 332, n = unknown
    At amino acid residue 81, Xaa = Tyr, His, Asn or Asp
<220> FEATURE:
<221> NAME/KEY: misc_feature
<222> LOCATION: (352)..(352)
<223> OTHER INFORMATION: At nucleotide 352, n = unknown

<400> SEQUENCE: 1

```
tttacatcat taataaacat aaatctaata aatcttgtgg atcaagatca agtttattag      60
tgagagtgtt ggatttgtga aatatttcaa a atg aat tct tta att gta aaa       112
                                  Met Asn Ser Leu Ile Val Lys
                                   1               5
att tct caa gga gct att gag ggg aag gaa atg att aat gat aat gga      160
Ile Ser Gln Gly Ala Ile Glu Gly Lys Glu Met Ile Asn Asp Asn Gly
        10                  15                  20
aag tcg ttt aga gga ttt ttg ggt ata cct tat gct aaa ccg cct ata      208
Lys Ser Phe Arg Gly Phe Leu Gly Ile Pro Tyr Ala Lys Pro Pro Ile
 25                  30                  35
gga aat ctt ana ttt aag cct cct caa aag cct gat gat tgg aat gat      256
Gly Asn Leu Xaa Phe Lys Pro Pro Gln Lys Pro Asp Asp Trp Asn Asp
 40                  45                  50                  55
gtt cga cca gct act gaa naa gca aat ggt tgt aga tcg aaa cat atg      304
Val Arg Pro Ala Thr Glu Xaa Ala Asn Gly Cys Arg Ser Lys His Met
                 60                  65                  70
ctg cag cat cat att att gga gac naa nat tgt cta tac cta aac gtn      352
Leu Gln His His Ile Ile Gly Asp Xaa Xaa Cys Leu Tyr Leu Asn Val
             75                  80                  85
tat gtt cca ttg act tcc aaa ttg gag aaa cta cca gta atg ttc tgg g    401
Tyr Val Pro Leu Thr Ser Lys Leu Glu Lys Leu Pro Val Met Phe Trp
         90                  95                 100
```

<210> SEQ ID NO 2
<211> LENGTH: 103
<212> TYPE: PRT
<213> ORGANISM: Ctenocephalides felis
<220> FEATURE:
<221> NAME/KEY: misc_feature
<222> LOCATION: (43)..(43)
<223> OTHER INFORMATION: The 'Xaa' at location 43 stands for Lys, Arg,
    Thr, or Ile.

```
<220> FEATURE:
<221> NAME/KEY: misc_feature
<222> LOCATION: (62)..(62)
<223> OTHER INFORMATION: The 'Xaa' at location 62 stands for Lys, Glu,
      Gln.
<220> FEATURE:
<221> NAME/KEY: misc_feature
<222> LOCATION: (80)..(80)
<223> OTHER INFORMATION: The 'Xaa' at location 80 stands for Lys, Glu,
      Gln.
<220> FEATURE:
<221> NAME/KEY: misc_feature
<222> LOCATION: (81)..(81)
<223> OTHER INFORMATION: The 'Xaa' at location 81 stands for Asn, Asp,
      His, or Tyr.

<400> SEQUENCE: 2
```

Met Asn Ser Leu Ile Val Lys Ile Ser Gln Gly Ala Ile Glu Gly Lys
1               5                   10                  15

Glu Met Ile Asn Asp Asn Gly Lys Ser Phe Arg Gly Phe Leu Gly Ile
            20                  25                  30

Pro Tyr Ala Lys Pro Pro Ile Gly Asn Leu Xaa Phe Lys Pro Pro Gln
        35                  40                  45

Lys Pro Asp Asp Trp Asn Asp Val Arg Pro Ala Thr Glu Xaa Ala Asn
    50                  55                  60

Gly Cys Arg Ser Lys His Met Leu Gln His His Ile Ile Gly Asp Xaa
65                  70                  75                  80

Xaa Cys Leu Tyr Leu Asn Val Tyr Val Pro Leu Thr Ser Lys Leu Glu
                85                  90                  95

Lys Leu Pro Val Met Phe Trp
                100

```
<210> SEQ ID NO 3
<211> LENGTH: 401
<212> TYPE: DNA
<213> ORGANISM: Ctenocephalides felis
<220> FEATURE:
<221> NAME/KEY: misc_feature
<222> LOCATION: (50)..(50)
<223> OTHER INFORMATION: n = unknown
<220> FEATURE:
<221> NAME/KEY: misc_feature
<222> LOCATION: (70)..(70)
<223> OTHER INFORMATION: n = unknown
<220> FEATURE:
<221> NAME/KEY: misc_feature
<222> LOCATION: (73)..(73)
<223> OTHER INFORMATION: n = unknown
<220> FEATURE:
<221> NAME/KEY: misc_feature
<222> LOCATION: (127)..(127)
<223> OTHER INFORMATION: n = unknown
<220> FEATURE:
<221> NAME/KEY: misc_feature
<222> LOCATION: (183)..(183)
<223> OTHER INFORMATION: n = unknown

<400> SEQUENCE: 3
cccagaacat tactggtagt ttctccaatt tggaagtcaa tggaacatan acgtttaggt      60
atagacaatn ttngtctcca ataatatgat gctgcagcat atgtttcgat ctacaaccat    120
ttgcttnttc agtagctggt cgaacatcat tccaatcatc aggctttttga ggaggcttaa   180 atntaagatt tcctataggc ggtttagcat aaggtatacc caaaaatcct ctaaacgact    240
ttccattatc attaatcatt tccttcccct caatagctcc ttgagaaatt tttacaatta    300
aagaattcat tttgaaatat ttcacaaatc caacactctc actaataaac ttgatcttga    360
```
tccacaagat ttattagatt tatgtttatt aatgatgtaa a                                401

<210> SEQ ID NO 4
<211> LENGTH: 364
<212> TYPE: DNA
<213> ORGANISM: Ctenocephalides felis
<220> FEATURE:
<221> NAME/KEY: CDS
<222> LOCATION: (2)..(364)
<223> OTHER INFORMATION:

<400> SEQUENCE: 4

```
g tct cgt gtt att ttt tta agt tgt att ttt ttg ttt agt ttt aat ttt          49
  Ser Arg Val Ile Phe Leu Ser Cys Ile Phe Leu Phe Ser Phe Asn Phe
  1               5                  10                  15 ata aac tgt gat tcc ccg act gta act ttg ccc caa ggc gaa ttg gtt            97
Ile Asn Cys Asp Ser Pro Thr Val Thr Leu Pro Gln Gly Glu Leu Val
            20                  25                  30 gga aaa gct ttg acg aac gaa aat gga aaa gag tat ttt agc tac aca           145
Gly Lys Ala Leu Thr Asn Glu Asn Gly Lys Glu Tyr Phe Ser Tyr Thr
        35                  40                  45 ggt gta cct tat gct aaa cct cct gtt gga gaa ctt aga ttt aag cct           193
Gly Val Pro Tyr Ala Lys Pro Pro Val Gly Glu Leu Arg Phe Lys Pro
    50                  55                  60 cca cag aaa gct gag cca tgg caa ggt gtt ttc aac gcc aca tta tac           241
Pro Gln Lys Ala Glu Pro Trp Gln Gly Val Phe Asn Ala Thr Leu Tyr
65                  70                  75                  80 gga aat gtg tgt aaa tct tta aat ttc ttc ttg aag aaa att gaa gga           289
Gly Asn Val Cys Lys Ser Leu Asn Phe Phe Leu Lys Lys Ile Glu Gly
                85                  90                  95 gac gaa gac tgc ttg gta gta aac gtg tac gca cca aaa aca act tct           337
Asp Glu Asp Cys Leu Val Val Asn Val Tyr Ala Pro Lys Thr Thr Ser
            100                 105                 110 gat aaa aaa ctt cca gta ttt ttc tgg                                        364
Asp Lys Lys Leu Pro Val Phe Phe Trp
        115                 120
```

<210> SEQ ID NO 5
<211> LENGTH: 121
<212> TYPE: PRT
<213> ORGANISM: Ctenocephalides felis

<400> SEQUENCE: 5

```
Ser Arg Val Ile Phe Leu Ser Cys Ile Phe Leu Phe Ser Phe Asn Phe
1               5                  10                  15

Ile Asn Cys Asp Ser Pro Thr Val Thr Leu Pro Gln Gly Glu Leu Val
            20                  25                  30

Gly Lys Ala Leu Thr Asn Glu Asn Gly Lys Glu Tyr Phe Ser Tyr Thr
        35                  40                  45

Gly Val Pro Tyr Ala Lys Pro Pro Val Gly Glu Leu Arg Phe Lys Pro
    50                  55                  60

Pro Gln Lys Ala Glu Pro Trp Gln Gly Val Phe Asn Ala Thr Leu Tyr
65                  70                  75                  80

Gly Asn Val Cys Lys Ser Leu Asn Phe Phe Leu Lys Lys Ile Glu Gly
                85                  90                  95

Asp Glu Asp Cys Leu Val Val Asn Val Tyr Ala Pro Lys Thr Thr Ser
            100                 105                 110

Asp Lys Lys Leu Pro Val Phe Phe Trp
        115                 120
```

<210> SEQ ID NO 6
<211> LENGTH: 364
<212> TYPE: DNA
<213> ORGANISM: Ctenocephalides felis

<400> SEQUENCE: 6

```
ccagaaaaat actggaagtt ttttatcaga agttgttttt ggtgcgtaca cgtttactac      60
caagcagtct tcgtctcctt caattttctt caagaagaaa tttaaagatt tacacacatt     120
tccgtataat gtggcgttga aaacaccttg ccatggctca gctttctgtg gaggcttaaa     180
tctaagttct ccaacaggag gtttagcata aggtacacct gtgtagctaa aatactcttt     240
tccattttcg ttcgtcaaag cttttccaac caattcgcct tggggcaaag ttacagtcgg     300
ggaatcacag tttataaaat taaaactaaa caaaaaaata caacttaaaa aaataacacg     360
agac                                                                  364
```

<210> SEQ ID NO 7
<211> LENGTH: 421
<212> TYPE: DNA
<213> ORGANISM: Ctenocephalides felis
<220> FEATURE:
<221> NAME/KEY: CDS
<222> LOCATION: (113)..(421)
<223> OTHER INFORMATION:

<400> SEQUENCE: 7

```
tttacattac atcaaatcat attttatta gtatattttt tagaagaacc tagccaaaaa       60
atatggactt tagactgtga ttaatttatt ttacctgaga ttttcctta ca atg ggt      118
                                                         Met Gly
                                                           1 gat ctt caa gtg act ttg tta caa ggt tct ttg aga gga aaa gag caa       166
Asp Leu Gln Val Thr Leu Leu Gln Gly Ser Leu Arg Gly Lys Glu Gln
        5                   10                  15 att aat gaa aag gga aat gtg ttt tat agt tat tct gga att cca tat       214
Ile Asn Glu Lys Gly Asn Val Phe Tyr Ser Tyr Ser Gly Ile Pro Tyr
 20                  25                  30 gcc aaa cct cca gtt ggt gat cta aga ttc aag cca cct caa cct gca       262
Ala Lys Pro Pro Val Gly Asp Leu Arg Phe Lys Pro Pro Gln Pro Ala
 35                  40                  45                  50 gaa cct tgg tca ggt gtc ctt gat gct act aaa gaa ggg aat agt tgt       310
Glu Pro Trp Ser Gly Val Leu Asp Ala Thr Lys Glu Gly Asn Ser Cys
                55                  60                  65 aga tct gta cat ttt att aaa aag att aaa gta ggg gct gaa gat tgt       358
Arg Ser Val His Phe Ile Lys Lys Ile Lys Val Gly Ala Glu Asp Cys
                    70                  75                  80 cta tac ctc aat gtc tat gta cca aaa aca tca gag aaa tcc ctt ctt       406
Leu Tyr Leu Asn Val Tyr Val Pro Lys Thr Ser Glu Lys Ser Leu Leu
     85                  90                  95 cca gta atg gta tgg                                                   421
Pro Val Met Val Trp
        100
```

<210> SEQ ID NO 8
<211> LENGTH: 103
<212> TYPE: PRT
<213> ORGANISM: Ctenocephalides felis

<400> SEQUENCE: 8

```
Met Gly Asp Leu Gln Val Thr Leu Leu Gln Gly Ser Leu Arg Gly Lys
  1               5                  10                  15

Glu Gln Ile Asn Glu Lys Gly Asn Val Phe Tyr Ser Tyr Ser Gly Ile
```

|  | 20 |  |  |  | 25 |  |  |  | 30 |  |  |
|---|---|---|---|---|---|---|---|---|---|---|---|
| Pro | Tyr | Ala | Lys | Pro | Val | Gly | Asp | Leu | Arg | Phe | Lys | Pro | Pro | Gln |
|  |  | 35 |  |  |  | 40 |  |  |  | 45 |  |  |  |  |

| Pro | Ala | Glu | Pro | Trp | Ser | Gly | Val | Leu | Asp | Ala | Thr | Lys | Glu | Gly | Asn |
|---|---|---|---|---|---|---|---|---|---|---|---|---|---|---|---|
|  | 50 |  |  |  |  | 55 |  |  |  |  | 60 |  |  |  |  |

| Ser | Cys | Arg | Ser | Val | His | Phe | Ile | Lys | Lys | Ile | Lys | Val | Gly | Ala | Glu |
|---|---|---|---|---|---|---|---|---|---|---|---|---|---|---|---|
| 65 |  |  |  |  | 70 |  |  |  |  | 75 |  |  |  |  | 80 |

| Asp | Cys | Leu | Tyr | Leu | Asn | Val | Tyr | Val | Pro | Lys | Thr | Ser | Glu | Lys | Ser |
|---|---|---|---|---|---|---|---|---|---|---|---|---|---|---|---|
|  |  |  |  | 85 |  |  |  |  | 90 |  |  |  |  | 95 |  |

| Leu | Leu | Pro | Val | Met | Val | Trp |
|---|---|---|---|---|---|---|
|  |  |  |  | 100 |  |  |

<210> SEQ ID NO 9
<211> LENGTH: 421
<212> TYPE: DNA
<213> ORGANISM: Ctenocephalides felis

<400> SEQUENCE: 9

| ccataccatt actggaagaa gggatttctc tgatgttttt ggtacataga cattgaggta | 60 |
|---|---|
| tagacaatct tcagccccta ctttaatctt tttaataaaa tgtacagatc tacaactatt | 120 |
| cccttcttta gtagcatcaa ggacacctga ccaaggttct gcaggttgag gtggcttgaa | 180 |
| tcttagatca ccaactggag gtttggcata tggaattcca gataactat aaaacacatt | 240 |
| tcccttttca ttaatttgct cttttcctct caaagaacct tgtaacaaag tcacttgaag | 300 |
| atcacccatt gtaaaggaaa atctcaggta aaataaatta atcacagtct aaagtccata | 360 |
| ttttttggct aggttcttct aaaaaatata ctaataaaaa tatgatttga tgtaatgtaa | 420 |
| a | 421 |

<210> SEQ ID NO 10
<211> LENGTH: 524
<212> TYPE: DNA
<213> ORGANISM: Ctenocephalides felis
<220> FEATURE:
<221> NAME/KEY: CDS
<222> LOCATION: (113)..(523)
<223> OTHER INFORMATION:

<400> SEQUENCE: 10

| gaacgttgat acgatagaca tgtcgtcttc aaaacgtcta ttttatcata aacaaaacga | 60 |
|---|---|
| gataaataat aacaattaag caaccaaaat gcattaaaaa acacaataaa aa atg tta | 118 |
|  | Met Leu |
|  | 1 |

| cct cac agt agt gca tta gtt tta ttt tta ttt ttt tta ttt ttc tta | 166 |
|---|---|
| Pro His Ser Ser Ala Leu Val Leu Phe Leu Phe Phe Leu Phe Phe Leu |  |
| 5 | 10 | 15 |

| ttt aca cct atc ttg tgc ata cta tgg gat aac cta gat cag cat ttg | 214 |
|---|---|
| Phe Thr Pro Ile Leu Cys Ile Leu Trp Asp Asn Leu Asp Gln His Leu |  |
| 20 | 25 | 30 |

| tgc aga gtt caa ttt aac agg atc acg gaa gga aaa ccg ttc cga tat | 262 |
|---|---|
| Cys Arg Val Gln Phe Asn Arg Ile Thr Glu Gly Lys Pro Phe Arg Tyr |  |
| 35 | 40 | 45 | 50 |

| aaa gat cat agg aat gat gta tat tgt tct tat ttg gga att cct tat | 310 |
|---|---|
| Lys Asp His Arg Asn Asp Val Tyr Cys Ser Tyr Leu Gly Ile Pro Tyr |  |
| 55 | 60 | 65 |

| gcc gaa ccg cct att gga cca tta cga ttt cag tct cca aaa cca ata | 358 |
|---|---|
| Ala Glu Pro Pro Ile Gly Pro Leu Arg Phe Gln Ser Pro Lys Pro Ile |  |
| 70 | 75 | 80 |

```
tca aat cca aaa aca gga ttc gta cag gct cga act ttg gga gac aaa    406
Ser Asn Pro Lys Thr Gly Phe Val Gln Ala Arg Thr Leu Gly Asp Lys
        85                  90                  95 tgt ttc cag gaa agt cta ata tat tct tat gca gga agc gaa gat tgc    454
Cys Phe Gln Glu Ser Leu Ile Tyr Ser Tyr Ala Gly Ser Glu Asp Cys
    100                 105                 110 tta tat ctg aat ata ttc acg cca gag act gtt aat tct gcg aac aat    502
Leu Tyr Leu Asn Ile Phe Thr Pro Glu Thr Val Asn Ser Ala Asn Asn
115                 120                 125                 130 aca aaa tat cct gta atg ttc t                                      524
Thr Lys Tyr Pro Val Met Phe
                135
```

<210> SEQ ID NO 11
<211> LENGTH: 137
<212> TYPE: PRT
<213> ORGANISM: Ctenocephalides felis

<400> SEQUENCE: 11

```
Met Leu Pro His Ser Ser Ala Leu Val Leu Phe Leu Phe Phe Leu Phe
1               5                   10                  15

Phe Leu Phe Thr Pro Ile Leu Cys Ile Leu Trp Asp Asn Leu Asp Gln
            20                  25                  30

His Leu Cys Arg Val Gln Phe Asn Arg Ile Thr Glu Gly Lys Pro Phe
        35                  40                  45

Arg Tyr Lys Asp His Arg Asn Asp Val Tyr Cys Ser Tyr Leu Gly Ile
50                  55                  60

Pro Tyr Ala Glu Pro Pro Ile Gly Pro Leu Arg Phe Gln Ser Pro Lys
65                  70                  75                  80

Pro Ile Ser Asn Pro Lys Thr Gly Phe Val Gln Ala Arg Thr Leu Gly
                85                  90                  95

Asp Lys Cys Phe Gln Glu Ser Leu Ile Tyr Ser Tyr Ala Gly Ser Glu
            100                 105                 110

Asp Cys Leu Tyr Leu Asn Ile Phe Thr Pro Glu Thr Val Asn Ser Ala
        115                 120                 125

Asn Asn Thr Lys Tyr Pro Val Met Phe
    130                 135
```

<210> SEQ ID NO 12
<211> LENGTH: 524
<212> TYPE: DNA
<213> ORGANISM: Ctenocephalides felis

<400> SEQUENCE: 12

```
agaacattac aggatatttt gtattgttcg cagaattaac agtctctggc gtgaatatat    60
tcagatataa gcaatcttcg cttcctgcat aagaatatat tagactttcc tggaaacatt   120
tgtctcccaa agtcgagcc tgtacgaatc ctgtttttgg atttgatatt ggttttggag    180
actgaaatcg taatggtcca ataggcggtt cggcataagg aattcccaaa taagaacaat   240
atacatcatt cctatgatct ttatatcgga acggttttcc ttccgtgatc ctgttaaatt   300
gaactctgca caaatgctga tctaggttat cccatagtat gcacaagata ggtgtaaata   360
agaaaaataa aaaaaataaa aataaaacta atgcactact gtgaggtaac attttttatt   420
gtgttttta atgcattttg gttgcttaat tgttattatt tatctcgttt gtttatgat    480
aaaatagacg ttttgaagac gacatgtcta tcgtatcaac gttc                   524
```

<210> SEQ ID NO 13

```
<211> LENGTH: 1982
<212> TYPE: DNA
<213> ORGANISM: Ctenocephalides felis
<220> FEATURE:
<221> NAME/KEY: CDS
<222> LOCATION: (3)..(1517)
<223> OTHER INFORMATION:
<220> FEATURE:
<221> NAME/KEY: misc_feature
<222> LOCATION: (300)..(300)
<223> OTHER INFORMATION: At nucleotide 300, r = a or g
      At amino acid residue 100, Xaa = Asn or Asp

<400> SEQUENCE: 13
```

| | | | | | | | | | | | | | | | |
|---|---|---|---|---|---|---|---|---|---|---|---|---|---|---|---|
| at ttt agc tac aca ggt gta cct tat gct aaa cct cct gtt gga gaa | | | | | | | | | | | | | | | 47 |
| Phe Ser Tyr Thr Gly Val Pro Tyr Ala Lys Pro Pro Val Gly Glu | | | | | | | | | | | | | | | |
| 1 | | | 5 | | | | 10 | | | | | 15 | | | |

```
ctt aga ttt aag cct cca cag aaa gct gag cca tgg caa ggt gtt ttc      95
Leu Arg Phe Lys Pro Pro Gln Lys Ala Glu Pro Trp Gln Gly Val Phe
             20                  25                  30 aac gcc aca tta tac gga aat gtg tgt aaa tct tta aat ttc ttc ttg      143
Asn Ala Thr Leu Tyr Gly Asn Val Cys Lys Ser Leu Asn Phe Phe Leu
         35                  40                  45 aag aaa att gaa gga gac gaa gac tgc ttg gta gta aac gtg tac gca      191
Lys Lys Ile Glu Gly Asp Glu Asp Cys Leu Val Val Asn Val Tyr Ala
     50                  55                  60 cca aaa aca act tct gat aaa aaa ctt cca gta ttt ttc tgg gtt cat      239
Pro Lys Thr Thr Ser Asp Lys Lys Leu Pro Val Phe Phe Trp Val His
 65                  70                  75 ggt ggt ggt ttt gtg act gga tcc gga aat tta gaa ttc caa agc cca      287
Gly Gly Gly Phe Val Thr Gly Ser Gly Asn Leu Glu Phe Gln Ser Pro
 80                  85                  90                  95 gat tat tta gta rat ttt gat gtt att ttc gta act ttc aat tac cga      335
Asp Tyr Leu Val Xaa Phe Asp Val Ile Phe Val Thr Phe Asn Tyr Arg
                100                 105                 110 ttg gga cct ctc gga ttt ctg aat ttg gag ttg gag ggt gct cca gga      383
Leu Gly Pro Leu Gly Phe Leu Asn Leu Glu Leu Glu Gly Ala Pro Gly
             115                 120                 125 aat gta gga tta ttg gat cag gtg gca gct ctg aaa tgg acc aaa gaa      431
Asn Val Gly Leu Leu Asp Gln Val Ala Ala Leu Lys Trp Thr Lys Glu
         130                 135                 140 aac att gag aaa ttt ggt gga gat cca gaa aat att aca att ggt ggt      479
Asn Ile Glu Lys Phe Gly Gly Asp Pro Glu Asn Ile Thr Ile Gly Gly
     145                 150                 155 gtt tct gct ggt gga gca agt gtt cat tat ctt ttg tta tct cat aca      527
Val Ser Ala Gly Gly Ala Ser Val His Tyr Leu Leu Leu Ser His Thr
 160                 165                 170                 175 acc act gga ctt tac aaa agg gca att gct caa agt gga agt gct ttt      575
Thr Thr Gly Leu Tyr Lys Arg Ala Ile Ala Gln Ser Gly Ser Ala Phe
                 180                 185                 190 aat cca tgg gcc ttc caa aga cat cca gta aag cgt agt ctt caa ctt      623
Asn Pro Trp Ala Phe Gln Arg His Pro Val Lys Arg Ser Leu Gln Leu
             195                 200                 205 gct gag ata ttg ggt cat ccc aca aac aat act caa gat gct tta gaa      671
Ala Glu Ile Leu Gly His Pro Thr Asn Asn Thr Gln Asp Ala Leu Glu
         210                 215                 220 ttc tta caa aaa gcc ccc gta gac agt ctc ctg aag aaa atg cca gct      719
Phe Leu Gln Lys Ala Pro Val Asp Ser Leu Leu Lys Lys Met Pro Ala
     225                 230                 235 gaa aca gaa ggt gaa ata ata gaa gag ttt gtc ttc gta cca tca att      767
Glu Thr Glu Gly Glu Ile Ile Glu Glu Phe Val Phe Val Pro Ser Ile
 240                 245                 250                 255
```

-continued

| | |
|---|---|
| gaa aaa gtt ttc cca tcc cac caa cct ttc ttg gaa gaa tca cca ttg<br>Glu Lys Val Phe Pro Ser His Gln Pro Phe Leu Glu Glu Ser Pro Leu<br>260                  265                 270 | 815 |
| gcc aga atg aaa tcc gga tcc ttt aac aaa gta cct tta tta gtt gga<br>Ala Arg Met Lys Ser Gly Ser Phe Asn Lys Val Pro Leu Leu Val Gly<br>275                  280                 285 | 863 |
| ttt aac agt gca gaa gga ctt ttg ttc aaa ttc ttc atg aaa gaa aaa<br>Phe Asn Ser Ala Glu Gly Leu Leu Phe Lys Phe Phe Met Lys Glu Lys<br>290                  295                 300 | 911 |
| cca gag atg ctg aac caa gct gaa gca gat ttt gaa aga ctc gta cca<br>Pro Glu Met Leu Asn Gln Ala Glu Ala Asp Phe Glu Arg Leu Val Pro<br>305                  310                 315 | 959 |
| gcc gaa ttt gaa tta gtc cat gga tca gag gaa tcg aaa aaa ctt gca<br>Ala Glu Phe Glu Leu Val His Gly Ser Glu Glu Ser Lys Lys Leu Ala<br>320                  325                 330                 335 | 1007 |
| gaa aaa atc agg aag ttt tac ttt gac gat aaa ccc gtt cca gaa aat<br>Glu Lys Ile Arg Lys Phe Tyr Phe Asp Asp Lys Pro Val Pro Glu Asn<br>340                  345                 350 | 1055 |
| gaa cag aaa ttt att gac ttg ata gga gat att tgg ttt act aga ggt<br>Glu Gln Lys Phe Ile Asp Leu Ile Gly Asp Ile Trp Phe Thr Arg Gly<br>355                  360                 365 | 1103 |
| gtt gac aag cat gtc aag ttg tct gtg gag aaa caa gac gaa cca gtt<br>Val Asp Lys His Val Lys Leu Ser Val Glu Lys Gln Asp Glu Pro Val<br>370                  375                 380 | 1151 |
| tat tat tat gaa tat tcc ttc tcg gaa agt cat cct gca aaa gga aca<br>Tyr Tyr Tyr Glu Tyr Ser Phe Ser Glu Ser His Pro Ala Lys Gly Thr<br>385                  390                 395 | 1199 |
| ttt ggt gat cat aat ctg act ggt gca tgc cat gga gaa gaa ctt gtg<br>Phe Gly Asp His Asn Leu Thr Gly Ala Cys His Gly Glu Glu Leu Val<br>400                  405                 410                 415 | 1247 |
| aat tta ttc aaa gtc gag atg atg aag ctg gaa aaa gat aaa cct aat<br>Asn Leu Phe Lys Val Glu Met Met Lys Leu Glu Lys Asp Lys Pro Asn<br>420                  425                 430 | 1295 |
| gtt cta tta aca aaa gat aga gta ctt gcc atg tgg act aac ttc atc<br>Val Leu Leu Thr Lys Asp Arg Val Leu Ala Met Trp Thr Asn Phe Ile<br>435                  440                 445 | 1343 |
| aaa aat gga aat cct act cct gaa gta aca gaa tta ttg cca gtt aaa<br>Lys Asn Gly Asn Pro Thr Pro Glu Val Thr Glu Leu Leu Pro Val Lys<br>450                  455                 460 | 1391 |
| tgg gaa cct gcc aca aaa gac aag ttg aat tat ttg aac att gat gcc<br>Trp Glu Pro Ala Thr Lys Asp Lys Leu Asn Tyr Leu Asn Ile Asp Ala<br>465                  470                 475 | 1439 |
| acc tta act ttg gga aca aat cct gag gca aac cga gtc aaa ttt tgg<br>Thr Leu Thr Leu Gly Thr Asn Pro Glu Ala Asn Arg Val Lys Phe Trp<br>480                  485                 490                 495 | 1487 |
| gaa gac gcc aca aaa tct ttg cac ggt caa taataattta tgaaaattgt<br>Glu Asp Ala Thr Lys Ser Leu His Gly Gln<br>500                  505 | 1537 |
| tttaaatact ttaggtaata tattaggtaa ataaaaatta aaaataaca atttttatgt | 1597 |
| tttatgtatt ggcttatgtg tatcagttct aattttattt atttattctt gttttgcttg | 1657 |
| ttttgaaata tcatggtttt aatttcaaa acacaacgtc gtttgttttt agcaaaattt | 1717 |
| ccaatagata tgttatatta agtactctga agtattttta tatatacact aaaatcagta | 1777 |
| aaaatacatt aactaaaaat ataagatatt ttcaataatt tttttaaag aaaataccaa | 1837 |
| aaataaagta aaattccaaa cggaattttt gtttaactta aaaataaaat taactcttca | 1897 |
| ataattttga taattagtat ttctgatatc attagtgaaa attatatttt gataatacgt | 1957 |
| atttatattt aaaataaaat tatgt | 1982 |

<210> SEQ ID NO 14
<211> LENGTH: 505
<212> TYPE: PRT
<213> ORGANISM: Ctenocephalides felis
<220> FEATURE:
<221> NAME/KEY: misc_feature
<222> LOCATION: (100)..(100)
<223> OTHER INFORMATION: The 'Xaa' at location 100 stands for Asp, or Asn.

<400> SEQUENCE: 14

```
Phe Ser Tyr Thr Gly Val Pro Tyr Ala Lys Pro Pro Val Gly Glu Leu
 1               5                  10                  15

Arg Phe Lys Pro Pro Gln Lys Ala Glu Pro Trp Gln Gly Val Phe Asn
            20                  25                  30

Ala Thr Leu Tyr Gly Asn Val Cys Lys Ser Leu Asn Phe Phe Leu Lys
        35                  40                  45

Lys Ile Glu Gly Asp Glu Asp Cys Leu Val Val Asn Val Tyr Ala Pro
    50                  55                  60

Lys Thr Thr Ser Asp Lys Lys Leu Pro Val Phe Phe Trp Val His Gly
65                  70                  75                  80

Gly Gly Phe Val Thr Gly Ser Gly Asn Leu Glu Phe Gln Ser Pro Asp
                85                  90                  95

Tyr Leu Val Xaa Phe Asp Val Ile Phe Val Thr Phe Asn Tyr Arg Leu
            100                 105                 110

Gly Pro Leu Gly Phe Leu Asn Leu Glu Leu Glu Gly Ala Pro Gly Asn
        115                 120                 125

Val Gly Leu Leu Asp Gln Val Ala Ala Leu Lys Trp Thr Lys Glu Asn
    130                 135                 140

Ile Glu Lys Phe Gly Gly Asp Pro Glu Asn Ile Thr Ile Gly Gly Val
145                 150                 155                 160

Ser Ala Gly Gly Ala Ser Val His Tyr Leu Leu Ser His Thr Thr
                165                 170                 175

Thr Gly Leu Tyr Lys Arg Ala Ile Ala Gln Ser Gly Ser Ala Phe Asn
            180                 185                 190

Pro Trp Ala Phe Gln Arg His Pro Val Lys Arg Ser Leu Gln Leu Ala
        195                 200                 205

Glu Ile Leu Gly His Pro Thr Asn Asn Thr Gln Asp Ala Leu Glu Phe
    210                 215                 220

Leu Gln Lys Ala Pro Val Asp Ser Leu Leu Lys Lys Met Pro Ala Glu
225                 230                 235                 240

Thr Glu Gly Glu Ile Ile Glu Glu Phe Val Phe Val Pro Ser Ile Glu
                245                 250                 255

Lys Val Phe Pro Ser His Gln Pro Phe Leu Glu Glu Ser Pro Leu Ala
            260                 265                 270

Arg Met Lys Ser Gly Ser Phe Asn Lys Val Pro Leu Leu Val Gly Phe
        275                 280                 285

Asn Ser Ala Glu Gly Leu Leu Phe Lys Phe Met Lys Glu Lys Pro
    290                 295                 300

Glu Met Leu Asn Gln Ala Glu Ala Asp Phe Glu Arg Leu Val Pro Ala
305                 310                 315                 320

Glu Phe Glu Leu Val His Gly Ser Glu Glu Ser Lys Lys Leu Ala Glu
                325                 330                 335

Lys Ile Arg Lys Phe Tyr Phe Asp Asp Lys Pro Val Pro Glu Asn Glu
            340                 345                 350
```

```
Gln Lys Phe Ile Asp Leu Ile Gly Asp Ile Trp Phe Thr Arg Gly Val
        355                 360                 365

Asp Lys His Val Lys Leu Ser Val Glu Lys Gln Asp Glu Pro Val Tyr
370                 375                 380

Tyr Tyr Glu Tyr Ser Phe Ser Glu Ser His Pro Ala Lys Gly Thr Phe
385                 390                 395                 400

Gly Asp His Asn Leu Thr Gly Ala Cys His Gly Glu Leu Val Asn
                405                 410                 415

Leu Phe Lys Val Glu Met Met Lys Leu Glu Lys Asp Lys Pro Asn Val
                420                 425                 430

Leu Leu Thr Lys Asp Arg Val Leu Ala Met Trp Thr Asn Phe Ile Lys
                435                 440                 445

Asn Gly Asn Pro Thr Pro Glu Val Thr Glu Leu Leu Pro Val Lys Trp
        450                 455                 460

Glu Pro Ala Thr Lys Asp Lys Leu Asn Tyr Leu Asn Ile Asp Ala Thr
465                 470                 475                 480

Leu Thr Leu Gly Thr Asn Pro Glu Ala Asn Arg Val Lys Phe Trp Glu
                485                 490                 495

Asp Ala Thr Lys Ser Leu His Gly Gln
                500                 505

<210> SEQ ID NO 15
<211> LENGTH: 1982
<212> TYPE: DNA
<213> ORGANISM: Ctenocephalides felis

<400> SEQUENCE: 15
acataatttt attttaaata taaatacgta ttatcaaaat ataattttca ctaatgatat     60
cagaaatact aattatcaaa attattgaag agttaatttt atttttaagt taaacaaaaa    120
ttccgtttgg aattttactt tattttggt attttcttta aaaaaaatta ttgaaaatat    180
cttatatttt tagttaatgt attttttactg atttagtgt atatataaaa atacttcaga    240
gtacttaata taacatatct attggaaatt ttgctaaaaa caaacgacgt tgtgttttga    300 aaattaaaaac catgatattt caaacaagc aaaacaagaa taaataaata aaattagaac    360
tgatacacat aagccaatac ataaaacata aaaattgtta tttttaatt tttatttacc    420 taatatatta cctaaagtat ttaaaacaat tttcataaat tattattgac cgtgcaaaga    480
ttttgtggcg tcttcccaaa atttgactcg gtttgcctca ggatttgttc ccaaagttaa    540
ggtggcatca atgttcaaat aattcaactt gtcttttgtg gcaggttccc atttaactgg    600
caataattct gttacttcag gagtaggatt tccattttg atgaagttag tccacatggc    660
aagtactcta tcttttgtta atagaacatt aggtttatct ttttccagct tcatcatctc    720
gactttgaat aaattcacaa gttcttctcc atggcatgca ccagtcagat tatgatcacc    780
aaatgttcct tttgcaggat gactttccga gaaggaatat tcataataat aaactggttc    840
gtcttgtttc tccacagaca acttgacatg cttgtcaaca cctctagtaa accaaatatc    900
tcctatcaag tcaataaatt tctgttcatt ttctggaacg ggtttatcgt caaagtaaaa    960
cttcctgatt ttttctgcaa gttttttcga ttcctctgat ccatggacta attcaaattc   1020
ggctggtacg agtctttcaa aatctgcttc agcttggttc agcatctctg ttttttcttt   1080
catgaagaat ttgaacaaaa gtccttctgc actgttaaat ccaactaata aagtactttt   1140
gttaaaggat ccggatttca ttctggccaa tggtgattct tccaagaaag gttggtggga   1200
```

```
tgggaaaact ttttcaattg atggtacgaa gacaaactct tctattattt caccttctgt    1260
ttcagctggc atttcttca ggagactgtc tacgggggct ttttgtaaga attctaaagc    1320
atcttgagta ttgtttgtgg gatgacccaa tatctcagca agttgaagac tacgctttac    1380
tggatgtctt tggaaggccc atggattaaa agcacttcca ctttgagcaa ttgcccttt    1440 gtaaagtcca gtggttgtat gagataacaa aagataatga acacttgctc caccagcaga    1500
aacaccacca attgtaatat tttctggatc tccaccaaat ttctcaatgt tttctttggt    1560
ccatttcaga gctgccacct gatccaataa tcctacattt cctggagcac cctccaactc    1620
caaattcaga aatccgagag gtcccaatcg gtaattgaaa gttacgaaaa taacatcaaa    1680
atytactaaa taatctgggc tttggaattc taaatttccg gatccagtca caaaccacc    1740 accatgaacc cagaaaaata ctggaagttt tttatcagaa gttgttttg gtgcgtacac    1800 gtttactacc aagcagtctt cgtctccttc aattttcttc aagaagaaat ttaaagattt    1860
acacacattt ccgtataatg tggcgttgaa acaccttgc catggctcag ctttctgtgg    1920
aggcttaaat ctaagttctc caacaggagg tttagcataa ggtacacctg tgtagctaaa    1980
at                                                                    1982
```

<210> SEQ ID NO 16
<211> LENGTH: 1515
<212> TYPE: DNA
<213> ORGANISM: Ctenocephalides felis
<220> FEATURE:
<221> NAME/KEY: exon
<222> LOCATION: (1)..(1515)
<223> OTHER INFORMATION:
<220> FEATURE:
<221> NAME/KEY: misc_feature
<222> LOCATION: (298)..(298)
<223> OTHER INFORMATION: At nucleotide 298, r = a or g
      At amino acid residue 100, Xaa = Asn or Asp

<400> SEQUENCE: 16

```
ttt agc tac aca ggt gta cct tat gct aaa cct cct gtt gga gaa ctt       48
Phe Ser Tyr Thr Gly Val Pro Tyr Ala Lys Pro Pro Val Gly Glu Leu
1               5                  10                  15 aga ttt aag cct cca cag aaa gct gag cca tgg caa ggt gtt ttc aac       96
Arg Phe Lys Pro Pro Gln Lys Ala Glu Pro Trp Gln Gly Val Phe Asn
                20                  25                  30 gcc aca tta tac gga aat gtg tgt aaa tct tta aat ttc ttc ttg aag      144
Ala Thr Leu Tyr Gly Asn Val Cys Lys Ser Leu Asn Phe Phe Leu Lys
            35                  40                  45 aaa att gaa gga gac gaa gac tgc ttg gta gta aac gtg tac gca cca      192
Lys Ile Glu Gly Asp Glu Asp Cys Leu Val Val Asn Val Tyr Ala Pro
    50                  55                  60 aaa aca act tct gat aaa aaa ctt cca gta ttt ttc tgg gtt cat ggt      240
Lys Thr Thr Ser Asp Lys Lys Leu Pro Val Phe Phe Trp Val His Gly
65                  70                  75                  80 ggt ggt ttt gtg act gga tcc gga aat tta gaa ttc caa agc cca gat      288
Gly Gly Phe Val Thr Gly Ser Gly Asn Leu Glu Phe Gln Ser Pro Asp
                85                  90                  95 tat tta gta rat ttt gat gtt att ttc gta act ttc aat tac cga ttg      336
Tyr Leu Val Xaa Phe Asp Val Ile Phe Val Thr Phe Asn Tyr Arg Leu
                100                 105                 110 gga cct ctc gga ttt ctg aat ttg gag ttg gag ggt gct cca gga aat      384
Gly Pro Leu Gly Phe Leu Asn Leu Glu Leu Glu Gly Ala Pro Gly Asn
            115                 120                 125 gta gga tta ttg gat cag gtg gca gct ctg aaa tgg acc aaa gaa aac      432
Val Gly Leu Leu Asp Gln Val Ala Ala Leu Lys Trp Thr Lys Glu Asn
```

```
                130                 135                 140
att gag aaa ttt ggt gga gat cca gaa aat att aca att ggt ggt gtt      480
Ile Glu Lys Phe Gly Gly Asp Pro Glu Asn Ile Thr Ile Gly Gly Val
145                 150                 155                 160 tct gct ggt gga gca agt gtt cat tat ctt ttg tta tct cat aca acc      528
Ser Ala Gly Gly Ala Ser Val His Tyr Leu Leu Leu Ser His Thr Thr
                165                 170                 175 act gga ctt tac aaa agg gca att gct caa agt gga agt gct ttt aat      576
Thr Gly Leu Tyr Lys Arg Ala Ile Ala Gln Ser Gly Ser Ala Phe Asn
            180                 185                 190 cca tgg gcc ttc caa aga cat cca gta aag cgt agt ctt caa ctt gct      624
Pro Trp Ala Phe Gln Arg His Pro Val Lys Arg Ser Leu Gln Leu Ala
        195                 200                 205 gag ata ttg ggt cat ccc aca aac aat act caa gat gct tta gaa ttc      672
Glu Ile Leu Gly His Pro Thr Asn Asn Thr Gln Asp Ala Leu Glu Phe
    210                 215                 220 tta caa aaa gcc ccc gta gac agt ctc ctg aag aaa atg cca gct gaa      720
Leu Gln Lys Ala Pro Val Asp Ser Leu Leu Lys Lys Met Pro Ala Glu
225                 230                 235                 240 aca gaa ggt gaa ata ata gaa gag ttt gtc ttc gta cca tca att gaa      768
Thr Glu Gly Glu Ile Ile Glu Glu Phe Val Phe Val Pro Ser Ile Glu
                245                 250                 255 aaa gtt ttc cca tcc cac caa cct ttc ttg gaa gaa tca cca ttg gcc      816
Lys Val Phe Pro Ser His Gln Pro Phe Leu Glu Glu Ser Pro Leu Ala
            260                 265                 270 aga atg aaa tcc gga tcc ttt aac aaa gta cct tta tta gtt gga ttt      864
Arg Met Lys Ser Gly Ser Phe Asn Lys Val Pro Leu Leu Val Gly Phe
        275                 280                 285 aac agt gca gaa gga ctt ttg ttc aaa ttc ttc atg aaa gaa aaa cca      912
Asn Ser Ala Glu Gly Leu Leu Phe Lys Phe Phe Met Lys Glu Lys Pro
    290                 295                 300 gag atg ctg aac caa gct gaa gca gat ttt gaa aga ctc gta cca gcc      960
Glu Met Leu Asn Gln Ala Glu Ala Asp Phe Glu Arg Leu Val Pro Ala
305                 310                 315                 320 gaa ttt gaa tta gtc cat gga tca gag gaa tcg aaa aaa ctt gca gaa     1008
Glu Phe Glu Leu Val His Gly Ser Glu Glu Ser Lys Lys Leu Ala Glu
                325                 330                 335 aaa atc agg aag ttt tac ttt gac gat aaa ccc gtt cca gaa aat gaa     1056
Lys Ile Arg Lys Phe Tyr Phe Asp Asp Lys Pro Val Pro Glu Asn Glu
            340                 345                 350 cag aaa ttt att gac ttg ata gga gat att tgg ttt act aga ggt gtt     1104
Gln Lys Phe Ile Asp Leu Ile Gly Asp Ile Trp Phe Thr Arg Gly Val
        355                 360                 365 gac aag cat gtc aag ttg tct gtg gag aaa caa gac gaa cca gtt tat     1152
Asp Lys His Val Lys Leu Ser Val Glu Lys Gln Asp Glu Pro Val Tyr
    370                 375                 380 tat tat gaa tat tcc ttc tcg gaa agt cat cct gca aaa gga aca ttt     1200
Tyr Tyr Glu Tyr Ser Phe Ser Glu Ser His Pro Ala Lys Gly Thr Phe
385                 390                 395                 400 ggt gat cat aat ctg act ggt gca tgc cat gga gaa gaa ctt gtg aat     1248
Gly Asp His Asn Leu Thr Gly Ala Cys His Gly Glu Glu Leu Val Asn
                405                 410                 415 tta ttc aaa gtc gag atg atg aag ctg gaa aaa gat aaa cct aat gtt     1296
Leu Phe Lys Val Glu Met Met Lys Leu Glu Lys Asp Lys Pro Asn Val
            420                 425                 430 cta tta aca aaa gat aga gta ctt gcc atg tgg act aac ttc atc aaa     1344
Leu Leu Thr Lys Asp Arg Val Leu Ala Met Trp Thr Asn Phe Ile Lys
        435                 440                 445 aat gga aat cct act cct gaa gta aca gaa tta ttg cca gtt aaa tgg     1392
```

| | | | | | | | | | | | | |
|---|---|---|---|---|---|---|---|---|---|---|---|---|
| Asn | Gly | Asn | Pro | Thr | Pro | Glu | Val | Thr | Glu | Leu | Leu | Pro | Val | Lys | Trp |
| | | 450 | | | | 455 | | | | 460 | | | | gaa cct gcc aca aaa gac aag ttg aat tat ttg aac att gat gcc acc    1440
Glu Pro Ala Thr Lys Asp Lys Leu Asn Tyr Leu Asn Ile Asp Ala Thr
465             470              475              480 tta act ttg gga aca aat cct gag gca aac cga gtc aaa ttt tgg gaa    1488
Leu Thr Leu Gly Thr Asn Pro Glu Ala Asn Arg Val Lys Phe Trp Glu
            485              490              495 gac gcc aca aaa tct ttg cac ggt caa                                 1515
Asp Ala Thr Lys Ser Leu His Gly Gln
            500              505

<210> SEQ ID NO 17
<211> LENGTH: 1515
<212> TYPE: DNA
<213> ORGANISM: Ctenocephalides felis

<400> SEQUENCE: 17
ttgaccgtgc aaagattttg tggcgtcttc ccaaaatttg actcggtttg cctcaggatt    60
tgttcccaaa gttaaggtgg catcaatgtt caaataattc aacttgtctt ttgtggcagg   120
ttcccattta actggcaata attctgttac ttcaggagta ggatttccat ttttgatgaa   180
gttagtccac atggcaagta ctctatcttt tgttaataga acattaggtt tatcttttc   240
cagcttcatc atctcgactt tgaataaatt cacaagttct tctccatggc atgcaccagt   300
cagattatga tcaccaaatg ttcctttttgc aggatgactt ccgagaagg aatattcata   360
ataataaact ggttcgtctt gtttctccac agacaacttg acatgcttgt caacacctct   420
agtaaaccaa atatctccta tcaagtcaat aaatttctgt tcattttctg aacgggttt   480
atcgtcaaag taaaacttcc tgattttttc tgcaagtttt ttcgattcct ctgatccatg   540
gactaattca aattcggctg gtacgagtct ttcaaaatct gcttcagctt ggttcagcat   600
ctctggtttt tctttcatga agaatttgaa caaaagtcct tctgcactgt taaatccaac   660
taataaaggt actttgttaa aggatccgga tttcattctg ccaatggtg attcttccaa   720
gaaaggttgg tgggatggga aactttttc aattgatggt acgaagacaa actcttctat   780
tatttcacct tctgttttcag ctggcatttt cttcaggaga ctgtctacgg ggcttttg   840
taagaattct aaagcatctt gagtattgtt tgtgggatga cccaatatct cagcaagttg   900
aagactacgc tttactggat gtcttttggaa ggcccatgga ttaaaagcac ttccactttg   960
agcaattgcc ctttttgtaaa gtccagtggt tgtatgagat aacaaaagat aatgaacact  1020
tgctccacca gcagaaacac caccaattgt aatattttct ggatctccac caaatttctc  1080
aatgttttct ttggtccatt tcagagctgc cacctgatcc aataatccta catttcctgg  1140
agcaccctcc aactccaaat tcagaaatcc gagaggtccc aatcggtaat tgaaagttac  1200
gaaaataaca tcaaaatyta ctaaataatc tgggctttgg aattctaaat ttccggatcc  1260
agtcacaaaa ccaccaccat gaacccagaa aaatactgga agtttttat cagaagttgt  1320
ttttggtgcg tacacgttta ctaccaagca gtcttcgtct ccttcaattt tcttcaagaa  1380
gaaatttaaa gatttacaca catttccgta taatgtggcg ttgaaaacac cttgccatgg  1440
ctcagctttc tgtggaggct taaatctaag ttctccaaca ggaggtttag cataaggtac  1500
acctgtgtag ctaaa                                                  1515

<210> SEQ ID NO 18
<211> LENGTH: 1792
<212> TYPE: DNA

-continued

```
<213> ORGANISM: Ctenocephalides felis
<220> FEATURE:
<221> NAME/KEY: CDS
<222> LOCATION: (49)..(1701)
<223> OTHER INFORMATION:
<220> FEATURE:
<221> NAME/KEY: misc_feature
<222> LOCATION: (1758)..(1758)
<223> OTHER INFORMATION: n = unknown
<220> FEATURE:
<221> NAME/KEY: misc_feature
<222> LOCATION: (1768)..(1768)
<223> OTHER INFORMATION: n = unknown

<400> SEQUENCE: 18
actgtgtgct aataattcag tacacacagt caatagtcta gatccaag atg tct cgt         57
                                                    Met Ser Arg
                                                      1 gtt att ttt tta agt tgt att ttt ttg ttt agt ttt aat ttt ata aaa         105
Val Ile Phe Leu Ser Cys Ile Phe Leu Phe Ser Phe Asn Phe Ile Lys
      5                  10                  15 tgt gat ccc ccg act gta act ttg ccc cag ggc gaa ttg gtt gga aaa         153
Cys Asp Pro Pro Thr Val Thr Leu Pro Gln Gly Glu Leu Val Gly Lys
 20                  25                  30                  35 gct ttg acg aac gaa aat gga aaa gag tat ttt agc tac aca ggt gtg         201
Ala Leu Thr Asn Glu Asn Gly Lys Glu Tyr Phe Ser Tyr Thr Gly Val
                 40                  45                  50 cct tat gct aaa cct cca gtt gga gaa ctt aga ttt aag cct cca cag         249
Pro Tyr Ala Lys Pro Pro Val Gly Glu Leu Arg Phe Lys Pro Pro Gln
             55                  60                  65 aaa gct gag cca tgg aat ggt gtt ttc aac gcc aca tca cat gga aat         297
Lys Ala Glu Pro Trp Asn Gly Val Phe Asn Ala Thr Ser His Gly Asn
         70                  75                  80 gtg tgc aaa gct ttg aat ttc ttc ttg aaa aaa att gaa gga gac gaa         345
Val Cys Lys Ala Leu Asn Phe Phe Leu Lys Lys Ile Glu Gly Asp Glu
     85                  90                  95 gac tgc ttg ttg gtg aat gtg tac gca cca aaa aca act tct gac aaa         393
Asp Cys Leu Leu Val Asn Val Tyr Ala Pro Lys Thr Thr Ser Asp Lys
100                 105                 110                 115 aaa ctt cca gta ttt ttc tgg gtt cat ggt ggc ggt ttt gtg act gga         441
Lys Leu Pro Val Phe Phe Trp Val His Gly Gly Gly Phe Val Thr Gly
                120                 125                 130 tcc gga aat tta gaa ttt caa agc cca gat tat tta gta aat tat gat         489
Ser Gly Asn Leu Glu Phe Gln Ser Pro Asp Tyr Leu Val Asn Tyr Asp
            135                 140                 145 gtt att ttt gta act ttc aat tac cga ttg gga cca ctc gga ttt ttg         537
Val Ile Phe Val Thr Phe Asn Tyr Arg Leu Gly Pro Leu Gly Phe Leu
        150                 155                 160 aat ttg gag ttg gaa ggt gct cct gga aat gta gga tta ttg gat cag         585
Asn Leu Glu Leu Glu Gly Ala Pro Gly Asn Val Gly Leu Leu Asp Gln
    165                 170                 175 gta gca gct ttg aaa tgg acc aaa gaa aat att gag aaa ttt ggt gga         633
Val Ala Ala Leu Lys Trp Thr Lys Glu Asn Ile Glu Lys Phe Gly Gly
180                 185                 190                 195 gat cca gaa aat att aca att ggt ggt gtt tct gct ggt gga gca agt         681
Asp Pro Glu Asn Ile Thr Ile Gly Gly Val Ser Ala Gly Gly Ala Ser
                200                 205                 210 gtt cat tat ctt tta ttg tca cat aca acc act gga ctt tac aaa agg         729
Val His Tyr Leu Leu Leu Ser His Thr Thr Thr Gly Leu Tyr Lys Arg
            215                 220                 225 gca att gct caa agt gga agt gct tta aat cca tgg gcc ttc caa aga         777
Ala Ile Ala Gln Ser Gly Ser Ala Leu Asn Pro Trp Ala Phe Gln Arg
        230                 235                 240
```

-continued

| | |
|---|---|
| cat cca gta aag cgt agt ctt caa ctt gct gag ata tta ggt cat ccc<br>His Pro Val Lys Arg Ser Leu Gln Leu Ala Glu Ile Leu Gly His Pro<br>245               250               255 | 825 |
| aca aac aac act caa gat gct tta gaa ttc tta caa aaa gcc cca gta<br>Thr Asn Asn Thr Gln Asp Ala Leu Glu Phe Leu Gln Lys Ala Pro Val<br>260               265             270              275 | 873 |
| gac agt ctc ctg aaa aaa atg cca gct gaa aca gaa ggt gaa ata ata<br>Asp Ser Leu Leu Lys Lys Met Pro Ala Glu Thr Glu Gly Glu Ile Ile<br>                 280               285              290 | 921 |
| gaa gag ttc gtc ttc gta cca tca att gaa aaa gtt ttc cca tcc cac<br>Glu Glu Phe Val Phe Val Pro Ser Ile Glu Lys Val Phe Pro Ser His<br>        295               300              305 | 969 |
| caa cct ttc ttg gaa gaa tca cca ttg gcc aga atg aaa tct gga tcc<br>Gln Pro Phe Leu Glu Glu Ser Pro Leu Ala Arg Met Lys Ser Gly Ser<br>            310               315              320 | 1017 |
| ttt aac aaa gta cct tta tta gtt gga ttc aac agc gca gaa gga ctt<br>Phe Asn Lys Val Pro Leu Leu Val Gly Phe Asn Ser Ala Glu Gly Leu<br>325               330              335 | 1065 |
| ttg tac aaa ttc ttt atg aaa gaa aaa cca gag atg ctg aac caa gct<br>Leu Tyr Lys Phe Phe Met Lys Glu Lys Pro Glu Met Leu Asn Gln Ala<br>340               345             350              355 | 1113 |
| gaa gca gat ttc gaa aga ctc gta cca gcc gaa ttt gaa tta gcc cat<br>Glu Ala Asp Phe Glu Arg Leu Val Pro Ala Glu Phe Glu Leu Ala His<br>                 360               365              370 | 1161 |
| gga tca gaa gaa tcg aaa aaa ctt gca gaa aaa atc agg aag ttt tac<br>Gly Ser Glu Glu Ser Lys Lys Leu Ala Glu Lys Ile Arg Lys Phe Tyr<br>        375               380              385 | 1209 |
| ttt gac gat aaa ccc gtt cct gaa aat gag cag aaa ttt att gac ttg<br>Phe Asp Asp Lys Pro Val Pro Glu Asn Glu Gln Lys Phe Ile Asp Leu<br>            390               395              400 | 1257 |
| ata gga gat att tgg ttt act aga ggc att gac aag cat gtc aag ttg<br>Ile Gly Asp Ile Trp Phe Thr Arg Gly Ile Asp Lys His Val Lys Leu<br>405               410              415 | 1305 |
| tct gta gaa aaa caa gac gag cca gta tat tat tat gaa tat tct ttc<br>Ser Val Glu Lys Gln Asp Glu Pro Val Tyr Tyr Tyr Glu Tyr Ser Phe<br>420               425             430              435 | 1353 |
| tct gaa agt cat cct gca aaa gga aca ttt ggt gac cat aac ttg act<br>Ser Glu Ser His Pro Ala Lys Gly Thr Phe Gly Asp His Asn Leu Thr<br>                 440               445              450 | 1401 |
| gga gca tgt cat ggt gaa gaa ctt gtg aat tta ttc aaa gtc gag atg<br>Gly Ala Cys His Gly Glu Glu Leu Val Asn Leu Phe Lys Val Glu Met<br>        455               460              465 | 1449 |
| atg aag ctg gaa aaa gat aaa ccg aat gtt tta tta aca aaa gat agg<br>Met Lys Leu Glu Lys Asp Lys Pro Asn Val Leu Leu Thr Lys Asp Arg<br>            470               475              480 | 1497 |
| gta ctt gct atg tgg acg aac ttc atc aaa aat gga aat cct act cct<br>Val Leu Ala Met Trp Thr Asn Phe Ile Lys Asn Gly Asn Pro Thr Pro<br>485               490              495 | 1545 |
| gaa gta act gaa tta ttg cca gtt aaa tgg gaa cct gcc aca aaa gac<br>Glu Val Thr Glu Leu Leu Pro Val Lys Trp Glu Pro Ala Thr Lys Asp<br>500               505             510              515 | 1593 |
| aag ttg aat tat ttg aac att gat gcc acc tta act ttg gga aca aat<br>Lys Leu Asn Tyr Leu Asn Ile Asp Ala Thr Leu Thr Leu Gly Thr Asn<br>            520               525              530 | 1641 |
| cca gaa gaa acc cga gtc aaa tty tgg gaa gat gca aca aaa act ttg<br>Pro Glu Glu Thr Arg Val Lys Phe Trp Glu Asp Ala Thr Lys Thr Leu<br>                 535               540              545 | 1689 |
| cac agt caa taa aaatgtatga aaattgtttt aattatttta ggtaatacat<br>His Ser Gln | 1741 |

```
                550
taggtaaata aaaattnaaa aataacnaaa aaaaaaaaaa aaaaaaaaaa a              1792
```

<210> SEQ ID NO 19
<211> LENGTH: 550
<212> TYPE: PRT
<213> ORGANISM: Ctenocephalides felis

<400> SEQUENCE: 19

```
Met Ser Arg Val Ile Phe Leu Ser Cys Ile Phe Leu Phe Ser Phe Asn
1               5                   10                  15

Phe Ile Lys Cys Asp Pro Pro Thr Val Thr Leu Pro Gln Gly Glu Leu
            20                  25                  30

Val Gly Lys Ala Leu Thr Asn Glu Asn Gly Lys Glu Tyr Phe Ser Tyr
        35                  40                  45

Thr Gly Val Pro Tyr Ala Lys Pro Pro Val Gly Glu Leu Arg Phe Lys
    50                  55                  60

Pro Pro Gln Lys Ala Glu Pro Trp Asn Gly Val Phe Asn Ala Thr Ser
65                  70                  75                  80

His Gly Asn Val Cys Lys Ala Leu Asn Phe Phe Leu Lys Lys Ile Glu
                85                  90                  95

Gly Asp Glu Asp Cys Leu Leu Val Asn Val Tyr Ala Pro Lys Thr Thr
            100                 105                 110

Ser Asp Lys Lys Leu Pro Val Phe Phe Trp Val His Gly Gly Gly Phe
        115                 120                 125

Val Thr Gly Ser Gly Asn Leu Glu Phe Gln Ser Pro Asp Tyr Leu Val
    130                 135                 140

Asn Tyr Asp Val Ile Phe Val Thr Phe Asn Tyr Arg Leu Gly Pro Leu
145                 150                 155                 160

Gly Phe Leu Asn Leu Glu Leu Glu Gly Ala Pro Gly Asn Val Gly Leu
                165                 170                 175

Leu Asp Gln Val Ala Ala Leu Lys Trp Thr Lys Glu Asn Ile Glu Lys
            180                 185                 190

Phe Gly Gly Asp Pro Glu Asn Ile Thr Ile Gly Gly Val Ser Ala Gly
        195                 200                 205

Gly Ala Ser Val His Tyr Leu Leu Ser His Thr Thr Thr Gly Leu
    210                 215                 220

Tyr Lys Arg Ala Ile Ala Gln Ser Gly Ser Ala Leu Asn Pro Trp Ala
225                 230                 235                 240

Phe Gln Arg His Pro Val Lys Arg Ser Leu Gln Leu Ala Glu Ile Leu
                245                 250                 255

Gly His Pro Thr Asn Asn Thr Gln Asp Ala Leu Glu Phe Leu Gln Lys
            260                 265                 270

Ala Pro Val Asp Ser Leu Leu Lys Lys Met Pro Ala Glu Thr Glu Gly
        275                 280                 285

Glu Ile Ile Glu Glu Phe Val Phe Val Pro Ser Ile Glu Lys Val Phe
    290                 295                 300

Pro Ser His Gln Pro Phe Leu Glu Glu Ser Pro Leu Ala Arg Met Lys
305                 310                 315                 320

Ser Gly Ser Phe Asn Lys Val Pro Leu Leu Val Gly Phe Asn Ser Ala
                325                 330                 335

Glu Gly Leu Leu Tyr Lys Phe Phe Met Lys Glu Lys Pro Glu Met Leu
            340                 345                 350

Asn Gln Ala Glu Ala Asp Phe Glu Arg Leu Val Pro Ala Glu Phe Glu
```

-continued

```
                355                 360                 365
Leu Ala His Gly Ser Glu Glu Ser Lys Lys Leu Ala Glu Lys Ile Arg
    370                 375                 380
Lys Phe Tyr Phe Asp Asp Lys Pro Val Pro Glu Asn Glu Gln Lys Phe
385                 390                 395                 400
Ile Asp Leu Ile Gly Asp Ile Trp Phe Thr Arg Gly Ile Asp Lys His
                405                 410                 415
Val Lys Leu Ser Val Glu Lys Gln Asp Glu Pro Val Tyr Tyr Tyr Glu
                420                 425                 430
Tyr Ser Phe Ser Glu Ser His Pro Ala Lys Gly Thr Phe Gly Asp His
            435                 440                 445
Asn Leu Thr Gly Ala Cys His Gly Glu Glu Leu Val Asn Leu Phe Lys
    450                 455                 460
Val Glu Met Met Lys Leu Glu Lys Asp Lys Pro Asn Val Leu Leu Thr
465                 470                 475                 480
Lys Asp Arg Val Leu Ala Met Trp Thr Asn Phe Ile Lys Asn Gly Asn
                485                 490                 495
Pro Thr Pro Glu Val Thr Glu Leu Leu Pro Val Lys Trp Glu Pro Ala
                500                 505                 510
Thr Lys Asp Lys Leu Asn Tyr Leu Asn Ile Asp Ala Thr Leu Thr Leu
            515                 520                 525
Gly Thr Asn Pro Glu Glu Thr Arg Val Lys Phe Trp Glu Asp Ala Thr
    530                 535                 540
Lys Thr Leu His Ser Gln
545                 550
```

<210> SEQ ID NO 20
<211> LENGTH: 1792
<212> TYPE: DNA
<213> ORGANISM: Ctenocephalides felis
<220> FEATURE:
<221> NAME/KEY: misc_feature
<222> LOCATION: (25)..(25)
<223> OTHER INFORMATION: n = unknown
<220> FEATURE:
<221> NAME/KEY: misc_feature
<222> LOCATION: (35)..(35)
<223> OTHER INFORMATION: n = unknown

<400> SEQUENCE: 20

```
tttttttttt tttttttttt ttttngttat tttnaattt ttatttacct aatgtattac    60
ctaaaataat taaaacaatt ttcatacatt tttattgact gtgcaaagtt tttgtggcat   120
cttcccaraa tttgactcgg gtttcttctg gatttgttcc caaagttaag gtggcatcaa   180
tgttcaaata attcaacttg tcttttgtgg caggttccca tttaactggc aataattcag   240
ttacttcagg agtaggattt ccattttga tgaagttcgt ccacatagca agtaccctat    300
cttttgttaa taaacattc ggtttatctt tttccagctt catcatctcg actttgaata   360
aattcacaag ttcttcacca tgacatgctc cagtcaagtt atggtcacca atgttccttt   420
tgcaggatg actttcagag aaagaatatt cataataata tactggctcg tcttgttttt   480
ctacagacaa cttgacatgc ttgtcaatgc ctctagtaaa ccaaatatct cctatcaagt   540
caataaattt ctgctcattt tcaggaacgg gtttatcgtc aaagtaaaac ttcctgattt   600
tttctgcaag tttttttcgat tcttctgatc catgggctaa ttcaaattcg gctggtacga   660
gtctttcgaa atctgcttca gcttggttca gcatctctgg ttttttcttc ataaagaatt   720
tgtacaaaag tccttctgcg ctgttgaatc caactaataa aggtactttg ttaaaggatc   780
```

-continued

```
cagatttcat tctggccaat ggtgattctt ccaagaaagg ttggtgggat gggaaaactt      840
tttcaattga tggtacgaag acgaactctt ctattatttc accttctgtt tcagctggca      900 ttttttttcag gagactgtct actggggctt tttgtaagaa ttctaaagca tcttgagtgt     960
tgtttgtggg atgacctaat atctcagcaa gttgaagact acgctttact ggatgtcttt    1020
ggaaggccca tggatttaaa gcacttccac tttgagcaat tgcccttttg taaagtccag    1080
tggttgtatg tgacaataaa agataatgaa cacttgctcc accagcagaa acaccaccaa    1140
ttgtaatatt ttctggatct ccaccaaatt tctcaatatt ttctttggtc catttcaaag    1200
ctgctacctg atccaataat cctacatttc caggagcacc ttccaactcc aaattcaaaa    1260
atccgagtgg tcccaatcgg taattgaaag ttacaaaaat aacatcataa tttactaaat    1320
aatctgggct ttgaaattct aaatttccgg atccagtcac aaaaccgcca ccatgaaccc    1380
agaaaaatac tggaagtttt ttgtcagaag ttgttttttgg tgcgtacaca ttcaccaaca    1440
agcagtcttc gtctccttca attttttttca agaagaaatt caaagctttg cacacatttc    1500
catgtgatgt ggcgttgaaa acaccattcc atggctcagc tttctgtgga ggcttaaatc    1560
taagttctcc aactggaggt ttagcataag gcacacctgt gtagctaaaa tactcttttc    1620
cattttcgtt cgtcaaagct tttccaacca attcgccctg gggcaaagtt acagtcgggg    1680
gatcacattt tataaaatta aaactaaaca aaaaaataca acttaaaaaa ataacacgag    1740
acatcttgga tctagactat tgactgtgtg tactgaatta ttagcacaca gt             1792
```

<210> SEQ ID NO 21
<211> LENGTH: 1650
<212> TYPE: DNA
<213> ORGANISM: Ctenocephalides felis
<220> FEATURE:
<221> NAME/KEY: exon
<222> LOCATION: (1)..(1650)
<223> OTHER INFORMATION:

<400> SEQUENCE: 21

```
atg tct cgt gtt att ttt tta agt tgt att ttt ttg ttt agt ttt aat      48
Met Ser Arg Val Ile Phe Leu Ser Cys Ile Phe Leu Phe Ser Phe Asn
 1               5                  10                  15 ttt ata aaa tgt gat ccc ccg act gta act ttg ccc cag ggc gaa ttg      96
Phe Ile Lys Cys Asp Pro Pro Thr Val Thr Leu Pro Gln Gly Glu Leu
                20                  25                  30 gtt gga aaa gct ttg acg aac gaa aat gga aaa gag tat ttt agc tac    144
Val Gly Lys Ala Leu Thr Asn Glu Asn Gly Lys Glu Tyr Phe Ser Tyr
            35                  40                  45 aca ggt gtg cct tat gct aaa cct cca gtt gga gaa ctt aga ttt aag    192
Thr Gly Val Pro Tyr Ala Lys Pro Pro Val Gly Glu Leu Arg Phe Lys
        50                  55                  60 cct cca cag aaa gct gag cca tgg aat ggt gtt ttc aac gcc aca tca    240
Pro Pro Gln Lys Ala Glu Pro Trp Asn Gly Val Phe Asn Ala Thr Ser
 65                  70                  75                  80 cat gga aat gtg tgc aaa gct ttg aat ttc ttc ttg aaa aaa att gaa    288
His Gly Asn Val Cys Lys Ala Leu Asn Phe Phe Leu Lys Lys Ile Glu
                85                  90                  95 gga gac gaa gac tgc ttg ttg gtg aat gtg tac gca cca aaa aca act    336
Gly Asp Glu Asp Cys Leu Leu Val Asn Val Tyr Ala Pro Lys Thr Thr
                100                 105                 110 tct gac aaa aaa ctt cca gta ttt ttc tgg gtt cat ggt ggc ggt ttt    384
Ser Asp Lys Lys Leu Pro Val Phe Phe Trp Val His Gly Gly Gly Phe
            115                 120                 125
```

```
gtg act gga tcc gga aat tta gaa ttt caa agc cca gat tat tta gta        432
Val Thr Gly Ser Gly Asn Leu Glu Phe Gln Ser Pro Asp Tyr Leu Val
    130                 135                 140 aat tat gat gtt att ttt gta act ttc aat tac cga ttg gga cca ctc        480
Asn Tyr Asp Val Ile Phe Val Thr Phe Asn Tyr Arg Leu Gly Pro Leu
145                 150                 155                 160 gga ttt ttg aat ttg gag ttg gaa ggt gct cct gga aat gta gga tta        528
Gly Phe Leu Asn Leu Glu Leu Glu Gly Ala Pro Gly Asn Val Gly Leu
                165                 170                 175 ttg gat cag gta gca gct ttg aaa tgg acc aaa gaa aat att gag aaa        576
Leu Asp Gln Val Ala Ala Leu Lys Trp Thr Lys Glu Asn Ile Glu Lys
            180                 185                 190 ttt ggt gga gat cca gaa aat att aca att ggt ggt gtt tct gct ggt        624
Phe Gly Gly Asp Pro Glu Asn Ile Thr Ile Gly Gly Val Ser Ala Gly
        195                 200                 205 gga gca agt gtt cat tat ctt tta ttg tca cat aca acc act gga ctt        672
Gly Ala Ser Val His Tyr Leu Leu Leu Ser His Thr Thr Thr Gly Leu
    210                 215                 220 tac aaa agg gca att gct caa agt gga agt gct tta aat cca tgg gcc        720
Tyr Lys Arg Ala Ile Ala Gln Ser Gly Ser Ala Leu Asn Pro Trp Ala
225                 230                 235                 240 ttc caa aga cat cca gta aag cgt agt ctt caa ctt gct gag ata tta        768
Phe Gln Arg His Pro Val Lys Arg Ser Leu Gln Leu Ala Glu Ile Leu
                245                 250                 255 ggt cat ccc aca aac aac act caa gat gct tta gaa ttc tta caa aaa        816
Gly His Pro Thr Asn Asn Thr Gln Asp Ala Leu Glu Phe Leu Gln Lys
            260                 265                 270 gcc cca gta gac agt ctc ctg aaa aaa atg cca gct gaa aca gaa ggt        864
Ala Pro Val Asp Ser Leu Leu Lys Lys Met Pro Ala Glu Thr Glu Gly
        275                 280                 285 gaa ata ata gaa gag ttc gtc ttc gta cca tca att gaa aaa gtt ttc        912
Glu Ile Ile Glu Glu Phe Val Phe Val Pro Ser Ile Glu Lys Val Phe
    290                 295                 300 cca tcc cac caa cct ttc ttg gaa gaa tca cca ttg gcc aga atg aaa        960
Pro Ser His Gln Pro Phe Leu Glu Glu Ser Pro Leu Ala Arg Met Lys
305                 310                 315                 320 tct gga tcc ttt aac aaa gta cct tta tta gtt gga ttc aac agc gca        1008
Ser Gly Ser Phe Asn Lys Val Pro Leu Leu Val Gly Phe Asn Ser Ala
                325                 330                 335 gaa gga ctt ttg tac aaa ttc ttt atg aaa gaa aaa cca gag atg ctg        1056
Glu Gly Leu Leu Tyr Lys Phe Phe Met Lys Glu Lys Pro Glu Met Leu
            340                 345                 350 aac caa gct gaa gca gat ttc gaa aga ctc gta cca gcc gaa ttt gaa        1104
Asn Gln Ala Glu Ala Asp Phe Glu Arg Leu Val Pro Ala Glu Phe Glu
        355                 360                 365 tta gcc cat gga tca gaa gaa tcg aaa aaa ctt gca gaa aaa atc agg        1152
Leu Ala His Gly Ser Glu Glu Ser Lys Lys Leu Ala Glu Lys Ile Arg
    370                 375                 380 aag ttt tac ttt gac gat aaa ccc gtt cct gaa aat gag cag aaa ttt        1200
Lys Phe Tyr Phe Asp Asp Lys Pro Val Pro Glu Asn Glu Gln Lys Phe
385                 390                 395                 400 att gac ttg ata gga gat att tgg ttt act aga ggc att gac aag cat        1248
Ile Asp Leu Ile Gly Asp Ile Trp Phe Thr Arg Gly Ile Asp Lys His
                405                 410                 415 gtc aag ttg tct gta gaa aaa caa gac gag cca gta tat tat gaa        1296
Val Lys Leu Ser Val Glu Lys Gln Asp Glu Pro Val Tyr Tyr Tyr Glu
            420                 425                 430 tat tct ttc tct gaa agt cat cct gca aaa gga aca ttt ggt gac cat        1344
Tyr Ser Phe Ser Glu Ser His Pro Ala Lys Gly Thr Phe Gly Asp His
    435                 440                 445
```

```
aac ttg act gga gca tgt cat ggt gaa gaa ctt gtg aat tta ttc aaa      1392
Asn Leu Thr Gly Ala Cys His Gly Glu Glu Leu Val Asn Leu Phe Lys
        450                 455                 460 gtc gag atg atg aag ctg gaa aaa gat aaa ccg aat gtt tta tta aca      1440
Val Glu Met Met Lys Leu Glu Lys Asp Lys Pro Asn Val Leu Leu Thr
465                 470                 475                 480 aaa gat agg gta ctt gct atg tgg acg aac ttc atc aaa aat gga aat      1488
Lys Asp Arg Val Leu Ala Met Trp Thr Asn Phe Ile Lys Asn Gly Asn
                485                 490                 495 cct act cct gaa gta act gaa tta ttg cca gtt aaa tgg gaa cct gcc      1536
Pro Thr Pro Glu Val Thr Glu Leu Leu Pro Val Lys Trp Glu Pro Ala
            500                 505                 510 aca aaa gac aag ttg aat tat ttg aac att gat gcc acc tta act ttg      1584
Thr Lys Asp Lys Leu Asn Tyr Leu Asn Ile Asp Ala Thr Leu Thr Leu
        515                 520                 525 gga aca aat cca gaa gaa acc cga gtc aaa tty tgg gaa gat gcc aca      1632
Gly Thr Asn Pro Glu Glu Thr Arg Val Lys Phe Trp Glu Asp Ala Thr
    530                 535                 540 aaa act ttg cac agt caa                                              1650
Lys Thr Leu His Ser Gln
545                 550

<210> SEQ ID NO 22
<211> LENGTH: 1650
<212> TYPE: DNA
<213> ORGANISM: Ctenocephalides felis

<400> SEQUENCE: 22
ttgactgtgc aaagtttttg tggcatcttc ccaraatttg actcgggttt cttctggatt      60
tgttcccaaa gttaaggtgg catcaatgtt caaataattc aacttgtctt tgtggcagg     120 ttcccattta actggcaata attcagttac ttcaggagta ggatttccat ttttgatgaa     180
gttcgtccac atagcaagta ccctatcttt tgttaataaa acattcggtt tatcttttc     240 cagcttcatc atctcgactt tgaataaatt cacaagttct tcaccatgac atgctccagt     300
caagttatgg tcaccaaatg ttcctttgc aggatgactt tcagagaaag aatattcata     360
ataatatact ggctcgtctt gttttctac agacaacttg acatgcttgt caatgcctct     420
agtaaaccaa atatctccta tcaagtcaat aaatttctgc tcattttcag gaacgggttt     480
atcgtcaaag taaaacttcc tgattttttc tgcaagtttt ttcgattctt ctgatccatg     540
ggctaattca aattcggctg gtacgagtct ttcgaaatct gcttcagctt ggttcagcat     600
ctctggtttt tctttcataa agaatttgta caaaagtcct tctgcgctgt tgaatccaac     660
taataaaggt actttgttaa aggatccaga tttcattctg gccaatggtg attcttccaa     720
gaaaggttgg tgggatggga aacttttttc aattgatggt acgaagacga actcttctat     780
tatttcacct tctgtttcag ctggcatttt tttcaggaga ctgtctactg ggctttttg     840 taagaattct aaagcatctt gagtgttgtt tgtgggatga cctaatatct cagcaagttg     900
aagactacgc tttactggat gtctttggaa ggcccatgga tttaaagcac ttccactttg     960
agcaattgcc cttttgtaaa gtccagtggt tgtatgtgac aataaaagat aatgaacact    1020
tgctccacca gcagaaacac caccaattgt aatattttct ggatctccac caaatttctc    1080
aatattttct ttggtccatt tcaaagctgc tacctgatcc aataatccta catttccagg    1140
agcaccttcc aactccaaat tcaaaaatcc gagtggtccc aatcggtaat tgaaagttac    1200
aaaaataaca tcataatttta ctaaataatc tgggctttga aattctaaat ttccggatcc    1260
```

-continued

```
agtcacaaaa ccgccaccat gaacccagaa aaatactgga agttttttgt cagaagttgt        1320
ttttggtgcg tacacattca ccaacaagca gtcttcgtct ccttcaattt ttttcaagaa        1380
gaaattcaaa gctttgcaca catttccatg tgatgtggcg ttgaaaacac cattccatgg        1440
ctcagctttc tgtggaggct taaatctaag ttctccaact ggaggtttag cataaggcac        1500
acctgtgtag ctaaaatact cttttccatt ttcgttcgtc aaagcttttc caaccaattc        1560
gccctggggc aaagttacag tcggggatc acatttata aaattaaaac taaacaaaaa         1620
aatacaactt aaaaaaataa cacgagacat                                        1650

<210> SEQ ID NO 23
<211> LENGTH: 1590
<212> TYPE: DNA
<213> ORGANISM: Ctenocephalides felis
<220> FEATURE:
<221> NAME/KEY: exon
<222> LOCATION: (1)..(1590)
<223> OTHER INFORMATION:

<400> SEQUENCE: 23 gat ccc ccg act gta act ttg ccc cag ggc gaa ttg gtt gga aaa gct          48
Asp Pro Pro Thr Val Thr Leu Pro Gln Gly Glu Leu Val Gly Lys Ala
1               5                   10                  15 ttg acg aac gaa aat gga aaa gag tat ttt agc tac aca ggt gtg cct          96
Leu Thr Asn Glu Asn Gly Lys Glu Tyr Phe Ser Tyr Thr Gly Val Pro
                20                  25                  30 tat gct aaa cct cca gtt gga gaa ctt aga ttt aag cct cca cag aaa         144
Tyr Ala Lys Pro Pro Val Gly Glu Leu Arg Phe Lys Pro Pro Gln Lys
            35                  40                  45 gct gag cca tgg aat ggt gtt ttc aac gcc aca tca cat gga aat gtg         192
Ala Glu Pro Trp Asn Gly Val Phe Asn Ala Thr Ser His Gly Asn Val
        50                  55                  60 tgc aaa gct ttg aat ttc ttc ttg aaa aaa att gaa gga gac gaa gac         240
Cys Lys Ala Leu Asn Phe Phe Leu Lys Lys Ile Glu Gly Asp Glu Asp
65                  70                  75                  80 tgc ttg ttg gtg aat gtg tac gca cca aaa aca act tct gac aaa aaa         288
Cys Leu Leu Val Asn Val Tyr Ala Pro Lys Thr Thr Ser Asp Lys Lys
                85                  90                  95 ctt cca gta ttt ttc tgg gtt cat ggt ggc ggt ttt gtg act gga tcc         336
Leu Pro Val Phe Phe Trp Val His Gly Gly Gly Phe Val Thr Gly Ser
            100                 105                 110 gga aat tta gaa ttt caa agc cca gat tat tta gta aat tat gat gtt         384
Gly Asn Leu Glu Phe Gln Ser Pro Asp Tyr Leu Val Asn Tyr Asp Val
        115                 120                 125 att ttt gta act ttc aat tac cga ttg gga cca ctc gga ttt ttg aat         432
Ile Phe Val Thr Phe Asn Tyr Arg Leu Gly Pro Leu Gly Phe Leu Asn
    130                 135                 140 ttg gag ttg gaa ggt gct cct gga aat gta gga tta ttg gat cag gta         480
Leu Glu Leu Glu Gly Ala Pro Gly Asn Val Gly Leu Leu Asp Gln Val
145                 150                 155                 160 gca gct ttg aaa tgg acc aaa gaa aat att gag aaa ttt ggt gga gat         528
Ala Ala Leu Lys Trp Thr Lys Glu Asn Ile Glu Lys Phe Gly Gly Asp
                165                 170                 175 cca gaa aat att aca att ggt ggt gtt tct gct ggt gga gca agt gtt         576
Pro Glu Asn Ile Thr Ile Gly Gly Val Ser Ala Gly Gly Ala Ser Val
            180                 185                 190 cat tat ctt tta ttg tca cat aca acc act gga ctt tac aaa agg gca         624
His Tyr Leu Leu Leu Ser His Thr Thr Thr Gly Leu Tyr Lys Arg Ala
        195                 200                 205 att gct caa agt gga agt gct tta aat cca tgg gcc ttc caa aga cat         672
```

```
Ile Ala Gln Ser Gly Ser Ala Leu Asn Pro Trp Ala Phe Gln Arg His
    210                 215                 220 cca gta aag cgt agt ctt caa ctt gct gag ata tta ggt cat ccc aca      720
Pro Val Lys Arg Ser Leu Gln Leu Ala Glu Ile Leu Gly His Pro Thr
225                 230                 235                 240 aac aac act caa gat gct tta gaa ttc tta caa aaa gcc cca gta gac      768
Asn Asn Thr Gln Asp Ala Leu Glu Phe Leu Gln Lys Ala Pro Val Asp
                245                 250                 255 agt ctc ctg aaa aaa atg cca gct gaa aca gaa ggt gaa ata ata gaa      816
Ser Leu Leu Lys Lys Met Pro Ala Glu Thr Glu Gly Glu Ile Ile Glu
            260                 265                 270 gag ttc gtc ttc gta cca tca att gaa aaa gtt ttc cca tcc cac caa      864
Glu Phe Val Phe Val Pro Ser Ile Glu Lys Val Phe Pro Ser His Gln
        275                 280                 285 cct ttc ttg gaa gaa tca cca ttg gcc aga atg aaa tct gga tcc ttt      912
Pro Phe Leu Glu Glu Ser Pro Leu Ala Arg Met Lys Ser Gly Ser Phe
    290                 295                 300 aac aaa gta cct tta tta gtt gga ttc aac agc gca gaa gga ctt ttg      960
Asn Lys Val Pro Leu Leu Val Gly Phe Asn Ser Ala Glu Gly Leu Leu
305                 310                 315                 320 tac aaa ttc ttt atg aaa gaa aaa cca gag atg ctg aac caa gct gaa     1008
Tyr Lys Phe Phe Met Lys Glu Lys Pro Glu Met Leu Asn Gln Ala Glu
                325                 330                 335 gca gat ttc gaa aga ctc gta cca gcc gaa ttt gaa tta gcc cat gga     1056
Ala Asp Phe Glu Arg Leu Val Pro Ala Glu Phe Glu Leu Ala His Gly
            340                 345                 350 tca gaa gaa tcg aaa aaa ctt gca gaa aaa atc agg aag ttt tac ttt     1104
Ser Glu Glu Ser Lys Lys Leu Ala Glu Lys Ile Arg Lys Phe Tyr Phe
        355                 360                 365 gac gat aaa ccc gtt cct gaa aat gag cag aaa ttt att gac ttg ata     1152
Asp Asp Lys Pro Val Pro Glu Asn Glu Gln Lys Phe Ile Asp Leu Ile
    370                 375                 380 gga gat att tgg ttt act aga ggc att gac aag cat gtc aag ttg tct     1200
Gly Asp Ile Trp Phe Thr Arg Gly Ile Asp Lys His Val Lys Leu Ser
385                 390                 395                 400 gta gaa aaa caa gac gag cca gta tat tat tat gaa tat tct ttc tct     1248
Val Glu Lys Gln Asp Glu Pro Val Tyr Tyr Tyr Glu Tyr Ser Phe Ser
                405                 410                 415 gaa agt cat cct gca aaa gga aca ttt ggt gac cat aac ttg act gga     1296
Glu Ser His Pro Ala Lys Gly Thr Phe Gly Asp His Asn Leu Thr Gly
            420                 425                 430 gca tgt cat ggt gaa gaa ctt gtg aat tta ttc aaa gtc gag atg atg     1344
Ala Cys His Gly Glu Glu Leu Val Asn Leu Phe Lys Val Glu Met Met
        435                 440                 445 aag ctg gaa aaa gat aaa ccg aat gtt tta tta aca aaa gat agg gta     1392
Lys Leu Glu Lys Asp Lys Pro Asn Val Leu Leu Thr Lys Asp Arg Val
    450                 455                 460 ctt gct atg tgg acg aac ttc atc aaa aat gga aat cct act cct gaa     1440
Leu Ala Met Trp Thr Asn Phe Ile Lys Asn Gly Asn Pro Thr Pro Glu
465                 470                 475                 480 gta act gaa tta ttg cca gtt aaa tgg gaa cct gcc aca aaa gac aag     1488
Val Thr Glu Leu Leu Pro Val Lys Trp Glu Pro Ala Thr Lys Asp Lys
                485                 490                 495 ttg aat tat ttg aac att gat gcc acc tta act ttg gga aca aat cca     1536
Leu Asn Tyr Leu Asn Ile Asp Ala Thr Leu Thr Leu Gly Thr Asn Pro
            500                 505                 510 gaa gaa acc cga gtc aaa tty tgg gaa gat gcc aca aaa act ttg cac     1584
Glu Glu Thr Arg Val Lys Phe Trp Glu Asp Ala Thr Lys Thr Leu His
        515                 520                 525
```

-continued

```
agt caa                                                                      1590
Ser Gln
    530

<210> SEQ ID NO 24
<211> LENGTH: 2836
<212> TYPE: DNA
<213> ORGANISM: Ctenocephalides felis
<220> FEATURE:
<221> NAME/KEY: CDS
<222> LOCATION: (99)..(1889)
<223> OTHER INFORMATION:
<220> FEATURE:
<221> NAME/KEY: misc_feature
<222> LOCATION: (2278)..(2278)
<223> OTHER INFORMATION: n = unknown

<400> SEQUENCE: 24
tagacatgtc gtcttcaaaa cgtctatttt atcataaaca aaacgagata aataataaca     60
attaagcaac caaaatgcat taaaaaacac aataaaaa atg tta cct cac agt agt    116
                                          Met Leu Pro His Ser Ser
                                            1               5 gca tta gtt tta ttt tta ttt ttt tta ttt ttc tta ttt aca cct atc      164
Ala Leu Val Leu Phe Leu Phe Phe Leu Phe Phe Leu Phe Thr Pro Ile
         10                  15                  20 ttg tgc ata cta tgg gat aac cta gat cag cat ttg tgc aga gtt caa      212
Leu Cys Ile Leu Trp Asp Asn Leu Asp Gln His Leu Cys Arg Val Gln
     25                  30                  35 ttt aac ggg atc acg gaa gga aaa ccg ttc cga tat aaa gat cat agg      260
Phe Asn Gly Ile Thr Glu Gly Lys Pro Phe Arg Tyr Lys Asp His Arg
 40                  45                  50 aat gat gta tat tgt tct tat ttg gga att cct tat gcc gaa ccg cct      308
Asn Asp Val Tyr Cys Ser Tyr Leu Gly Ile Pro Tyr Ala Glu Pro Pro
 55                  60                  65                  70 ttt gga cca tta cga ttt cag tct cca aaa cca ata tca aat cca aaa      356
Phe Gly Pro Leu Arg Phe Gln Ser Pro Lys Pro Ile Ser Asn Pro Lys
                 75                  80                  85 aca gga ttc gta cag gct cga act ttg gga gac aaa tgt ttc cag gaa      404
Thr Gly Phe Val Gln Ala Arg Thr Leu Gly Asp Lys Cys Phe Gln Glu
             90                  95                 100 agt cta ata tat tct tat gca gga agc gaa gat tgc tta tat ctg aat      452
Ser Leu Ile Tyr Ser Tyr Ala Gly Ser Glu Asp Cys Leu Tyr Leu Asn
        105                 110                 115 ata ttc acg cca gag act gtt aat tct gcg aac aat aca aaa tat cct      500
Ile Phe Thr Pro Glu Thr Val Asn Ser Ala Asn Asn Thr Lys Tyr Pro
    120                 125                 130 gta atg ttc tgg atc cat gga ggc gca ttc aac caa gga tca gga tct      548
Val Met Phe Trp Ile His Gly Gly Ala Phe Asn Gln Gly Ser Gly Ser
135                 140                 145                 150 tat aat ttt ttt gga cct gat tat ttg atc agg gaa gga att att ttg      596
Tyr Asn Phe Phe Gly Pro Asp Tyr Leu Ile Arg Glu Gly Ile Ile Leu
                155                 160                 165 gtc act atc aac tat aga tta gga gtt ttc ggt ttt cta tca gcg ccg      644
Val Thr Ile Asn Tyr Arg Leu Gly Val Phe Gly Phe Leu Ser Ala Pro
            170                 175                 180 gaa tgg gat atc cat gga aat atg ggt cta aaa gac cag aga ttg gca      692
Glu Trp Asp Ile His Gly Asn Met Gly Leu Lys Asp Gln Arg Leu Ala
        185                 190                 195 cta aaa tgg gtt tac gac aac atc gaa aag ttt ggt gga gac aga gaa      740
Leu Lys Trp Val Tyr Asp Asn Ile Glu Lys Phe Gly Gly Asp Arg Glu
    200                 205                 210 aaa att aca att gct gga gaa tct gct gga gca gca agt gtc cat ttt      788
```

```
Lys Ile Thr Ile Ala Gly Glu Ser Ala Gly Ala Ala Ser Val His Phe
215                 220                 225                 230 ctg atg atg gac aac tcg act aga aaa tac tac caa agg gcc att ttg        836
Leu Met Met Asp Asn Ser Thr Arg Lys Tyr Tyr Gln Arg Ala Ile Leu
                    235                 240                 245 cag agt ggg aca tta cta aat ccg act gct aat caa att caa ctt ctg        884
Gln Ser Gly Thr Leu Leu Asn Pro Thr Ala Asn Gln Ile Gln Leu Leu
                250                 255                 260 cat aga ttt gaa aaa ctc aaa caa gtg cta aac atc acg caa aaa caa        932
His Arg Phe Glu Lys Leu Lys Gln Val Leu Asn Ile Thr Gln Lys Gln
            265                 270                 275 gaa ctc cta aac ctg gat aaa aac cta att tta cga gca gcc tta aac        980
Glu Leu Leu Asn Leu Asp Lys Asn Leu Ile Leu Arg Ala Ala Leu Asn
        280                 285                 290 aga gtt cct gat agc aac gac cat gac cga gac aca gta cca gta ttt       1028
Arg Val Pro Asp Ser Asn Asp His Asp Arg Asp Thr Val Pro Val Phe
295                 300                 305                 310 aat cca gtc tta gaa tca cca gaa tct cca gat cca ata aca ttt cca       1076
Asn Pro Val Leu Glu Ser Pro Glu Ser Pro Asp Pro Ile Thr Phe Pro
                    315                 320                 325 tct gcc ttg gaa aga atg aga aat ggt gaa ttt cct gat gtc gat gtc       1124
Ser Ala Leu Glu Arg Met Arg Asn Gly Glu Phe Pro Asp Val Asp Val
                330                 335                 340 atc att ggt ttc aat agt gct gaa ggt tta aga tct atg gca aga gta       1172
Ile Ile Gly Phe Asn Ser Ala Glu Gly Leu Arg Ser Met Ala Arg Val
            345                 350                 355 acc aga gga aac atg gaa gtt cac aag act ttg aca aat ata gaa agg       1220
Thr Arg Gly Asn Met Glu Val His Lys Thr Leu Thr Asn Ile Glu Arg
        360                 365                 370 gct ata cct aga gat gct aat att tgg aaa aat cca aat ggt att gag       1268
Ala Ile Pro Arg Asp Ala Asn Ile Trp Lys Asn Pro Asn Gly Ile Glu
375                 380                 385                 390 gag aaa aaa cta ata aaa atg ctt aca gag ttt tat gac caa gtg aaa       1316
Glu Lys Lys Leu Ile Lys Met Leu Thr Glu Phe Tyr Asp Gln Val Lys
                    395                 400                 405 gaa caa aac gat gac att gaa gcc tac gtc caa cta aaa ggc gat gct       1364
Glu Gln Asn Asp Asp Ile Glu Ala Tyr Val Gln Leu Lys Gly Asp Ala
                410                 415                 420 ggt tac ctc caa gga atc tac cgt acc ttg aaa gcc ata ttt ttc aat       1412
Gly Tyr Leu Gln Gly Ile Tyr Arg Thr Leu Lys Ala Ile Phe Phe Asn
            425                 430                 435 gaa ttc aga agg aat tcc aat ttg tat ttg tac agg tta tca gac gat       1460
Glu Phe Arg Arg Asn Ser Asn Leu Tyr Leu Tyr Arg Leu Ser Asp Asp
        440                 445                 450 acg tat agt gta tat aaa agt tat atc ttg ccc tat cga tgg ggt tcc       1508
Thr Tyr Ser Val Tyr Lys Ser Tyr Ile Leu Pro Tyr Arg Trp Gly Ser
455                 460                 465                 470 ttg cca gga gtt agt cat ggt gat gat tta gga tat ctt ttt gca aac       1556
Leu Pro Gly Val Ser His Gly Asp Asp Leu Gly Tyr Leu Phe Ala Asn
                    475                 480                 485 tcg ttg gat gtt cct att ttg gga aca acg cac att tct ata ccg caa       1604
Ser Leu Asp Val Pro Ile Leu Gly Thr Thr His Ile Ser Ile Pro Gln
                490                 495                 500 gat gct atg cag act ctg gaa agg atg gtc agg atc tgg acc aat ttt       1652
Asp Ala Met Gln Thr Leu Glu Arg Met Val Arg Ile Trp Thr Asn Phe
            505                 510                 515 gta aag aat gga aaa cct aca tca aac act gaa gat gca tca tgt gat       1700
Val Lys Asn Gly Lys Pro Thr Ser Asn Thr Glu Asp Ala Ser Cys Asp
        520                 525                 530
```

| | | |
|---|---|---|
| aca aaa aga cat tta aac gac att ttt tgg gaa cca tac aac gac gaa<br>Thr Lys Arg His Leu Asn Asp Ile Phe Trp Glu Pro Tyr Asn Asp Glu<br>535                     540                     545                     550 | 1748 |
| gaa cca aaa tat ttg gac atg gga aaa gaa aat ttt gaa atg aaa aat<br>Glu Pro Lys Tyr Leu Asp Met Gly Lys Glu Asn Phe Glu Met Lys Asn<br>                  555                     560                     565 | 1796 |
| att ttg gaa cta aaa cgc atg atg ctt tgg gat gaa gtt tat aga aat<br>Ile Leu Glu Leu Lys Arg Met Met Leu Trp Asp Glu Val Tyr Arg Asn<br>570                     575                     580 | 1844 |
| gcg aat ttg cgg ttt aga gtc tgt aat gaa gaa agt att aga tga<br>Ala Asn Leu Arg Phe Arg Val Cys Asn Glu Glu Ser Ile Arg<br>        585                     590                     595 | 1889 |
| gtttttttaa ttttacatac agccgagagg aaacatgact aaaattggaa agaaaaatca | 1949 |
| gaaaagaaa aatcacatgg accatagtaa ctttattaca tgatttagtt tcaagtgtat | 2009 |
| caagaaaact tattgcatca agaaaatat tattttgcca aaattcttgg aaaaacactt | 2069 |
| tttatgactg acatggccca taattgaagc tttttcttct tttaccaaat cgccaaattt | 2129 |
| tgtagcgtca gacacattta tttatgacat ggcaattaat gtgttaaaca ttcaactcta | 2189 |
| tattaaaaat ggtagtattt tctaataaga aggttatata aaaagacttg aaaataataa | 2249 |
| gatttgctcg gctatatata aaaacttanc gtctcgttat gctaaacttt tttgatggta | 2309 |
| aaaatatgtt gattttccta ataatctaag atattatatt ttagattaaa ttaaaatatg | 2369 |
| atattttcaa ttaattaatt ttagttttaa atgtactata tttaccagta ctatgaaact | 2429 |
| atttaaata tattttttat tacaatattt atttctcaaa aatgtttagt gtaacaagac | 2489 |
| cattaaatta gagttaatgt tgtaaattaa actatttttt atctatcaca accgcttaat | 2549 |
| tggtgcaaag aaaaatttta ctgtgataat atttgacatt tacacaatat tacgaattgt | 2609 |
| aaactcacaa ttatgtgaat attgtttttt gttaaaaaaa catacatgac ttttctatat | 2669 |
| cattttatat tacggtgata tggattaatg tcaacatgta aaatacaaat gcggttgtta | 2729 |
| aaaataatct gtattaaaat tgttatataa aatctgaata aatgtacttt taagtaaaaa | 2789 |
| aaaaaaaaaa aaaaaaaaaa aaaaaaaaaa aaaaaaaaaa aaaaaaa | 2836 |

<210> SEQ ID NO 25
<211> LENGTH: 596
<212> TYPE: PRT
<213> ORGANISM: Ctenocephalides felis

<400> SEQUENCE: 25

Met Leu Pro His Ser Ser Ala Leu Val Leu Phe Leu Phe Phe Leu Phe
1                 5                    10                 15

Phe Leu Phe Thr Pro Ile Leu Cys Ile Leu Trp Asp Asn Leu Asp Gln
               20                   25                    30

His Leu Cys Arg Val Gln Phe Asn Gly Ile Thr Glu Gly Lys Pro Phe
            35                     40                    45

Arg Tyr Lys Asp His Arg Asn Asp Val Tyr Cys Ser Tyr Leu Gly Ile
50                  55                    60

Pro Tyr Ala Glu Pro Pro Gly Leu Arg Phe Gln Ser Pro Lys
65                 70                   75                    80

Pro Ile Ser Asn Pro Lys Thr Gly Phe Val Gln Ala Arg Thr Leu Gly
               85                   90                    95

Asp Lys Cys Phe Gln Glu Ser Leu Ile Tyr Ser Tyr Ala Gly Ser Glu
           100                   105                  110

Asp Cys Leu Tyr Leu Asn Ile Phe Thr Pro Glu Thr Val Asn Ser Ala
       115                   120                  125

```
Asn Asn Thr Lys Tyr Pro Val Met Phe Trp Ile His Gly Gly Ala Phe
130                 135                 140
Asn Gln Gly Ser Gly Ser Tyr Asn Phe Phe Gly Pro Asp Tyr Leu Ile
145                 150                 155                 160
Arg Glu Gly Ile Ile Leu Val Thr Ile Asn Tyr Arg Leu Gly Val Phe
                165                 170                 175
Gly Phe Leu Ser Ala Pro Glu Trp Asp Ile His Gly Asn Met Gly Leu
                180                 185                 190
Lys Asp Gln Arg Leu Ala Leu Lys Trp Val Tyr Asp Asn Ile Glu Lys
                195                 200                 205
Phe Gly Gly Asp Arg Glu Lys Ile Thr Ile Ala Gly Glu Ser Ala Gly
210                 215                 220
Ala Ala Ser Val His Phe Leu Met Met Asp Asn Ser Thr Arg Lys Tyr
225                 230                 235                 240
Tyr Gln Arg Ala Ile Leu Gln Ser Gly Thr Leu Leu Asn Pro Thr Ala
                245                 250                 255
Asn Gln Ile Gln Leu Leu His Arg Phe Glu Lys Leu Lys Gln Val Leu
                260                 265                 270
Asn Ile Thr Gln Lys Gln Glu Leu Leu Asn Leu Asp Lys Asn Leu Ile
                275                 280                 285
Leu Arg Ala Ala Leu Asn Arg Val Pro Asp Ser Asn Asp His Asp Arg
290                 295                 300
Asp Thr Val Pro Val Phe Asn Pro Val Leu Glu Ser Pro Glu Ser Pro
305                 310                 315                 320
Asp Pro Ile Thr Phe Pro Ser Ala Leu Glu Arg Met Arg Asn Gly Glu
                325                 330                 335
Phe Pro Asp Val Asp Val Ile Ile Gly Phe Asn Ser Ala Glu Gly Leu
                340                 345                 350
Arg Ser Met Ala Arg Val Thr Arg Gly Asn Met Glu Val His Lys Thr
                355                 360                 365
Leu Thr Asn Ile Glu Arg Ala Ile Pro Arg Asp Ala Asn Ile Trp Lys
370                 375                 380
Asn Pro Asn Gly Ile Glu Glu Lys Lys Leu Ile Lys Met Leu Thr Glu
385                 390                 395                 400
Phe Tyr Asp Gln Val Lys Glu Gln Asn Asp Asp Ile Glu Ala Tyr Val
                405                 410                 415
Gln Leu Lys Gly Asp Ala Gly Tyr Leu Gln Gly Ile Tyr Arg Thr Leu
                420                 425                 430
Lys Ala Ile Phe Phe Asn Glu Phe Arg Arg Asn Ser Asn Leu Tyr Leu
                435                 440                 445
Tyr Arg Leu Ser Asp Asp Thr Tyr Ser Val Tyr Lys Ser Tyr Ile Leu
                450                 455                 460
Pro Tyr Arg Trp Gly Ser Leu Pro Gly Val Ser His Gly Asp Asp Leu
465                 470                 475                 480
Gly Tyr Leu Phe Ala Asn Ser Leu Asp Val Pro Ile Leu Gly Thr Thr
                485                 490                 495
His Ile Ser Ile Pro Gln Asp Ala Met Gln Thr Leu Glu Arg Met Val
                500                 505                 510
Arg Ile Trp Thr Asn Phe Val Lys Asn Gly Lys Pro Thr Ser Asn Thr
                515                 520                 525
Glu Asp Ala Ser Cys Asp Thr Lys Arg His Leu Asn Asp Ile Phe Trp
530                 535                 540
```

| Glu | Pro | Tyr | Asn | Asp | Glu | Pro | Lys | Tyr | Leu | Asp | Met | Gly | Lys | Glu |
| 545 | | | | | 550 | | | | | 555 | | | | 560 |

Asn Phe Glu Met Lys Asn Ile Leu Glu Leu Lys Arg Met Met Leu Trp
              565                 570                 575

Asp Glu Val Tyr Arg Asn Ala Asn Leu Arg Phe Arg Val Cys Asn Glu
          580                 585                 590

Glu Ser Ile Arg
       595

<210> SEQ ID NO 26
<211> LENGTH: 2836
<212> TYPE: DNA
<213> ORGANISM: Ctenocephalides felis
<220> FEATURE:
<221> NAME/KEY: misc_feature
<222> LOCATION: (559)..(559)
<223> OTHER INFORMATION: n = unknown

<400> SEQUENCE: 26

```
tttttttttt tttttttttt tttttttttt tttttttttt tttttttttt ttacttaaaa      60
gtacatttat tcagatttta tataacaatt ttaatacaga ttattttttaa caaccgcatt    120
tgtattttac atgttgacat taatccatat caccgtaata taaatgata tagaaaagtc      180
atgtatgttt ttttaacaaa aaacaatatt cacataattg tgagtttaca attcgtaata    240
ttgtgtaaat gtcaaatatt atcacagtaa aattttttctt tgcaccaatt aagcggttgt   300
gatagataaa aaatagttta atttacaaca ttaactctaa tttaatggtc ttgttacact    360
aaacattttt gagaaataaa tattgtaata aaaaatatat ttaaaatagt ttcatagtac    420
tggtaaatat agtacattta aaactaaaat taattaattg aaaatatcat atttttaattt   480
aatctaaaat ataatatctt agattattag gaaaatcaac atattttttac catcaaaaaa   540
gtttagcata acgagacgnt aagtttttat atatagccga gcaaatctta ttattttcaa    600
gtctttttat ataaccttct tattagaaaa tactaccatt tttaatatag agttgaatgt    660
ttaacacatt aattgccatg tcataaataa atgtgtctga cgctacaaaa tttggcgatt    720
tggtaaaaga agaaaaagct tcaattatgg gccatgtcag tcataaaaag tgttttttcca   780
agaattttgg caaataaata tttttctttga tgcaataagt tttcttgata cacttgaaac   840
taaatcatgt aataaagtta ctatggtcca tgtgattttt cttttttctga tttttctttc   900
caattttagt catgtttcct ctcggctgta tgtaaaatta aaaaaactca tctaatactt    960
tcttcattac agactctaaa ccgcaaattc gcatttctat aaacttcatc ccaaagcatc   1020
atgcgtttta gttccaaaat attttttcatt tcaaaatttt cttttcccat gtccaaatat   1080
tttggttctt cgtcgttgta tggttcccaa aaaatgtcgt ttaaatgtct ttttgtatca   1140
catgatgcat cttcagtgtt tgatgtaggt tttccattct ttacaaaatt ggtccagatc   1200
ctgaccatcc tttccagagt ctgcatagca tcttgcggta tagaaatgtg cgttgttccc   1260
aaaataggaa catccaacga gtttgcaaaa agatatccta aatcatcacc atgactaact   1320
cctggcaagg aacccccatcg ataggggcaag atataacttt tatatacact atacgtatcg  1380
tctgataacc tgtacaaata caaattggaa ttccttctga attcattgaa aaatatggct   1440
ttcaaggtac ggtagattcc ttggaggtaa ccagcatcgc cttttagttg gacgtaggct   1500
tcaatgtcat cgtttgttc tttcacttgg tcataaaaact ctgtaagcat ttttattagt   1560
tttttctcct caataccatt tggattttttc caaatattag catctctagg tatagccctt   1620
tctatatttg tcaaagtctt gtgaacttcc atgtttcctc tggttactct tgccatagat   1680
```

-continued

```
cttaaacctt cagcactatt gaaaccaatg atgacatcga catcaggaaa ttcaccattt    1740
ctcattcttt ccaaggcaga tggaaatgtt attggatctg gagattctgg tgattctaag    1800
actggattaa atactggtac tgtgtctcgg tcatggtcgt tgctatcagg aactctgttt    1860
aaggctgctc gtaaaattag gttttatcc aggtttagga gttcttgttt ttgcgtgatg     1920
tttagcactt gtttgagttt ttcaaatcta tgcagaagtt gaatttgatt agcagtcgga    1980
tttagtaatg tcccactctg caaaatggcc ctttggtagt attttctagt cgagttgtcc    2040
atcatcagaa aatggacact tgctgctcca gcagattctc cagcaattgt aattttttct    2100
ctgtctccac caaacttttc gatgttgtcg taaacccatt ttagtgccaa tctctggtct    2160
tttagaccca tatttccatg gatatcccat tccggcgctg atagaaaacc gaaaactcct    2220
aatctatagt tgatagtgac caaaataatt ccttccctga tcaaataatc aggtccaaaa    2280
aaattataag atcctgatcc ttggttgaat gcgcctccat ggatccagaa cattacagga    2340
tattttgtat tgttcgcaga attaacagtc tctggcgtga atatattcag atataagcaa    2400
tcttcgcttc ctgcataaga atatattaga ctttcctgga acatttgtc tcccaaagtt     2460 cgagcctgta cgaatcctgt ttttggattt gatattggtt ttggagactg aaatcgtaat    2520
ggtccaaaag gcggttcggc ataaggaatt cccaaataag aacaatatac atcattccta    2580
tgatctttat atcggaacgg ttttccttcc gtgatcccgt taaattgaac tctgcacaaa    2640
tgctgatcta ggttatccca tagtatgcac aagataggtg taaataagaa aaataaaaaa    2700
aataaaaata aaactaatgc actactgtga ggtaacattt tttattgtgt tttttaatgc    2760
attttggttg cttaattgtt attatttatc tcgttttgtt tatgataaaa tagacgtttt    2820
gaagacgaca tgtcta                                                   2836

<210> SEQ ID NO 27
<211> LENGTH: 1710
<212> TYPE: DNA
<213> ORGANISM: Ctenocephalides felis
<220> FEATURE:
<221> NAME/KEY: exon
<222> LOCATION: (1)..(1710)
<223> OTHER INFORMATION:

<400> SEQUENCE: 27 tgg gat aac cta gat cag cat ttg tgc aga gtt caa ttt aac ggg atc      48
Trp Asp Asn Leu Asp Gln His Leu Cys Arg Val Gln Phe Asn Gly Ile
1               5                   10                  15 acg gaa gga aaa ccg ttc cga tat aaa gat cat agg aat gat gta tat      96
Thr Glu Gly Lys Pro Phe Arg Tyr Lys Asp His Arg Asn Asp Val Tyr
            20                  25                  30 tgt tct tat ttg gga att cct tat gcc gaa ccg cct ttt gga cca tta     144
Cys Ser Tyr Leu Gly Ile Pro Tyr Ala Glu Pro Pro Phe Gly Pro Leu
        35                  40                  45 cga ttt cag tct cca aaa cca ata tca aat cca aaa aca gga ttc gta     192
Arg Phe Gln Ser Pro Lys Pro Ile Ser Asn Pro Lys Thr Gly Phe Val
    50                  55                  60 cag gct cga act ttg gga gac aaa tgt ttc cag gaa agt cta ata tat     240
Gln Ala Arg Thr Leu Gly Asp Lys Cys Phe Gln Glu Ser Leu Ile Tyr
65                  70                  75                  80 tct tat gca gga agc gaa gat tgc tta tat ctg aat ata ttc acg cca     288
Ser Tyr Ala Gly Ser Glu Asp Cys Leu Tyr Leu Asn Ile Phe Thr Pro
                85                  90                  95 gag act gtt aat tct gcg aac aat aca aaa tat cct gta atg ttc tgg     336
Glu Thr Val Asn Ser Ala Asn Asn Thr Lys Tyr Pro Val Met Phe Trp
```

```
            100                 105                 110
atc cat gga ggc gca ttc aac caa gga tca gga tct tat aat ttt ttt    384
Ile His Gly Gly Ala Phe Asn Gln Gly Ser Gly Ser Tyr Asn Phe Phe
        115                 120                 125 gga cct gat tat ttg atc agg gaa gga att att ttg gtc act atc aac    432
Gly Pro Asp Tyr Leu Ile Arg Glu Gly Ile Ile Leu Val Thr Ile Asn
130                 135                 140 tat aga tta gga gtt ttc ggt ttt cta tca gcg ccg gaa tgg gat atc    480
Tyr Arg Leu Gly Val Phe Gly Phe Leu Ser Ala Pro Glu Trp Asp Ile
145                 150                 155                 160 cat gga aat atg ggt cta aaa gac cag aga ttg gca cta aaa tgg gtt    528
His Gly Asn Met Gly Leu Lys Asp Gln Arg Leu Ala Leu Lys Trp Val
                165                 170                 175 tac gac aac atc gaa aag ttt ggt gga gac aga gaa aaa att aca att    576
Tyr Asp Asn Ile Glu Lys Phe Gly Gly Asp Arg Glu Lys Ile Thr Ile
                180                 185                 190 gct gga gaa tct gct gga gca gca agt gtc cat ttt ctg atg atg gac    624
Ala Gly Glu Ser Ala Gly Ala Ala Ser Val His Phe Leu Met Met Asp
        195                 200                 205 aac tcg act aga aaa tac tac caa agg gcc att ttg cag agt ggg aca    672
Asn Ser Thr Arg Lys Tyr Tyr Gln Arg Ala Ile Leu Gln Ser Gly Thr
210                 215                 220 tta cta aat ccg act gct aat caa att caa ctt ctg cat aga ttt gaa    720
Leu Leu Asn Pro Thr Ala Asn Gln Ile Gln Leu Leu His Arg Phe Glu
225                 230                 235                 240 aaa ctc aaa caa gtg cta aac atc acg caa aaa caa gaa ctc cta aac    768
Lys Leu Lys Gln Val Leu Asn Ile Thr Gln Lys Gln Glu Leu Leu Asn
                245                 250                 255 ctg gat aaa aac cta att tta cga gca gcc tta aac aga gtt cct gat    816
Leu Asp Lys Asn Leu Ile Leu Arg Ala Ala Leu Asn Arg Val Pro Asp
                260                 265                 270 agc aac gac cat gac cga gac aca gta cca gta ttt aat cca gtc tta    864
Ser Asn Asp His Asp Arg Asp Thr Val Pro Val Phe Asn Pro Val Leu
        275                 280                 285 gaa tca cca gaa tct cca gat cca ata aca ttt cca tct gcc ttg gaa    912
Glu Ser Pro Glu Ser Pro Asp Pro Ile Thr Phe Pro Ser Ala Leu Glu
290                 295                 300 aga atg aga aat ggt gaa ttt cct gat gtc gat gtc atc att ggt ttc    960
Arg Met Arg Asn Gly Glu Phe Pro Asp Val Asp Val Ile Ile Gly Phe
305                 310                 315                 320 aat agt gct gaa ggt tta aga tct atg gca aga gta acc aga gga aac   1008
Asn Ser Ala Glu Gly Leu Arg Ser Met Ala Arg Val Thr Arg Gly Asn
                325                 330                 335 atg gaa gtt cac aag act ttg aca aat ata gaa agg gct ata cct aga   1056
Met Glu Val His Lys Thr Leu Thr Asn Ile Glu Arg Ala Ile Pro Arg
                340                 345                 350 gat gct aat att tgg aaa aat cca aat ggt att gag gag aaa aaa cta   1104
Asp Ala Asn Ile Trp Lys Asn Pro Asn Gly Ile Glu Glu Lys Lys Leu
        355                 360                 365 ata aaa atg ctt aca gag ttt tat gac caa gtg aaa gaa caa aac gat   1152
Ile Lys Met Leu Thr Glu Phe Tyr Asp Gln Val Lys Glu Gln Asn Asp
370                 375                 380 gac att gaa gcc tac gtc caa cta aaa ggc gat gct ggt tac ctc caa   1200
Asp Ile Glu Ala Tyr Val Gln Leu Lys Gly Asp Ala Gly Tyr Leu Gln
385                 390                 395                 400 gga atc tac cgt acc ttg aaa gcc ata ttt ttc aat gaa ttc aga agg   1248
Gly Ile Tyr Arg Thr Leu Lys Ala Ile Phe Phe Asn Glu Phe Arg Arg
                405                 410                 415 aat tcc aat ttg tat ttg tac agg tta tca gac gat acg tat agt gta   1296
```

```
Asn Ser Asn Leu Tyr Leu Tyr Arg Leu Ser Asp Asp Thr Tyr Ser Val
            420                 425                 430 tat aaa agt tat atc ttg ccc tat cga tgg ggt tcc ttg cca gga gtt      1344
Tyr Lys Ser Tyr Ile Leu Pro Tyr Arg Trp Gly Ser Leu Pro Gly Val
        435                 440                 445 agt cat ggt gat gat tta gga tat ctt ttt gca aac tcg ttg gat gtt      1392
Ser His Gly Asp Asp Leu Gly Tyr Leu Phe Ala Asn Ser Leu Asp Val
450                 455                 460 cct att ttg gga aca acg cac att tct ata ccg caa gat gct atg cag      1440
Pro Ile Leu Gly Thr Thr His Ile Ser Ile Pro Gln Asp Ala Met Gln
465                 470                 475                 480 act ctg gaa agg atg gtc agg atc tgg acc aat ttt gta aag aat gga      1488
Thr Leu Glu Arg Met Val Arg Ile Trp Thr Asn Phe Val Lys Asn Gly
                485                 490                 495 aaa cct aca tca aac act gaa gat gca tca tgt gat aca aaa aga cat      1536
Lys Pro Thr Ser Asn Thr Glu Asp Ala Ser Cys Asp Thr Lys Arg His
                500                 505                 510 tta aac gac att ttt tgg gaa cca tac aac gac gaa gaa cca aaa tat      1584
Leu Asn Asp Ile Phe Trp Glu Pro Tyr Asn Asp Glu Glu Pro Lys Tyr
            515                 520                 525 ttg gac atg gga aaa gaa aat ttt gaa atg aaa aat att ttg gaa cta      1632
Leu Asp Met Gly Lys Glu Asn Phe Glu Met Lys Asn Ile Leu Glu Leu
        530                 535                 540 aaa cgc atg atg ctt tgg gat gaa gtt tat aga aat gcg aat ttg cgg      1680
Lys Arg Met Met Leu Trp Asp Glu Val Tyr Arg Asn Ala Asn Leu Arg
545                 550                 555                 560 ttt aga gtc tgt aat gaa gaa agt att aga                              1710
Phe Arg Val Cys Asn Glu Glu Ser Ile Arg
                565                 570

<210> SEQ ID NO 28
<211> LENGTH: 1788
<212> TYPE: DNA
<213> ORGANISM: Ctenocephalides felis
<220> FEATURE:
<221> NAME/KEY: exon
<222> LOCATION: (1)..(1788)
<223> OTHER INFORMATION:

<400> SEQUENCE: 28 atg tta cct cac agt agt gca tta gtt tta ttt tta ttt ttt tta ttt      48
Met Leu Pro His Ser Ser Ala Leu Val Leu Phe Leu Phe Phe Leu Phe
1               5                   10                  15 ttc tta ttt aca cct atc ttg tgc ata cta tgg gat aac cta gat cag      96
Phe Leu Phe Thr Pro Ile Leu Cys Ile Leu Trp Asp Asn Leu Asp Gln
            20                  25                  30 cat ttg tgc aga gtt caa ttt aac ggg atc acg gaa gga aaa ccg ttc      144
His Leu Cys Arg Val Gln Phe Asn Gly Ile Thr Glu Gly Lys Pro Phe
        35                  40                  45 cga tat aaa gat cat agg aat gat gta tat tgt tct tat ttg gga att      192
Arg Tyr Lys Asp His Arg Asn Asp Val Tyr Cys Ser Tyr Leu Gly Ile
    50                  55                  60 cct tat gcc gaa ccg cct ttt gga cca tta cga ttt cag tct cca aaa      240
Pro Tyr Ala Glu Pro Pro Phe Gly Pro Leu Arg Phe Gln Ser Pro Lys
65                  70                  75                  80 cca ata tca aat cca aaa aca gga ttc gta cag gct cga act ttg gga      288
Pro Ile Ser Asn Pro Lys Thr Gly Phe Val Gln Ala Arg Thr Leu Gly
                85                  90                  95 gac aaa tgt ttc cag gaa agt cta ata tat tct tat gca gga agc gaa      336
Asp Lys Cys Phe Gln Glu Ser Leu Ile Tyr Ser Tyr Ala Gly Ser Glu
            100                 105                 110
```

```
gat tgc tta tat ctg aat ata ttc acg cca gag act gtt aat tct gcg      384
Asp Cys Leu Tyr Leu Asn Ile Phe Thr Pro Glu Thr Val Asn Ser Ala
        115                 120                 125 aac aat aca aaa tat cct gta atg ttc tgg atc cat gga ggc gca ttc      432
Asn Asn Thr Lys Tyr Pro Val Met Phe Trp Ile His Gly Gly Ala Phe
    130                 135                 140 aac caa gga tca gga tct tat aat ttt ttt gga cct gat tat ttg atc      480
Asn Gln Gly Ser Gly Ser Tyr Asn Phe Phe Gly Pro Asp Tyr Leu Ile
145                 150                 155                 160 agg gaa gga att att ttg gtc act atc aac tat aga tta gga gtt ttc      528
Arg Glu Gly Ile Ile Leu Val Thr Ile Asn Tyr Arg Leu Gly Val Phe
                165                 170                 175 ggt ttt cta tca gcg ccg gaa tgg gat atc cat gga aat atg ggt cta      576
Gly Phe Leu Ser Ala Pro Glu Trp Asp Ile His Gly Asn Met Gly Leu
            180                 185                 190 aaa gac cag aga ttg gca cta aaa tgg gtt tac gac aac atc gaa aag      624
Lys Asp Gln Arg Leu Ala Leu Lys Trp Val Tyr Asp Asn Ile Glu Lys
        195                 200                 205 ttt ggt gga gac aga gaa aaa att aca att gct gga gaa tct gct gga      672
Phe Gly Gly Asp Arg Glu Lys Ile Thr Ile Ala Gly Glu Ser Ala Gly
    210                 215                 220 gca gca agt gtc cat ttt ctg atg atg gac aac tcg act aga aaa tac      720
Ala Ala Ser Val His Phe Leu Met Met Asp Asn Ser Thr Arg Lys Tyr
225                 230                 235                 240 tac caa agg gcc att ttg cag agt ggg aca tta cta aat ccg act gct      768
Tyr Gln Arg Ala Ile Leu Gln Ser Gly Thr Leu Leu Asn Pro Thr Ala
                245                 250                 255 aat caa att caa ctt ctg cat aga ttt gaa aaa ctc aaa caa gtg cta      816
Asn Gln Ile Gln Leu Leu His Arg Phe Glu Lys Leu Lys Gln Val Leu
            260                 265                 270 aac atc acg caa aaa caa gaa ctc cta aac ctg gat aaa aac cta att      864
Asn Ile Thr Gln Lys Gln Glu Leu Leu Asn Leu Asp Lys Asn Leu Ile
        275                 280                 285 tta cga gca gcc tta aac aga gtt cct gat agc aac gac cat gac cga      912
Leu Arg Ala Ala Leu Asn Arg Val Pro Asp Ser Asn Asp His Asp Arg
    290                 295                 300 gac aca gta cca gta ttt aat cca gtc tta gaa tca cca gaa tct cca      960
Asp Thr Val Pro Val Phe Asn Pro Val Leu Glu Ser Pro Glu Ser Pro
305                 310                 315                 320 gat cca ata aca ttt cca tct gcc ttg gaa aga atg aga aat ggt gaa     1008
Asp Pro Ile Thr Phe Pro Ser Ala Leu Glu Arg Met Arg Asn Gly Glu
                325                 330                 335 ttt cct gat gtc gat gtc atc att ggt ttc aat agt gct gaa ggt tta     1056
Phe Pro Asp Val Asp Val Ile Ile Gly Phe Asn Ser Ala Glu Gly Leu
            340                 345                 350 aga tct atg gca aga gta acc aga gga aac atg gaa gtt cac aag act     1104
Arg Ser Met Ala Arg Val Thr Arg Gly Asn Met Glu Val His Lys Thr
        355                 360                 365 ttg aca aat ata gaa agg gct ata cct aga gat gct aat att tgg aaa     1152
Leu Thr Asn Ile Glu Arg Ala Ile Pro Arg Asp Ala Asn Ile Trp Lys
    370                 375                 380 aat cca aat ggt att gag gag aaa aaa cta ata aaa atg ctt aca gag     1200
Asn Pro Asn Gly Ile Glu Glu Lys Lys Leu Ile Lys Met Leu Thr Glu
385                 390                 395                 400 ttt tat gac caa gtg aaa gaa caa aac gat gac att gaa gcc tac gtc     1248
Phe Tyr Asp Gln Val Lys Glu Gln Asn Asp Asp Ile Glu Ala Tyr Val
                405                 410                 415 caa cta aaa ggc gat gct ggt tac ctc caa gga atc tac cgt acc ttg     1296
Gln Leu Lys Gly Asp Ala Gly Tyr Leu Gln Gly Ile Tyr Arg Thr Leu
            420                 425                 430
```

```
aaa gcc ata ttt ttc aat gaa ttc aga agg aat tcc aat ttg tat ttg     1344
Lys Ala Ile Phe Phe Asn Glu Phe Arg Arg Asn Ser Asn Leu Tyr Leu
        435                 440                 445 tac agg tta tca gac gat acg tat agt gta tat aaa agt tat atc ttg     1392
Tyr Arg Leu Ser Asp Asp Thr Tyr Ser Val Tyr Lys Ser Tyr Ile Leu
    450                 455                 460 ccc tat cga tgg ggt tcc ttg cca gga gtt agt cat ggt gat gat tta     1440
Pro Tyr Arg Trp Gly Ser Leu Pro Gly Val Ser His Gly Asp Asp Leu
465                 470                 475                 480 gga tat ctt ttt gca aac tcg ttg gat gtt cct att ttg gga aca acg     1488
Gly Tyr Leu Phe Ala Asn Ser Leu Asp Val Pro Ile Leu Gly Thr Thr
                485                 490                 495 cac att tct ata ccg caa gat gct atg cag act ctg gaa agg atg gtc     1536
His Ile Ser Ile Pro Gln Asp Ala Met Gln Thr Leu Glu Arg Met Val
            500                 505                 510 agg atc tgg acc aat ttt gta aag aat gga aaa cct aca tca aac act     1584
Arg Ile Trp Thr Asn Phe Val Lys Asn Gly Lys Pro Thr Ser Asn Thr
        515                 520                 525 gaa gat gca tca tgt gat aca aaa aga cat tta aac gac att ttt tgg     1632
Glu Asp Ala Ser Cys Asp Thr Lys Arg His Leu Asn Asp Ile Phe Trp
    530                 535                 540 gaa cca tac aac gac gaa gaa cca aaa tat ttg gac atg gga aaa gaa     1680
Glu Pro Tyr Asn Asp Glu Glu Pro Lys Tyr Leu Asp Met Gly Lys Glu
545                 550                 555                 560 aat ttt gaa atg aaa aat att ttg gaa cta aaa cgc atg atg ctt tgg     1728
Asn Phe Glu Met Lys Asn Ile Leu Glu Leu Lys Arg Met Met Leu Trp
                565                 570                 575 gat gaa gtt tat aga aat gcg aat ttg cgg ttt aga gtc tgt aat gaa     1776
Asp Glu Val Tyr Arg Asn Ala Asn Leu Arg Phe Arg Val Cys Asn Glu
            580                 585                 590 gaa agt att aga                                                     1788
Glu Ser Ile Arg
        595

<210> SEQ ID NO 29
<211> LENGTH: 1788
<212> TYPE: DNA
<213> ORGANISM: Ctenocephalides felis

<400> SEQUENCE: 29
tctaatactt tcttcattac agactctaaa ccgcaaattc gcatttctat aaacttcatc     60
ccaaagcatc atgcgtttta gttccaaaat attttcatt tcaaaatttt cttttcccat     120
gtccaaatat tttggttctt cgtcgttgta tggttcccaa aaaatgtcgt ttaaatgtct     180
ttttgtatca catgatgcat cttcagtgtt tgatgtaggt tttccattct ttacaaaatt     240
ggtccagatc ctgaccatcc tttccagagt ctgcatagca tcttgcggta tagaaatgtg     300
cgttgttccc aaaataggaa catccaacga gtttgcaaaa agatatccta aatcatcacc     360
atgactaact cctggcaagg aaccccatcg ataggcaag atataacttt tatatacact     420
atacgtatcg tctgataacc tgtacaaata caaattggaa ttccttctga attcattgaa     480
aaatatggct tcaaggtac ggtagattcc ttggaggtaa ccagcatcgc cttttagttg     540
gacgtaggct tcaatgtcat cgttttgttc tttcacttgg tcataaaact ctgtaagcat     600
ttttattagt tttttctcct caataccatt tggattttc caaatattag catctctagg     660 tatagcccctt tctatatttg tcaaagtctt gtgaacttcc atgtttcctc tggttactct     720
tgccatagat cttaaacctt cagcactatt gaaaccaatg atgacatcga catcaggaaa     780
```

```
ttcaccattt ctcattcttt ccaaggcaga tggaaatgtt attggatctg gagattctgg      840
tgattctaag actggattaa atactggtac tgtgtctcgg tcatggtcgt tgctatcagg      900
aactctgttt aaggctgctc gtaaaattag gtttttatcc aggtttagga gttcttgttt      960
ttgcgtgatg tttagcactt gtttgagttt ttcaaatcta tgcagaagtt gaatttgatt     1020
agcagtcgga tttagtaatg tcccactctg caaaatggcc ctttggtagt attttctagt     1080
cgagttgtcc atcatcagaa aatggacact tgctgctcca gcagattctc cagcaattgt     1140 aatttttttct ctgtctccac caaacttttc gatgttgtcg taaacccatt ttagtgccaa    1200
tctctggtct tttagaccca tatttccatg gatatcccat tccggcgctg atagaaaacc     1260
gaaaactcct aatctatagt tgatagtgac caaaataatt ccttccctga tcaaataatc     1320
aggtccaaaa aaattataag atcctgatcc ttggttgaat gcgcctccat ggatccagaa     1380
cattacagga tattttgtat tgttcgcaga attaacagtc tctggcgtga atatattcag     1440
atataagcaa tcttcgcttc ctgcataaga atatattaga ctttcctgga aacatttgtc     1500
tcccaaagtt cgagcctgta cgaatcctgt ttttggattt gatattggtt ttggagactg     1560
aaatcgtaat ggtccaaaag gcggttcggc ataaggaatt cccaaataag aacaatatac     1620
atcattccta tgatctttat atcggaacgg ttttccttcc gtgatcccgt taaattgaac     1680
tctgcacaaa tgctgatcta ggttatccca tagtatgcac aagataggtg taaataagaa     1740
aaataaaaaa aataaaaata aaactaatgc actactgtga ggtaacat                  1788
```

<210> SEQ ID NO 30
<211> LENGTH: 2801
<212> TYPE: DNA
<213> ORGANISM: Ctenocephalides felis
<220> FEATURE:
<221> NAME/KEY: CDS
<222> LOCATION: (99)..(1886)
<223> OTHER INFORMATION:
<220> FEATURE:
<221> NAME/KEY: misc_feature
<222> LOCATION: (2275)..(2275)
<223> OTHER INFORMATION: n = unknown

<400> SEQUENCE: 30

```
gacatgtcgt cttcaaaacg tctattttat cataaacaaa acgagataaa taataacaat       60
taagcatcca aaatgcatta aaaaaaacat cataaaaa atg tta cct cac agt gca      116
                                           Met Leu Pro His Ser Ala
                                             1               5 tta gtt tta ttt tta ttt ttt tta ttt ttc tta ttt aca cct gtc ttg         164
Leu Val Leu Phe Leu Phe Phe Leu Phe Phe Leu Phe Thr Pro Val Leu
        10                  15                  20 tgc ata cta tgg gat aac cta gat cag cat ttg tgc aga gtt caa ttt         212
Cys Ile Leu Trp Asp Asn Leu Asp Gln His Leu Cys Arg Val Gln Phe
    25                  30                  35 aac ggg atc acg gaa gga aaa ccg ttc cga tat aaa gat cat aaa aat         260
Asn Gly Ile Thr Glu Gly Lys Pro Phe Arg Tyr Lys Asp His Lys Asn
40                  45                  50 gat gta tat tgt tcc tat ttg gga att cct tat gca gaa ccg cct att         308
Asp Val Tyr Cys Ser Tyr Leu Gly Ile Pro Tyr Ala Glu Pro Pro Ile
55                  60                  65                  70 gga cca ttg cga ttt cag tct cca aaa cca ata tca aat cca aaa aca         356
Gly Pro Leu Arg Phe Gln Ser Pro Lys Pro Ile Ser Asn Pro Lys Thr
            75                  80                  85 gga ttc gtt cag gct cgg tct tta gga gac aaa tgt ttc cag gaa agt         404
Gly Phe Val Gln Ala Arg Ser Leu Gly Asp Lys Cys Phe Gln Glu Ser
        90                  95                 100
```

```
cta ata tat tct tat gca gga agc gaa gat tgc tta tat ctg aat ata        452
Leu Ile Tyr Ser Tyr Ala Gly Ser Glu Asp Cys Leu Tyr Leu Asn Ile
        105                 110                 115 ttc acg cca gag act gtt aat tct gcg aac aat aca aaa tat cct gta        500
Phe Thr Pro Glu Thr Val Asn Ser Ala Asn Asn Thr Lys Tyr Pro Val
    120                 125                 130 atg ttc tgg atc cat gga ggc gca ttc aac caa gga tca gga tct tat        548
Met Phe Trp Ile His Gly Gly Ala Phe Asn Gln Gly Ser Gly Ser Tyr
135                 140                 145                 150 aat ttt ttt gga cct gat tat ttg atc agg gaa gga att att ttg gtc        596
Asn Phe Phe Gly Pro Asp Tyr Leu Ile Arg Glu Gly Ile Ile Leu Val
                155                 160                 165 act atc aac tat aga tta gga gtt ttc ggt ttt cta tca gcg ccg gaa        644
Thr Ile Asn Tyr Arg Leu Gly Val Phe Gly Phe Leu Ser Ala Pro Glu
            170                 175                 180 tgg gat atc cat gga aat atg ggt cta aaa gac cag aga ttg gca cta        692
Trp Asp Ile His Gly Asn Met Gly Leu Lys Asp Gln Arg Leu Ala Leu
        185                 190                 195 aaa tgg gtt tat gac aac atc gaa aaa ttt ggt gga gac aga gat aaa        740
Lys Trp Val Tyr Asp Asn Ile Glu Lys Phe Gly Gly Asp Arg Asp Lys
    200                 205                 210 atc act ata gct gga gaa tct gct gga gca gca agt gtt cat ttt ctg        788
Ile Thr Ile Ala Gly Glu Ser Ala Gly Ala Ala Ser Val His Phe Leu
215                 220                 225                 230 atg atg gac aat tct act aga aaa tac tac caa agg gca att ttg cag        836
Met Met Asp Asn Ser Thr Arg Lys Tyr Tyr Gln Arg Ala Ile Leu Gln
                235                 240                 245 agt ggg aca tta ctc aat ccg act gct aat caa att caa cct ctg cat        884
Ser Gly Thr Leu Leu Asn Pro Thr Ala Asn Gln Ile Gln Pro Leu His
            250                 255                 260 aga ttt gaa aaa cta aaa caa gtg ctg aac atc acg caa aaa caa gaa        932
Arg Phe Glu Lys Leu Lys Gln Val Leu Asn Ile Thr Gln Lys Gln Glu
        265                 270                 275 ctc cta aat ctg gac aaa aat caa att ttg cga gca gcc tta aac aga        980
Leu Leu Asn Leu Asp Lys Asn Gln Ile Leu Arg Ala Ala Leu Asn Arg
    280                 285                 290 gtc cca gat aac aac gac cac gaa agg gac aca gta cca gta ttt aat       1028
Val Pro Asp Asn Asn Asp His Glu Arg Asp Thr Val Pro Val Phe Asn
295                 300                 305                 310 cca gtc cta gaa tca cca gaa tct cca gac cca ata aca ttt cca tct       1076
Pro Val Leu Glu Ser Pro Glu Ser Pro Asp Pro Ile Thr Phe Pro Ser
                315                 320                 325 gct tta gaa aga atg aga aat ggt gaa ttt cct gac gtt gat gtc atc       1124
Ala Leu Glu Arg Met Arg Asn Gly Glu Phe Pro Asp Val Asp Val Ile
            330                 335                 340 att gga ttc aat agt gct gaa ggt tta aga tct atg cca aga gta acc       1172
Ile Gly Phe Asn Ser Ala Glu Gly Leu Arg Ser Met Pro Arg Val Thr
        345                 350                 355 aga gga aac atg gaa gtt tac aag act ttg aca aat ata gag aga gct       1220
Arg Gly Asn Met Glu Val Tyr Lys Thr Leu Thr Asn Ile Glu Arg Ala
    360                 365                 370 ata cct aga gat gct aat att tgg aaa aat cct aat ggc att gag gag       1268
Ile Pro Arg Asp Ala Asn Ile Trp Lys Asn Pro Asn Gly Ile Glu Glu
375                 380                 385                 390 aaa aaa ctt ata aaa atg ctt aca gag ttt tat gac caa gtt aaa gaa       1316
Lys Lys Leu Ile Lys Met Leu Thr Glu Phe Tyr Asp Gln Val Lys Glu
                395                 400                 405 caa aac gat gac atc gaa gcc tat gtc caa cta aaa ggc gat gct ggt       1364
Gln Asn Asp Asp Ile Glu Ala Tyr Val Gln Leu Lys Gly Asp Ala Gly
```

```
                         410                  415                  420
tat ctc caa gga att tac cgt acc ttg aaa gcc ata ttt ttc aat gaa      1412
Tyr Leu Gln Gly Ile Tyr Arg Thr Leu Lys Ala Ile Phe Phe Asn Glu
            425                  430                  435 atc aaa aga aat tcc aac ttg tat ttg tat agg tta tca gat gat acg      1460
Ile Lys Arg Asn Ser Asn Leu Tyr Leu Tyr Arg Leu Ser Asp Asp Thr
    440                  445                  450 tat agt gta tat aaa agt tat atc ttg ccc tat cga tgg ggt tcc ttg      1508
Tyr Ser Val Tyr Lys Ser Tyr Ile Leu Pro Tyr Arg Trp Gly Ser Leu
455                  460                  465                  470 cca gga gtt agt cat ggt gat gat tta gga tat ctt ttt gca aac tct      1556
Pro Gly Val Ser His Gly Asp Asp Leu Gly Tyr Leu Phe Ala Asn Ser
                475                  480                  485 ttg gat gtt cct att ttg gga aca acg cac att tct ata ccg caa gat      1604
Leu Asp Val Pro Ile Leu Gly Thr Thr His Ile Ser Ile Pro Gln Asp
            490                  495                  500 gct atg cag act ctg gaa agg atg gtc agg atc tgg acc aat ttt gta      1652
Ala Met Gln Thr Leu Glu Arg Met Val Arg Ile Trp Thr Asn Phe Val
    505                  510                  515 aag aat gga aaa cct aca tca aac act gaa gat gca tca tgt gat aca      1700
Lys Asn Gly Lys Pro Thr Ser Asn Thr Glu Asp Ala Ser Cys Asp Thr
520                  525                  530 aaa aga cat tta aac gac att ttt tgg gaa cca tac aac gac gaa gaa      1748
Lys Arg His Leu Asn Asp Ile Phe Trp Glu Pro Tyr Asn Asp Glu Glu
535                  540                  545                  550 cca aaa tat ttg gac atg gga aaa gaa cat ttt gaa atg aaa aat att      1796
Pro Lys Tyr Leu Asp Met Gly Lys Glu His Phe Glu Met Lys Asn Ile
                555                  560                  565 ttg gaa cta aaa cgc atg atg ctt tgg gat gaa gtt tat aga aat gcg      1844
Leu Glu Leu Lys Arg Met Met Leu Trp Asp Glu Val Tyr Arg Asn Ala
            570                  575                  580 aat ttg cgg ttt aga gtc tgt aat gaa gaa agt att aga tga              1886
Asn Leu Arg Phe Arg Val Cys Asn Glu Glu Ser Ile Arg
    585                  590                  595 gttttttaa ttttacatac agccgagagg aaacatgact aaaattggaa agaaaaatca    1946 gaaaagaaa aatcacatgg accatagtaa ctttattaca tgatttagtt tcaagtgtat    2006
caagaaaact tattgcatca agaaaatat tattttgcca aaattcttgg aaaaacactt    2066
tttatgactg acatggccca taattgaagc ttttcttct tttaccaaat cgccaatttt    2126
tgtagcgtca gacacattta tttatgacat ggcaattaat gtgttaaaca ttcaactcta   2186
tattaaaaat ggtagtattt tctaataaga aggttatata aaaagacttg aaaataataa   2246
gatttgctcg gctatatata aaaacttanc gtctcgttat gctaaacttt tttgatggta   2306
aaaatatgtt gattttccta ataatctaag atattatatt ttagattaaa ttaaaatatg   2366
atattttcaa ttaattaatt ttagttttaa atgtactata tttaccagta ctatgaaact   2426
attttaaata tatttttat tacaatattt atttctcaaa aatgtttagt gtaacaagac    2486
cattaaatta gagttaatgt tgtaaattaa actattttt atctatcaca accgcttaat    2546
tggtgcaaag aaaaatttta ctgtgataat atttgacatt tacacaatat tacgaattgt   2606
aaactcacaa ttatgtgaat attgtttttt gttaaaaaaa catacatgac ttttctatat   2666
cattttatat tacggtgata tggattaatg tcaacatgta aaatacaaat gcggttgtta   2726
aaaataatct gtattaaaat tgttatataa aatctgaata aatgtacttt taagtaaaaa   2786
aaaaaaaaaa aaaaa                                                    2801
```

```
<210> SEQ ID NO 31
<211> LENGTH: 595
<212> TYPE: PRT
<213> ORGANISM: Ctenocephalides felis

<400> SEQUENCE: 31

Met Leu Pro His Ser Ala Leu Val Leu Phe Leu Phe Phe Leu Phe Phe
1               5                   10                  15

Leu Phe Thr Pro Val Leu Cys Ile Leu Trp Asp Asn Leu Asp Gln His
            20                  25                  30

Leu Cys Arg Val Gln Phe Asn Gly Ile Thr Glu Gly Lys Pro Phe Arg
        35                  40                  45

Tyr Lys Asp His Lys Asn Asp Val Tyr Cys Ser Tyr Leu Gly Ile Pro
    50                  55                  60

Tyr Ala Glu Pro Pro Ile Gly Pro Leu Arg Phe Gln Ser Pro Lys Pro
65                  70                  75                  80

Ile Ser Asn Pro Lys Thr Gly Phe Val Gln Ala Arg Ser Leu Gly Asp
                85                  90                  95

Lys Cys Phe Gln Glu Ser Leu Ile Tyr Ser Tyr Ala Gly Ser Glu Asp
            100                 105                 110

Cys Leu Tyr Leu Asn Ile Phe Thr Pro Glu Thr Val Asn Ser Ala Asn
        115                 120                 125

Asn Thr Lys Tyr Pro Val Met Phe Trp Ile His Gly Gly Ala Phe Asn
    130                 135                 140

Gln Gly Ser Gly Ser Tyr Asn Phe Phe Gly Pro Asp Tyr Leu Ile Arg
145                 150                 155                 160

Glu Gly Ile Ile Leu Val Thr Ile Asn Tyr Arg Leu Gly Val Phe Gly
                165                 170                 175

Phe Leu Ser Ala Pro Glu Trp Asp Ile His Gly Asn Met Gly Leu Lys
            180                 185                 190

Asp Gln Arg Leu Ala Leu Lys Trp Val Tyr Asp Asn Ile Glu Lys Phe
        195                 200                 205

Gly Gly Asp Arg Asp Lys Ile Thr Ile Ala Gly Glu Ser Ala Gly Ala
    210                 215                 220

Ala Ser Val His Phe Leu Met Met Asp Asn Ser Thr Arg Lys Tyr Tyr
225                 230                 235                 240

Gln Arg Ala Ile Leu Gln Ser Gly Thr Leu Leu Asn Pro Thr Ala Asn
                245                 250                 255

Gln Ile Gln Pro Leu His Arg Phe Glu Lys Leu Lys Gln Val Leu Asn
            260                 265                 270

Ile Thr Gln Lys Gln Glu Leu Leu Asn Leu Asp Lys Asn Gln Ile Leu
        275                 280                 285

Arg Ala Ala Leu Asn Arg Val Pro Asp Asn Asn Asp His Glu Arg Asp
    290                 295                 300

Thr Val Pro Val Phe Asn Pro Val Leu Glu Ser Pro Glu Ser Pro Asp
305                 310                 315                 320

Pro Ile Thr Phe Pro Ser Ala Leu Glu Arg Met Arg Asn Gly Glu Phe
                325                 330                 335

Pro Asp Val Asp Val Ile Ile Gly Phe Asn Ser Ala Glu Gly Leu Arg
            340                 345                 350

Ser Met Pro Arg Val Thr Arg Gly Asn Met Glu Val Tyr Lys Thr Leu
        355                 360                 365

Thr Asn Ile Glu Arg Ala Ile Pro Arg Asp Ala Asn Ile Trp Lys Asn
    370                 375                 380
```

```
Pro Asn Gly Ile Glu Glu Lys Lys Leu Ile Lys Met Leu Thr Glu Phe
385                 390                 395                 400

Tyr Asp Gln Val Lys Glu Gln Asn Asp Ile Glu Ala Tyr Val Gln
            405                 410                 415

Leu Lys Gly Asp Ala Gly Tyr Leu Gln Gly Ile Tyr Arg Thr Leu Lys
            420                 425                 430

Ala Ile Phe Phe Asn Glu Ile Lys Arg Asn Ser Asn Leu Tyr Leu Tyr
        435                 440                 445

Arg Leu Ser Asp Asp Thr Tyr Ser Val Tyr Lys Ser Tyr Ile Leu Pro
        450                 455                 460

Tyr Arg Trp Gly Ser Leu Pro Gly Val Ser His Gly Asp Asp Leu Gly
465                 470                 475                 480

Tyr Leu Phe Ala Asn Ser Leu Asp Val Pro Ile Leu Gly Thr Thr His
            485                 490                 495

Ile Ser Ile Pro Gln Asp Ala Met Gln Thr Leu Glu Arg Met Val Arg
            500                 505                 510

Ile Trp Thr Asn Phe Val Lys Asn Gly Lys Pro Thr Ser Asn Thr Glu
        515                 520                 525

Asp Ala Ser Cys Asp Thr Lys Arg His Leu Asn Asp Ile Phe Trp Glu
530                 535                 540

Pro Tyr Asn Asp Glu Glu Pro Lys Tyr Leu Asp Met Gly Lys Glu His
545                 550                 555                 560

Phe Glu Met Lys Asn Ile Leu Glu Leu Lys Arg Met Met Leu Trp Asp
            565                 570                 575

Glu Val Tyr Arg Asn Ala Asn Leu Arg Phe Arg Val Cys Asn Glu Glu
            580                 585                 590

Ser Ile Arg
        595

<210> SEQ ID NO 32
<211> LENGTH: 2801
<212> TYPE: DNA
<213> ORGANISM: Ctenocephalides felis
<220> FEATURE:
<221> NAME/KEY: misc_feature
<222> LOCATION: (527)..(527)
<223> OTHER INFORMATION: n = unknown at position 527

<400> SEQUENCE: 32
tttttttttt tttttttttt acttaaaagt acatttattc agattttata taacaatttt      60
aatacagatt attttttaaca accgcatttg tattttacat gttgacatta atccatatca    120
ccgtaatata aaatgatata gaaaagtcat gtatgttttt ttaacaaaaa acaatattca    180
cataattgtg agtttacaat tcgtaatatt gtgtaaatgt caaatattat cacagtaaaa    240
tttttctttg caccaattaa gcggttgtga tagataaaaa atagtttaat ttacaacatt    300
aactctaatt taatggtctt gttacactaa acattttga gaaataaata ttgtaataaa    360
aaatatattt aaaatagttt catagtactg gtaaatatag tacatttaaa actaaaatta    420
attaattgaa aatatcatat tttaatttaa tctaaaatat aatatcttag attattagga    480
aaatcaacat attttttacca tcaaaaaagt ttagcataac gagacgntaa gttttttatat    540 atagccgagc aaatcttatt attttcaagt cttttttatat aaccttctta ttagaaaata    600
ctaccatttt taatatagag ttgaatgttt aacacattaa ttgccatgtc ataaataaat    660
gtgtctgacg ctacaaaatt tggcgatttg gtaaagaag aaaaagcttc aattatgggc    720
catgtcagtc ataaaaagtg ttttttccaag aattttggca aataatatatt ttctttgatg    780
```

```
caataagttt tcttgataca cttgaaacta aatcatgtaa taaagttact atggtccatg    840
tgatttttct ttttctgatt tttctttcca attttagtca tgtttcctct cggctgtatg    900
taaaattaaa aaaactcatc taatactttc ttcattacag actctaaacc gcaaattcgc    960
atttctataa acttcatccc aaagcatcat gcgttttagt tccaaaatat ttttcatttc   1020
aaaatgttct tttcccatgt ccaaatattt tggttcttcg tcgttgtatg gttcccaaaa   1080
aatgtcgttt aaatgtcttt ttgtatcaca tgatgcatct tcagtgtttg atgtaggttt   1140
tccattcttt acaaaattgg tccagatcct gaccatcctt tccagagtct gcatagcatc   1200
ttgcggtata gaaatgtgcg ttgttcccaa aataggaaca tccaaagagt ttgcaaaaag   1260
atatcctaaa tcatcaccat gactaactcc tggcaaggaa ccccatcgat agggcaagat   1320
ataactttta tatacactat acgtatcatc tgataaccta tacaaataca agttggaatt   1380
tcttttgatt tcattgaaaa atatggcttt caaggtacgg taaattcctt ggagataacc   1440
agcatcgcct tttagttgga cataggcttc gatgtcatcg ttttgttctt taacttggtc   1500
ataaaactct gtaagcattt ttataagttt tttctcctca atgccattag gattttcca   1560
aatattagca tctctaggta tagctctctc tatatttgtc aaagtcttgt aaacttccat   1620
gtttcctctg gttactcttg gcatagatct taaaccttca gcactattga atccaatgat   1680
gacatcaacg tcaggaaatt caccatttct cattctttct aaagcagatg gaaatgttat   1740
tgggtctgga gattctggtg attctaggac tggattaaat actggtactg tgtcccttt с   1800
gtggtcgttg ttatctggga ctctgtttaa ggctgctcgc aaaatttgat ttttgtccag   1860
atttaggagt tcttgttttt gcgtgatgtt cagcacttgt tttagttttt caaatctatg   1920
cagaggttga atttgattag cagtcggatt gagtaatgtc ccactctgca aaattgccct   1980
ttggtagtat tttctagtag aattgtccat catcagaaaa tgaacacttg ctgctccagc   2040
agattctcca gctatagtga ttttatctct gtctccacca aattttcga tgttgtcata   2100
aacccatttt agtgccaatc tctggtcttt tagaccccata tttccatgga tatcccattc   2160
cggcgctgat agaaaaccga aaactcctaa tctatagttg atagtgacca aaataattcc   2220
ttccctgatc aaataatcag gtccaaaaaa attataagat cctgatcctt ggttgaatgc   2280
gcctccatgg atccagaaca ttacaggata ttttgtattg ttcgcagaat taacagtctc   2340
tggcgtgaat atattcagat ataagcaatc ttcgcttcct gcataagaat atattagact   2400
ttcctggaaa catttgtctc ctaaagaccg agcctgaacg aatcctgttt ttggatttga   2460
tattggtttt ggagactgaa atcgcaatgg tccataggc ggttctgcat aaggaattcc   2520
caaataggaa caatatacat cattttatg atctttatat cggaacggtt ttccttccgt   2580
gatcccgtta aattgaactc tgcacaaatg ctgatctagg ttatcccata gtatgcacaa   2640
gacaggtgta aataagaaaa ataaaaaaaa taaaataaaa actaatgcac tgtgaggtaa   2700
cattttttat gatgtttttt ttaatgcatt ttggatgctt aattgttatt atttatctcg   2760
ttttgtttat gataaaatag acgttttgaa gacgacatgt c                       2801
```

<210> SEQ ID NO 33
<211> LENGTH: 1710
<212> TYPE: DNA
<213> ORGANISM: Ctenocephalides felis
<220> FEATURE:
<221> NAME/KEY: exon
<222> LOCATION: (1)..(1710)
<223> OTHER INFORMATION:

-continued

```
<400> SEQUENCE: 33 tgg gat aac cta gat cag cat ttg tgc aga gtt caa ttt aac ggg atc      48
Trp Asp Asn Leu Asp Gln His Leu Cys Arg Val Gln Phe Asn Gly Ile
1               5                   10                  15 acg gaa gga aaa ccg ttc cga tat aaa gat cat aaa aat gat gta tat      96
Thr Glu Gly Lys Pro Phe Arg Tyr Lys Asp His Lys Asn Asp Val Tyr
            20                  25                  30 tgt tcc tat ttg gga att cct tat gca gaa ccg cct att gga cca ttg     144
Cys Ser Tyr Leu Gly Ile Pro Tyr Ala Glu Pro Pro Ile Gly Pro Leu
        35                  40                  45 cga ttt cag tct cca aaa cca ata tca aat cca aaa aca gga ttc gtt     192
Arg Phe Gln Ser Pro Lys Pro Ile Ser Asn Pro Lys Thr Gly Phe Val
    50                  55                  60 cag gct cgg tct tta gga gac aaa tgt ttc cag gaa agt cta ata tat     240
Gln Ala Arg Ser Leu Gly Asp Lys Cys Phe Gln Glu Ser Leu Ile Tyr
65                  70                  75                  80 tct tat gca gga agc gaa gat tgc tta tat ctg aat ata ttc acg cca     288
Ser Tyr Ala Gly Ser Glu Asp Cys Leu Tyr Leu Asn Ile Phe Thr Pro
                85                  90                  95 gag act gtt aat tct gcg aac aat aca aaa tat cct gta atg ttc tgg     336
Glu Thr Val Asn Ser Ala Asn Asn Thr Lys Tyr Pro Val Met Phe Trp
            100                 105                 110 atc cat gga ggc gca ttc aac caa gga tca gga tct tat aat ttt ttt     384
Ile His Gly Gly Ala Phe Asn Gln Gly Ser Gly Ser Tyr Asn Phe Phe
        115                 120                 125 gga cct gat tat ttg atc agg gaa gga att att ttg gtc act atc aac     432
Gly Pro Asp Tyr Leu Ile Arg Glu Gly Ile Ile Leu Val Thr Ile Asn
    130                 135                 140 tat aga tta gga gtt ttc ggt ttt cta tca gcg ccg gaa tgg gat atc     480
Tyr Arg Leu Gly Val Phe Gly Phe Leu Ser Ala Pro Glu Trp Asp Ile
145                 150                 155                 160 cat gga aat atg ggt cta aaa gac cag aga ttg gca cta aaa tgg gtt     528
His Gly Asn Met Gly Leu Lys Asp Gln Arg Leu Ala Leu Lys Trp Val
                165                 170                 175 tat gac aac atc gaa aaa ttt ggt gga gac aga gat aaa atc act ata     576
Tyr Asp Asn Ile Glu Lys Phe Gly Gly Asp Arg Asp Lys Ile Thr Ile
            180                 185                 190 gct gga gaa tct gct gga gca gca agt gtt cat ttt ctg atg atg gac     624
Ala Gly Glu Ser Ala Gly Ala Ala Ser Val His Phe Leu Met Met Asp
        195                 200                 205 aat tct act aga aaa tac tac caa agg gca att ttg cag agt ggg aca     672
Asn Ser Thr Arg Lys Tyr Tyr Gln Arg Ala Ile Leu Gln Ser Gly Thr
    210                 215                 220 tta ctc aat ccg act gct aat caa att caa cct ctg cat aga ttt gaa     720
Leu Leu Asn Pro Thr Ala Asn Gln Ile Gln Pro Leu His Arg Phe Glu
225                 230                 235                 240 aaa cta aaa caa gtg ctg aac atc acg caa aaa caa gaa ctc cta aat     768
Lys Leu Lys Gln Val Leu Asn Ile Thr Gln Lys Gln Glu Leu Leu Asn
                245                 250                 255 ctg gac aaa aat caa att ttg cga gca gcc tta aac aga gtc cca gat     816
Leu Asp Lys Asn Gln Ile Leu Arg Ala Ala Leu Asn Arg Val Pro Asp
            260                 265                 270 aac aac gac cac gaa agg gac aca gta cca gta ttt aat cca gtc cta     864
Asn Asn Asp His Glu Arg Asp Thr Val Pro Val Phe Asn Pro Val Leu
        275                 280                 285 gaa tca cca gaa tct cca gac cca ata aca ttt cca tct gct tta gaa     912
Glu Ser Pro Glu Ser Pro Asp Pro Ile Thr Phe Pro Ser Ala Leu Glu
    290                 295                 300 aga atg aga aat ggt gaa ttt cct gac gtt gat gtc atc att gga ttc     960
```

-continued

| | | |
|---|---|---|
| Arg Met Arg Asn Gly Glu Phe Pro Asp Val Asp Val Ile Ile Gly Phe<br>305                            310                         315                         320 | | |
| aat agt gct gaa ggt tta aga tct atg cca aga gta acc aga gga aac<br>Asn Ser Ala Glu Gly Leu Arg Ser Met Pro Arg Val Thr Arg Gly Asn<br>                        325                        330                        335 | | 1008 |
| atg gaa gtt tac aag act ttg aca aat ata gag aga gct ata cct aga<br>Met Glu Val Tyr Lys Thr Leu Thr Asn Ile Glu Arg Ala Ile Pro Arg<br>            340                        345                        350 | | 1056 |
| gat gct aat att tgg aaa aat cct aat ggc att gag gag aaa aaa ctt<br>Asp Ala Asn Ile Trp Lys Asn Pro Asn Gly Ile Glu Glu Lys Lys Leu<br>               355                        360                        365 | | 1104 |
| ata aaa atg ctt aca gag ttt tat gac caa gtt aaa gaa caa aac gat<br>Ile Lys Met Leu Thr Glu Phe Tyr Asp Gln Val Lys Glu Gln Asn Asp<br>370                            375                         380 | | 1152 |
| gac atc gaa gcc tat gtc caa cta aaa ggc gat gct ggt tat ctc caa<br>Asp Ile Glu Ala Tyr Val Gln Leu Lys Gly Asp Ala Gly Tyr Leu Gln<br>385                            390                        395                        400 | | 1200 |
| gga att tac cgt acc ttg aaa gcc ata ttt ttc aat gaa atc aaa aga<br>Gly Ile Tyr Arg Thr Leu Lys Ala Ile Phe Phe Asn Glu Ile Lys Arg<br>                        405                        410                        415 | | 1248 |
| aat tcc aac ttg tat ttg tat agg tta tca gat gat acg tat agt gta<br>Asn Ser Asn Leu Tyr Leu Tyr Arg Leu Ser Asp Asp Thr Tyr Ser Val<br>            420                        425                        430 | | 1296 |
| tat aaa agt tat atc ttg ccc tat cga tgg ggt tcc ttg cca gga gtt<br>Tyr Lys Ser Tyr Ile Leu Pro Tyr Arg Trp Gly Ser Leu Pro Gly Val<br>               435                        440                        445 | | 1344 |
| agt cat ggt gat gat tta gga tat ctt ttt gca aac tct ttg gat gtt<br>Ser His Gly Asp Asp Leu Gly Tyr Leu Phe Ala Asn Ser Leu Asp Val<br>            450                        455                        460 | | 1392 |
| cct att ttg gga aca acg cac att tct ata ccg caa gat gct atg cag<br>Pro Ile Leu Gly Thr Thr His Ile Ser Ile Pro Gln Asp Ala Met Gln<br>465                            470                        475                        480 | | 1440 |
| act ctg gaa agg atg gtc agg atc tgg acc aat ttt gta aag aat gga<br>Thr Leu Glu Arg Met Val Arg Ile Trp Thr Asn Phe Val Lys Asn Gly<br>               485                        490                        495 | | 1488 |
| aaa cct aca tca aac act gaa gat gca tca tgt gat aca aaa aga cat<br>Lys Pro Thr Ser Asn Thr Glu Asp Ala Ser Cys Asp Thr Lys Arg His<br>            500                        505                        510 | | 1536 |
| tta aac gac att ttt tgg gaa cca tac aac gac gaa gaa cca aaa tat<br>Leu Asn Asp Ile Phe Trp Glu Pro Tyr Asn Asp Glu Glu Pro Lys Tyr<br>               515                        520                        525 | | 1584 |
| ttg gac atg gga aaa gaa cat ttt gaa atg aaa aat att ttg gaa cta<br>Leu Asp Met Gly Lys Glu His Phe Glu Met Lys Asn Ile Leu Glu Leu<br>530                            535                        540 | | 1632 |
| aaa cgc atg atg ctt tgg gat gaa gtt tat aga aat gcg aat ttg cgg<br>Lys Arg Met Met Leu Trp Asp Glu Val Tyr Arg Asn Ala Asn Leu Arg<br>545                            550                        555                        560 | | 1680 |
| ttt aga gtc tgt aat gaa gaa agt att aga<br>Phe Arg Val Cys Asn Glu Glu Ser Ile Arg<br>            565                        570 | | 1710 |

<210> SEQ ID NO 34
<211> LENGTH: 1785
<212> TYPE: DNA
<213> ORGANISM: Ctenocephalides felis
<220> FEATURE:
<221> NAME/KEY: exon
<222> LOCATION: (1)..(1785)
<223> OTHER INFORMATION:

<400> SEQUENCE: 34

-continued

```
atg tta cct cac agt gca tta gtt tta ttt tta ttt ttt tta ttt ttc      48
Met Leu Pro His Ser Ala Leu Val Leu Phe Leu Phe Phe Leu Phe Phe
1               5                   10                  15 tta ttt aca cct gtc ttg tgc ata cta tgg gat aac cta gat cag cat      96
Leu Phe Thr Pro Val Leu Cys Ile Leu Trp Asp Asn Leu Asp Gln His
            20                  25                  30 ttg tgc aga gtt caa ttt aac ggg atc acg gaa gga aaa ccg ttc cga     144
Leu Cys Arg Val Gln Phe Asn Gly Ile Thr Glu Gly Lys Pro Phe Arg
        35                  40                  45 tat aaa gat cat aaa aat gat gta tat tgt tcc tat ttg gga att cct     192
Tyr Lys Asp His Lys Asn Asp Val Tyr Cys Ser Tyr Leu Gly Ile Pro
50                  55                  60 tat gca gaa ccg cct att gga cca ttg cga ttt cag tct cca aaa cca     240
Tyr Ala Glu Pro Pro Ile Gly Pro Leu Arg Phe Gln Ser Pro Lys Pro
65                  70                  75                  80 ata tca aat cca aaa aca gga ttc gtt cag gct cgg tct tta gga gac     288
Ile Ser Asn Pro Lys Thr Gly Phe Val Gln Ala Arg Ser Leu Gly Asp
            85                  90                  95 aaa tgt ttc cag gaa agt cta ata tat tct tat gca gga agc gaa gat     336
Lys Cys Phe Gln Glu Ser Leu Ile Tyr Ser Tyr Ala Gly Ser Glu Asp
        100                 105                 110 tgc tta tat ctg aat ata ttc acg cca gag act gtt aat tct gcg aac     384
Cys Leu Tyr Leu Asn Ile Phe Thr Pro Glu Thr Val Asn Ser Ala Asn
    115                 120                 125 aat aca aaa tat cct gta atg ttc tgg atc cat gga ggc gca ttc aac     432
Asn Thr Lys Tyr Pro Val Met Phe Trp Ile His Gly Gly Ala Phe Asn
130                 135                 140 caa gga tca gga tct tat aat ttt ttt gga cct gat tat ttg atc agg     480
Gln Gly Ser Gly Ser Tyr Asn Phe Phe Gly Pro Asp Tyr Leu Ile Arg
145                 150                 155                 160 gaa gga att att ttg gtc act atc aac tat aga tta gga gtt ttc ggt     528
Glu Gly Ile Ile Leu Val Thr Ile Asn Tyr Arg Leu Gly Val Phe Gly
            165                 170                 175 ttt cta tca gcg ccg gaa tgg gat atc cat gga aat atg ggt cta aaa     576
Phe Leu Ser Ala Pro Glu Trp Asp Ile His Gly Asn Met Gly Leu Lys
        180                 185                 190 gac cag aga ttg gca cta aaa tgg gtt tat gac aac atc gaa aaa ttt     624
Asp Gln Arg Leu Ala Leu Lys Trp Val Tyr Asp Asn Ile Glu Lys Phe
    195                 200                 205 ggt gga gac aga gat aaa atc act ata gct gga gaa tct gct gga gca     672
Gly Gly Asp Arg Asp Lys Ile Thr Ile Ala Gly Glu Ser Ala Gly Ala
210                 215                 220 gca agt gtt cat ttt ctg atg atg gac aat tct act aga aaa tac tac     720
Ala Ser Val His Phe Leu Met Met Asp Asn Ser Thr Arg Lys Tyr Tyr
225                 230                 235                 240 caa agg gca att ttg cag agt ggg aca tta ctc aat ccg act gct aat     768
Gln Arg Ala Ile Leu Gln Ser Gly Thr Leu Leu Asn Pro Thr Ala Asn
            245                 250                 255 caa att caa cct ctg cat aga ttt gaa aaa cta aaa caa gtg ctg aac     816
Gln Ile Gln Pro Leu His Arg Phe Glu Lys Leu Lys Gln Val Leu Asn
        260                 265                 270 atc acg caa aaa caa gaa ctc cta aat ctg gac aaa aat caa att ttg     864
Ile Thr Gln Lys Gln Glu Leu Leu Asn Leu Asp Lys Asn Gln Ile Leu
    275                 280                 285 cga gca gcc tta aac aga gtc cca gat aac aac gac cac gaa agg gac     912
Arg Ala Ala Leu Asn Arg Val Pro Asp Asn Asn Asp His Glu Arg Asp
290                 295                 300 aca gta cca gta ttt aat cca gtc cta gaa tca cca gaa tct cca gac     960
Thr Val Pro Val Phe Asn Pro Val Leu Glu Ser Pro Glu Ser Pro Asp
305                 310                 315                 320
```

```
cca ata aca ttt cca tct gct tta gaa aga atg aga aat ggt gaa ttt    1008
Pro Ile Thr Phe Pro Ser Ala Leu Glu Arg Met Arg Asn Gly Glu Phe
            325                 330                 335 cct gac gtt gat gtc atc att gga ttc aat agt gct gaa ggt tta aga    1056
Pro Asp Val Asp Val Ile Ile Gly Phe Asn Ser Ala Glu Gly Leu Arg
        340                 345                 350 tct atg cca aga gta acc aga gga aac atg gaa gtt tac aag act ttg    1104
Ser Met Pro Arg Val Thr Arg Gly Asn Met Glu Val Tyr Lys Thr Leu
        355                 360                 365 aca aat ata gag aga gct ata cct aga gat gct aat att tgg aaa aat    1152
Thr Asn Ile Glu Arg Ala Ile Pro Arg Asp Ala Asn Ile Trp Lys Asn
    370                 375                 380 cct aat ggc att gag gag aaa aaa ctt ata aaa atg ctt aca gag ttt    1200
Pro Asn Gly Ile Glu Glu Lys Lys Leu Ile Lys Met Leu Thr Glu Phe
385                 390                 395                 400 tat gac caa gtt aaa gaa caa aac gat gac atc gaa gcc tat gtc caa    1248
Tyr Asp Gln Val Lys Glu Gln Asn Asp Asp Ile Glu Ala Tyr Val Gln
                405                 410                 415 cta aaa ggc gat gct ggt tat ctc caa gga att tac cgt acc ttg aaa    1296
Leu Lys Gly Asp Ala Gly Tyr Leu Gln Gly Ile Tyr Arg Thr Leu Lys
            420                 425                 430 gcc ata ttt ttc aat gaa atc aaa aga aat tcc aac ttg tat ttg tat    1344
Ala Ile Phe Phe Asn Glu Ile Lys Arg Asn Ser Asn Leu Tyr Leu Tyr
        435                 440                 445 agg tta tca gat gat acg tat agt gta tat aaa agt tat atc ttg ccc    1392
Arg Leu Ser Asp Asp Thr Tyr Ser Val Tyr Lys Ser Tyr Ile Leu Pro
    450                 455                 460 tat cga tgg ggt tcc ttg cca gga gtt agt cat ggt gat gat tta gga    1440
Tyr Arg Trp Gly Ser Leu Pro Gly Val Ser His Gly Asp Asp Leu Gly
465                 470                 475                 480 tat ctt ttt gca aac tct ttg gat gtt cct att ttg gga aca acg cac    1488
Tyr Leu Phe Ala Asn Ser Leu Asp Val Pro Ile Leu Gly Thr Thr His
                485                 490                 495 att tct ata ccg caa gat gct atg cag act ctg gaa agg atg gtc agg    1536
Ile Ser Ile Pro Gln Asp Ala Met Gln Thr Leu Glu Arg Met Val Arg
            500                 505                 510 atc tgg acc aat ttt gta aag aat gga aaa cct aca tca aac act gaa    1584
Ile Trp Thr Asn Phe Val Lys Asn Gly Lys Pro Thr Ser Asn Thr Glu
        515                 520                 525 gat gca tca tgt gat aca aaa aga cat tta aac gac att ttt tgg gaa    1632
Asp Ala Ser Cys Asp Thr Lys Arg His Leu Asn Asp Ile Phe Trp Glu
    530                 535                 540 cca tac aac gac gaa gaa cca aaa tat ttg gac atg gga aaa gaa cat    1680
Pro Tyr Asn Asp Glu Glu Pro Lys Tyr Leu Asp Met Gly Lys Glu His
545                 550                 555                 560 ttt gaa atg aaa aat att ttg gaa cta aaa cgc atg atg ctt tgg gat    1728
Phe Glu Met Lys Asn Ile Leu Glu Leu Lys Arg Met Met Leu Trp Asp
                565                 570                 575 gaa gtt tat aga aat gcg aat ttg cgg ttt aga gtc tgt aat gaa gaa    1776
Glu Val Tyr Arg Asn Ala Asn Leu Arg Phe Arg Val Cys Asn Glu Glu
            580                 585                 590 agt att aga                                                         1785
Ser Ile Arg
        595

<210> SEQ ID NO 35
<211> LENGTH: 1785
<212> TYPE: DNA
<213> ORGANISM: Ctenocephalides felis
```

<400> SEQUENCE: 35

```
tctaatactt tcttcattac agactctaaa ccgcaaattc gcatttctat aaacttcatc      60
ccaaagcatc atgcgtttta gttccaaaat atttttcatt tcaaaatgtt cttttcccat     120
gtccaaatat tttggttctt cgtcgttgta tggttcccaa aaaatgtcgt ttaaatgtct     180
ttttgtatca catgatgcat cttcagtgtt tgatgtaggt tttccattct ttacaaaatt     240
ggtccagatc ctgaccatcc tttccagagt ctgcatagca tcttgcggta tagaaatgtg     300
cgttgttccc aaaataggaa catccaaaga gtttgcaaaa agatatccta aatcatcacc     360
atgactaact cctggcaagg aaccccatcg ataggcaag atataacttt tatatacact      420
atacgtatca tctgataacc tatacaaata caagttggaa tttcttttga tttcattgaa     480
aaatatggct ttcaaggtac ggtaaattcc ttggagataa ccagcatcgc cttttagttg     540
gacataggct tcgatgtcat cgttttgttc tttaacttgg tcataaaact ctgtaagcat     600
ttttataagt ttttctcct caatgccatt aggattttc caaatattag catctctagg       660
tatagctctc tctatatttg tcaaagtctt gtaaacttcc atgtttcctc tggttactct     720
tggcatagat cttaaacctt cagcactatt gaatccaatg atgacatcaa cgtcaggaaa     780
ttcaccattt ctcattcttt ctaaagcaga tggaaatgtt attgggtctg gagattctgg     840
tgattctagg actggattaa atactggtac tgtgtcccctt tcgtggtcgt tgttatctgg    900
gactctgttt aaggctgctc gcaaaatttg atttttgtcc agatttagga gttcttgttt     960
ttgcgtgatg ttcagcactt gttttagttt ttcaaatcta tgcagaggtt gaatttgatt    1020
agcagtcgga ttgagtaatg tcccactctg caaaattgcc ctttggtagt attttctagt    1080
agaattgtcc atcatcagaa aatgaacact tgctgctcca gcagattctc cagctatagt    1140
gattttatct ctgtctccac caaattttc gatgttgtca taaacccatt ttagtgccaa     1200
tctctggtct tttagaccca tatttccatg gatatcccat tccggcgctg atagaaaacc    1260
gaaaactcct aatctatagt tgatagtgac caaaataatt ccttccctga tcaaataatc    1320
aggtccaaaa aaattataag atcctgatcc ttggttgaat gcgcctccat ggatccagaa    1380
cattacagga tattttgtat tgttcgcaga attaacagtc tctggcgtga atatattcag    1440
atataagcaa tcttcgcttc ctgcataaga atatattaga ctttcctgga aacatttgtc    1500
tcctaaagac cgagcctgaa cgaatcctgt ttttggattt gatattggtt ttggagactg    1560
aaatcgcaat ggtccaatag gcggttctgc ataaggaatt cccaaatagg aacaatatac    1620
atcattttta tgatctttat atcggaacgg ttttccttcc gtgatcccgt taaattgaac    1680
tctgcacaaa tgctgatcta ggttatccca tagtatgcac aagacaggtg taaataagaa    1740
aaataaaaaa aataaaaata aaactaatgc actgtgaggt aacat                    1785
```

<210> SEQ ID NO 36
<211> LENGTH: 2007
<212> TYPE: DNA
<213> ORGANISM: Ctenocephalides felis
<220> FEATURE:
<221> NAME/KEY: CDS
<222> LOCATION: (11)..(1594)
<223> OTHER INFORMATION:

<400> SEQUENCE: 36

```
agttccaacg atg gct gat cta caa gtg act ttg ctt caa ggt act tta      49
            Met Ala Asp Leu Gln Val Thr Leu Leu Gln Gly Thr Leu
              1               5                  10 aaa gga aaa gag caa att agt gaa aaa gga aat gtg ttc cat agt tat    97
```

|     |     |     |     |     |     |     |     |     |     |     |     |     |     |     |     |
| --- | --- | --- | --- | --- | --- | --- | --- | --- | --- | --- | --- | --- | --- | --- | --- |
| Lys | Gly | Lys | Glu | Gln | Ile | Ser | Glu | Lys | Gly | Asn | Val | Phe | His | Ser | Tyr |
|     | 15  |     |     |     |     | 20  |     |     |     |     | 25  |     |     |     |     |

```
tct gga att cca tat gcc aaa cct cct gta ggt gat cta aga ttt aag         145
Ser Gly Ile Pro Tyr Ala Lys Pro Pro Val Gly Asp Leu Arg Phe Lys
30              35                  40                  45 cca cct caa cct gca gaa cct tgg tca ggt gtt ctt gat gct agt aaa         193
Pro Pro Gln Pro Ala Glu Pro Trp Ser Gly Val Leu Asp Ala Ser Lys
                50                  55                  60 gaa ggg aat agt tgt aga tca gta cat ttt att aaa aaa att aaa gta         241
Glu Gly Asn Ser Cys Arg Ser Val His Phe Ile Lys Lys Ile Lys Val
            65                  70                  75 ggg gct gaa gat tgt tta tac ctc aat gtc tat gta cca aaa aca tca         289
Gly Ala Glu Asp Cys Leu Tyr Leu Asn Val Tyr Val Pro Lys Thr Ser
        80                  85                  90 gag aaa tca ctt ctt cca gta atg gta tgg ata cat gga gga ggc ttc         337
Glu Lys Ser Leu Leu Pro Val Met Val Trp Ile His Gly Gly Gly Phe
    95                  100                 105 ttc atg gga tct gga aat agt gat atg tat ggt cct gaa tat ttg atg         385
Phe Met Gly Ser Gly Asn Ser Asp Met Tyr Gly Pro Glu Tyr Leu Met
110                 115                 120                 125 gat tat gga att gtt ctg gtt act ttc aat tat cga tta ggt gtt ttg         433
Asp Tyr Gly Ile Val Leu Val Thr Phe Asn Tyr Arg Leu Gly Val Leu
                130                 135                 140 gga ttt ttg aac ctg gga ata gaa gaa gcg cct ggc aat gtt ggt ttg         481
Gly Phe Leu Asn Leu Gly Ile Glu Glu Ala Pro Gly Asn Val Gly Leu
            145                 150                 155 atg gac cag gtt gaa gct cta aaa tgg gta aaa aac aat att gca tcc         529
Met Asp Gln Val Glu Ala Leu Lys Trp Val Lys Asn Asn Ile Ala Ser
        160                 165                 170 ttt ggt ggt gac ccc aac aat gtg act att ttt gga gaa tca gca ggt         577
Phe Gly Gly Asp Pro Asn Asn Val Thr Ile Phe Gly Glu Ser Ala Gly
    175                 180                 185 ggt gca agt gtt cat tat ttg atg tta tca gat ctt tcc aaa gga ctt         625
Gly Ala Ser Val His Tyr Leu Met Leu Ser Asp Leu Ser Lys Gly Leu
190                 195                 200                 205 ttt cat aaa gcg atc tca caa agt gga agt gct ttt aat cct tgg gca         673
Phe His Lys Ala Ile Ser Gln Ser Gly Ser Ala Phe Asn Pro Trp Ala
                210                 215                 220 ctt caa cat gat aat aat aaa gaa aat gca ttc cgc ctc tgc aaa ctt         721
Leu Gln His Asp Asn Asn Lys Glu Asn Ala Phe Arg Leu Cys Lys Leu
            225                 230                 235 ctg ggt cat cct gtc gat aac gag aca gaa gct cta aaa atc ctt cgt         769
Leu Gly His Pro Val Asp Asn Glu Thr Glu Ala Leu Lys Ile Leu Arg
        240                 245                 250 caa gcc ccc ata gat gat ctt ata gac aac aga ata aaa cca aaa gac         817
Gln Ala Pro Ile Asp Asp Leu Ile Asp Asn Arg Ile Lys Pro Lys Asp
    255                 260                 265 aaa ggc caa ctt att ata gac tat cct ttt cta cca aca ata gaa aaa         865
Lys Gly Gln Leu Ile Ile Asp Tyr Pro Phe Leu Pro Thr Ile Glu Lys
270                 275                 280                 285 cgt tat caa aat ttt gaa cca ttc ttg gac cag tct cca tta tca aaa         913
Arg Tyr Gln Asn Phe Glu Pro Phe Leu Asp Gln Ser Pro Leu Ser Lys
                290                 295                 300 atg caa tca ggc aat ttc aca aaa gtc cca ttt ata tgt gga tac aac         961
Met Gln Ser Gly Asn Phe Thr Lys Val Pro Phe Ile Cys Gly Tyr Asn
            305                 310                 315 agt gct gaa gga att tta ggt tta atg gac ttc aag gat gac cca aat        1009
Ser Ala Glu Gly Ile Leu Gly Leu Met Asp Phe Lys Asp Asp Pro Asn
        320                 325                 330
```

```
ata ttt gag aag ttt gaa gct gat ttt gaa aga ttt gta cca gta gat      1057
Ile Phe Glu Lys Phe Glu Ala Asp Phe Glu Arg Phe Val Pro Val Asp
    335                 340                 345 ttg aat cta act tta agg tct aag gaa tct aaa aaa ttg gct gaa gaa      1105
Leu Asn Leu Thr Leu Arg Ser Lys Glu Ser Lys Lys Leu Ala Glu Glu
350                 355                 360                 365 atg aga aag ttt tat tac caa gac gaa cct gtt tct tca gac aac aaa      1153
Met Arg Lys Phe Tyr Tyr Gln Asp Glu Pro Val Ser Ser Asp Asn Lys
                370                 375                 380 gaa aaa ttt gtc agt gtt att agt gat act tgg ttt ttg aga ggg att      1201
Glu Lys Phe Val Ser Val Ile Ser Asp Thr Trp Phe Leu Arg Gly Ile
            385                 390                 395 aaa aat act gca aga tat ata att gaa cat tcc tca gaa ccg tta tat      1249
Lys Asn Thr Ala Arg Tyr Ile Ile Glu His Ser Ser Glu Pro Leu Tyr
        400                 405                 410 tta tat gtt tat agt ttt gat gat ttt ggt ttt ttg aag aaa ctt gta      1297
Leu Tyr Val Tyr Ser Phe Asp Asp Phe Gly Phe Leu Lys Lys Leu Val
    415                 420                 425 tta gat cct aat att gaa gga gca gct cat gga gat gag ctg gga tat      1345
Leu Asp Pro Asn Ile Glu Gly Ala Ala His Gly Asp Glu Leu Gly Tyr
430                 435                 440                 445 ctt ttc aag atg agt ttt aca gaa ttt cca aaa gat tta cca agt gca      1393
Leu Phe Lys Met Ser Phe Thr Glu Phe Pro Lys Asp Leu Pro Ser Ala
                450                 455                 460 gtg gtg aat agg gaa cga ttg ttg caa ctt tgg aca aat ttt gca aaa      1441
Val Val Asn Arg Glu Arg Leu Leu Gln Leu Trp Thr Asn Phe Ala Lys
            465                 470                 475 aca gga aat ccc act cct gaa atc aat gat gtt ata aca aca aaa tgg      1489
Thr Gly Asn Pro Thr Pro Glu Ile Asn Asp Val Ile Thr Thr Lys Trp
        480                 485                 490 gat aaa gct act gag gaa aaa tca gat cat atg gat atc gat aat act      1537
Asp Lys Ala Thr Glu Glu Lys Ser Asp His Met Asp Ile Asp Asn Thr
    495                 500                 505 ttg aga atg att cca gat cct gat gca aaa cga ctt aga ttt tgg aat      1585
Leu Arg Met Ile Pro Asp Pro Asp Ala Lys Arg Leu Arg Phe Trp Asn
510                 515                 520                 525 aaa ttt tta tgataaatat accaattatc gattttatta tagagtttct              1634
Lys Phe Leu gtattagtat aattatcacg tttagatgta cgagattcaa ttggctctaa ttgaagtata    1694
tttcgatttc aaatttactc tgattattgg aaaaaaagct tttacagttg taataatcaa    1754
gaagtaggtg gtaaatttag aacaaattct gttttagtga tttgcgcatt caacagatgg    1814
tgtactgtgc ctaaatttgt cgctcttctt gaagaactga actaaaaatg tgattaatgg    1874
acgccacatt atttatattt gatattatta ccatctttgt atcatatttg cttttatttt    1934 ttcattttt ttttatttca aatatattgt ttttttataa aaaaaaaaa aaaaaaaaa       1994 aaaaaaaaa aaa                                                        2007

<210> SEQ ID NO 37
<211> LENGTH: 528
<212> TYPE: PRT
<213> ORGANISM: Ctenocephalides felis

<400> SEQUENCE: 37

Met Ala Asp Leu Gln Val Thr Leu Leu Gln Gly Thr Leu Lys Gly Lys
1               5                   10                  15

Glu Gln Ile Ser Glu Lys Gly Asn Val Phe His Ser Tyr Ser Gly Ile
            20                  25                  30
```

```
Pro Tyr Ala Lys Pro Val Gly Asp Leu Arg Phe Lys Pro Pro Gln
        35                  40                  45

Pro Ala Glu Pro Trp Ser Gly Val Leu Asp Ala Ser Lys Glu Gly Asn
    50                  55                  60

Ser Cys Arg Ser Val His Phe Ile Lys Lys Ile Lys Val Gly Ala Glu
65                  70                  75                  80

Asp Cys Leu Tyr Leu Asn Val Tyr Val Pro Lys Thr Ser Glu Lys Ser
                85                  90                  95

Leu Leu Pro Val Met Val Trp Ile His Gly Gly Phe Phe Met Gly
            100                 105                 110

Ser Gly Asn Ser Asp Met Tyr Gly Pro Glu Tyr Leu Met Asp Tyr Gly
        115                 120                 125

Ile Val Leu Val Thr Phe Asn Tyr Arg Leu Gly Val Leu Gly Phe Leu
    130                 135                 140

Asn Leu Gly Ile Glu Glu Ala Pro Gly Asn Val Gly Leu Met Asp Gln
145                 150                 155                 160

Val Glu Ala Leu Lys Trp Val Lys Asn Asn Ile Ala Ser Phe Gly Gly
                165                 170                 175

Asp Pro Asn Asn Val Thr Ile Phe Gly Glu Ser Ala Gly Gly Ala Ser
            180                 185                 190

Val His Tyr Leu Met Leu Ser Asp Leu Ser Lys Gly Leu Phe His Lys
    195                 200                 205

Ala Ile Ser Gln Ser Gly Ser Ala Phe Asn Pro Trp Ala Leu Gln His
    210                 215                 220

Asp Asn Asn Lys Glu Asn Ala Phe Arg Leu Cys Lys Leu Leu Gly His
225                 230                 235                 240

Pro Val Asp Asn Glu Thr Glu Ala Leu Lys Ile Leu Arg Gln Ala Pro
                245                 250                 255

Ile Asp Asp Leu Ile Asp Asn Arg Ile Lys Pro Lys Asp Lys Gly Gln
            260                 265                 270

Leu Ile Ile Asp Tyr Pro Phe Leu Pro Thr Ile Glu Lys Arg Tyr Gln
    275                 280                 285

Asn Phe Glu Pro Phe Leu Asp Gln Ser Pro Leu Ser Lys Met Gln Ser
290                 295                 300

Gly Asn Phe Thr Lys Val Pro Phe Ile Cys Gly Tyr Asn Ser Ala Glu
305                 310                 315                 320

Gly Ile Leu Gly Leu Met Asp Phe Lys Asp Asp Pro Asn Ile Phe Glu
            325                 330                 335

Lys Phe Glu Ala Asp Phe Glu Arg Phe Val Pro Val Asp Leu Asn Leu
            340                 345                 350

Thr Leu Arg Ser Lys Glu Ser Lys Leu Ala Glu Met Arg Lys
        355                 360                 365

Phe Tyr Tyr Gln Asp Glu Pro Val Ser Ser Asp Asn Lys Glu Lys Phe
    370                 375                 380

Val Ser Val Ile Ser Asp Thr Trp Phe Leu Arg Gly Ile Lys Asn Thr
385                 390                 395                 400

Ala Arg Tyr Ile Ile Glu His Ser Ser Glu Pro Leu Tyr Leu Tyr Val
                405                 410                 415

Tyr Ser Phe Asp Asp Phe Gly Leu Lys Lys Leu Val Leu Asp Pro
            420                 425                 430

Asn Ile Glu Gly Ala Ala His Gly Asp Glu Leu Gly Tyr Leu Phe Lys
    435                 440                 445

Met Ser Phe Thr Glu Phe Pro Lys Asp Leu Pro Ser Ala Val Val Asn
```

| | | | | | | | | | | | | |
|---|---|---|---|---|---|---|---|---|---|---|---|---|
| | 450 | | | | 455 | | | | 460 | | | |
| Arg | Glu | Arg | Leu | Leu | Gln | Leu | Trp | Thr | Asn | Phe | Ala | Lys | Thr | Gly | Asn |
| 465 | | | | | 470 | | | | | 475 | | | | | 480 |

Pro Thr Pro Glu Ile Asn Asp Val Ile Thr Thr Lys Trp Asp Lys Ala
              485                    490                    495

Thr Glu Glu Lys Ser Asp His Met Asp Ile Asp Asn Thr Leu Arg Met
         500                    505                    510

Ile Pro Asp Pro Asp Ala Lys Arg Leu Arg Phe Trp Asn Lys Phe Leu
        515                    520                    525

<210> SEQ ID NO 38
<211> LENGTH: 2007
<212> TYPE: DNA
<213> ORGANISM: Ctenocephalides felis

<400> SEQUENCE: 38

```
ttttttttttt tttttttttt tttttttttt ttttttataaa aaaacaatat atttgaaata    60
aaaaaaaaat gaaaaaataa aagcaaatat gatacaaaga tggtaataat atcaaatata   120
aataatgtgg cgtccattaa tcacattttt agttcagttc ttcaagaaga gcgacaaatt   180
taggcacagt acaccatctg ttgaatgcgc aaatcactaa aacagaattt gttctaaatt   240
taccacctac ttcttgatta ttacaactgt aaaagctttt tttccaataa tcagagtaaa   300
tttgaaatcg aaatatactt caattagagc caattgaatc tcgtacatct aaacgtgata   360
attatactaa tacagaaact ctaataaaa atcgataatt ggtatattta tcataaaaat   420
ttattccaaa atctaagtcg ttttgcatca ggatctggaa tcattctcaa agtattatcg   480
atatccatat gatctgattt ttcctcagta gctttatccc attttgttgt tataacatca   540
ttgatttcag gagtgggatt tcctgttttt gcaaatttg tccaaagttg caacaatcgt   600
tccctattca ccactgcact tggtaaatct tttggaaatt ctgtaaaact catcttgaaa   660
agatatccca gctcatctcc atgagctgct ccttcaatat taggatctaa tacaagtttc   720
ttcaaaaac caaaatcatc aaaactataa acatataaat ataacggttc tgaggaatgt   780
tcaattatat atcttgcagt attttttaatc cctctcaaaa accaagtatc actaataaca   840
ctgacaaatt tttctttgtt gtctgaagaa acaggttcgt cttggtaata aaactttctc   900
atttcttcag ccaattttt agattcctta gaccttaaag ttagattcaa atctactggt   960
acaaatcttt caaaatcagc ttcaaacttc tcaaatatat ttgggtcatc cttgaagtcc  1020
attaaaccta aaattccttc agcactgttg tatccacata taaatgggac ttttgtgaaa  1080
ttgcctgatt gcatttttga taatggagac tggtccaaga atggttcaaa attttgataa  1140
cgttttttcta ttgttggtag aaaaggatag tctataataa gttggccttt gtcttttggt  1200
tttattctgt tgtctataag atcatctatg ggggcttgac gaaggatttt tagagcttct  1260
gtctcgttat cgacaggatg acccagaagt ttgcagaggc ggaatgcatt ttctttatta  1320
ttatcatgtt gaagtgccca aggattaaaa gcacttccac tttgtgagat cgctttatga  1380
aaagtccctt tggaaagatc tgataacatc aaataatgaa cacttgcacc acctgctgat  1440
tctccaaaaa tagtcacatt gttggggtca ccaccaaagg atgcaatatt gttttttacc  1500
cattttagag cttcaacctg gtccatcaaa ccaacattgc caggcgcttc ttctattccc  1560
aggttcaaaa atcccaaaac acctaatcga taattgaaag taaccagaac aattccataa  1620
tccatcaaat attcaggacc atacatatca ctatttccag atcccatgaa gaagcctcct  1680
ccatgtatcc ataccattac tggaagaagt gatttctctg atgtttttgg tacatagaca  1740
```

```
ttgaggtata aacaatcttc agcccctact ttaattttt  taataaaatg tactgatcta    1800
caactattcc cttctttact agcatcaaga acacctgacc aaggttctgc aggttgaggt    1860
ggcttaaatc ttagatcacc tacaggaggt ttggcatatg gaattccaga ataactatgg    1920
aacacatttc cttttcact aatttgctct tttcctttta aagtaccttg aagcaaagtc     1980
acttgtagat cagccatcgt tggaact                                        2007
```

<210> SEQ ID NO 39
<211> LENGTH: 12
<212> TYPE: PRT
<213> ORGANISM: Peptide

<400> SEQUENCE: 39

Asp Pro Pro Thr Val Thr Leu Pro Gln Gly Glu Leu
1               5                   10

<210> SEQ ID NO 40
<211> LENGTH: 22
<212> TYPE: PRT
<213> ORGANISM: Peptide
<220> FEATURE:
<221> NAME/KEY: MISC_FEATURE
<222> LOCATION: (21)..(21)
<223> OTHER INFORMATION: Xaa = unknown

<400> SEQUENCE: 40

Asp Pro Pro Thr Val Thr Leu Pro Gln Gly Glu Leu Val Gly Lys Ala
1               5                   10                  15

Thr Asn Glu Asn Xaa Lys
            20

<210> SEQ ID NO 41
<211> LENGTH: 12
<212> TYPE: PRT
<213> ORGANISM: Peptide

<400> SEQUENCE: 41

Asp Pro Pro Thr Val Thr Leu Pro Gln Gly Glu Leu
1               5                   10

<210> SEQ ID NO 42
<211> LENGTH: 21
<212> TYPE: PRT
<213> ORGANISM: Peptide

<400> SEQUENCE: 42

Asp Pro Pro Thr Val Thr Leu Pro Gln Gly Glu Leu Val Gly Lys Ala
1               5                   10                  15

Leu Ser Asn Glu Asn
            20

<210> SEQ ID NO 43
<211> LENGTH: 8
<212> TYPE: PRT
<213> ORGANISM: Peptide

<400> SEQUENCE: 43

Asp Pro Pro Thr Val Thr Leu Pro
1               5

<210> SEQ ID NO 44
<211> LENGTH: 23

```
<212> TYPE: PRT
<213> ORGANISM: Peptide

<400> SEQUENCE: 44

Asp Pro Pro Thr Val Thr Leu Pro Gln Gly Glu Leu Val Gly Lys Ala
1               5                   10                  15

Leu Thr Asn Glu Asn Gly Lys
            20

<210> SEQ ID NO 45
<211> LENGTH: 20
<212> TYPE: DNA
<213> ORGANISM: Artificial sequence
<220> FEATURE:
<223> OTHER INFORMATION: Synthetic Primer

<400> SEQUENCE: 45
aattaaccct cactaaaggg                                           20

<210> SEQ ID NO 46
<211> LENGTH: 17
<212> TYPE: DNA
<213> ORGANISM: Artificial sequence
<220> FEATURE:
<223> OTHER INFORMATION: Synthetic Primer

<400> SEQUENCE: 46
ardccdccdc crtrdat                                              17

<210> SEQ ID NO 47
<211> LENGTH: 38
<212> TYPE: DNA
<213> ORGANISM: Artificial sequence
<220> FEATURE:
<223> OTHER INFORMATION: Synthetic Primer

<400> SEQUENCE: 47
tgtgctcgag atgggataac ctagatcagc atttgtgc                       38

<210> SEQ ID NO 48
<211> LENGTH: 35
<212> TYPE: DNA
<213> ORGANISM: Artificial sequence
<220> FEATURE:
<223> OTHER INFORMATION: Synthetic Primer

<400> SEQUENCE: 48
ttaaggtacc tcatctaata cttccttcat tacag                          35

<210> SEQ ID NO 49
<211> LENGTH: 36
<212> TYPE: DNA
<213> ORGANISM: Artificial sequence
<220> FEATURE:
<223> OTHER INFORMATION: Synthetic Primer

<400> SEQUENCE: 49
aaaactgcag tataaatatg ttacctcaca gtagtg                         36

<210> SEQ ID NO 50
<211> LENGTH: 34
<212> TYPE: DNA
<213> ORGANISM: Artificial sequence
<220> FEATURE:
<223> OTHER INFORMATION: Synthetic Primer
```

<400> SEQUENCE: 50
tgctctagat tatctaatac ttccttcatt acag    34

<210> SEQ ID NO 51
<211> LENGTH: 1584
<212> TYPE: DNA
<213> ORGANISM: Ctenocephalides felis
<220> FEATURE:
<221> NAME/KEY: exon
<222> LOCATION: (1)..(1584)
<223> OTHER INFORMATION:

<400> SEQUENCE: 51

| | | |
|---|---|---|
| atg gct gat cta caa gtg act ttg ctt caa ggt act tta aaa gga aaa<br>Met Ala Asp Leu Gln Val Thr Leu Leu Gln Gly Thr Leu Lys Gly Lys<br>1               5                   10              15 | 48 |
| gag caa att agt gaa aaa gga aat gtg ttc cat agt tat tct gga att<br>Glu Gln Ile Ser Glu Lys Gly Asn Val Phe His Ser Tyr Ser Gly Ile<br>               20                  25                 30 | 96 |
| cca tat gcc aaa cct cct gta ggt gat cta aga ttt aag cca cct caa<br>Pro Tyr Ala Lys Pro Pro Val Gly Asp Leu Arg Phe Lys Pro Pro Gln<br>           35                  40              45 | 144 |
| cct gca gaa cct tgg tca ggt gtt ctt gat gct agt aaa gaa ggg aat<br>Pro Ala Glu Pro Trp Ser Gly Val Leu Asp Ala Ser Lys Glu Gly Asn<br>50                   55                   60 | 192 |
| agt tgt aga tca gta cat ttt att aaa aaa att aaa gta ggg gct gaa<br>Ser Cys Arg Ser Val His Phe Ile Lys Lys Ile Lys Val Gly Ala Glu<br>65                   70                  75              80 | 240 |
| gat tgt tta tac ctc aat gtc tat gta cca aaa aca tca gag aaa tca<br>Asp Cys Leu Tyr Leu Asn Val Tyr Val Pro Lys Thr Ser Glu Lys Ser<br>                 85                  90              95 | 288 |
| ctt ctt cca gta atg gta tgg ata cat gga gga ggc ttc ttc atg gga<br>Leu Leu Pro Val Met Val Trp Ile His Gly Gly Gly Phe Phe Met Gly<br>                100               105              110 | 336 |
| tct gga aat agt gat atg tat ggt cct gaa tat ttg atg gat tat gga<br>Ser Gly Asn Ser Asp Met Tyr Gly Pro Glu Tyr Leu Met Asp Tyr Gly<br>               115              120              125 | 384 |
| att gtt ctg gtt act ttc aat tat cga tta ggt gtt ttg gga ttt ttg<br>Ile Val Leu Val Thr Phe Asn Tyr Arg Leu Gly Val Leu Gly Phe Leu<br>130                  135               140 | 432 |
| aac ctg gga ata gaa gaa gcg cct ggc aat gtt ggt ttg atg gac cag<br>Asn Leu Gly Ile Glu Glu Ala Pro Gly Asn Val Gly Leu Met Asp Gln<br>145                150               155              160 | 480 |
| gtt gaa gct cta aaa tgg gta aaa aac aat att gca tcc ttt ggt ggt<br>Val Glu Ala Leu Lys Trp Val Lys Asn Asn Ile Ala Ser Phe Gly Gly<br>               165              170              175 | 528 |
| gac ccc aac aat gtg act att ttt gga gaa tca gca ggt ggt gca agt<br>Asp Pro Asn Asn Val Thr Ile Phe Gly Glu Ser Ala Gly Gly Ala Ser<br>               180              185              190 | 576 |
| gtt cat tat ttg atg tta tca gat ctt tcc aaa gga ctt ttt cat aaa<br>Val His Tyr Leu Met Leu Ser Asp Leu Ser Lys Gly Leu Phe His Lys<br>               195              200              205 | 624 |
| gcg atc tca caa agt gga agt gct ttt aat cct tgg gca ctt caa cat<br>Ala Ile Ser Gln Ser Gly Ser Ala Phe Asn Pro Trp Ala Leu Gln His<br>           210                  215              220 | 672 |
| gat aat aat aaa gaa aat gca ttc cgc ctc tgc aaa ctt ctg ggt cat<br>Asp Asn Asn Lys Glu Asn Ala Phe Arg Leu Cys Lys Leu Leu Gly His<br>225                  230               235              240 | 720 |
| cct gtc gat aac gag aca gaa gct cta aaa atc ctt cgt caa gcc ccc<br>Pro Val Asp Asn Glu Thr Glu Ala Leu Lys Ile Leu Arg Gln Ala Pro<br>               245              250              255 | 768 |

```
ata gat gat ctt ata gac aac aga ata aaa cca aaa gac aaa ggc caa      816
Ile Asp Asp Leu Ile Asp Asn Arg Ile Lys Pro Lys Asp Lys Gly Gln
            260                 265                 270 ctt att ata gac tat cct ttt cta cca aca ata gaa aaa cgt tat caa      864
Leu Ile Ile Asp Tyr Pro Phe Leu Pro Thr Ile Glu Lys Arg Tyr Gln
                275                 280                 285 aat ttt gaa cca ttc ttg gac cag tct cca tta tca aaa atg caa tca      912
Asn Phe Glu Pro Phe Leu Asp Gln Ser Pro Leu Ser Lys Met Gln Ser
290                 295                 300 ggc aat ttc aca aaa gtc cca ttt ata tgt gga tac aac agt gct gaa      960
Gly Asn Phe Thr Lys Val Pro Phe Ile Cys Gly Tyr Asn Ser Ala Glu
305                 310                 315                 320 gga att tta ggt tta atg gac ttc aag gat gac cca aat ata ttt gag     1008
Gly Ile Leu Gly Leu Met Asp Phe Lys Asp Asp Pro Asn Ile Phe Glu
            325                 330                 335 aag ttt gaa gct gat ttt gaa aga ttt gta cca gta gat ttg aat cta     1056
Lys Phe Glu Ala Asp Phe Glu Arg Phe Val Pro Val Asp Leu Asn Leu
                340                 345                 350 act tta agg tct aag gaa tct aaa aaa ttg gct gaa gaa atg aga aag     1104
Thr Leu Arg Ser Lys Glu Ser Lys Lys Leu Ala Glu Glu Met Arg Lys
                    355                 360                 365 ttt tat tac caa gac gaa cct gtt tct tca gac aac aaa gaa aaa ttt     1152
Phe Tyr Tyr Gln Asp Glu Pro Val Ser Ser Asp Asn Lys Glu Lys Phe
370                 375                 380 gtc agt gtt att agt gat act tgg ttt ttg aga ggg att aaa aat act     1200
Val Ser Val Ile Ser Asp Thr Trp Phe Leu Arg Gly Ile Lys Asn Thr
385                 390                 395                 400 gca aga tat ata att gaa cat tcc tca gaa ccg tta tat tta tat gtt     1248
Ala Arg Tyr Ile Ile Glu His Ser Ser Glu Pro Leu Tyr Leu Tyr Val
            405                 410                 415 tat agt ttt gat gat ttt ggt ttt ttg aag aaa ctt gta tta gat cct     1296
Tyr Ser Phe Asp Asp Phe Gly Phe Leu Lys Lys Leu Val Leu Asp Pro
                420                 425                 430 aat att gaa gga gca gct cat gga gat gag ctg gga tat ctt ttc aag     1344
Asn Ile Glu Gly Ala Ala His Gly Asp Glu Leu Gly Tyr Leu Phe Lys
                    435                 440                 445 atg agt ttt aca gaa ttt cca aaa gat tta cca agt gca gtg gtg aat     1392
Met Ser Phe Thr Glu Phe Pro Lys Asp Leu Pro Ser Ala Val Val Asn
    450                 455                 460 agg gaa cga ttg ttg caa ctt tgg aca aat ttt gca aaa aca gga aat     1440
Arg Glu Arg Leu Leu Gln Leu Trp Thr Asn Phe Ala Lys Thr Gly Asn
465                 470                 475                 480 ccc act cct gaa atc aat gat gtt ata aca aca aaa tgg gat aaa gct     1488
Pro Thr Pro Glu Ile Asn Asp Val Ile Thr Thr Lys Trp Asp Lys Ala
            485                 490                 495 act gag gaa aaa tca gat cat atg gat atc gat aat act ttg aga atg     1536
Thr Glu Glu Lys Ser Asp His Met Asp Ile Asp Asn Thr Leu Arg Met
                500                 505                 510 att cca gat cct gat gca aaa cga ctt aga ttt tgg aat aaa ttt tta     1584
Ile Pro Asp Pro Asp Ala Lys Arg Leu Arg Phe Trp Asn Lys Phe Leu
                    515                 520                 525

<210> SEQ ID NO 52
<211> LENGTH: 1584
<212> TYPE: DNA
<213> ORGANISM: Ctenocephalides felis

<400> SEQUENCE: 52
taaaaattta ttccaaaatc taagtcgttt tgcatcagga tctggaatca ttctcaaagt     60
```

```
attatcgata tccatatgat ctgattttc ctcagtagct ttatcccatt ttgttgttat    120
aacatcattg atttcaggag tgggatttcc tgtttttgca aaatttgtcc aaagttgcaa    180
caatcgttcc ctattcacca ctgcacttgg taaatctttt ggaaattctg taaaactcat    240
cttgaaaaga tatcccagct catctccatg agctgctcct tcaatattag gatctaatac    300
aagtttcttc aaaaaaccaa aatcatcaaa actataaaca tataaatata acggttctga    360
ggaatgttca attatatatc ttgcagtatt tttaatccct ctcaaaaacc aagtatcact    420
aataacactg acaaatttt ctttgttgtc tgaagaaaca ggttcgtctt ggtaataaaa    480
ctttctcatt tcttcagcca attttttaga ttccttagac cttaaagtta gattcaaatc    540
tactggtaca aatctttcaa aatcagcttc aaacttctca aatatatttg ggtcatcctt    600
gaagtccatt aaacctaaaa ttccttcagc actgttgtat ccacatataa atgggacttt    660
tgtgaaattg cctgattgca ttttgataa tggagactgg tccaagaatg gttcaaaatt    720
ttgataacgt ttttctattg ttggtagaaa aggatagtct ataataagtt ggcctttgtc    780
ttttggtttt attctgttgt ctataagatc atctatgggg gcttgacgaa ggattttag    840 agcttctgtc tcgttatcga caggatgacc cagaagtttg cagaggcgga atgcattttc    900
tttattatta tcatgttgaa gtgcccaagg attaaaagca cttccacttt gtgagatcgc    960
tttatgaaaa agtcctttgg aaagatctga taacatcaaa taatgaacac ttgcaccacc   1020
tgctgattct ccaaaaatag tcacattgtt ggggtcacca ccaaaggatg caatattgtt   1080
ttttacccat tttagagctt caacctggtc catcaaacca acattgccag gcgcttcttc   1140
tattcccagg ttcaaaaatc ccaaaacacc taatcgataa ttgaaagtaa ccagaacaat   1200
tccataatcc atcaaatatt caggaccata catatcacta tttccagatc ccatgaagaa   1260
gcctcctcca tgtatccata ccattactgg aagaagtgat ttctctgatg tttttggtac   1320
atagacattg aggtataaac aatcttcagc ccctacttta attttttaa taaaatgtac   1380 tgatctacaa ctattccctt ctttactagc atcaagaaca cctgaccaag gttctgcagg   1440
ttgaggtggc ttaaatctta gatcacctac aggaggtttg gcatatggaa ttccagaata   1500
actatggaac acatttcctt tttcactaat ttgctctttt ccttttaaag taccttgaag   1560
caaagtcact tgtagatcag ccat                                        1584
```

<210> SEQ ID NO 53
<211> LENGTH: 530
<212> TYPE: PRT
<213> ORGANISM: Ctenocephalides felis

<400> SEQUENCE: 53

```
Asp Pro Pro Thr Val Thr Leu Pro Gln Gly Glu Leu Val Gly Lys Ala
1               5                   10                  15

Leu Thr Asn Glu Asn Gly Lys Glu Tyr Phe Ser Tyr Thr Gly Val Pro
            20                  25                  30

Tyr Ala Lys Pro Pro Val Gly Glu Leu Arg Phe Lys Pro Pro Gln Lys
        35                  40                  45

Ala Glu Pro Trp Asn Gly Val Phe Asn Ala Thr Ser His Gly Asn Val
    50                  55                  60

Cys Lys Ala Leu Asn Phe Phe Leu Lys Lys Ile Glu Gly Asp Glu Asp
65                  70                  75                  80

Cys Leu Leu Val Asn Val Tyr Ala Pro Lys Thr Thr Ser Asp Lys Lys
                85                  90                  95
```

-continued

```
Leu Pro Val Phe Phe Trp Val His Gly Gly Phe Val Thr Gly Ser
        100                 105                 110

Gly Asn Leu Glu Phe Gln Ser Pro Asp Tyr Leu Val Asn Tyr Asp Val
            115                 120                 125

Ile Phe Val Thr Phe Asn Tyr Arg Leu Gly Pro Leu Gly Phe Leu Asn
        130                 135                 140

Leu Glu Leu Glu Gly Ala Pro Gly Asn Val Gly Leu Leu Asp Gln Val
145                 150                 155                 160

Ala Ala Leu Lys Trp Thr Lys Glu Asn Ile Glu Lys Phe Gly Gly Asp
                165                 170                 175

Pro Glu Asn Ile Thr Ile Gly Gly Val Ser Ala Gly Gly Ala Ser Val
                180                 185                 190

His Tyr Leu Leu Leu Ser His Thr Thr Gly Leu Tyr Lys Arg Ala
        195                 200                 205

Ile Ala Gln Ser Gly Ser Ala Leu Asn Pro Trp Ala Phe Gln Arg His
        210                 215                 220

Pro Val Lys Arg Ser Leu Gln Leu Ala Glu Ile Leu Gly His Pro Thr
225                 230                 235                 240

Asn Asn Thr Gln Asp Ala Leu Glu Phe Leu Gln Lys Ala Pro Val Asp
                245                 250                 255

Ser Leu Leu Lys Lys Met Pro Ala Glu Thr Glu Gly Glu Ile Ile Glu
                260                 265                 270

Glu Phe Val Phe Val Pro Ser Ile Glu Lys Val Phe Pro Ser His Gln
            275                 280                 285

Pro Phe Leu Glu Glu Ser Pro Leu Ala Arg Met Lys Ser Gly Ser Phe
        290                 295                 300

Asn Lys Val Pro Leu Leu Val Gly Phe Asn Ser Ala Glu Gly Leu Leu
305                 310                 315                 320

Tyr Lys Phe Phe Met Lys Glu Lys Pro Glu Met Leu Asn Gln Ala Glu
                325                 330                 335

Ala Asp Phe Glu Arg Leu Val Pro Ala Glu Phe Glu Leu Ala His Gly
                340                 345                 350

Ser Glu Glu Ser Lys Lys Leu Ala Glu Lys Ile Arg Lys Phe Tyr Phe
            355                 360                 365

Asp Asp Lys Pro Val Pro Glu Asn Glu Gln Lys Phe Ile Asp Leu Ile
        370                 375                 380

Gly Asp Ile Trp Phe Thr Arg Gly Ile Asp Lys His Val Lys Leu Ser
385                 390                 395                 400

Val Glu Lys Gln Asp Glu Pro Val Tyr Tyr Glu Tyr Ser Phe Ser
                405                 410                 415

Glu Ser His Pro Ala Lys Gly Thr Phe Gly Asp His Asn Leu Thr Gly
                420                 425                 430

Ala Cys His Gly Glu Glu Leu Val Asn Leu Phe Lys Val Glu Met Met
        435                 440                 445

Lys Leu Glu Lys Asp Lys Pro Asn Val Leu Leu Thr Lys Asp Arg Val
450                 455                 460

Leu Ala Met Trp Thr Asn Phe Ile Lys Asn Gly Asn Pro Thr Pro Glu
465                 470                 475                 480

Val Thr Glu Leu Leu Pro Val Lys Trp Glu Pro Ala Thr Lys Asp Lys
                485                 490                 495

Leu Asn Tyr Leu Asn Ile Asp Ala Thr Leu Thr Leu Gly Thr Asn Pro
            500                 505                 510

Glu Glu Thr Arg Val Lys Phe Trp Glu Asp Ala Thr Lys Thr Leu His
```

Ser Gln
    530

<210> SEQ ID NO 54
<211> LENGTH: 570
<212> TYPE: PRT
<213> ORGANISM: Ctenocephalides felis

<400> SEQUENCE: 54

Trp Asp Asn Leu Asp Gln His Leu Cys Arg Val Gln Phe Asn Gly Ile
1               5                   10                  15

Thr Glu Gly Lys Pro Phe Arg Tyr Lys Asp His Arg Asn Asp Val Tyr
            20                  25                  30

Cys Ser Tyr Leu Gly Ile Pro Tyr Ala Glu Pro Pro Phe Gly Pro Leu
        35                  40                  45

Arg Phe Gln Ser Pro Lys Pro Ile Ser Asn Pro Lys Thr Gly Phe Val
    50                  55                  60

Gln Ala Arg Thr Leu Gly Asp Lys Cys Phe Gln Glu Ser Leu Ile Tyr
65                  70                  75                  80

Ser Tyr Ala Gly Ser Glu Asp Cys Leu Tyr Leu Asn Ile Phe Thr Pro
                85                  90                  95

Glu Thr Val Asn Ser Ala Asn Asn Thr Lys Tyr Pro Val Met Phe Trp
            100                 105                 110

Ile His Gly Gly Ala Phe Asn Gln Gly Ser Gly Ser Tyr Asn Phe Phe
        115                 120                 125

Gly Pro Asp Tyr Leu Ile Arg Glu Gly Ile Ile Leu Val Thr Ile Asn
    130                 135                 140

Tyr Arg Leu Gly Val Phe Gly Phe Leu Ser Ala Pro Glu Trp Asp Ile
145                 150                 155                 160

His Gly Asn Met Gly Leu Lys Asp Gln Arg Leu Ala Leu Lys Trp Val
                165                 170                 175

Tyr Asp Asn Ile Glu Lys Phe Gly Gly Asp Arg Glu Lys Ile Thr Ile
            180                 185                 190

Ala Gly Glu Ser Ala Gly Ala Ala Ser Val His Phe Leu Met Met Asp
        195                 200                 205

Asn Ser Thr Arg Lys Tyr Tyr Gln Arg Ala Ile Leu Gln Ser Gly Thr
    210                 215                 220

Leu Leu Asn Pro Thr Ala Asn Gln Ile Gln Leu Leu His Arg Phe Glu
225                 230                 235                 240

Lys Leu Lys Gln Val Leu Asn Ile Thr Gln Lys Gln Glu Leu Leu Asn
                245                 250                 255

Leu Asp Lys Asn Leu Ile Leu Arg Ala Ala Leu Asn Arg Val Pro Asp
            260                 265                 270

Ser Asn Asp His Asp Arg Asp Thr Val Pro Val Phe Asn Pro Val Leu
    275                 280                 285

Glu Ser Pro Glu Ser Pro Asp Pro Ile Thr Phe Pro Ser Ala Leu Glu
    290                 295                 300

Arg Met Arg Asn Gly Glu Phe Pro Asp Val Asp Val Ile Ile Gly Phe
305                 310                 315                 320

Asn Ser Ala Glu Gly Leu Arg Ser Met Ala Arg Val Thr Arg Gly Asn
                325                 330                 335

Met Glu Val His Lys Thr Leu Asn Ile Glu Arg Ala Ile Pro Arg
            340                 345                 350

```
Asp Ala Asn Ile Trp Lys Asn Pro Asn Gly Ile Glu Glu Lys Lys Leu
            355                 360                 365

Ile Lys Met Leu Thr Glu Phe Tyr Asp Gln Val Lys Glu Gln Asn Asp
    370                 375                 380

Asp Ile Glu Ala Tyr Val Gln Leu Lys Gly Asp Ala Gly Tyr Leu Gln
385                 390                 395                 400

Gly Ile Tyr Arg Thr Leu Lys Ala Ile Phe Phe Asn Glu Phe Arg Arg
                405                 410                 415

Asn Ser Asn Leu Tyr Leu Tyr Arg Leu Ser Asp Asp Thr Tyr Ser Val
            420                 425                 430

Tyr Lys Ser Tyr Ile Leu Pro Tyr Arg Trp Gly Ser Leu Pro Gly Val
            435                 440                 445

Ser His Gly Asp Asp Leu Gly Tyr Leu Phe Ala Asn Ser Leu Asp Val
    450                 455                 460

Pro Ile Leu Gly Thr Thr His Ile Ser Ile Pro Gln Asp Ala Met Gln
465                 470                 475                 480

Thr Leu Glu Arg Met Val Arg Ile Trp Thr Asn Phe Val Lys Asn Gly
                485                 490                 495

Lys Pro Thr Ser Asn Thr Glu Asp Ala Ser Cys Asp Thr Lys Arg His
            500                 505                 510

Leu Asn Asp Ile Phe Trp Glu Pro Tyr Asn Asp Glu Pro Lys Tyr
            515                 520                 525

Leu Asp Met Gly Lys Glu Asn Phe Glu Met Lys Asn Ile Leu Glu Leu
            530                 535                 540

Lys Arg Met Met Leu Trp Asp Glu Val Tyr Arg Asn Ala Asn Leu Arg
545                 550                 555                 560

Phe Arg Val Cys Asn Glu Gly Ser Ile Arg
                565                 570

<210> SEQ ID NO 55
<211> LENGTH: 570
<212> TYPE: PRT
<213> ORGANISM: Ctenocephalides felis

<400> SEQUENCE: 55

Trp Asp Asn Leu Asp Gln His Leu Cys Arg Val Gln Phe Asn Gly Ile
1               5                   10                  15

Thr Glu Gly Lys Pro Phe Arg Tyr Lys Asp His Lys Asn Asp Val Tyr
            20                  25                  30

Cys Ser Tyr Leu Gly Ile Pro Tyr Ala Glu Pro Ile Gly Pro Leu
            35                  40                  45

Arg Phe Gln Ser Pro Lys Pro Ile Ser Asn Pro Lys Thr Gly Phe Val
    50                  55                  60

Gln Ala Arg Ser Leu Gly Asp Lys Cys Phe Gln Glu Ser Leu Ile Tyr
65                  70                  75                  80

Ser Tyr Ala Gly Ser Glu Asp Cys Leu Tyr Leu Asn Ile Phe Thr Pro
                85                  90                  95

Glu Thr Val Asn Ser Ala Asn Asn Thr Lys Tyr Pro Val Met Phe Trp
            100                 105                 110

Ile His Gly Gly Ala Phe Asn Gln Gly Ser Gly Ser Tyr Asn Phe Phe
    115                 120                 125

Gly Pro Asp Tyr Leu Ile Arg Glu Gly Ile Ile Leu Val Thr Ile Asn
    130                 135                 140

Tyr Arg Leu Gly Val Phe Gly Phe Leu Ser Ala Pro Glu Trp Asp Ile
145                 150                 155                 160
```

-continued

```
His Gly Asn Met Gly Leu Lys Asp Gln Arg Leu Ala Leu Lys Trp Val
            165                 170                 175
Tyr Asp Asn Ile Glu Lys Phe Gly Gly Asp Arg Asp Lys Ile Thr Ile
            180                 185                 190
Ala Gly Glu Ser Ala Gly Ala Ala Ser Val His Phe Leu Met Met Asp
            195                 200                 205
Asn Ser Thr Arg Lys Tyr Tyr Gln Arg Ala Ile Leu Gln Ser Gly Thr
210                 215                 220
Leu Leu Asn Pro Thr Ala Asn Gln Ile Gln Pro Leu His Arg Phe Glu
225                 230                 235                 240
Lys Leu Lys Gln Val Leu Asn Ile Thr Gln Lys Gln Glu Leu Leu Asn
            245                 250                 255
Leu Asp Lys Asn Gln Ile Leu Arg Ala Ala Leu Asn Arg Val Pro Asp
            260                 265                 270
Asn Asn Asp His Glu Arg Asp Thr Val Pro Val Phe Asn Pro Val Leu
            275                 280                 285
Glu Ser Pro Glu Ser Pro Asp Pro Ile Thr Phe Pro Ser Ala Leu Glu
            290                 295                 300
Arg Met Arg Asn Gly Glu Phe Pro Asp Val Asp Val Ile Ile Gly Phe
305                 310                 315                 320
Asn Ser Ala Glu Gly Leu Arg Ser Met Pro Arg Val Thr Arg Gly Asn
            325                 330                 335
Met Glu Val Tyr Lys Thr Leu Thr Asn Ile Glu Arg Ala Ile Pro Arg
            340                 345                 350
Asp Ala Asn Ile Trp Lys Asn Pro Asn Gly Ile Glu Glu Lys Lys Leu
            355                 360                 365
Ile Lys Met Leu Thr Glu Phe Tyr Asp Gln Val Lys Glu Gln Asn Asp
            370                 375                 380
Asp Ile Glu Ala Tyr Val Gln Leu Lys Gly Asp Ala Gly Tyr Leu Gln
385                 390                 395                 400
Gly Ile Tyr Arg Thr Leu Lys Ala Ile Phe Phe Asn Glu Ile Lys Arg
            405                 410                 415
Asn Ser Asn Leu Tyr Leu Tyr Arg Leu Ser Asp Asp Thr Tyr Ser Val
            420                 425                 430
Tyr Lys Ser Tyr Ile Leu Pro Tyr Arg Trp Gly Ser Leu Pro Gly Val
            435                 440                 445
Ser His Gly Asp Asp Leu Gly Tyr Leu Phe Ala Asn Ser Leu Asp Val
            450                 455                 460
Pro Ile Leu Gly Thr Thr His Ile Ser Ile Pro Gln Asp Ala Met Gln
465                 470                 475                 480
Thr Leu Glu Arg Met Val Arg Ile Trp Thr Asn Phe Val Lys Asn Gly
            485                 490                 495
Lys Pro Thr Ser Asn Thr Glu Asp Ala Ser Cys Asp Thr Lys Arg His
            500                 505                 510
Leu Asn Asp Ile Phe Trp Glu Pro Tyr Asn Asp Glu Glu Pro Lys Tyr
            515                 520                 525
Leu Asp Met Gly Lys Glu His Phe Glu Met Lys Asn Ile Leu Glu Leu
            530                 535                 540
Lys Arg Met Met Leu Trp Asp Glu Val Tyr Arg Asn Ala Asn Leu Arg
545                 550                 555                 560
Phe Arg Val Cys Asn Glu Gly Ser Ile Arg
            565                 570
```

<210> SEQ ID NO 56
<211> LENGTH: 20
<212> TYPE: DNA
<213> ORGANISM: Artificial sequence
<220> FEATURE:
<223> OTHER INFORMATION: Synthetic Primer

<400> SEQUENCE: 56
gtgcgtacac gtttactacc                                                          20

<210> SEQ ID NO 57
<211> LENGTH: 2144
<212> TYPE: DNA
<213> ORGANISM: Ctenocephalides felis
<220> FEATURE:
<221> NAME/KEY: CDS
<222> LOCATION: (30)..(1682)
<223> OTHER INFORMATION:
<220> FEATURE:
<221> NAME/KEY: misc_feature
<222> LOCATION: (462)..(462)
<223> OTHER INFORMATION: At nucleotide 462, r = a or g
      At amino acid residue 145, Xaa = Asn or Asp

<400> SEQUENCE: 57

| gtacacatag tcaatagtct agatccaag | atg | tct | cgt | gtt | att | ttt | tta | agt | 53 |
|---|---|---|---|---|---|---|---|---|---|
| | Met | Ser | Arg | Val | Ile | Phe | Leu | Ser | |
| | 1 | | | | 5 | | | | |

| tgt | att | ttt | ttg | ttt | agt | ttt | aat | ttt | ata | aaa | tgt | gat | tcc | ccg | act | 101 |
|---|---|---|---|---|---|---|---|---|---|---|---|---|---|---|---|---|
| Cys | Ile | Phe | Leu | Phe | Ser | Phe | Asn | Phe | Ile | Lys | Cys | Asp | Ser | Pro | Thr | |
| 10 | | | | | 15 | | | | | 20 | | | | | | |

| gta | act | ttg | ccc | caa | ggc | gaa | ttg | gtt | gga | aaa | gct | ttg | acg | aac | gaa | 149 |
|---|---|---|---|---|---|---|---|---|---|---|---|---|---|---|---|---|
| Val | Thr | Leu | Pro | Gln | Gly | Glu | Leu | Val | Gly | Lys | Ala | Leu | Thr | Asn | Glu | |
| 25 | | | | 30 | | | | | 35 | | | | | | 40 | |

| aat | gga | aaa | gag | tat | ttt | agc | tac | aca | ggt | gta | cct | tat | gct | aaa | cct | 197 |
|---|---|---|---|---|---|---|---|---|---|---|---|---|---|---|---|---|
| Asn | Gly | Lys | Glu | Tyr | Phe | Ser | Tyr | Thr | Gly | Val | Pro | Tyr | Ala | Lys | Pro | |
| | | | | 45 | | | | | 50 | | | | | 55 | | |

| cct | gtt | gga | gaa | ctt | aga | ttt | aag | cct | cca | cag | aaa | gct | gag | cca | tgg | 245 |
|---|---|---|---|---|---|---|---|---|---|---|---|---|---|---|---|---|
| Pro | Val | Gly | Glu | Leu | Arg | Phe | Lys | Pro | Pro | Gln | Lys | Ala | Glu | Pro | Trp | |
| | | 60 | | | | | 65 | | | | | 70 | | | | |

| caa | ggt | gtt | ttc | aac | gcc | aca | tta | tac | gga | aat | gtg | tgt | aaa | tct | tta | 293 |
|---|---|---|---|---|---|---|---|---|---|---|---|---|---|---|---|---|
| Gln | Gly | Val | Phe | Asn | Ala | Thr | Leu | Tyr | Gly | Asn | Val | Cys | Lys | Ser | Leu | |
| | 75 | | | | | 80 | | | | | 85 | | | | | |

| aat | ttc | ttc | ttg | aag | aaa | att | gaa | gga | gac | gaa | gac | tgc | ttg | gta | gta | 341 |
|---|---|---|---|---|---|---|---|---|---|---|---|---|---|---|---|---|
| Asn | Phe | Phe | Leu | Lys | Lys | Ile | Glu | Gly | Asp | Glu | Asp | Cys | Leu | Val | Val | |
| 90 | | | | | 95 | | | | | 100 | | | | | | |

| aac | gtg | tac | gca | cca | aaa | aca | act | tct | gat | aaa | aaa | ctt | cca | gta | ttt | 389 |
|---|---|---|---|---|---|---|---|---|---|---|---|---|---|---|---|---|
| Asn | Val | Tyr | Ala | Pro | Lys | Thr | Thr | Ser | Asp | Lys | Lys | Leu | Pro | Val | Phe | |
| 105 | | | | 110 | | | | | 115 | | | | | 120 | | |

| ttc | tgg | gtt | cat | ggt | ggt | ggt | ttt | gtg | act | gga | tcc | gga | aat | tta | gaa | 437 |
|---|---|---|---|---|---|---|---|---|---|---|---|---|---|---|---|---|
| Phe | Trp | Val | His | Gly | Gly | Gly | Phe | Val | Thr | Gly | Ser | Gly | Asn | Leu | Glu | |
| | | | 125 | | | | | 130 | | | | | 135 | | | |

| ttc | caa | agc | cca | gat | tat | tta | gta | rat | ttt | gat | gtt | att | ttc | gta | act | 485 |
|---|---|---|---|---|---|---|---|---|---|---|---|---|---|---|---|---|
| Phe | Gln | Ser | Pro | Asp | Tyr | Leu | Val | Xaa | Phe | Asp | Val | Ile | Phe | Val | Thr | |
| | | | 140 | | | | | 145 | | | | | 150 | | | |

| ttc | aat | tac | cga | ttg | gga | cct | ctc | gga | ttt | ctg | aat | ttg | gag | ttg | gag | 533 |
|---|---|---|---|---|---|---|---|---|---|---|---|---|---|---|---|---|
| Phe | Asn | Tyr | Arg | Leu | Gly | Pro | Leu | Gly | Phe | Leu | Asn | Leu | Glu | Leu | Glu | |
| | | 155 | | | | | 160 | | | | | 165 | | | | |

| ggt | gct | cca | gga | aat | gta | gga | tta | ttg | gat | cag | gtg | gca | gct | ctg | aaa | 581 |
|---|---|---|---|---|---|---|---|---|---|---|---|---|---|---|---|---|
| Gly | Ala | Pro | Gly | Asn | Val | Gly | Leu | Leu | Asp | Gln | Val | Ala | Ala | Leu | Lys | |
| | 170 | | | | | 175 | | | | | 180 | | | | | |

| tgg | acc | aaa | gaa | aac | att | gag | aaa | ttt | ggt | gga | gat | cca | gaa | aat | att | 629 |
|---|---|---|---|---|---|---|---|---|---|---|---|---|---|---|---|---|
| Trp | Thr | Lys | Glu | Asn | Ile | Glu | Lys | Phe | Gly | Gly | Asp | Pro | Glu | Asn | Ile | |

-continued

| | | | |
|---|---|---|---|
| 185 | 190 | 195 | 200 |

| | | |
|---|---|---|
| aca att ggt ggt gtt tct gct ggt gga gca agt gtt cat tat ctt ttg<br>Thr Ile Gly Gly Val Ser Ala Gly Gly Ala Ser Val His Tyr Leu Leu<br>    205              210              215 | | 677 |
| tta tct cat aca acc act gga ctt tac aaa agg gca att gct caa agt<br>Leu Ser His Thr Thr Thr Gly Leu Tyr Lys Arg Ala Ile Ala Gln Ser<br>        220              225              230 | | 725 |
| gga agt gct ttt aat cca tgg gcc ttc caa aga cat cca gta aag cgt<br>Gly Ser Ala Phe Asn Pro Trp Ala Phe Gln Arg His Pro Val Lys Arg<br>        235              240              245 | | 773 |
| agt ctt caa ctt gct gag ata ttg ggt cat ccc aca aac aat act caa<br>Ser Leu Gln Leu Ala Glu Ile Leu Gly His Pro Thr Asn Asn Thr Gln<br>    250              255              260 | | 821 |
| gat gct tta gaa ttc tta caa aaa gcc ccc gta gac agt ctc ctg aag<br>Asp Ala Leu Glu Phe Leu Gln Lys Ala Pro Val Asp Ser Leu Leu Lys<br>265              270              275              280 | | 869 |
| aaa atg cca gct gaa aca gaa ggt gaa ata ata gaa gag ttt gtc ttc<br>Lys Met Pro Ala Glu Thr Glu Gly Glu Ile Ile Glu Glu Phe Val Phe<br>        285              290              295 | | 917 |
| gta cca tca att gaa aaa gtt ttc cca tcc cac caa cct ttc ttg gaa<br>Val Pro Ser Ile Glu Lys Val Phe Pro Ser His Gln Pro Phe Leu Glu<br>    300              305              310 | | 965 |
| gaa tca cca ttg gcc aga atg aaa tcc gga tcc ttt aac aaa gta cct<br>Glu Ser Pro Leu Ala Arg Met Lys Ser Gly Ser Phe Asn Lys Val Pro<br>    315              320              325 | | 1013 |
| tta tta gtt gga ttt aac agt gca gaa gga ctt ttg ttc aaa ttc ttc<br>Leu Leu Val Gly Phe Asn Ser Ala Glu Gly Leu Leu Phe Lys Phe Phe<br>    330              335              340 | | 1061 |
| atg aaa gaa aaa cca gag atg ctg aac caa gct gaa gca gat ttt gaa<br>Met Lys Glu Lys Pro Glu Met Leu Asn Gln Ala Glu Ala Asp Phe Glu<br>345              350              355              360 | | 1109 |
| aga ctc gta cca gcc gaa ttt gaa tta gtc cat gga tca gag gaa tcg<br>Arg Leu Val Pro Ala Glu Phe Glu Leu Val His Gly Ser Glu Glu Ser<br>        365              370              375 | | 1157 |
| aaa aaa ctt gca gaa aaa atc agg aag ttt tac ttt gac gat aaa ccc<br>Lys Lys Leu Ala Glu Lys Ile Arg Lys Phe Tyr Phe Asp Asp Lys Pro<br>        380              385              390 | | 1205 |
| gtt cca gaa aat gaa cag aaa ttt att gac ttg ata gga gat att tgg<br>Val Pro Glu Asn Glu Gln Lys Phe Ile Asp Leu Ile Gly Asp Ile Trp<br>        395              400              405 | | 1253 |
| ttt act aga ggt gtt gac aag cat gtc aag ttg tct gtg gag aaa caa<br>Phe Thr Arg Gly Val Asp Lys His Val Lys Leu Ser Val Glu Lys Gln<br>    410              415              420 | | 1301 |
| gac gaa cca gtt tat tat tat gaa tat tcc ttc tcg gaa agt cat cct<br>Asp Glu Pro Val Tyr Tyr Tyr Glu Tyr Ser Phe Ser Glu Ser His Pro<br>425              430              435              440 | | 1349 |
| gca aaa gga aca ttt ggt gat cat aat ctg act ggt gca tgc cat gga<br>Ala Lys Gly Thr Phe Gly Asp His Asn Leu Thr Gly Ala Cys His Gly<br>        445              450              455 | | 1397 |
| gaa gaa ctt gtg aat tta ttc aaa gtc gag atg atg aag ctg gaa aaa<br>Glu Glu Leu Val Asn Leu Phe Lys Val Glu Met Met Lys Leu Glu Lys<br>        460              465              470 | | 1445 |
| gat aaa cct aat gtt cta tta aca aaa gat aga gta ctt gcc atg tgg<br>Asp Lys Pro Asn Val Leu Leu Thr Lys Asp Arg Val Leu Ala Met Trp<br>        475              480              485 | | 1493 |
| act aac ttc atc aaa aat gga aat cct act cct gaa gta aca gaa tta<br>Thr Asn Phe Ile Lys Asn Gly Asn Pro Thr Pro Glu Val Thr Glu Leu<br>    490              495              500 | | 1541 |
| ttg cca gtt aaa tgg gaa cct gcc aca aaa gac aag ttg aat tat ttg | | 1589 |

| | | | | | | | | | | | | | | | |
|---|---|---|---|---|---|---|---|---|---|---|---|---|---|---|---|
| Leu | Pro | Val | Lys | Trp | Glu | Pro | Ala | Thr | Lys | Asp | Lys | Leu | Asn | Tyr | Leu |
| 505 | | | | | 510 | | | | 515 | | | | | | 520 |

| | | | | | | | | | | | | | | |
|---|---|---|---|---|---|---|---|---|---|---|---|---|---|---|
| aac | att | gat | gcc | acc | tta | act | ttg | gga | aca | aat | cct | gag | gca | aac | cga | 1637 |
| Asn | Ile | Asp | Ala | Thr | Leu | Thr | Leu | Gly | Thr | Asn | Pro | Glu | Ala | Asn | Arg |
| | | | | 525 | | | | | 530 | | | | | 535 | |

| | | | | | | | | | | | |
|---|---|---|---|---|---|---|---|---|---|---|---|
| gtc | aaa | ttt | tgg | gaa | gac | gcc | aca | aaa | tct | ttg | cac | ggt | caa | taa | 1682 |
| Val | Lys | Phe | Trp | Glu | Asp | Ala | Thr | Lys | Ser | Leu | His | Gly | Gln |
| | | | 540 | | | | | 545 | | | | | 550 |

```
taatttatga aaattgtttt aaatacttta ggtaatatat taggtaaata aaaattaaaa    1742
aataacaatt tttatgtttt atgtattggc ttatgtgtat cagttctaat tttatttatt    1802
tattcttgtt ttgcttgttt tgaaatatca tggttttaat tttcaaaaca caacgtcgtt    1862
tgtttttagc aaaatttcca atagatatgt tatattaagt actctgaagt attttatat    1922 atacactaaa atcagtaaaa atacattaac taaaaatata agatattttc aataattttt    1982
tttaaagaaa ataccaaaaa taaagtaaaa ttccaaacgg aatttttgtt taacttaaaa    2042
ataaaattaa ctcttcaata attttgataa ttagtatttc tgatatcatt agtgaaaatt    2102
atattttgat aatacgtatt tatatttaaa ataaaattat gt                        2144

<210> SEQ ID NO 58
<211> LENGTH: 550
<212> TYPE: PRT
<213> ORGANISM: Ctenocephalides felis
<220> FEATURE:
<221> NAME/KEY: misc_feature
<222> LOCATION: (145)..(145)
<223> OTHER INFORMATION: The 'Xaa' at location 145 stands for Asp, or
      Asn.

<400> SEQUENCE: 58
```

| | | | | | | | | | | | | | | | |
|---|---|---|---|---|---|---|---|---|---|---|---|---|---|---|---|
| Met | Ser | Arg | Val | Ile | Phe | Leu | Ser | Cys | Ile | Phe | Leu | Phe | Ser | Phe | Asn |
| 1 | | | | 5 | | | | | 10 | | | | | 15 | |

| | | | | | | | | | | | | | | | |
|---|---|---|---|---|---|---|---|---|---|---|---|---|---|---|---|
| Phe | Ile | Lys | Cys | Asp | Ser | Pro | Thr | Val | Thr | Leu | Pro | Gln | Gly | Glu | Leu |
| | | | 20 | | | | | 25 | | | | | 30 | | |

| | | | | | | | | | | | | | | | |
|---|---|---|---|---|---|---|---|---|---|---|---|---|---|---|---|
| Val | Gly | Lys | Ala | Leu | Thr | Asn | Glu | Asn | Gly | Lys | Glu | Tyr | Phe | Ser | Tyr |
| | | 35 | | | | | 40 | | | | | 45 | | | |

| | | | | | | | | | | | | | | | |
|---|---|---|---|---|---|---|---|---|---|---|---|---|---|---|---|
| Thr | Gly | Val | Pro | Tyr | Ala | Lys | Pro | Pro | Val | Gly | Glu | Leu | Arg | Phe | Lys |
| | 50 | | | | | 55 | | | | | 60 | | | | |

| | | | | | | | | | | | | | | | |
|---|---|---|---|---|---|---|---|---|---|---|---|---|---|---|---|
| Pro | Pro | Gln | Lys | Ala | Glu | Pro | Trp | Gln | Gly | Val | Phe | Asn | Ala | Thr | Leu |
| 65 | | | | | 70 | | | | | 75 | | | | | 80 |

| | | | | | | | | | | | | | | | |
|---|---|---|---|---|---|---|---|---|---|---|---|---|---|---|---|
| Tyr | Gly | Asn | Val | Cys | Lys | Ser | Leu | Asn | Phe | Phe | Leu | Lys | Lys | Ile | Glu |
| | | | | 85 | | | | | 90 | | | | | 95 | |

| | | | | | | | | | | | | | | | |
|---|---|---|---|---|---|---|---|---|---|---|---|---|---|---|---|
| Gly | Asp | Glu | Asp | Cys | Leu | Val | Val | Asn | Val | Tyr | Ala | Pro | Lys | Thr | Thr |
| | | | 100 | | | | | 105 | | | | | 110 | | |

| | | | | | | | | | | | | | | | |
|---|---|---|---|---|---|---|---|---|---|---|---|---|---|---|---|
| Ser | Asp | Lys | Lys | Leu | Pro | Val | Phe | Phe | Trp | Val | His | Gly | Gly | Gly | Phe |
| | | 115 | | | | | 120 | | | | | 125 | | | |

| | | | | | | | | | | | | | | | |
|---|---|---|---|---|---|---|---|---|---|---|---|---|---|---|---|
| Val | Thr | Gly | Ser | Gly | Asn | Leu | Glu | Phe | Gln | Ser | Pro | Asp | Tyr | Leu | Val |
| | 130 | | | | | 135 | | | | | 140 | | | | |

| | | | | | | | | | | | | | | | |
|---|---|---|---|---|---|---|---|---|---|---|---|---|---|---|---|
| Xaa | Phe | Asp | Val | Ile | Phe | Val | Thr | Phe | Asn | Tyr | Arg | Leu | Gly | Pro | Leu |
| 145 | | | | | 150 | | | | | 155 | | | | | 160 |

| | | | | | | | | | | | | | | | |
|---|---|---|---|---|---|---|---|---|---|---|---|---|---|---|---|
| Gly | Phe | Leu | Asn | Leu | Glu | Leu | Glu | Gly | Ala | Pro | Gly | Asn | Val | Gly | Leu |
| | | | | 165 | | | | | 170 | | | | | 175 | |

| | | | | | | | | | | | | | | | |
|---|---|---|---|---|---|---|---|---|---|---|---|---|---|---|---|
| Leu | Asp | Gln | Val | Ala | Ala | Leu | Lys | Trp | Thr | Lys | Glu | Asn | Ile | Glu | Lys |
| | | | 180 | | | | | 185 | | | | | 190 | | |

| | | | | | | | | | | | | | | | |
|---|---|---|---|---|---|---|---|---|---|---|---|---|---|---|---|
| Phe | Gly | Gly | Asp | Pro | Glu | Asn | Ile | Thr | Ile | Gly | Gly | Val | Ser | Ala | Gly |
| | | 195 | | | | | 200 | | | | | 205 | | | |

```
Gly Ala Ser Val His Tyr Leu Leu Ser His Thr Thr Gly Leu
    210                 215                 220

Tyr Lys Arg Ala Ile Ala Gln Ser Gly Ser Ala Phe Asn Pro Trp Ala
225                 230                 235                 240

Phe Gln Arg His Pro Val Lys Arg Ser Leu Gln Leu Ala Glu Ile Leu
                245                 250                 255

Gly His Pro Thr Asn Asn Thr Gln Asp Ala Leu Glu Phe Leu Gln Lys
            260                 265                 270

Ala Pro Val Asp Ser Leu Leu Lys Lys Met Pro Ala Glu Thr Glu Gly
            275                 280                 285

Glu Ile Ile Glu Glu Phe Val Phe Pro Ser Ile Glu Lys Val Phe
290                 295                 300

Pro Ser His Gln Pro Phe Leu Glu Glu Ser Pro Leu Ala Arg Met Lys
305                 310                 315                 320

Ser Gly Ser Phe Asn Lys Val Pro Leu Leu Val Gly Phe Asn Ser Ala
                325                 330                 335

Glu Gly Leu Leu Phe Lys Phe Met Lys Glu Lys Pro Glu Met Leu
            340                 345                 350

Asn Gln Ala Glu Ala Asp Phe Glu Arg Leu Val Pro Ala Glu Phe Glu
            355                 360                 365

Leu Val His Gly Ser Glu Glu Ser Lys Lys Leu Ala Glu Lys Ile Arg
    370                 375                 380

Lys Phe Tyr Phe Asp Asp Lys Pro Val Pro Glu Asn Glu Gln Lys Phe
385                 390                 395                 400

Ile Asp Leu Ile Gly Asp Ile Trp Phe Thr Arg Gly Val Asp Lys His
                405                 410                 415

Val Lys Leu Ser Val Glu Lys Gln Asp Glu Pro Val Tyr Tyr Tyr Glu
                420                 425                 430

Tyr Ser Phe Ser Glu Ser His Pro Ala Lys Gly Thr Phe Gly Asp His
            435                 440                 445

Asn Leu Thr Gly Ala Cys His Gly Glu Glu Leu Val Asn Leu Phe Lys
    450                 455                 460

Val Glu Met Met Lys Leu Glu Lys Asp Lys Pro Asn Val Leu Leu Thr
465                 470                 475                 480

Lys Asp Arg Val Leu Ala Met Trp Thr Asn Phe Ile Lys Asn Gly Asn
                485                 490                 495

Pro Thr Pro Glu Val Thr Glu Leu Leu Pro Val Lys Trp Glu Pro Ala
            500                 505                 510

Thr Lys Asp Lys Leu Asn Tyr Leu Asn Ile Asp Ala Thr Leu Thr Leu
            515                 520                 525

Gly Thr Asn Pro Glu Ala Asn Arg Val Lys Phe Trp Glu Asp Ala Thr
    530                 535                 540

Lys Ser Leu His Gly Gln
545                 550

<210> SEQ ID NO 59
<211> LENGTH: 2144
<212> TYPE: DNA
<213> ORGANISM: Ctenocephalides felis

<400> SEQUENCE: 59
acataatttt attttaaata taaatacgta ttatcaaaat ataattttca ctaatgatat      60
cagaaatact aattatcaaa attattgaag agttaatttt attttaagt taaacaaaaa     120 ttccgtttgg aattttactt tattttggt attttcttta aaaaaaatta ttgaaaatat     180
```

-continued

```
cttatatttt tagttaatgt atttttactg attttagtgt atatataaaa atacttcaga       240
gtacttaata taacatatct attggaaatt ttgctaaaaa caaacgacgt tgtgttttga       300
aaattaaaac catgatattt caaaacaagc aaaacaagaa taaataaata aaattagaac       360
tgatacacat aagccaatac ataaaacata aaaattgtta tttttttaatt tttatttacc      420
taatatatta cctaaagtat ttaaaacaat tttcataaat tattattgac cgtgcaaaga       480
ttttgtggcg tcttcccaaa atttgactcg gtttgcctca ggatttgttc ccaaagttaa       540
ggtggcatca atgttcaaat aattcaactt gtcttttgtg gcaggttccc atttaactgg       600
caataattct gttacttcag gagtaggatt tccattttg atgaagttag tccacatggc        660
aagtactcta tctttgtta atagaacatt aggtttatct ttttccagct tcatcatctc        720
gactttgaat aaattcacaa gttcttctcc atggcatgca ccagtcagat tatgatcacc       780
aaatgttcct tttgcaggat gactttccga gaaggaatat tcataataat aaactggttc      840
gtcttgtttc tccacagaca acttgacatg cttgtcaaca cctctagtaa accaaatatc      900
tcctatcaag tcaataaatt tctgttcatt ttctggaacg ggtttatcgt caaagtaaaa      960
cttcctgatt ttttctgcaa gttttttcga ttcctctgat ccatggacta attcaaattc     1020
ggctggtacg agtcttttcaa aatctgcttc agcttggttc agcatctctg gttttttcttt    1080
catgaagaat ttgaacaaaa gtccttctgc actgttaaat ccaactaata aggtactttt     1140
gttaaaggat ccggatttca ttctggccaa tggtgattct tccaagaaag gttggtggga     1200
tgggaaaact ttttcaattg atggtacgaa gacaaactct tctattattt caccttctgt     1260
ttcagctggc atttttcttca ggagactgtc tacgggggct ttttgtaaga attctaaagc    1320
atcttgagta ttgtttgtgg gatgacccaa tatctcagca agttgaagac tacgctttac     1380
tggatgtctt tggaaggccc atggattaaa agcacttcca ctttgagcaa ttgccctttt     1440
gtaaagtcca gtggttgtat gagataacaa aagataatga acacttgctc caccagcaga    1500
aacaccacca attgtaatat tttctggatc tccaccaaat ttctcaatgt tttctttggt    1560
ccatttcaga gctgccacct gatccaataa tcctacattt cctggagcac cctccaactc    1620
caaattcaga aatccgagag gtcccaatcg gtaattgaaa gttacgaaaa taacatcaaa    1680
atytactaaa taatctgggc tttggaattc taaatttccg gatccagtca caaaaccacc    1740
accatgaacc cagaaaaata ctggaagttt tttatcagaa gttgttttttg gtgcgtacac    1800
gtttactacc aagcagtctt cgtctccttc aattttcttc aagaagaaat ttaaagattt    1860
acacacattt ccgtataatg tggcgttgaa aacaccttgc catggctcag ctttctgtgg    1920
aggcttaaat ctaagttctc caacaggagg tttagcataa ggtacacctg tgtagctaaa    1980
atactctttt ccattttcgt tcgtcaaagc ttttccaacc aattcgcctt ggggcaaagt    2040
tacagtcggg gaatcacatt ttataaaatt aaaactaaac aaaaaaatac aacttaaaaa    2100
aataacacga gacatcttgg atctagacta ttgactatgt gtac                     2144
```

<210> SEQ ID NO 60
<211> LENGTH: 1650
<212> TYPE: DNA
<213> ORGANISM: Ctenocephalides felis
<220> FEATURE:
<221> NAME/KEY: exon
<222> LOCATION: (1)..(1650)
<223> OTHER INFORMATION:
<220> FEATURE:
<221> NAME/KEY: misc_feature
<222> LOCATION: (433)..(433)

<223> OTHER INFORMATION: At nucleotide 433, r = a or g
At amino acid residue 145, Xaa = Asn or Asp

<400> SEQUENCE: 60

| | | | | | | | | | | | | | | | | |
|---|---|---|---|---|---|---|---|---|---|---|---|---|---|---|---|---|
| atg | tct | cgt | gtt | att | ttt | tta | agt | tgt | att | ttt | ttg | ttt | agt | ttt | aat | 48 |
| Met | Ser | Arg | Val | Ile | Phe | Leu | Ser | Cys | Ile | Phe | Leu | Phe | Ser | Phe | Asn | |
| 1 | | | | 5 | | | | | 10 | | | | | 15 | | |
| ttt | ata | aaa | tgt | gat | tcc | ccg | act | gta | act | ttg | ccc | caa | ggc | gaa | ttg | 96 |
| Phe | Ile | Lys | Cys | Asp | Ser | Pro | Thr | Val | Thr | Leu | Pro | Gln | Gly | Glu | Leu | |
| | | | 20 | | | | | 25 | | | | | 30 | | | |
| gtt | gga | aaa | gct | ttg | acg | aac | gaa | aat | gga | aaa | gag | tat | ttt | agc | tac | 144 |
| Val | Gly | Lys | Ala | Leu | Thr | Asn | Glu | Asn | Gly | Lys | Glu | Tyr | Phe | Ser | Tyr | |
| | | 35 | | | | | 40 | | | | | 45 | | | | |
| aca | ggt | gta | cct | tat | gct | aaa | cct | cct | gtt | gga | gaa | ctt | aga | ttt | aag | 192 |
| Thr | Gly | Val | Pro | Tyr | Ala | Lys | Pro | Pro | Val | Gly | Glu | Leu | Arg | Phe | Lys | |
| | 50 | | | | | 55 | | | | | 60 | | | | | |
| cct | cca | cag | aaa | gct | gag | cca | tgg | caa | ggt | gtt | ttc | aac | gcc | aca | tta | 240 |
| Pro | Pro | Gln | Lys | Ala | Glu | Pro | Trp | Gln | Gly | Val | Phe | Asn | Ala | Thr | Leu | |
| 65 | | | | | 70 | | | | | 75 | | | | | 80 | |
| tac | gga | aat | gtg | tgt | aaa | tct | tta | aat | ttc | ttc | ttg | aag | aaa | att | gaa | 288 |
| Tyr | Gly | Asn | Val | Cys | Lys | Ser | Leu | Asn | Phe | Phe | Leu | Lys | Lys | Ile | Glu | |
| | | | | 85 | | | | | 90 | | | | | 95 | | |
| gga | gac | gaa | gac | tgc | ttg | gta | gta | aac | gtg | tac | gca | cca | aaa | aca | act | 336 |
| Gly | Asp | Glu | Asp | Cys | Leu | Val | Val | Asn | Val | Tyr | Ala | Pro | Lys | Thr | Thr | |
| | | | 100 | | | | | 105 | | | | | 110 | | | |
| tct | gat | aaa | aaa | ctt | cca | gta | ttt | ttc | tgg | gtt | cat | ggt | ggt | ggt | ttt | 384 |
| Ser | Asp | Lys | Lys | Leu | Pro | Val | Phe | Phe | Trp | Val | His | Gly | Gly | Gly | Phe | |
| | | 115 | | | | | 120 | | | | | 125 | | | | |
| gtg | act | gga | tcc | gga | aat | tta | gaa | ttc | caa | agc | cca | gat | tat | tta | gta | 432 |
| Val | Thr | Gly | Ser | Gly | Asn | Leu | Glu | Phe | Gln | Ser | Pro | Asp | Tyr | Leu | Val | |
| | 130 | | | | | 135 | | | | | 140 | | | | | |
| rat | ttt | gat | gtt | att | ttc | gta | act | ttc | aat | tac | cga | ttg | gga | cct | ctc | 480 |
| Xaa | Phe | Asp | Val | Ile | Phe | Val | Thr | Phe | Asn | Tyr | Arg | Leu | Gly | Pro | Leu | |
| 145 | | | | | 150 | | | | | 155 | | | | | 160 | |
| gga | ttt | ctg | aat | ttg | gag | ttg | gag | ggt | gct | cca | gga | aat | gta | gga | tta | 528 |
| Gly | Phe | Leu | Asn | Leu | Glu | Leu | Glu | Gly | Ala | Pro | Gly | Asn | Val | Gly | Leu | |
| | | | | 165 | | | | | 170 | | | | | 175 | | |
| ttg | gat | cag | gtg | gca | gct | ctg | aaa | tgg | acc | aaa | gaa | aac | att | gag | aaa | 576 |
| Leu | Asp | Gln | Val | Ala | Ala | Leu | Lys | Trp | Thr | Lys | Glu | Asn | Ile | Glu | Lys | |
| | | | 180 | | | | | 185 | | | | | 190 | | | |
| ttt | ggt | gga | gat | cca | gaa | aat | att | aca | att | ggt | ggt | gtt | tct | gct | ggt | 624 |
| Phe | Gly | Gly | Asp | Pro | Glu | Asn | Ile | Thr | Ile | Gly | Gly | Val | Ser | Ala | Gly | |
| | | 195 | | | | | 200 | | | | | 205 | | | | |
| gga | gca | agt | gtt | cat | tat | ctt | ttg | tta | tct | cat | aca | acc | act | gga | ctt | 672 |
| Gly | Ala | Ser | Val | His | Tyr | Leu | Leu | Leu | Ser | His | Thr | Thr | Thr | Gly | Leu | |
| | 210 | | | | | 215 | | | | | 220 | | | | | |
| tac | aaa | agg | gca | att | gct | caa | agt | gga | agt | gct | ttt | aat | cca | tgg | gcc | 720 |
| Tyr | Lys | Arg | Ala | Ile | Ala | Gln | Ser | Gly | Ser | Ala | Phe | Asn | Pro | Trp | Ala | |
| 225 | | | | | 230 | | | | | 235 | | | | | 240 | |
| ttc | caa | aga | cat | cca | gta | aag | cgt | agt | ctt | caa | ctt | gct | gag | ata | ttg | 768 |
| Phe | Gln | Arg | His | Pro | Val | Lys | Arg | Ser | Leu | Gln | Leu | Ala | Glu | Ile | Leu | |
| | | | | 245 | | | | | 250 | | | | | 255 | | |
| ggt | cat | ccc | aca | aac | aat | act | caa | gat | gct | tta | gaa | ttc | tta | caa | aaa | 816 |
| Gly | His | Pro | Thr | Asn | Asn | Thr | Gln | Asp | Ala | Leu | Glu | Phe | Leu | Gln | Lys | |
| | | | 260 | | | | | 265 | | | | | 270 | | | |
| gcc | ccc | gta | gac | agt | ctc | ctg | aag | aaa | atg | cca | gct | gaa | aca | gaa | ggt | 864 |
| Ala | Pro | Val | Asp | Ser | Leu | Leu | Lys | Lys | Met | Pro | Ala | Glu | Thr | Glu | Gly | |
| | | 275 | | | | | 280 | | | | | 285 | | | | |
| gaa | ata | ata | gaa | gag | ttt | gtc | ttc | gta | cca | tca | att | gaa | aaa | gtt | ttc | 912 |
| Glu | Ile | Ile | Glu | Glu | Phe | Val | Phe | Val | Pro | Ser | Ile | Glu | Lys | Val | Phe | |

|  |  |  |  |  |  |  |  |  |  |  |  |  |  |  |  |  |
|---|---|---|---|---|---|---|---|---|---|---|---|---|---|---|---|---|
| | | | 290 | | | | 295 | | | | 300 | | | | | |
| cca | tcc | cac | caa | cct | ttc | ttg | gaa | gaa | tca | cca | ttg | gcc | aga | atg | aaa | 960 |
| Pro | Ser | His | Gln | Pro | Phe | Leu | Glu | Glu | Ser | Pro | Leu | Ala | Arg | Met | Lys | |
| 305 | | | | 310 | | | | 315 | | | | 320 | | | | |
| tcc | gga | tcc | ttt | aac | aaa | gta | cct | tta | tta | gtt | gga | ttt | aac | agt | gca | 1008 |
| Ser | Gly | Ser | Phe | Asn | Lys | Val | Pro | Leu | Leu | Val | Gly | Phe | Asn | Ser | Ala | |
| | | | | 325 | | | | | 330 | | | | | 335 | | |
| gaa | gga | ctt | ttg | ttc | aaa | ttc | ttc | atg | aaa | gaa | aaa | cca | gag | atg | ctg | 1056 |
| Glu | Gly | Leu | Leu | Phe | Lys | Phe | Phe | Met | Lys | Glu | Lys | Pro | Glu | Met | Leu | |
| | | | 340 | | | | | 345 | | | | | 350 | | | |
| aac | caa | gct | gaa | gca | gat | ttt | gaa | aga | ctc | gta | cca | gcc | gaa | ttt | gaa | 1104 |
| Asn | Gln | Ala | Glu | Ala | Asp | Phe | Glu | Arg | Leu | Val | Pro | Ala | Glu | Phe | Glu | |
| | | 355 | | | | | 360 | | | | | 365 | | | | |
| tta | gtc | cat | gga | tca | gag | gaa | tcg | aaa | aaa | ctt | gca | gaa | aaa | atc | agg | 1152 |
| Leu | Val | His | Gly | Ser | Glu | Glu | Ser | Lys | Lys | Leu | Ala | Glu | Lys | Ile | Arg | |
| 370 | | | | | 375 | | | | | 380 | | | | | | |
| aag | ttt | tac | ttt | gac | gat | aaa | ccc | gtt | cca | gaa | aat | gaa | cag | aaa | ttt | 1200 |
| Lys | Phe | Tyr | Phe | Asp | Asp | Lys | Pro | Val | Pro | Glu | Asn | Glu | Gln | Lys | Phe | |
| 385 | | | | 390 | | | | 395 | | | | 400 | | | | |
| att | gac | ttg | ata | gga | gat | att | tgg | ttt | act | aga | ggt | gtt | gac | aag | cat | 1248 |
| Ile | Asp | Leu | Ile | Gly | Asp | Ile | Trp | Phe | Thr | Arg | Gly | Val | Asp | Lys | His | |
| | | | | 405 | | | | | 410 | | | | | 415 | | |
| gtc | aag | ttg | tct | gtg | gag | aaa | caa | gac | gaa | cca | gtt | tat | tat | tat | gaa | 1296 |
| Val | Lys | Leu | Ser | Val | Glu | Lys | Gln | Asp | Glu | Pro | Val | Tyr | Tyr | Tyr | Glu | |
| | | | 420 | | | | | 425 | | | | | 430 | | | |
| tat | tcc | ttc | tcg | gaa | agt | cat | cct | gca | aaa | gga | aca | ttt | ggt | gat | cat | 1344 |
| Tyr | Ser | Phe | Ser | Glu | Ser | His | Pro | Ala | Lys | Gly | Thr | Phe | Gly | Asp | His | |
| | | 435 | | | | | 440 | | | | | 445 | | | | |
| aat | ctg | act | ggt | gca | tgc | cat | gga | gaa | gaa | ctt | gtg | aat | tta | ttc | aaa | 1392 |
| Asn | Leu | Thr | Gly | Ala | Cys | His | Gly | Glu | Glu | Leu | Val | Asn | Leu | Phe | Lys | |
| | | | | 450 | | | | | 455 | | | | | 460 | | |
| gtc | gag | atg | atg | aag | ctg | gaa | aaa | gat | aaa | cct | aat | gtt | cta | tta | aca | 1440 |
| Val | Glu | Met | Met | Lys | Leu | Glu | Lys | Asp | Lys | Pro | Asn | Val | Leu | Leu | Thr | |
| 465 | | | | | 470 | | | | | 475 | | | | | 480 | |
| aaa | gat | aga | gta | ctt | gcc | atg | tgg | act | aac | ttc | atc | aaa | aat | gga | aat | 1488 |
| Lys | Asp | Arg | Val | Leu | Ala | Met | Trp | Thr | Asn | Phe | Ile | Lys | Asn | Gly | Asn | |
| | | | | 485 | | | | | 490 | | | | | 495 | | |
| cct | act | cct | gaa | gta | aca | gaa | tta | ttg | cca | gtt | aaa | tgg | gaa | cct | gcc | 1536 |
| Pro | Thr | Pro | Glu | Val | Thr | Glu | Leu | Leu | Pro | Val | Lys | Trp | Glu | Pro | Ala | |
| | | | 500 | | | | | 505 | | | | | 510 | | | |
| aca | aaa | gac | aag | ttg | aat | tat | ttg | aac | att | gat | gcc | acc | tta | act | ttg | 1584 |
| Thr | Lys | Asp | Lys | Leu | Asn | Tyr | Leu | Asn | Ile | Asp | Ala | Thr | Leu | Thr | Leu | |
| | | 515 | | | | | 520 | | | | | 525 | | | | |
| gga | aca | aat | cct | gag | gca | aac | cga | gtc | aaa | ttt | tgg | gaa | gac | gcc | aca | 1632 |
| Gly | Thr | Asn | Pro | Glu | Ala | Asn | Arg | Val | Lys | Phe | Trp | Glu | Asp | Ala | Thr | |
| | | 530 | | | | | 535 | | | | | 540 | | | | |
| aaa | tct | ttg | cac | ggt | caa | | | | | | | | | | | 1650 |
| Lys | Ser | Leu | His | Gly | Gln | | | | | | | | | | | |
| 545 | | | | 550 | | | | | | | | | | | | |

<210> SEQ ID NO 61
<211> LENGTH: 1650
<212> TYPE: DNA
<213> ORGANISM: Ctenocephalides felis

<400> SEQUENCE: 61

| | |
|---|---|
| ttgaccgtgc aaagattttg tggcgtcttc ccaaaatttg actcggtttg cctcaggatt | 60 |
| tgttcccaaa gttaaggtgg catcaatgtt caaataattc aacttgtctt ttgtggcagg | 120 |
| ttcccattta actggcaata attctgttac ttcaggagta ggatttccat ttttgatgaa | 180 |

```
gttagtccac atggcaagta ctctatcttt tgttaataga acattaggtt tatcttttc        240 cagcttcatc atctcgactt tgaataaatt cacaagttct tctccatggc atgcaccagt       300
cagattatga tcaccaaatg ttccttttgc aggatgactt tccgagaagg aatattcata       360
ataataaact ggttcgtctt gtttctccac agacaacttg acatgcttgt caacacctct      420
agtaaaccaa atatctccta tcaagtcaat aaatttctgt tcattttctg gaacgggttt       480
atcgtcaaag taaaacttcc tgattttttc tgcaagtttt ttcgattcct ctgatccatg       540
gactaattca aattcggctg gtacgagtct ttcaaaatct gcttcagctt ggttcagcat       600
ctctggtttt tctttcatga agaatttgaa caaaagtcct tctgcactgt taaatccaac       660
taataaaggt actttgttaa aggatccgga tttcattctg gccaatggtg attcttccaa       720
gaaaggttgg tgggatggga aaacttttc aattgatggt acgaagacaa actcttctat       780
tatttcacct tctgtttcag ctggcatttt cttcaggaga ctgtctacgg gggcttttg       840 taagaattct aaagcatctt gagtattgtt tgtgggatga cccaatatct cagcaagttg       900
aagactacgc tttactggat gtctttggaa ggcccatgga ttaaaagcac ttccactttg       960
agcaattgcc cttttgtaaa gtccagtggt tgtatgagat aacaaaagat aatgaacact      1020
tgctccacca gcagaaacac caccaattgt aatattttct ggatctccac caaatttctc      1080
aatgttttct ttggtccatt tcagagctgc cacctgatcc aataatccta catttcctgg      1140
agcaccctcc aactccaaat tcagaaatcc gagaggtccc aatcggtaat tgaaagttac      1200
gaaaataaca tcaaaatyta ctaaataatc tgggctttgg aattctaaat ttccggatcc      1260
agtcacaaaa ccaccaccat gaacccagaa aaatactgga agttttttat cagaagttgt      1320
ttttggtgcg tacacgttta ctaccaagca gtcttcgtct ccttcaattt tcttcaagaa      1380
gaaatttaaa gatttacaca catttccgta taatgtggcg ttgaaaacac cttgccatgg      1440
ctcagctttc tgtggaggct taaatctaag ttctccaaca ggaggtttag cataaggtac      1500
acctgtgtag ctaaaatact cttttccatt ttcgttcgtc aaagcttttc caaccaattc      1560 gccttgggc aaagttacag tcggggaatc acattttata aaattaaaac taaacaaaaa       1620
aatacaactt aaaaaaataa cacgagacat                                        1650
```

<210> SEQ ID NO 62
<211> LENGTH: 29
<212> TYPE: DNA
<213> ORGANISM: Artificial sequence
<220> FEATURE:
<223> OTHER INFORMATION: Synthetic Primer

<400> SEQUENCE: 62

```
aaactcgagt cccccgactg taactttgc                                         29
```

<210> SEQ ID NO 63
<211> LENGTH: 36
<212> TYPE: DNA
<213> ORGANISM: Artificial sequence
<220> FEATURE:
<223> OTHER INFORMATION: Synthetic Primer

<400> SEQUENCE: 63

```
tcatctgcag ttattgactg tgcaaagttt ttgtgg                                 36
```

<210> SEQ ID NO 64
<211> LENGTH: 32
<212> TYPE: DNA

```
<213> ORGANISM: Artificial sequence
<220> FEATURE:
<223> OTHER INFORMATION: Synthetic Primer

<400> SEQUENCE: 64
ttccggatcc ggctgatcta caagtgactt tg                                 32

<210> SEQ ID NO 65
<211> LENGTH: 34
<212> TYPE: DNA
<213> ORGANISM: Artificial sequence
<220> FEATURE:
<223> OTHER INFORMATION: Synthetic Primer

<400> SEQUENCE: 65
tggtactcga gtcataaaaa tttattccaa aatc                               34

<210> SEQ ID NO 66
<211> LENGTH: 39
<212> TYPE: DNA
<213> ORGANISM: Artificial sequence
<220> FEATURE:
<223> OTHER INFORMATION: Synthetic Primer

<400> SEQUENCE: 66
aaaactgcag tataaatatg ttacctcaca gtgcattag                          39

<210> SEQ ID NO 67
<211> LENGTH: 1987
<212> TYPE: DNA
<213> ORGANISM: Ctenocephalides felis
<220> FEATURE:
<221> NAME/KEY: CDS
<222> LOCATION: (231)..(1820)
<223> OTHER INFORMATION:

<400> SEQUENCE: 67
aattcacagt gtaaataatt ttatttgata taaatgtatt taattttttat tttaatctaa  60 ttttaattta aatatatata gttttatta taaaaaaata ttttttttat gatcgaaaag   120
aaatttttat ttatgtttat gagtgtgtgt tttggctatg atttacatta tttttgagct  180
agtataaaat taaaccatat tatattttgg atatataata acattttata atg tgt     236
                                                        Met Cys
                                                          1 gat cca tta cta aaa aca aca aca tat gga att ctg aaa ggc aag aaa   284
Asp Pro Leu Leu Lys Thr Thr Thr Tyr Gly Ile Leu Lys Gly Lys Lys
        5                   10                  15 gtt gta aac gaa aat ggt aaa att tac tat agt tac aca ggt ata ccc   332
Val Val Asn Glu Asn Gly Lys Ile Tyr Tyr Ser Tyr Thr Gly Ile Pro
 20                  25                  30 tat gca aaa tct cct gta aat gat ctc aga ttc aag cca cca caa aaa   380
Tyr Ala Lys Ser Pro Val Asn Asp Leu Arg Phe Lys Pro Pro Gln Lys
 35                  40                  45                  50 ctt gat cct tgg aat ggt gtt ttt gac gcc act cag tat gga aat aat   428
Leu Asp Pro Trp Asn Gly Val Phe Asp Ala Thr Gln Tyr Gly Asn Asn
                55                  60                  65 tgt gct gct ggg aaa tgg ttt ttg aaa tca gct ggg ggt tgc gaa gat   476
Cys Ala Ala Gly Lys Trp Phe Leu Lys Ser Ala Gly Gly Cys Glu Asp
            70                  75                  80 tgc ctt tac tta aat atc tat gtc cca caa aac act tca gaa aat cct   524
Cys Leu Tyr Leu Asn Ile Tyr Val Pro Gln Asn Thr Ser Glu Asn Pro
        85                  90                  95 ttg cca gta atg ttt tgg att cat gga gga gca ttt gtg gtc gga tca   572
```

```
                                                                                         -continued Leu Pro Val Met Phe Trp Ile His Gly Gly Ala Phe Val Gly Ser
    100                 105                 110 gga aat tct gat ata cat ggt cct gat tat tta ata gaa tat gat att     620
Gly Asn Ser Asp Ile His Gly Pro Asp Tyr Leu Ile Glu Tyr Asp Ile
115                 120                 125                 130 atc tta gta act att aat tat cgt cta gga cca ctt ggt ttt ctt aat     668
Ile Leu Val Thr Ile Asn Tyr Arg Leu Gly Pro Leu Gly Phe Leu Asn
                135                 140                 145 ttg gaa atc gaa gat gcg cct ggg aat gtt gga ttg atg gat caa gtt     716
Leu Glu Ile Glu Asp Ala Pro Gly Asn Val Gly Leu Met Asp Gln Val
            150                 155                 160 gca gcc cta aaa tgg gta aat gaa aat att gca acc ttt agt gga gac     764
Ala Ala Leu Lys Trp Val Asn Glu Asn Ile Ala Thr Phe Ser Gly Asp
        165                 170                 175 cca aaa aat att aca att tgt gga gca act gct gga gct gca agt gta     812
Pro Lys Asn Ile Thr Ile Cys Gly Ala Thr Ala Gly Ala Ala Ser Val
    180                 185                 190 cat tat cac att ttg tca caa ctt acc aaa ggt tta ttc cac aag gct     860
His Tyr His Ile Leu Ser Gln Leu Thr Lys Gly Leu Phe His Lys Ala
195                 200                 205                 210 ata gca caa agt gga agt gct ttt aat ccc tgg gct ttc caa aaa aat     908
Ile Ala Gln Ser Gly Ser Ala Phe Asn Pro Trp Ala Phe Gln Lys Asn
                215                 220                 225 cct gtt aag aat gca ctt cga cta tgc aaa acc tta ggc ctt acc aca     956
Pro Val Lys Asn Ala Leu Arg Leu Cys Lys Thr Leu Gly Leu Thr Thr
            230                 235                 240 aac aac ctt caa gaa gcc ttg gat ttt ttg aaa aac cta cca gta gaa    1004
Asn Asn Leu Gln Glu Ala Leu Asp Phe Leu Lys Asn Leu Pro Val Glu
        245                 250                 255 aca ttg tta aat acc aaa tta ccc caa gaa att gat ggt caa ctg ctg    1052
Thr Leu Leu Asn Thr Lys Leu Pro Gln Glu Ile Asp Gly Gln Leu Leu
    260                 265                 270 gat gac ttc gtg ttt gta cct tcg att gaa aaa aca ttt cca gaa caa    1100
Asp Asp Phe Val Phe Val Pro Ser Ile Glu Lys Thr Phe Pro Glu Gln
275                 280                 285                 290 gat tcg tac tta act gac ttg cca ata cca ata ata aat tca gga aaa    1148
Asp Ser Tyr Leu Thr Asp Leu Pro Ile Pro Ile Ile Asn Ser Gly Lys
                295                 300                 305 ttc cac aaa gtt cca ttg ttg aca ggt tac aac agt gcc gaa ggc aat    1196
Phe His Lys Val Pro Leu Leu Thr Gly Tyr Asn Ser Ala Glu Gly Asn
            310                 315                 320 cta ttt ttc atg tac tta aaa aca gat cca gat tta tta aat aaa ttt    1244
Leu Phe Phe Met Tyr Leu Lys Thr Asp Pro Asp Leu Leu Asn Lys Phe
        325                 330                 335 gaa gct gat ttt gaa aga ttt ata cca act gac tta gaa tta cct ttg    1292
Glu Ala Asp Phe Glu Arg Phe Ile Pro Thr Asp Leu Glu Leu Pro Leu
    340                 345                 350 cga tca caa aaa tct att gca ctg ggt gaa gca atc agg gaa ttt tat    1340
Arg Ser Gln Lys Ser Ile Ala Leu Gly Glu Ala Ile Arg Glu Phe Tyr
355                 360                 365                 370 ttc caa aac aaa acc ata tca gaa aat atg cag aat ttt gta gat gtt    1388
Phe Gln Asn Lys Thr Ile Ser Glu Asn Met Gln Asn Phe Val Asp Val
                375                 380                 385 tta agt gat aat tgg ttt aca cgt gga att gat gag caa gta aag tta    1436
Leu Ser Asp Asn Trp Phe Thr Arg Gly Ile Asp Glu Gln Val Lys Leu
            390                 395                 400 act gtt aaa aat cag gaa gaa cca gtt ttt tat tat gtt tat aat ttt    1484
Thr Val Lys Asn Gln Glu Glu Pro Val Phe Tyr Tyr Val Tyr Asn Phe
        405                 410                 415
```

```
gat gaa aat tct cca agt cgg aaa gtt ttt ggt gat ttt gga ata aaa    1532
Asp Glu Asn Ser Pro Ser Arg Lys Val Phe Gly Asp Phe Gly Ile Lys
    420                 425                 430 ggc ggt ggt cat gct gat gaa ttg ggt aat ata ttt aaa gcc aaa agt    1580
Gly Gly Gly His Ala Asp Glu Leu Gly Asn Ile Phe Lys Ala Lys Ser
435                 440                 445                 450 gca aat ttt ggg aag gaa aca cca aat gct gtg ttg gtt cag aga agg    1628
Ala Asn Phe Gly Lys Glu Thr Pro Asn Ala Val Leu Val Gln Arg Arg
                455                 460                 465 atg ctg gag atg tgg act aat ttt gct aaa ttt gga aat cct act cca    1676
Met Leu Glu Met Trp Thr Asn Phe Ala Lys Phe Gly Asn Pro Thr Pro
            470                 475                 480 gct att acg gat aca ctt cca ata aaa tgg gaa cct gct ttt aaa gaa    1724
Ala Ile Thr Asp Thr Leu Pro Ile Lys Trp Glu Pro Ala Phe Lys Glu
        485                 490                 495 aat atg act ttt gtt caa att gac att gat tta aat ttg agt act gat    1772
Asn Met Thr Phe Val Gln Ile Asp Ile Asp Leu Asn Leu Ser Thr Asp
    500                 505                 510 cca cta aaa agt cgt atg gaa ttt ggg aat aaa ata aaa tta tta aaa    1820
Pro Leu Lys Ser Arg Met Glu Phe Gly Asn Lys Ile Lys Leu Leu Lys
515                 520                 525                 530 taagtaacta tacttagcta aaccataata taccaaataa tagtatagga atacttcaca    1880
attttttgtt acttcgttaa gtaaatttaa tttttttataa aaccaacttt tacgaataaa    1940
aaatgtaatt attttggaaa aaaaaagaa aaaaaaaaa aaaaaac                    1987

<210> SEQ ID NO 68
<211> LENGTH: 530
<212> TYPE: PRT
<213> ORGANISM: Ctenocephalides felis

<400> SEQUENCE: 68

Met Cys Asp Pro Leu Leu Lys Thr Thr Thr Tyr Gly Ile Leu Lys Gly
1               5                   10                  15

Lys Lys Val Val Asn Glu Asn Gly Lys Ile Tyr Tyr Ser Tyr Thr Gly
            20                  25                  30

Ile Pro Tyr Ala Lys Ser Pro Val Asn Asp Leu Arg Phe Lys Pro Pro
        35                  40                  45

Gln Lys Leu Asp Pro Trp Asn Gly Val Phe Asp Ala Thr Gln Tyr Gly
    50                  55                  60

Asn Asn Cys Ala Ala Gly Lys Trp Phe Leu Lys Ser Ala Gly Gly Cys
65                  70                  75                  80

Glu Asp Cys Leu Tyr Leu Asn Ile Tyr Val Pro Gln Asn Thr Ser Glu
                85                  90                  95

Asn Pro Leu Pro Val Met Phe Trp Ile His Gly Gly Ala Phe Val Val
            100                 105                 110

Gly Ser Gly Asn Ser Asp Ile His Gly Pro Asp Tyr Leu Ile Glu Tyr
        115                 120                 125

Asp Ile Ile Leu Val Thr Ile Asn Tyr Arg Leu Gly Pro Leu Gly Phe
    130                 135                 140

Leu Asn Leu Glu Ile Glu Asp Ala Pro Gly Asn Val Gly Leu Met Asp
145                 150                 155                 160

Gln Val Ala Ala Leu Lys Trp Val Asn Glu Asn Ile Ala Thr Phe Ser
                165                 170                 175

Gly Asp Pro Lys Asn Ile Thr Ile Cys Gly Ala Thr Ala Gly Ala Ala
            180                 185                 190

Ser Val His Tyr His Ile Leu Ser Gln Leu Thr Lys Gly Leu Phe His
```

-continued

```
            195                 200                 205
Lys Ala Ile Ala Gln Ser Gly Ser Ala Phe Asn Pro Trp Ala Phe Gln
            210                 215                 220
Lys Asn Pro Val Lys Asn Ala Leu Arg Leu Cys Lys Thr Leu Gly Leu
225                 230                 235                 240
Thr Thr Asn Asn Leu Gln Glu Ala Leu Asp Phe Leu Lys Asn Leu Pro
                245                 250                 255
Val Glu Thr Leu Leu Asn Thr Lys Leu Pro Gln Glu Ile Asp Gly Gln
            260                 265                 270
Leu Leu Asp Asp Phe Val Phe Val Pro Ser Ile Glu Lys Thr Phe Pro
            275                 280                 285
Glu Gln Asp Ser Tyr Leu Thr Asp Leu Pro Ile Pro Ile Ile Asn Ser
290                 295                 300
Gly Lys Phe His Lys Val Pro Leu Leu Thr Gly Tyr Asn Ser Ala Glu
305                 310                 315                 320
Gly Asn Leu Phe Phe Met Tyr Leu Lys Thr Asp Pro Asp Leu Leu Asn
                325                 330                 335
Lys Phe Glu Ala Asp Phe Glu Arg Phe Ile Pro Thr Asp Leu Glu Leu
            340                 345                 350
Pro Leu Arg Ser Gln Lys Ser Ile Ala Leu Gly Glu Ala Ile Arg Glu
            355                 360                 365
Phe Tyr Phe Gln Asn Lys Thr Ile Ser Glu Asn Met Gln Asn Phe Val
370                 375                 380
Asp Val Leu Ser Asp Asn Trp Phe Thr Arg Gly Ile Asp Glu Gln Val
385                 390                 395                 400
Lys Leu Thr Val Lys Asn Gln Glu Glu Pro Val Phe Tyr Tyr Val Tyr
                405                 410                 415
Asn Phe Asp Glu Asn Ser Pro Ser Arg Lys Val Phe Gly Asp Phe Gly
                420                 425                 430
Ile Lys Gly Gly Gly His Ala Asp Glu Leu Gly Asn Ile Phe Lys Ala
            435                 440                 445
Lys Ser Ala Asn Phe Gly Lys Glu Thr Pro Asn Ala Val Leu Val Gln
    450                 455                 460
Arg Arg Met Leu Glu Met Trp Thr Asn Phe Ala Lys Phe Gly Asn Pro
465                 470                 475                 480
Thr Pro Ala Ile Thr Asp Thr Leu Pro Ile Lys Trp Glu Pro Ala Phe
                485                 490                 495
Lys Glu Asn Met Thr Phe Val Gln Ile Asp Ile Asp Leu Asn Leu Ser
                500                 505                 510
Thr Asp Pro Leu Lys Ser Arg Met Glu Phe Gly Asn Lys Ile Lys Leu
            515                 520                 525
Leu Lys
    530
```

<210> SEQ ID NO 69
<211> LENGTH: 1987
<212> TYPE: DNA
<213> ORGANISM: Ctenocephalides felis

<400> SEQUENCE: 69

```
gtttttttt tttttttttc tttttttttt ccaaaataat tacatttttt attcgtaaaa    60
gttggtttta taaaaatta aatttactta acgaagtaac aaaaaattgt gaagtattcc   120
tatactatta tttggtatat tatggtttag ctaagtatag ttacttattt taataatttt   180
```

```
attttattcc caaattccat acgactttt  agtggatcag tactcaaatt taaatcaatg    240
tcaatttgaa caaaagtcat attttctttta aaagcaggtt cccattttat tggaagtgta    300
tccgtaatag ctggagtagg atttccaaat ttagcaaaat tagtccacat ctccagcatc    360
cttctctgaa ccaacacagc atttggtgtt tccttcccaa aatttgcact tttggcttta    420
aatatattac ccaattcatc agcatgacca ccgccttta  ttccaaaatc accaaaaact    480
ttccgacttg gagaattttc atcaaaatta taaacataat aaaaaactgg ttcttcctga    540
tttttaacag ttaactttac ttgctcatca attccacgtg taaaccaatt atcacttaaa    600
acatctacaa aattctgcat attttctgat atggttttgt tttggaaata aaattccctg    660
attgcttcac ccagtgcaat agatttttgt gatcgcaaag gtaattctaa gtcagttggt    720
ataaatcttt caaaatcagc ttcaaattta tttaataaat ctggatctgt ttttaagtac    780
atgaaaaata gattgccttc ggcactgttg taacctgtca acaatggaac tttgtggaat    840
tttcctgaat ttattattgg tattggcaag tcagttaagt acgaatcttg ttctggaaat    900
gttttttcaa tcgaaggtac aaacacgaag tcatccagca gttgaccatc aatttcttgg    960
ggtaatttgg tatttaacaa tgtttctact ggtaggtttt tcaaaaaatc caaggcttct   1020
tgaaggttgt ttgtggtaag gcctaaggtt ttgcatagtc gaagtgcatt cttaacagga   1080
tttttttgga aagcccaggg attaaaagca cttccacttt gtgctatagc cttgtggaat   1140
aaacctttgg taagttgtga caaaatgtga taatgtacac ttgcagctcc agcagttgct   1200
ccacaaattg taatattttt tgggtctcca ctaaaggttg caatattttc atttaccat    1260 tttagggctg caacttgatc catcaatcca acattcccag gcgcatcttc gatttccaaa   1320
ttaagaaaac caagtggtcc tagacgataa ttaatagtta ctaagataat atcatattct   1380
attaaataat caggaccatg tatatcagaa tttcctgatc cgaccacaaa tgctcctcca   1440
tgaatccaaa acattactgg caaggatttt tctgaagtgt tttgtgggac atagatattt   1500
aagtaaaggc aatcttcgca accccccagct gatttcaaaa accatttccc agcagcacaa   1560
ttatttccat actgagtggc gtcaaaaaca ccattccaag gatcaagttt ttgtggtggc   1620
ttgaatctga gatcatttac aggagatttt gcatagggta tacctgtgta actatagtaa   1680
attttaccat tttcgtttac aactttcttg cctttcagaa ttccatatgt tgttgttttt   1740
agtaatggat cacacattat aaaatgttat tatatatcca aaatataata tggtttaatt   1800
ttatactagc tcaaaaataa tgtaaatcat agccaaaaca cacactcata aacataaata   1860
aaaatttctt ttcgatcata aaaaaatat ttttttataa ataaaactat atatatttaa    1920
attaaaatta gattaaaata aaaattaaat acatttatat caaataaaat tatttacact   1980
gtgaatt                                                             1987
```

<210> SEQ ID NO 70
<211> LENGTH: 1590
<212> TYPE: DNA
<213> ORGANISM: Ctenocephalides felis
<220> FEATURE:
<221> NAME/KEY: exon
<222> LOCATION: (1)..(1590)
<223> OTHER INFORMATION:

<400> SEQUENCE: 70

```
atg tgt gat cca tta cta aaa aca aca aca tat gga att ctg aaa ggc      48
Met Cys Asp Pro Leu Leu Lys Thr Thr Thr Tyr Gly Ile Leu Lys Gly
1               5                   10                  15 aag aaa gtt gta aac gaa aat ggt aaa att tac tat agt tac aca ggt      96
```

-continued

```
Lys Lys Val Val Asn Glu Asn Gly Lys Ile Tyr Tyr Ser Tyr Thr Gly
         20              25              30 ata ccc tat gca aaa tct cct gta aat gat ctc aga ttc aag cca cca        144
Ile Pro Tyr Ala Lys Ser Pro Val Asn Asp Leu Arg Phe Lys Pro Pro
         35              40              45 caa aaa ctt gat cct tgg aat ggt gtt ttt gac gcc act cag tat gga        192
Gln Lys Leu Asp Pro Trp Asn Gly Val Phe Asp Ala Thr Gln Tyr Gly
 50              55              60 aat aat tgt gct gct ggg aaa tgg ttt ttg aaa tca gct ggg ggt tgc        240
Asn Asn Cys Ala Ala Gly Lys Trp Phe Leu Lys Ser Ala Gly Gly Cys
 65              70              75              80 gaa gat tgc ctt tac tta aat atc tat gtc cca caa aac act tca gaa        288
Glu Asp Cys Leu Tyr Leu Asn Ile Tyr Val Pro Gln Asn Thr Ser Glu
                 85              90              95 aat cct ttg cca gta atg ttt tgg att cat gga gga gca ttt gtg gtc        336
Asn Pro Leu Pro Val Met Phe Trp Ile His Gly Gly Ala Phe Val Val
         100             105             110 gga tca gga aat tct gat ata cat ggt cct gat tat tta ata gaa tat        384
Gly Ser Gly Asn Ser Asp Ile His Gly Pro Asp Tyr Leu Ile Glu Tyr
         115             120             125 gat att atc tta gta act att aat tat cgt cta gga cca ctt ggt ttt        432
Asp Ile Ile Leu Val Thr Ile Asn Tyr Arg Leu Gly Pro Leu Gly Phe
 130             135             140 ctt aat ttg gaa atc gaa gat gcg cct ggg aat gtt gga ttg atg gat        480
Leu Asn Leu Glu Ile Glu Asp Ala Pro Gly Asn Val Gly Leu Met Asp
145             150             155             160 caa gtt gca gcc cta aaa tgg gta aat gaa aat att gca acc ttt agt        528
Gln Val Ala Ala Leu Lys Trp Val Asn Glu Asn Ile Ala Thr Phe Ser
                 165             170             175 gga gac cca aaa aat att aca att tgt gga gca act gct gga gct gca        576
Gly Asp Pro Lys Asn Ile Thr Ile Cys Gly Ala Thr Ala Gly Ala Ala
         180             185             190 agt gta cat tat cac att ttg tca caa ctt acc aaa ggt tta ttc cac        624
Ser Val His Tyr His Ile Leu Ser Gln Leu Thr Lys Gly Leu Phe His
         195             200             205 aag gct ata gca caa agt gga agt gct ttt aat ccc tgg gct ttc caa        672
Lys Ala Ile Ala Gln Ser Gly Ser Ala Phe Asn Pro Trp Ala Phe Gln
         210             215             220 aaa aat cct gtt aag aat gca ctt cga cta tgc aaa acc tta ggc ctt        720
Lys Asn Pro Val Lys Asn Ala Leu Arg Leu Cys Lys Thr Leu Gly Leu
225             230             235             240 acc aca aac aac ctt caa gaa gcc ttg gat ttt ttg aaa aac cta cca        768
Thr Thr Asn Asn Leu Gln Glu Ala Leu Asp Phe Leu Lys Asn Leu Pro
                 245             250             255 gta gaa aca ttg tta aat acc aaa tta ccc caa gaa att gat ggt caa        816
Val Glu Thr Leu Leu Asn Thr Lys Leu Pro Gln Glu Ile Asp Gly Gln
         260             265             270 ctg ctg gat gac ttc gtg ttt gta cct tcg att gaa aaa aca ttt cca        864
Leu Leu Asp Asp Phe Val Phe Val Pro Ser Ile Glu Lys Thr Phe Pro
         275             280             285 gaa caa gat tcg tac tta act gac ttg cca ata cca ata ata aat tca        912
Glu Gln Asp Ser Tyr Leu Thr Asp Leu Pro Ile Pro Ile Ile Asn Ser
         290             295             300 gga aaa ttc cac aaa gtt cca ttg ttg aca ggt tac aac agt gcc gaa        960
Gly Lys Phe His Lys Val Pro Leu Leu Thr Gly Tyr Asn Ser Ala Glu
305             310             315             320 ggc aat cta ttt ttc atg tac tta aaa aca gat cca gat tta tta aat       1008
Gly Asn Leu Phe Phe Met Tyr Leu Lys Thr Asp Pro Asp Leu Leu Asn
                 325             330             335
```

| | | | | | | | | | | | | | | | | |
|---|---|---|---|---|---|---|---|---|---|---|---|---|---|---|---|---|
| aaa | ttt | gaa | gct | gat | ttt | gaa | aga | ttt | ata | cca | act | gac | tta | gaa | tta | 1056 |
| Lys | Phe | Glu | Ala | Asp | Phe | Glu | Arg | Phe | Ile | Pro | Thr | Asp | Leu | Glu | Leu | |
| | | | 340 | | | | 345 | | | | | 350 | | | | |
| cct | ttg | cga | tca | caa | aaa | tct | att | gca | ctg | ggt | gaa | gca | atc | agg | gaa | 1104 |
| Pro | Leu | Arg | Ser | Gln | Lys | Ser | Ile | Ala | Leu | Gly | Glu | Ala | Ile | Arg | Glu | |
| | | 355 | | | | | 360 | | | | | 365 | | | | |
| ttt | tat | ttc | caa | aac | aaa | acc | ata | tca | gaa | aat | atg | cag | aat | ttt | gta | 1152 |
| Phe | Tyr | Phe | Gln | Asn | Lys | Thr | Ile | Ser | Glu | Asn | Met | Gln | Asn | Phe | Val | |
| | 370 | | | | | 375 | | | | | 380 | | | | | |
| gat | gtt | tta | agt | gat | aat | tgg | ttt | aca | cgt | gga | att | gat | gag | caa | gta | 1200 |
| Asp | Val | Leu | Ser | Asp | Asn | Trp | Phe | Thr | Arg | Gly | Ile | Asp | Glu | Gln | Val | |
| 385 | | | | | 390 | | | | | 395 | | | | | 400 | |
| aag | tta | act | gtt | aaa | aat | cag | gaa | gaa | cca | gtt | ttt | tat | tat | gtt | tat | 1248 |
| Lys | Leu | Thr | Val | Lys | Asn | Gln | Glu | Glu | Pro | Val | Phe | Tyr | Tyr | Val | Tyr | |
| | | | | 405 | | | | | 410 | | | | | 415 | | |
| aat | ttt | gat | gaa | aat | tct | cca | agt | cgg | aaa | gtt | ttt | ggt | gat | ttt | gga | 1296 |
| Asn | Phe | Asp | Glu | Asn | Ser | Pro | Ser | Arg | Lys | Val | Phe | Gly | Asp | Phe | Gly | |
| | | | 420 | | | | | 425 | | | | | 430 | | | |
| ata | aaa | ggc | ggt | ggt | cat | gct | gat | gaa | ttg | ggt | aat | ata | ttt | aaa | gcc | 1344 |
| Ile | Lys | Gly | Gly | Gly | His | Ala | Asp | Glu | Leu | Gly | Asn | Ile | Phe | Lys | Ala | |
| | | 435 | | | | | 440 | | | | | 445 | | | | |
| aaa | agt | gca | aat | ttt | ggg | aag | gaa | aca | cca | aat | gct | gtg | ttg | gtt | cag | 1392 |
| Lys | Ser | Ala | Asn | Phe | Gly | Lys | Glu | Thr | Pro | Asn | Ala | Val | Leu | Val | Gln | |
| | 450 | | | | | 455 | | | | | 460 | | | | | |
| aga | agg | atg | ctg | gag | atg | tgg | act | aat | ttt | gct | aaa | ttt | gga | aat | cct | 1440 |
| Arg | Arg | Met | Leu | Glu | Met | Trp | Thr | Asn | Phe | Ala | Lys | Phe | Gly | Asn | Pro | |
| 465 | | | | | 470 | | | | | 475 | | | | | 480 | |
| act | cca | gct | att | acg | gat | aca | ctt | cca | ata | aaa | tgg | gaa | cct | gct | ttt | 1488 |
| Thr | Pro | Ala | Ile | Thr | Asp | Thr | Leu | Pro | Ile | Lys | Trp | Glu | Pro | Ala | Phe | |
| | | | | 485 | | | | | 490 | | | | | 495 | | |
| aaa | gaa | aat | atg | act | ttt | gtt | caa | att | gac | att | gat | tta | aat | ttg | agt | 1536 |
| Lys | Glu | Asn | Met | Thr | Phe | Val | Gln | Ile | Asp | Ile | Asp | Leu | Asn | Leu | Ser | |
| | | | 500 | | | | | 505 | | | | | 510 | | | |
| act | gat | cca | cta | aaa | agt | cgt | atg | gaa | ttt | ggg | aat | aaa | ata | aaa | tta | 1584 |
| Thr | Asp | Pro | Leu | Lys | Ser | Arg | Met | Glu | Phe | Gly | Asn | Lys | Ile | Lys | Leu | |
| | | | 515 | | | | | 520 | | | | | 525 | | | |
| tta | aaa | | | | | | | | | | | | | | | 1590 |
| Leu | Lys | | | | | | | | | | | | | | | |
| | 530 | | | | | | | | | | | | | | | |

<210> SEQ ID NO 71
<211> LENGTH: 1590
<212> TYPE: DNA
<213> ORGANISM: Ctenocephalides felis

<400> SEQUENCE: 71

```
ttttaataat tttattttat tcccaaattc catacgactt tttagtggat cagtactcaa      60
atttaaatca atgtcaattt gaacaaaagt catattttct ttaaaagcag gttcccatttt    120
tattggaagt gtatccgtaa tagctggagt aggatttcca aatttagcaa aattagtcca    180
catctccagc atccttctct gaaccaacac agcatttggt gtttccttcc caaaatttgc    240
acttttggct ttaaatatat tacccaattc atcagcatga ccaccgcctt ttattccaaa    300
atcaccaaaa actttccgac ttggagaatt tcatcaaaa ttataaacat aataaaaaac    360
tggttcttcc tgattttaa cagttaactt tacttgctca tcaattccac gtgtaaacca    420
attatcactt aaaacatcta caaaattctg catattttct gatatggttt tgttttggaa    480
ataaaattcc ctgattgctt cacccagtgc aatagatttt tgtgatcgca aaggtaattc    540
taagtcagtt ggtataaatc tttcaaaatc agcttcaaat ttatttaata aatctggatc    600
```

```
tgtttttaag tacatgaaaa atagattgcc ttcggcactg ttgtaacctg tcaacaatgg      660
aactttgtgg aatttccctg aatttattat tggtattggc aagtcagtta agtacgaatc      720
ttgttctgga aatgtttttt caatcgaagg tacaaacacg aagtcatcca gcagttgacc      780
atcaatttct tggggtaatt tggtatttaa caatgtttct actggtaggt ttttcaaaaa      840
atccaaggct tcttgaaggt tgtttgtggt aaggcctaag gttttgcata gtcgaagtgc      900
attcttaaca ggattttttt ggaaagccca gggattaaaa gcacttccac tttgtgctat      960
agccttgtgg aataaacctt tggtaagttg tgacaaaatg tgataatgta cacttgcagc     1020
tccagcagtt gctccacaaa ttgtaatatt ttttgggtct ccactaaagg ttgcaatatt     1080
ttcatttacc catttaggg ctgcaacttg atccatcaat ccaacattcc caggcgcatc     1140
ttcgatttcc aaattaagaa aaccaagtgg tcctagacga taattaatag ttactaagat     1200
aatatcatat tctattaaat aatcaggacc atgtatatca gaatttcctg atccgaccac     1260
aaatgctcct ccatgaatcc aaaacattac tggcaaagga ttttctgaag tgttttgtgg     1320
gacatagata tttaagtaaa ggcaatcttc gcaaccccca gctgatttca aaaaccattt     1380
cccagcagca caattatttc catactgagt ggcgtcaaaa acaccattcc aaggatcaag     1440
tttttgtggt ggcttgaatc tgagatcatt tacaggagat tttgcatagg gtatacctgt     1500
gtaactatag taaattttac cattttcgtt tacaactttc ttgcctttca gaattccata     1560
tgttgttgtt tttagtaatg gatcacacat                                      1590

<210> SEQ ID NO 72
<211> LENGTH: 650
<212> TYPE: DNA
<213> ORGANISM: Ctenocephalides felis
<220> FEATURE:
<221> NAME/KEY: CDS
<222> LOCATION: (3)..(650)
<223> OTHER INFORMATION:

<400> SEQUENCE: 72 gg atc cat gga ggc gca ttc aac caa gga tca gga tct tat aat ttt         47
   Ile His Gly Gly Ala Phe Asn Gln Gly Ser Gly Ser Tyr Asn Phe
   1               5                   10                  15 ttt gga cct gat tat ttg atc agg gaa gga att att ttg gtc act atc       95
Phe Gly Pro Asp Tyr Leu Ile Arg Glu Gly Ile Ile Leu Val Thr Ile
            20                  25                  30 aac tat aga tta gga gtt ttc ggt ttt cta tca gcg ccg gaa tgg gat      143
Asn Tyr Arg Leu Gly Val Phe Gly Phe Leu Ser Ala Pro Glu Trp Asp
        35                  40                  45 atc cat gga aat atg ggt cta aaa gac cag aga ttg gca cta aaa tgg      191
Ile His Gly Asn Met Gly Leu Lys Asp Gln Arg Leu Ala Leu Lys Trp
    50                  55                  60 gtt tac gac aac atc gaa aag ttt ggt gga gac aga gaa aaa att aca      239
Val Tyr Asp Asn Ile Glu Lys Phe Gly Gly Asp Arg Glu Lys Ile Thr
65                  70                  75 att gct gga gaa tct gct gga gca gca agt gtc cat ttt ctg atg atg      287
Ile Ala Gly Glu Ser Ala Gly Ala Ala Ser Val His Phe Leu Met Met
80                  85                  90                  95 gac aac tcg act aga aaa tac tac caa agg gcc att ttg cag agt ggg      335
Asp Asn Ser Thr Arg Lys Tyr Tyr Gln Arg Ala Ile Leu Gln Ser Gly
                100                 105                 110 aca tta cta aat ccg act gct aat caa att caa ctt ctg cat aga ttt      383
Thr Leu Leu Asn Pro Thr Ala Asn Gln Ile Gln Leu Leu His Arg Phe
            115                 120                 125
```

```
gaa aaa ctc aaa caa gtg cta aac atc acg caa aaa caa gaa ctc cta      431
Glu Lys Leu Lys Gln Val Leu Asn Ile Thr Gln Lys Gln Glu Leu Leu
        130                 135                 140 aac ctg gat aaa aac cta att tta cga gca gcc tta aac aga gtt cct      479
Asn Leu Asp Lys Asn Leu Ile Leu Arg Ala Ala Leu Asn Arg Val Pro
    145                 150                 155 gat agc aac gac cat gac cga gac aca gta cca gta ttt aat cca gtc      527
Asp Ser Asn Asp His Asp Arg Asp Thr Val Pro Val Phe Asn Pro Val
160                 165                 170                 175 tta gaa tca cca gaa tct cca gat cca ata aca ttt cca tct gcc ttg      575
Leu Glu Ser Pro Glu Ser Pro Asp Pro Ile Thr Phe Pro Ser Ala Leu
                180                 185                 190 gaa aga atg aga aat ggt gaa ttt cct gat gtc gat gtc atc att ggt      623
Glu Arg Met Arg Asn Gly Glu Phe Pro Asp Val Asp Val Ile Ile Gly
            195                 200                 205 ttc aat agt gct gaa ggt tta aga tct                                  650
Phe Asn Ser Ala Glu Gly Leu Arg Ser
        210                 215

<210> SEQ ID NO 73
<211> LENGTH: 216
<212> TYPE: PRT
<213> ORGANISM: Ctenocephalides felis

<400> SEQUENCE: 73

Ile His Gly Gly Ala Phe Asn Gln Gly Ser Gly Ser Tyr Asn Phe Phe
1               5                   10                  15

Gly Pro Asp Tyr Leu Ile Arg Glu Gly Ile Ile Leu Val Thr Ile Asn
            20                  25                  30

Tyr Arg Leu Gly Val Phe Gly Phe Leu Ser Ala Pro Glu Trp Asp Ile
        35                  40                  45

His Gly Asn Met Gly Leu Lys Asp Gln Arg Leu Ala Leu Lys Trp Val
    50                  55                  60

Tyr Asp Asn Ile Glu Lys Phe Gly Gly Asp Arg Glu Lys Ile Thr Ile
65                  70                  75                  80

Ala Gly Glu Ser Ala Gly Ala Ala Ser Val His Phe Leu Met Met Asp
                85                  90                  95

Asn Ser Thr Arg Lys Tyr Tyr Gln Arg Ala Ile Leu Gln Ser Gly Thr
            100                 105                 110

Leu Leu Asn Pro Thr Ala Asn Gln Ile Gln Leu Leu His Arg Phe Glu
        115                 120                 125

Lys Leu Lys Gln Val Leu Asn Ile Thr Gln Lys Gln Glu Leu Leu Asn
    130                 135                 140

Leu Asp Lys Asn Leu Ile Leu Arg Ala Ala Leu Asn Arg Val Pro Asp
145                 150                 155                 160

Ser Asn Asp His Asp Arg Asp Thr Val Pro Val Phe Asn Pro Val Leu
                165                 170                 175

Glu Ser Pro Glu Ser Pro Asp Pro Ile Thr Phe Pro Ser Ala Leu Glu
            180                 185                 190

Arg Met Arg Asn Gly Glu Phe Pro Asp Val Asp Val Ile Ile Gly Phe
        195                 200                 205

Asn Ser Ala Glu Gly Leu Arg Ser
    210                 215

<210> SEQ ID NO 74
<211> LENGTH: 15
<212> TYPE: PRT
<213> ORGANISM: Peptide
```

-continued

```
<220> FEATURE:
<221> NAME/KEY: MISC_FEATURE
<222> LOCATION: (3)..(3)
<223> OTHER INFORMATION: Xaa = unknown
<220> FEATURE:
<221> NAME/KEY: MISC_FEATURE
<222> LOCATION: (5)..(5)
<223> OTHER INFORMATION: Xaa = unknown
<220> FEATURE:
<221> NAME/KEY: MISC_FEATURE
<222> LOCATION: (6)..(6)
<223> OTHER INFORMATION: Xaa = unknown

<400> SEQUENCE: 74

Asp Leu Xaa Val Xaa Xaa Leu Gln Gly Thr Leu Lys Gly Lys Glu
1               5                   10                  15

<210> SEQ ID NO 75
<211> LENGTH: 31
<212> TYPE: DNA
<213> ORGANISM: Artificial sequence
<220> FEATURE:
<223> OTHER INFORMATION: Synthetic Primer

<400> SEQUENCE: 75
cgcggatccg ctgatctaca agtgactttg c                              31

<210> SEQ ID NO 76
<211> LENGTH: 1488
<212> TYPE: DNA
<213> ORGANISM: Ctenocephalides felis
<220> FEATURE:
<221> NAME/KEY: exon
<222> LOCATION: (3)..(1487)
<223> OTHER INFORMATION:

<400> SEQUENCE: 76 cc cag ggc gaa ttg gtt gga aaa gct ttg acg aac gaa aat gga aaa    47
   Gln Gly Glu Leu Val Gly Lys Ala Leu Thr Asn Glu Asn Gly Lys
   1               5                   10                  15 gag tat ttt agc tac aca ggt gtg cct tat gct aaa cct cca gtt gga   95
Glu Tyr Phe Ser Tyr Thr Gly Val Pro Tyr Ala Lys Pro Pro Val Gly
                20                  25                  30 gaa ctt aga ttt aag cct cca cag aaa gct gag cca tgg aat ggt gtt   143
Glu Leu Arg Phe Lys Pro Pro Gln Lys Ala Glu Pro Trp Asn Gly Val
            35                  40                  45 ttc aac gcc aca tca cat gga aat gtg tgc aaa gct ttg aat ttc ttc   191
Phe Asn Ala Thr Ser His Gly Asn Val Cys Lys Ala Leu Asn Phe Phe
        50                  55                  60 ttg aaa aaa att gaa gga gac gaa gac tgc ttg ttg gtg aat gtg tac   239
Leu Lys Lys Ile Glu Gly Asp Glu Asp Cys Leu Leu Val Asn Val Tyr
    65                  70                  75 gca cca aaa aca act tct gac aaa aaa ctt cca gta ttt ttc tgg gtt   287
Ala Pro Lys Thr Thr Ser Asp Lys Lys Leu Pro Val Phe Phe Trp Val
80                  85                  90                  95 cat ggt ggc ggt ttt gtg act gga tcc gga aat tta gaa ttt caa agc   335
His Gly Gly Gly Phe Val Thr Gly Ser Gly Asn Leu Glu Phe Gln Ser
                100                 105                 110 cca gat tat tta gta aat tat gat gtt att ttt gta act ttc aat tac   383
Pro Asp Tyr Leu Val Asn Tyr Asp Val Ile Phe Val Thr Phe Asn Tyr
            115                 120                 125 cga ttg gga cca ctc gga ttt ttg aat ttg gag ttg gaa ggt gct cct   431
Arg Leu Gly Pro Leu Gly Phe Leu Asn Leu Glu Leu Glu Gly Ala Pro
        130                 135                 140 gga aat gta gga tta ttg gat cag gta gca gct ttg aaa tgg acc aaa   479
```

```
Gly Asn Val Gly Leu Leu Asp Gln Val Ala Ala Leu Lys Trp Thr Lys
        145                 150                 155 gaa aat att gag aaa ttt ggt gga gat cca gaa aat att aca att ggt        527
Glu Asn Ile Glu Lys Phe Gly Gly Asp Pro Glu Asn Ile Thr Ile Gly
160                 165                 170                 175 ggt gtt tct gct ggt gga gca agt gtt cat tat ctt tta ttg tca cat        575
Gly Val Ser Ala Gly Gly Ala Ser Val His Tyr Leu Leu Leu Ser His
                180                 185                 190 aca acc act gga ctt tac aaa agg gca att gct caa agt gga agt gct        623
Thr Thr Thr Gly Leu Tyr Lys Arg Ala Ile Ala Gln Ser Gly Ser Ala
        195                 200                 205 tta aat cca tgg gcc ttc caa aga cat cca gta aag cgt agt ctt caa        671
Leu Asn Pro Trp Ala Phe Gln Arg His Pro Val Lys Arg Ser Leu Gln
        210                 215                 220 ctt gct gag ata tta ggt cat ccc aca aac aac act caa gat gct tta        719
Leu Ala Glu Ile Leu Gly His Pro Thr Asn Asn Thr Gln Asp Ala Leu
225                 230                 235 gaa ttc tta caa aaa gcc cca gta gac agt ctc ctg aaa aaa atg cca        767
Glu Phe Leu Gln Lys Ala Pro Val Asp Ser Leu Leu Lys Lys Met Pro
240                 245                 250                 255 gct gaa aca gaa ggt gaa ata ata gaa gag ttc gtc ttc gta cca tca        815
Ala Glu Thr Glu Gly Glu Ile Ile Glu Glu Phe Val Phe Val Pro Ser
                260                 265                 270 att gaa aaa gtt ttc cca tcc cac caa cct ttc ttg gaa gaa tca cca        863
Ile Glu Lys Val Phe Pro Ser His Gln Pro Phe Leu Glu Glu Ser Pro
        275                 280                 285 ttg gcc aga atg aaa tct gga tcc ttt aac aaa gta cct tta tta gtt        911
Leu Ala Arg Met Lys Ser Gly Ser Phe Asn Lys Val Pro Leu Leu Val
        290                 295                 300 gga ttc aac agc gca gaa gga ctt ttg tac aaa ttc ttt atg aaa gaa        959
Gly Phe Asn Ser Ala Glu Gly Leu Leu Tyr Lys Phe Phe Met Lys Glu
        305                 310                 315 aaa cca gag atg ctg aac caa gct gaa gca gat ttc gaa aga ctc gta       1007
Lys Pro Glu Met Leu Asn Gln Ala Glu Ala Asp Phe Glu Arg Leu Val
320                 325                 330                 335 cca gcc gaa ttt gaa tta gcc cat gga tca gaa gaa tcg aaa aaa ctt       1055
Pro Ala Glu Phe Glu Leu Ala His Gly Ser Glu Glu Ser Lys Lys Leu
                340                 345                 350 gca gaa aaa atc agg aag ttt tac ttt gac gat aaa ccc gtt cct gaa       1103
Ala Glu Lys Ile Arg Lys Phe Tyr Phe Asp Asp Lys Pro Val Pro Glu
        355                 360                 365 aat gag cag aaa ttt att gac ttg ata gga gat att tgg ttt act aga       1151
Asn Glu Gln Lys Phe Ile Asp Leu Ile Gly Asp Ile Trp Phe Thr Arg
        370                 375                 380 ggc att gac aag cat gtc aag ttg tct gta gaa aaa caa gac gag cca       1199
Gly Ile Asp Lys His Val Lys Leu Ser Val Glu Lys Gln Asp Glu Pro
385                 390                 395 gta tat tat tat gaa tat tct ttc tct gaa agt cat cct gca aaa gga       1247
Val Tyr Tyr Tyr Glu Tyr Ser Phe Ser Glu Ser His Pro Ala Lys Gly
400                 405                 410                 415 aca ttt ggt gac cat aac ttg act gga gca tgt cat ggt gaa gaa ctt       1295
Thr Phe Gly Asp His Asn Leu Thr Gly Ala Cys His Gly Glu Glu Leu
                420                 425                 430 gtg aat tta ttc aaa gtc gag atg atg aag ctg gaa aaa gat aaa ccg       1343
Val Asn Leu Phe Lys Val Glu Met Met Lys Leu Glu Lys Asp Lys Pro
        435                 440                 445 aat gtt tta tta aca aaa gat agg gta ctt gct atg tgg acg aac ttc       1391
Asn Val Leu Leu Thr Lys Asp Arg Val Leu Ala Met Trp Thr Asn Phe
        450                 455                 460
```

-continued

```
atc aaa aat gga aat cct act cct gaa gta act gaa tta ttg cca gtt       1439
Ile Lys Asn Gly Asn Pro Thr Pro Glu Val Thr Glu Leu Leu Pro Val
    465                 470                 475 aaa tgg gaa cct gcc aca aaa gac aag ttg aat tat ttg aac att gat g     1488
Lys Trp Glu Pro Ala Thr Lys Asp Lys Leu Asn Tyr Leu Asn Ile Asp
480                 485                 490                 495
```